(12) United States Patent
Lu et al.

(10) Patent No.: US 7,781,414 B2
(45) Date of Patent: Aug. 24, 2010

(54) TARGETS FOR TUMOR GROWTH INHIBITION

(75) Inventors: Patrick Y. Lu, Rockville, MD (US);
Frank Y. Xie, Germantown, MD (US);
Martin C. Woodle, Bethesda, MD (US);
Yijia Liu, Gaithersburg, MD (US);
Quinn Q. Tang, Gaithersburg, MD (US);
Jun Xu, Germantown, MD (US)

(73) Assignee: Intradigm Corporation, Palo Alto, CA (US)

(*) Notice: Subject to any disclaimer, the term of this patent is extended or adjusted under 35 U.S.C. 154(b) by 378 days.

(21) Appl. No.: 10/551,667

(22) PCT Filed: Apr. 1, 2004

(86) PCT No.: PCT/US2004/010059

§ 371 (c)(1),
(2), (4) Date: Jul. 18, 2006

(87) PCT Pub. No.: WO2004/089284

PCT Pub. Date: Oct. 21, 2004

(65) Prior Publication Data

US 2007/0003519 A1    Jan. 4, 2007

Related U.S. Application Data

(60) Provisional application No. 60/458,948, filed on Apr. 1, 2003, provisional application No. 60/489,504, filed on Jul. 24, 2003.

(51) Int. Cl.
*A61K 31/70* (2006.01)
*C07H 21/04* (2006.01)
*C07H 21/00* (2006.01)
*C12P 19/34* (2006.01)

(52) U.S. Cl. .................. 514/44; 536/23.1; 536/24.5; 536/25.3; 435/91.1

(58) Field of Classification Search .......... None
See application file for complete search history.

(56) References Cited

U.S. PATENT DOCUMENTS

| 5,801,154 | A  | 9/1998  | Baracchini et al. |
| 6,309,636 | B1 | 10/2001 | Do Couto et al. |
| 6,506,559 | B1 | 1/2003  | Fire et al. |
| 2006/0211637 | A1 | 9/2006 | Scaria et al. |

FOREIGN PATENT DOCUMENTS

| WO | WO 95/15171 | 6/1995 |
| WO | WO 00/06723 | 2/2000 |
| WO | WO 00/30667 | 6/2000 |
| WO | WO 03/00928 | 1/2003 |
| WO | WO 03/70771 | 8/2003 |
| WO | WO 2004/013310 A2 | 2/2004 |

OTHER PUBLICATIONS

Opalinska et al. Nature Reviews Drug Discovery, 2002, vol. 1, p. 503-514.*
Yan et al. Molecular Cancer Therapeutics 2008, vol. 7, pp. 1355-1364.*
Cai et al., "Induction of glucose regulated proteins during growth of a murine tumor," *J. Cell Physiol.*, 154:229-237 (1993).
Carmon et al., "Characterization of novel breast carcinoma-associated BA46-derived peptides in HLA-A2.1/Db-beta2m transgenic mice," *Journal of Clinical Investigation*, 110:453-462 (2002).
Couto et al., "Cloning and sequence analysis of human breast epithelial antigen BA46 reveals an RGD cell adhesion sequence presented on an epidermal growth factor-like domain," *DNA and Cell Biology*; 15:281-286 (1996).
GenBank Accession No. AAA02490.
GenBank Accession No. AAH14425.
GenBank Accession No. AK026010.
GenBank Accession No. AK056708.
GenBank Accession No. BAB15318.
GenBank Accession No. BC014425.
GenBank Accession No. M99624.
GenBank Accession No. NM_022450.
GenBank Accession No. Z69719.
Gorza et al., "Reduced amount of the glucose-regulated protein GRP94 in skeletal myoblasts results in loss of fusion competence," *The FASEB Journal*, 14:461-475 (2000).
Taylor et al., "Antisense oligonucleotides: a systematic high-throughput approach to target validation and gene function determination," *Drug Discovery Today*, 4:562-567 (1999).
U.S. Appl. No. 60/401,029, filed Aug. 6, 2002, Xie et al.

* cited by examiner

*Primary Examiner*—Tracy Vivlemore
(74) *Attorney, Agent, or Firm*—Ropes & Gray LLP; Jane T. Gunnison; Alla Brukman

(57) ABSTRACT

The present invention relates to methods for treating cancers by manipulating a target gene expression by up-regulation, silencing and/or down-regulation of the gene, such as EGFR-RP, TRA1, MFGE8, TNFSF13 and ZFP236, respectively. The methods are useful in treating cancers and/or inhibiting tumor growth by enhancing expression of a gene that is validated as a target such as ICT1030, for protein, peptide drug and gene therapy modalities; or by RNA interference to silence and/or down-regulate targets such as ICT1024, ICT1025 and ICT1031 and ICB1003 that are validated for antibody, small molecule and other inhibitor drug modalities.

31 Claims, 48 Drawing Sheets

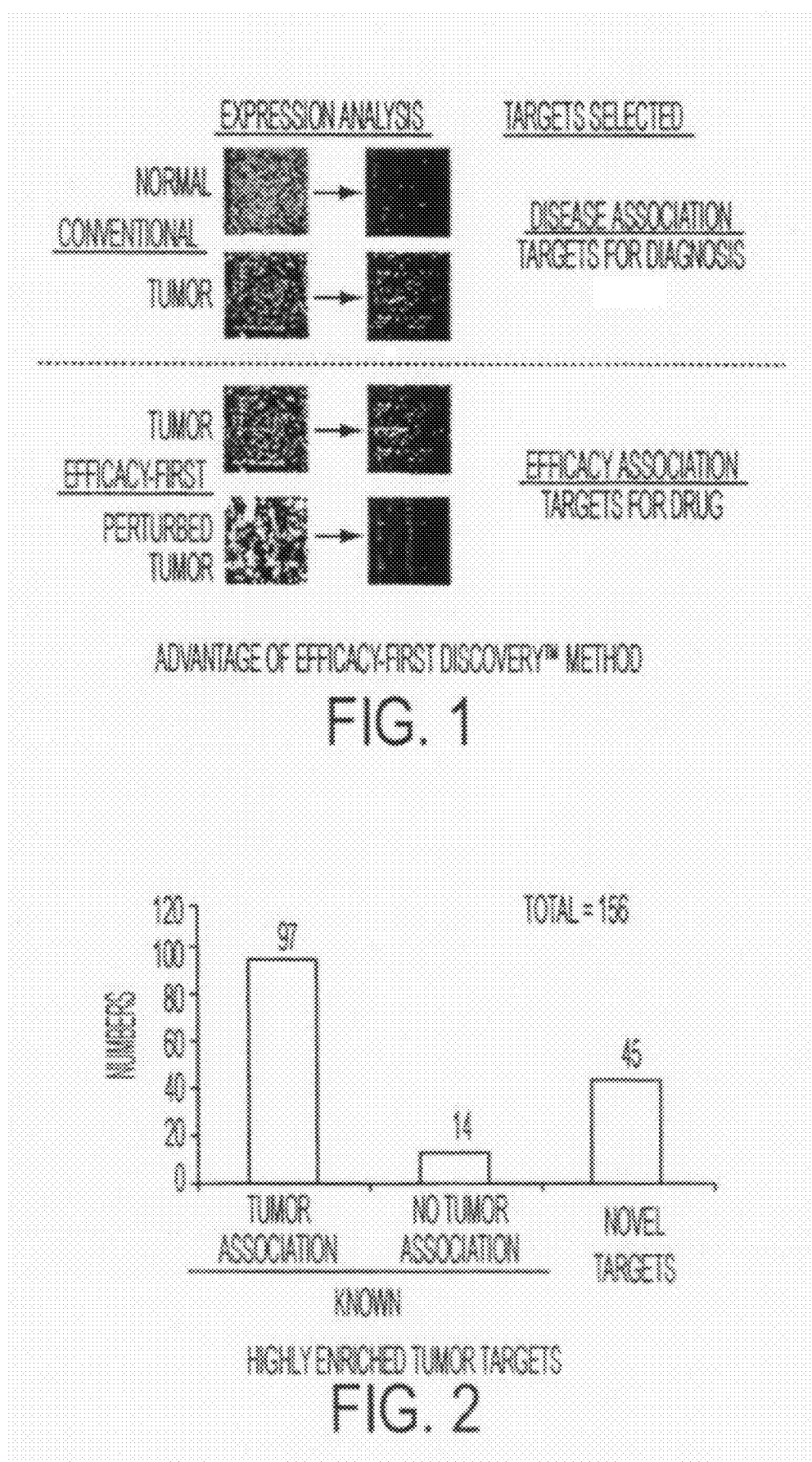

Consensus in rhomboid family

```
                              10        20        30        40        50        60
                     ....*....|....*....|....*....|....*....|....*....|....*....|
Human     consensus     1   PLQPGQLWR--LITSMPLHAGILHLLFNMLSLLFFGIPLERRLGSVRFLLLYLLSGLAG-  57
Yeast     gi 9963865   99   ALRNWQVYR--LVTYIPVYENPISLLCGAIIIWRFAGNPERTVGTVRHCFFTVIPAIFS- 155
Bacteria  gi 3738201   47   LLQKRQLYE--IITYVTLHLSMLHIVFNFVSLLPAMSQFEKKQGTLACILVTVIPYTLFp 104
Yeast     gi 1653749   49   PRSLEGLRG--IVFAPPLHADPGHLIANSVPFVVLAWLVMLQ-EVSDFWIVTIITMVVG- 104
Human     gi 13621505  60   sksnarpvvaigdsDIYSYRIWS-FFCQWINTIFCWSNRRRPLGLTPPFLLLYVLSGVMG- 117
Bacteria  gi 20139804 103   PEKREEAWR--FISYMLVHAgVQHILGNLCMQLVLGIPLEMVHKGLRVGLVYLAGVIAG- 159
Human     gi 1169951  129   PTLKFEFWR--YFTHALMHPSLMHILFNLLWWWYLGGAVEKRLGSGKLIVIRSISALLS- 185
Bacteria  gi 11066250 198   SNPASKVLCspMLLSTPSHPSLFHMAANMYVLWSPSSSIVNILGQEQPMAVYLSAGVIS- 256
Human     gi 13813618  68   yLVIKGYYSe-LFTSIPITNSFVDPIFNPISLYVIYLIFGSRAGKHEYGIPILAGILGN- 125
Plant     gi 9294149  242   IFKHKDLKR--LFLSAFYHVNEPHLVYNMMSLLWKGIKLETSMGSSEFASMVFTLIGMS- 298

70        80        90       100       110       120
                     ....*....|....*....|....*....|....*....|....*....|....*....|
Human     consensus    58   SLLSLLLSPAS-----TPSVGASGAIFGLLGALLVLLPLNRILLLNP--GAALFLLLGII 110
Yeast     gi 9963865  156   AIIFLSPEAVSs----LSKLGEVEDARGFTPVAPAMLGVTTVRSRMRraLVFGMVVPSVL 211
Bacteria  gi 3738201  105   GIMHLIVYHFFlrkdyVSIAGLSGWAFAFISASCVHSPQRLISPFN-----LFSIPAYCF 159
Yeast     gi 1653749  105   GLGVWLIAPPN-----TVTVGASILIFGYLGFLLFRGWFQKNLASIV1-SIVVLVLYGSA 158
Human     gi 13621505 118   NAFTFWLTPETv------AAGASTSLFGLFAAIVVLSFLGKNQALKDl-GKSYQTLIV-V 169
Bacteria  gi 20139804 160   SLASSIFDPLR------YLVGASGGVYALMGGYFMNVLVNFQEMIPA--FGIFRLLIIIL 211
Human     gi 1169951  186   GYVQQKFSGPW--------FGGLSGVVYALMGYVWLRGERDPQSG--------IYLQRGLI 230
Bacteria  gi 11066250 257   NFVSYLGKVATqr--yGPSLGASGAIMTVLAAVCTKIPBGR-LA-------IIFLPMFTF 306
Human     gi 13813618 126   LLTVIFYSPFT------LSSGASGGIFGLLSYYTFYDFLKKDNLG----VYGLVFLVSVF 175
Plant     gi 9294149  299   QGVTLLLAKSL-----LLLFDYDRAYYNEYAVGFSGVLFAMKVVLNSq-AEDYSSVYGIL 352

130       140       150       160       170
                     ....*....|....*....|....*....|....*....|....*....|.
Human     consensus   111   LLNLLLGL---LPGISNFG-----------HLGGLLAGLLLGFLLLRRPR 146
Yeast     gi 9963865  212   VPWLLLGAswlIPQTSFLS-----------NVCGLSIGLAYAHLLLFHRP 250
Bacteria  gi 3738201  160   PIIYLIMTtilVPKASPIG-----------HASGAVMGYCTPFMLGSIPL 198
Yeast     gi 1653749  159   LWGLLPGR----AGVSWQG-----------HLFGFIGGAIAAWLIAREKH 193
Human     gi 13621505 170   NLLMNLP----MPNVSMAG-----------HIGGVVGGALLSIVFPTKMR 204
Bacteria  gi 20139804 212   IIVLDNGF---ALYRRFFVpedqsp-vsfaaHIAGGPAGMSIGYTVFSCPD 258
Human     gi 1169951  231   IFALIWIV---AGWFDLFGmsma-----ngaHIAGLAVGLAMAPVDSLNAR 273
Bacteria  gi 11066250 307   TAGNALKA---IIAMDTAGmilqwkffdhaaHLGGALFGIWYVTYGHELIW 354
Human     gi 13813618 176   GVSDLIFP-----NVNVVA-----------HIGGILGGIMYAVVYYLIRS 209
Plant     gi 9294149  353   VPTKYAAWa-eLILVQMFVpnas-----flqHLGGILAGIIYLKLKGSYSG 397
```

FIG. 12

Human rhomboid Proteins
Human Rhomboid Family Protein Alignments

```
ICT-1024    1 msearrdstsslgrkpppwlkldipsavpltae--eps------flqplrrqaflrsvsmpaetahisspphelrrpvlqrqtsitqtlirrgtadwfgvskdsdstqkwqrksirhcsqry
HRhomboid 2 1 ------------------------------------------------------------------------------------------------------------------------
HRhomboid 3 1 ------------------------------------------------------------------------------------------------------------------------
HRhomboid 4 1 mgeh--------------------pspqpavaacaeae-----rieelepeaeerlpaaped------hwkv----------lfdqfdpqmtgyi------stgkfrslleshssk--
HRhomboid 5 1 ------------------------------------------------------------------------------------------------------------mawrg----waqrg-wgcqqaw
HRhomboid 6 1 mgrrsrgintglilllsqifhvginnippvtla--tlalniwfflnp--------------------qkplysscslvekcyqq---------kd------wqr-------------

ICT-1024  114 gtklkpqvlreldlpsgdnvsltstetpplryvgpcqlgmqkiidplargrafrvaddtaeglsapphtpvtpgaaslcfssrsgfhrlprrkresvakmsfraaaalmkgrsvrdgtf
HRhomboid 2   1 ------------------------------------------------------------------------------------------------------mnlmmgremkee-
HRhomboid 3   1 ------------------------------------------------------------------------------------------------msvahmslqaaaallkgrsvldatg
HRhomboid 4  70 --------------ldphkrevllaladshadg-----------------------qigydifvslmsnk---rsnsi
HRhomboid 5  18 g--------asvggrsceeltavltppqll-----grfnf----------------fiqqkcgfrkaprk--veprrsdpgts
HRhomboid 6  68 -------------------llsplhh------add------------------wh--lyfnmasmlwkginle- ICT-1024  234 rra---r--rrsftpasfleedtdfpdeldtsffaregilheelstypdevfespseaalkdwekapeqadltggaldrselershlmplergwrkqkegaappphkvrlrgevvsta
HRhomboid 2  13 -------------------leee---------------------------ekmred----gggkdrakskkvh
HRhomboid 3  26 --rvvkrsfafpsfleedvdgadtfdssifsk-----eemssmpddvfesspplsa-syfrgiphsa--spvspdgvqipl----keygrapvp
HRhomboid 4 108 rqailqg--nrrlsskalleekglslsqrl-------irhvayetlprei-----------------drkwyydsyfcppp
HRhomboid 5  71 gea----------yvitafsvltgvvyllllqfavaefmdep--dfkrsc--avgfsgylfalkvlnnhy--ykrsalippve----etvfypsp-
HRhomboid 6  97 rrl---g--srwfa-----------------------facwvel---------------cpggfvni ICT-1024  349 gprrgqtiavpvrtkl-farekrpyglqmvgrltnrtyrkridsfvkrqiedmddhrpfftywlfvhslvtilavciygiap-vgfsqhetvdsvlrnrgvyenvkyvqqenfwigpsse
HRhomboid 2  36 --rj--vskw-mlpek-----srgtyleranccfpp------pvfiisislae--laviiy-----------------tvtllevaff-------lyngvi-------
HRhomboid 3 109 gprrgkriaskvkhfafdrkrhyglgvvgnwlnrsyrrsisstvqrqlesfdshrpfftywltfvhviitlvictygiap-vgfaqhvttqlvlrmkgvyesvkyiqqenfwvgpssi
HRhomboid 4 163 ---pwfmi-----------------------gcafgsaa-iw--qyesiks--rvqsyfdgik------
HRhomboid 5  93 ---ypirsl-i----kpl-----------fftvgft------vaihlfspgtsfaghla------gilvglmytq-------
HRhomboid 6 166 ---lgfpv-----------pnr-----------------------------------------gplkk
```

FIG. 13

```
ICT-1024    467 alihlgakfspcmrqdpqvhstfirsarerehsaccvvmdrsgcvqtseeecsstlavwvkwpihpsap---elaghkrqfgsvchqdprvcdepssedphewpediktkwpicktknsagn
HRhomboid 2  78 ---------------------------------------------------------------yavw--------kpqkqw----------------------------------------
HRhomboid 3 228 dlihlgakfspcirkdgieqlvlrerdlerdsgccvqndhsgciqtqrkdcsetlatfvkwqddtqppmdksdlgqkrtsgavchqdprtceepassgahiwpdditkwpicteqarsn
HRhomboid 4 183 ----------------------------------------------------slgqfvqvthpr--------------------------------------------------yknslvy
HRhomboid 5 137 -----adwldsir--pqkegdfr--keinkw-----wmnlsdgqttvtgiiaanylvfclwrv-------------------------------------------------pslqrtmiry
HRhomboid 6 213 im-----------------------------------------eacaggfsssvgyp-----------------------------------------------------------sgssqy ICT-1024    584 htnhphmdcviltgrpccigtkgrceiitsreycdfmrgyfheeatlcsqvhcmddvcgll--pfl-npeypdqfyrlwlslflhagilhclvslcfqmtvlrdleklagwhriafiylsg
HRhomboid 2  88 -----------------------------------------------itldt-------gilespfiyspekreeawrfisymlvhaqvqhilgnlcmglvlqiplemvhkglrvglvylagv
HRhomboid 3 348 htgflhmdceikrpccigtkgsceittreycefmhgyfheeatlcsqvhcldkvcgll--pfl-npeypdqfyrlwlslflhagvvhclvsvvfqmtilrdleklagwhriaiifilsg
HRhomboid 4 204 h-----------------------------------------------------------pqlraqvwrylytyifmhagiehlginvvlqllvgvplemvhgatriglvvvagv
HRhomboid 5 196 ftsnp------------------------------askvlcs---------------------pml----------------lstfshfslfhmaanmyvlwststssivmilggeqfmavylsag
HRhomboid 6 243 qdyyph------grp------dhyeeaprnydtytaglseeeq-----------------------leralqasl-----------------------------------------wdr------g ICT-1024    701 vtgmlasaiflp------yraevpagsqfgilaclfvelfqs--wqllarpwraff--kllavvlflfftgl-lpw--i-----------dnf-------ahlsgflsglflsfafl
HRhomboid 2 157 iagslassiflp------lrylvgasggvyalmggyfmnvlvh-fqemipafgifr--llililvldmgf-aly--r----------rffvpedgspvsfaahiagpfag--msiqyt
HRhomboid 3 465 itgmlasaiflp------yraevpagsqtfgilaclfvelfqs-wpllerpwkafi--nlsavlflficgl-lpw--i-----------dnl-------ahifgflsgllllafafl
HRhomboid 4 259 vagslavsvadm------tapvvgssggyyalvsahlanivmn-wsgmkcqfkllr--mavalicmsmefgr-avw--lrfhpsayppcphpsfv-----ahlggvavgitlgvvvl
HRhomboid 5 254 visnifvsylgkvatgrygpslgasgaimtvlaavctkipegrlalifilpmfftagnalkaiiamdtagmilgwkff-----------dha-------ahlggalfgiw
HRhomboid 6 287 ntrnspp---p-------ygfhlspe ICT-1024    788 pyisfqkfdlyrkrcqililfgvvflgllaglvvlfyypvrceweefltcipftdkfceekyeldaqlh---
HRhomboid 2 253 vfsctdkallkdprfwlai----------------------------aaylacvlfa-vflmiflspan---
HRhomboid 3 552 pyiltgtsdkyrkralilvsllafaglfaalvlwlylyipinwpwiehltcfpftsrfceekyeldqvlh--
HRhomboid 4 359 rn------yegrlqdqslwwifvamyt-vflvfavf---wnifayti-----ldlklppppp
HRhomboid 5 345 -yvtygheliwknr-----------------eplvkiwheirtngpkkggsk-----
HRhomboid 6 303 -----emrrqrl]
```

FIG. 13(continued)

(SEQ ID NO:58) ICT1024 PROTEIN (855 AA) CODING REGION: 1670-3637

```
   1  TCAATATTGG CCATTAGCCA TATTATTCAT TGGTTATATA GCATAAATCA ATATTGGCTA
  61  TTGGCCATTG CATACGTTGT ATCTATATCA TAATATGTAC ATTTATATTG GCTCATGTCC
 121  AATATGACCG CCATGTTGGC ATTGATTATT GACTAGTTAT TAATAGTAAT CAATTACGGG
 181  GTCATTAGTT CATAGCCCAT ATATGGAGTT CCGCGTTACA TAACTTACGG TAAATGGCCC
 241  GCCTGGCTGA CCGCCCAACG ACCCCGCCC ATTGACGTCA ATAATGACGT ATGTTCCCAT
 301  AGTAACGCCA ATAGGGACTT TCCATTGACG TCAATGGGTG GAGTATTTAC GGTAAACTGC
 361  CCACTTGGCA GTACATCAAG TGTATCATAT GCCAAGTCCG CCCCCTATTG ACGTCAATGA
 421  CGGTAAATGG CCCGCCTGGC ATTATGCCCA GTACATGACC TTACGGGACT TTCCTACTTG
 481  GCAGTACATC TACGTATTAG TCATCGCTAT TACCATGGTG ATGCGGTTTT GGCAGTACAC
 541  CAATGGGCGT GGATAGCGGT TTGACTCACG GGGATTTCCA AGTCTCCACC CCATTGACGT
 601  CAATGGGAGT TTGTTTTGGC ACCAAAATCA ACGGGACTTT CCAAAATGTC GTAATAACCC
 661  CGCCCCGTTG ACGCAAATGG GCGGTAGGCG TGTACGGTGG GAGGTCTATA TAAGCAGAGC
 721  TCGTTTAGTG AACCGTCAGA TCACTAGAAG CTTTATTGCG GTAGTTTATC ACAGTTAAAT
 781  TGCTAACGCA GTCAGTGCTT CTGACACAAC AGTCTCGAAC TTAAGCTGCA GAAGTTGGTC
 841  GTGAGGCACT GGGCAGGTAA GTATCAAGGT TACAAGACAG GTTTAAGGAG ACCAATAGAA
 901  ACTGGGCTTG TCGAGACAGA GAAGACTCTT GCGTTTCTGA TAGGCACCTA TTGGTCTTAC
 961  TGACATCCAC TTTGCCTTTC TCTCCACAGG TGTCCACTCC CAGTTCAATT ACAGCTCTTA
1021  AGGCTAGAGT ACTTAATACG ACTCACTATA GGCTAGCCTC GAGAATTCCA TGAGTGAGGC
1081  CCGCAGGGAC AGCACGAGCA GCCTGCAGCG CAAGAAGCCA CCCTGGCTAA AGCTGGACAT
1141  TCCCTCTGCG GTGCCCCTGA CGGCAGAAGA GCCCAGCTTC CTGCAGCCCC TGAGGCGACA
1201  GGCTTTCCTG AGGAGTGTGA GTATGCCAGC CGAGACAGCC ACATCTCTT CACCCCACCA
1261  TGAGCTCCGG CGGCCGGTGC TGCAACGCCA GACGTCCATC ACACAGACCA TCCGCAGGGG
1321  GACCGCCGAC TGGTTTGGAG TGAGCAAGGA CAGTGACAGC ACCCAGAAAT GGCAGCGCAA
1381  GAGCATCCGT CACTGCAGCC AGCGCTACGG GAAGCTGAAG CCCCAGGTCC TCCGGGAGCT
1441  GGACCTGCCC AGCCAGGACA CGTGTCGCT GACCAGCACC GAGACGCCAC CCCCACTCTA
1501  CGTGGGGCCA TGCCAGCTGG GCATGCAGAA GATCATAGAC CCCCTGGCCC GTGGCCGTGC
1561  CTTCCGTGTG GCAGATGACA CTGCGGAAGG CCTGAGTGCC CCACACACTC CCGTCACGCC
1621  GGGTGCTGCC TCCCTCTGCT CCTTCTCCAG CTCCCGCTCA GGTTTCCACC GGCTCCCGCG
1681  GCGGCGCAAG CGAGAGTCGG TGGCCAAGAT GAGCTTCCGG GCGGCCGCAG CGCTGATGAA
1741  AGGCCGCTCC GTTAGGGATG GCACCTTTCG CCGGGCACGG CGTCGAAGCT TCACTCCAGC
1801  TAGCTTTCTG GAGGAGGACA CAACTGATTT CCCCGATGAG CTGGACACAT CCTTCTTTGC
1861  CCGGGAAGGT ATCCTCCATG AAGAGCTGTC CACATACCCG GATGAAGTTT TCGAGTCCCC
1921  ATCGGAGGCA GCGCTAAAGG ACTGGGAGAA GGCACCGGAG CAGGCGGACC TCACCGGCGG
1981  GGCCCTGGAC CGCAGCGAGC TTGAGCGCAG CCACCTGATG CTGCCCTTGG AGCGAGGCTG
2041  GCGGAAGCAG AAGGAGGGCG CCGCAGCCCC GCAGCCCAAG GTGCGGCTCC GACAGGAGGT
2101  GGTGAGCACC GCGGGGCCGC GACGGGCCA GCGTATCGCG GTGCCGGTGC GCAAGCTCTT
```

FIG. 25

```
2161  CGCCCGGGAG AAGCGGCCGT ATGGGCTGGG CATGGTGGGA CGGCTCACCA ACCGCACCTA
2221  CCGCAAGCGC ATCGACAGCT TCGTCAAGCG CCAGATCGAG GACATGGACG ACCACAGGCC
2281  CTTCTTCACC TACTGGCTTA CCTTCGTGCA CTCGCTCGTC ACCATCCTAG CCGTGTGCAT
2341  CTATGGCATC GCGCCCGTGG GCTTCTCGCA GCATGAGACG GTGGACTCGG TGCTGCGGAA
2401  CCGCGGGGTC TACGAGAACG TCAAGTACGT GCAGCAGGAG AACTTCTGGA TCGGGCCCAG
2461  CTCGGAGGCC CTCATCCACC TGGGCGCCAA GTTTTCGCCC TGCATGCGCC AGGACCCGCA
2521  GGTGCACAGC TTCATTCGCT CGGCGCGCGA GCGCGAGAAG CACTCCGCCT GCTGCGTGCG
2581  CAACGACAGG TCGGGCTGCG TGCAGACCTC GGAGGAGGAG TGCTCGTCCA CGCTGGCAGT
2641  GTGGGTGAAG TGGCCCATCC ATCCCAGCGC CCAGAGCTT GCGGGCCACA AGAGACAGTT
2701  TGGCTCTGTC TGCCACCAGG ATCCCAGGGT GTGTGATGAG CCCTCCTCCG AAGACCCTCA
2761  TGAGTGGCCA GAAGACATCA CCAAGTGGCC GATCTGCACC AAAAACAGCG CTGGGAACCA
2821  CACCAACCAT CCCCACATGG ACTGTGTCAT CACAGGACGG CCCTGCTGCA TTGGCACCAA
2881  GGGCAGGTGT GAGATCACCT CCCGGGAGTA CTGTGACTTC ATGAGGGGCT ACTTCCATGA
2941  GGAGGCCACG CTCTGCTCTC AGGTGCACTG CATGGATGAT GTGTGTGGGC TCCTGCCTTT
3001  TCTCAACCCC GAGGTGCCTG ACCAGTTCTA CCGCCTGTGG CTATCCCTCT TCCTGCACGC
3061  CGGGATCTTG CACTGCCTGG TGTCCATCTG CTTCCAGATG ACTGTCCTGC GGGACCTGGA
3121  GAAGCTGGCA GGCTGGCACC GCATAGCCAT CATCTACCTG CTGAGTGGTG TCACCGGCAA
3181  CCTGGCCAGT GCCATCTTCC TGCCATACCG AGCAGAGGTG GGTCCTGCTG GCTCCCAGTT
3241  CGGCATCCTG GCCTGCCTCT TCGTGGAGCT CTTCCAGAGC TGGCAGATCC TGGCGCGGCC
3301  CTGGCGTGCC TTCTTCAAGC TGCTGGCTGT GGTGCTCTTC CTCTTCACCT TTGGGCTGCT
3361  GCCGTGGATT GACAACTTTG CCCACATCTC GGGGTTCATC AGTGGCCTCT TCCTCTCCTT
3421  CGCCTTCTTG CCCTACATCA GCTTTGGCAA GTTCGACCTG TACCGGAAAC GCTGCCAGAT
3481  CATCATCTTT CAGGTGGTCT TCCTGGGCCT CCTGGCTGGC CTGGTGGTCC TCTTCTACGT
3541  CTATCCTGTC CGCTGTGAGT GGTGTGAGTT CCTCACCTGC ATCCCCTTCA CTGACAAGTT
3601  CTGTGAGAAG TACGAACTGG ACGCTCAGCT CCACTGAGTC GACCCGGGCG GCCGCTTCGA
3661  GCAGACATGA TAAGATACAT TGATGAGTTT GGACAAACCA CAACTAGAAT GCAGTGAAAA
3721  AAATGCTTTA TTTGTGAAAT TTGTGATGCT ATTGCTTTAT TTGTAACCAT TATAAGCTGC
3781  AATAAACAAG TTAACAACAA CAATTGCATT CATTTTATGT TTCAGGTTCA GGGGGAGATG
3841  TGGGAGGTTT TTTAAAGCAA GTAAAACCTC TACAAATGTG GTAAAATCGA TAAGGATCCG
3901  GGCTGGCGTA ATAGCGAAGA GGCCCGCACC GATCGCCCTT CCCAACAGTT GCGCAGCCTG
3961  AATGGCGAAT GGACGCGCCC TGTAGCGGCG CATTAAGCGC GGCGGGTGTG GTGGTTACGC
4021  GCAGCGTGAC CGCTACACTT GCCAGCGCCC TAGCGCCCGC TCCTTTCGCT TTCTTCCCTT
4081  CCTTTCTCGC CACGTTCGCC GGCTTTCCCC GTCAAGCTCT AAATCGGGGG CTCCCTTTAG
4141  GGTTCCGATT TAGAGCTTTA CGGCACCTCG ACCGCAAAAA ACTTGATTTG GGTGATGGTT
4201  CACGTAGTGG GCCATCGCCC TGATAGACGG TTTTTCGCCC TTTGACGTTG GAGTCCACGT
4261  TCTTTAATAG TGGACTCTTG TTCCAAACTG GAACAACACT CAACCCTATC TCGGTCTATT
4321  CTTTTGATTT ATAAGGGATT TTGCCGATTT CGGCCTATTG GTTAAAAAAT GAGCTGATTT
```

FIG. 25 (continued)

```
4381  AACAAATATT TAACGCGAAT TTTAACAAAA TATTAACGTT TACAATTTCG CCTGATGCGG
4441  TATTTTCTCC TTACGCATCT GTGCGGTATT TCACACCGCA TATGGTGCAC TCTCAGTACA
4501  ATCTGCTCTG ATGCCGCATA GTTAAGCCAG CCCCGACACC CGCCAACACC CGCTGACGCG
4561  CCCTGACGGG CTTGTCTGCT CCCGGCATCC GCTTACAGAC AAGCTGTGAC CGTCTCCGGG
4621  AGCTGCATGT GTCAGAGGTT TTCACCGTCA TCACCGAAAC GCGCGAGACG AAAGGGCCTC
4681  GTGATACGCC TATTTTTATA GGTTAATGTC ATGATAATAA TGGTTTCTTA GACGTCAGGT
4741  GGCACTTTTC GGGGAAATGT GCGCGGAACC CCTATTTGTT TATTTTTCTA AATACATTCA
4801  AATATGTATC CGCTCATGAG ACAATAACCC TGATAAATGC TTCAATAATA TTGAAAAAGG
4861  AAGAGTATGA GTATTCAACA TTTCCGTGTC GCCCTTATTC CCTTTTTTGC GGCATTTTGC
4921  CTTCCTGTTT TTGCTCACCC AGAAACGCTG GTGAAAGTAA AAGATGCTGA AGATCAGTTG
4981  GGTGCACGAG TGGGTTACAT CGAACTGGAT CTCAACAGCG GTAAGATCCT TGAGAGTTTT
5041  CGCCCCGAAG AACGTTTTCC AATGATGAGC ACTTTTAAAG TTCTGCTATG TGGCGCGGTA
5101  TTATCCCGTA TTGACGCCGG GCAAGAGCAA CTCGGTCGCC GCATACACTA TTCTCAGAAT
5161  GACTTGGTTG AGTACTCACC AGTCACAGAA AAGCATCTTA CGGATGGCAT GACAGTAAGA
5221  GAATTATGCA GTGCTGCCAT AACCATGAGT GATAACACTG CGGCCAACTT ACTTCTGACA
5281  ACGATCGGAG GACCGAAGGA GCTAACCGCT TTTTTGCACA ACATGGGGGA TCATGTAACT
5341  CGCCTTGATC GTTGGGAACC GGAGCTGAAT GAAGCCATAC CAAACGACGA GCGTGACACC
5401  ACGATGCCTG TAGCAATGGC AACAACGTTG CGCAAACTAT TAACTGGCGA ACTACTTACT
5461  CTAGCTTCCC GGCAACAATT AATAGACTGG ATGGAGGCGG ATAAAGTTGC AGGACCACTT
5521  CTGCGCTCGG CCCTTCCGGC TGGCTGGTTT ATTGCTGATA AATCTGGAGC CGGTGAGCGT
5581  GGGTCTCGCG GTATCATTGC AGCACTGGGG CCAGATGGTA AGCCCTCCCG TATCGTAGTT
5641  ATCTACACGA CGGGGAGTCA GGCAACTATG GATGAACGAA ATAGACAGAT CGCTGAGATA
5701  GGTGCCTCAC TGATTAAGCA TTGGTAACTG TCAGACCAAG TTTACTCATA TATACTTTAG
5761  ATTGATTTAA AACTTCATTT TTAATTTAAA AGGATCTAGG TGAAGATCCT TTTTGATAAT
5821  CTCATGACCA AAATCCCTTA ACGTGAGTTT TCGTTCCACT GAGCGTCAGA CCCCGTAGAA
5881  AAGATCAAAG GATCTTCTTG AGATCCTTTT TTTCTGCGCG TAATCTGCTG CTTGCAAACA
5941  AAAAAACCAC CGCTACCAGC GGTGGTTTGT TTGCCGGATC AAGAGCTACC AACTCTTTTT
6001  CCGAAGGTAA CTGGCTTCAG CAGAGCGCAG ATACCAAATA CTGTCCTTCT AGTGTAGCCG
6061  TAGTTAGGCC ACCACTTCAA GAACTCTGTA GCACCGCCTA CATACCTCGC TCTGCTAATC
6121  CTGTTACCAG TGGCTGCTGC CAGTGGCGAT AAGTCGTGTC TTACCGGGTT GGACTCAAGA
6181  CGATAGTTAC CGGATAAGGC GCAGCGGTCG GGCTGAACGG GGGGTTCGTG CACACAGCCC
6241  AGCTTGGAGC GAACGACCTA CACCGAACTG AGATACCTAC AGCGTGAGCT ATGAGAAAGC
6301  GCCACGCTTC CCGAAGGGAG AAAGGCGGAC AGGTATCCGG TAAGCGGCAG GGTCGGAACA
6361  GGAGAGCGCA CGAGGGAGCT TCCAGGGGGA AACGCCTGGT ATCTTTATAG TCCTGTCGGG
6421  TTTCGCCACC TCTGACTTGA GCGTCGATTT TTGTGATGCT CGTCAGGGGG GCGGAGCCTA
6481  TGGAAAAACG CCAGCAACGC GGCCTTTTTA CGGTTCCTGG CCTTTTGCTG GCCTTTTGCT
6541  CACATGGCTC GACAGATCT
```

(SEQ ID NO:60) ICT1024 N TERMINUS 553 AA CODING REGION: 1070-2731

```
   1 TCAATATTGG CCATTAGC CA TATTATTCAT TGGTTATATA GCATAAATCA ATATTGGCTA
  61 TTGGCCATTG CATACGTTGT ATCTATATCA TAATATGTAC ATTTATATTG GCTCATGTCC
 121 AATATGACCG CCATGTTGGC ATTGATTATT GACTAGTTAT TAATAGTAAT CAATTACGGG
 181 GTCATTAGTT CATAGCCCAT ATATGGAGTT CCGCGTTACA TAACTTACGG TAAATGGCCC
 241 GCCTGGCTGA CCGCCCAACG ACCCCGCCC ATTGACGTCA ATAATGACGT ATGTTCCCAT
 301 AGTAACGCCA ATAGGGACTT TCCATTGACG TCAATGGGTG GAGTATTTAC GGTAAACTGC
 361 CCACTTGGCA GTACATCAAG TGTATCATAT GCCAAGTCCG CCCCCTATTG ACGTCAATGA
 421 CGGTAAATGG CCCGCCTGGC ATTATGCCCA GTACATGACC TTACGGGACT TTCCTACTTG
 481 GCAGTACATC TACGTATTAG TCATCGCTAT TACCATGGTG ATGCGGTTTT GGCAGTACAC
 541 CAATGGGCGT GGATAGCGGT TTGACTCACG GGGATTTCCA AGTCTCCACC CCATTGACGT
 601 CAATGGGAGT TTGTTTTGGC ACCAAAATCA ACGGGACTTT CCAAAATGTC GTAATAACCC
 661 CGCCCCGTTG ACGCAAATGG GCGGTAGGCG TGTACGGTGG GAGGTCTATA TAAGCAGAGC
 721 TCGTTTAGTG AACCGTCAGA TCACTAGAAG CTTTATTGCG GTAGTTTATC ACAGTTAAAT
 781 TGCTAACGCA GTCAGTGCTT CTGACACAAC AGTCTCGAAC TTAAGCTGCA GAAGTTGGTC
 841 GTGAGGCACT GGGCAGGTAA GTATCAAGGT TACAAGACAG GTTTAAGGAG ACCAATAGAA
 901 ACTGGGCTTG TCGAGACAGA GAAGACTCTT GCGTTTCTGA TAGGCACCTA TTGGTCTTAC
 961 TGACATCCAC TTTGCCTTTC TCTCCACAGG TGTCCACTCC CAGTTCAATT ACAGCTCTTA
1021 AGGCTAGAGT ACTTAATACG ACTCACTATA GGCTAGCCTC GAGAATTCCA TGAGTGAGGC
1081 CCGCAGGGAC AGCACGAGCA GCCTGCAGCG CAAGAAGCCA CCCTGGCTAA AGCTGGACAT
1141 TCCCTCTGCG GTGCCCCTGA CGGCAGAAGA GCCCAGCTTC CTGCAGCCCC TGAGGCGACA
1201 GGCTTTCCTG AGGAGTGTGA GTATGCCAGC CGAGACAGCC CACATCTCTT CACCCCACCA
1261 TGAGCTCCGG CGGCCGGTGC TGCAACGCCA GACGTCCATC ACACAGACCA TCCGCAGGGG
1321 GACCGCCGAC TGGTTTGGAG TGAGCAAGGA CAGTGACAGC ACCCAGAAAT GGCAGCGCAA
1381 GAGCATCCGT CACTGCAGCC AGCGCTACGG GAAGCTGAAG CCCCAGGTCC TCCGGGAGCT
1441 GGACCTGCCC AGCCAGGACA ACGTGTCGCT GACCAGCACC GAGACGCCAC CCCACTCTA
1501 CGTGGGGCCA TGCCAGCTGG GCATGCAGAA GATCATAGAC CCCCTGGCCC GTGGCCGTGC
1561 CTTCCGTGTG GCAGATGACA CTGCGGAAGG CCTGAGTGCC CCACACACTC CCGTCACGCC
1621 GGGTGCTGCC TCCCTCTGCT CCTTCTCCAG CTCCCGCTCA GGTTTCCACC GGCTCCCGCG
1681 GCGGCGCAAG CGAGAGTCGG TGGCCAAGAT GAGCTTCCGG GCGGCCGCAG CGCTGATGAA
1741 AGGCCGCTCC GTTAGGGATG GCACCTTTCG CCGGGCACGG CGTCGAAGCT TCACTCCAGC
1801 TAGCTTTCTG GAGGAGGACA CAACTGATTT CCCCGATGAG CTGGACACAT CCTTCTTTGC
1861 CCGGGAAGGT ATCCTCCATG AAGAGCTGTC CACATACCCG GATGAAGTTT TCGAGTCCCC
1921 ATCGGAGGCA GCGCTAAAGG ACTGGGAGAA GGCACCGGAG CAGGCGGACC TCACCGGCGG
1981 GGCCCTGGAC CGCAGCGAGC TTGAGCGCAG CCACCTGATG CTGCCCTTGG AGCGAGGCTG
2041 GCGGAAGCAG AAGGAGGGCG CCGCAGCCCC GCAGCCCAAG GTGCGGCTCC GACAGGAGGT
2101 GGTGAGCACC GCGGGGCCGC GACGGGGCCA GCGTATCGCG GTGCCGGTGC GCAAGCTCTT
```

FIG. 26

```
2161 CGCCCGGGAG AAGCGGCCGT ATGGGCTGGG CATGGTGGGA CGGCTCACCA ACCGCACCTA
2221 CCGCAAGCGC ATCGACAGCT TCGTCAAGCG CCAGATCGAG GACATGGACG ACCACAGGCC
2281 CTTCTTCACC TACTGGCTTA CCTTCGTGCA CTCGCTCGTC ACCATCCTAG CCGTGTGCAT
2341 CTATGGCATC GCGCCCGTGG GCTTCTCGCA GCATGAGACG GTGGACTCGG TGCTGCGGAA
2401 CCGCGGGGTC TACGAGAACG TCAAGTACGT GCAGCAGGAG AACTTCTGGA TCGGGCCCAG
2461 CTCGGAGGCC CTCATCCACC TGGGCGCCAA GTTTTCGCCC TGCATGCGCC AGGACCCGCA
2521 GGTGCACAGC TTCATTCGCT CGGCGCGCGA GCGCGAGAAG CACTCCGCCT GCTGCGTGCG
2581 CAACGACAGG TCGGGCTGCG TGCAGACCTC GGAGGAGGAG TGCTCGTCCA CGCTGGCAGT
2641 GTGGGTGAAG TGGCCCATCC ATCCCAGCGC CCCAGAGCTT GCGGGCCACA AGAGACAGTT
2701 TGGCTCTGTC TGCCACCAGG ATCCCAGGTG AGTCGACCCG GCGGCCGCT TCGAGCAGAC
2761 ATGATAAGAT ACATTGATGA GTTTGGACAA ACCACAACTA GAATGCAGTG AAAAAAATGC
2821 TTTATTTGTG AAATTTGTGA TGCTATTGCT TTATTTGTAA CCATTATAAG CTGCAATAAA
2881 CAAGTTAACA ACAACAATTG CATTCATTTT ATGTTTCAGG TTCAGGGGGA GATGTGGGAG
2941 GTTTTTTAAA GCAAGTAAAA CCTCTACAAA TGTGGTAAAA TCGATAAGGA TCCGGGCTGG
3001 CGTAATAGCG AAGAGGCCCG CACCGATCGC CCTTCCCAAC AGTTGCGCAG CCTGAATGGC
3061 GAATGGACGC GCCCTGTAGC GGCGCATTAA GCGCGGCGGG TGTGGTGGTT ACGCGCAGCG
3121 TGACCGCTAC ACTTGCCAGC GCCCTAGCGC CCGCTCCTTT CGCTTTCTTC CCTTCCTTTC
3181 TCGCCACGTT CGCCGGCTTT CCCCGTCAAG CTCTAAATCG GGGCTCCCT TTAGGGTTCC
3241 GATTTAGAGC TTTACGGCAC CTCGACCGCA AAAACTTGA TTTGGGTGAT GGTTCACGTA
3301 GTGGGCCATC GCCCTGATAG ACGGTTTTTC GCCCTTTGAC GTTGGAGTCC ACGTTCTTTA
3361 ATAGTGGACT CTTGTTCCAA ACTGGAACAA CACTCAACCC TATCTCGGTC TATTCTTTTG
3421 ATTTATAAGG GATTTTGCCG ATTTCGGCCT ATTGGTTAAA AAATGAGCTG ATTTAACAAA
3481 TATTTAACGC GAATTTTAAC AAAATATTAA CGTTTACAAT TTCGCCTGAT GCGGTATTTT
3541 CTCCTTACGC ATCTGTGCGG TATTTCACAC CGCATATGGT GCACTCTCAG TACAATCTGC
3601 TCTGATGCCG CATAGTTAAG CCAGCCCCGA CACCCGCCAA CACCCGCTGA CGCGCCCTGA
3661 CGGGCTTGTC TGCTCCCGGC ATCCGCTTAC AGACAAGCTG TGACCGTCTC CGGGAGCTGC
3721 ATGTGTCAGA GGTTTTCACC GTCATCACCG AAACGCGCGA GACGAAAGGG CCTCGTGATA
3781 CGCCTATTTT TATAGGTTAA TGTCATGATA ATAATGGTTT CTTAGACGTC AGGTGGCACT
3841 TTTCGGGGAA ATGTGCGCGG AACCCCTATT TGTTTATTTT TCTAAATACA TTCAAATATG
3901 TATCCGCTCA TGAGACAATA ACCCTGATAA ATGCTTCAAT AATATTGAAA AAGGAAGAGT
3961 ATGAGTATTC AACATTTCCG TGTCGCCCTT ATTCCCTTTT TTGCGGCATT TTGCCTTCCT
4021 GTTTTTGCTC ACCCAGAAAC GCTGGTGAAA GTAAAAGATG CTGAAGATCA GTTGGGTGCA
4081 CGAGTGGGTT ACATCGAACT GGATCTCAAC AGCGGTAAGA TCCTTGAGAG TTTTCGCCCC
4141 GAAGAACGTT TTCCAATGAT GAGCACTTTT AAAGTTCTGC TATGTGGCGC GGTATTATCC
4201 CGTATTGACG CCGGGCAAGA GCAACTCGGT CGCCGCATAC ACTATTCTCA GAATGACTTG
4261 GTTGAGTACT CACCAGTCAC AGAAAAGCAT CTTACGGATG GCATGACAGT AAGAGAATTA
4321 TGCAGTGCTG CCATAACCAT GAGTGATAAC ACTGCGGCCA ACTTACTTCT GACAACGATC
```

FIG. 26 (continued)

```
4381 GGAGGACCGA AGGAGCTAAC CGCTTTTTTG CACAACATGG GGGATCATGT AACTCGCCTT
4441 GATCGTTGGG AACCGGAGCT GAATGAAGCC ATACCAAACG ACGAGCGTGA CACCACGATG
4501 CCTGTAGCAA TGGCAACAAC GTTGCGCAAA CTATTAACTG GCGAACTACT TACTCTAGCT
4561 TCCCGGCAAC AATTAATAGA CTGGATGGAG GCGGATAAAG TTGCAGGACC ACTTCTGCGC
4621 TCGGCCCTTC CGGCTGGCTG GTTTATTGCT GATAAATCTG GAGCCGGTGA GCGTGGGTCT
4681 CGCGGTATCA TTGCAGCACT GGGGCCAGAT GGTAAGCCCT CCCGTATCGT AGTTATCTAC
4741 ACGACGGGGA GTCAGGCAAC TATGGATGAA CGAAATAGAC AGATCGCTGA GATAGGTGCC
4801 TCACTGATTA AGCATTGGTA ACTGTCAGAC CAAGTTTACT CATATATACT TTAGATTGAT
4861 TTAAAACTTC ATTTTTAATT TAAAAGGATC TAGGTGAAGA TCCTTTTTGA TAATCTCATG
4921 ACCAAAATCC CTTAACGTGA GTTTTCGTTC CACTGAGCGT CAGACCCCGT AGAAAAGATC
4981 AAAGGATCTT CTTGAGATCC TTTTTTTCTG CGCGTAATCT GCTGCTTGCA AACAAAAAAA
5041 CCACCGCTAC CAGCGGTGGT TTGTTTGCCG GATCAAGAGC TACCAACTCT TTTTCCGAAG
5101 GTAACTGGCT TCAGCAGAGC GCAGATACCA AATACTGTCC TTCTAGTGTA GCCGTAGTTA
5161 GGCCACCACT TCAAGAACTC TGTAGCACCG CCTACATACC TCGCTCTGCT AATCCTGTTA
5221 CCAGTGGCTG CTGCCAGTGG CGATAAGTCG TGTCTTACCG GGTTGGACTC AAGACGATAG
5281 TTACCGGATA AGGCGCAGCG GTCGGGCTGA ACGGGGGGTT CGTGCACACA GCCCAGCTTG
5341 GAGCGAACGA CCTACACCGA ACTGAGATAC CTACAGCGTG AGCTATGAGA AAGCGCCACG
5401 CTTCCCGAAG GGAGAAAGGC GGACAGGTAT CCGGTAAGCG GCAGGGTCGG AACAGGAGAG
5461 CGCACGAGGG AGCTTCCAGG GGGAAACGCC TGGTATCTTT ATAGTCCTGT CGGGTTTCGC
5521 CACCTCTGAC TTGAGCGTCG ATTTTGTGA TGCTCGTCAG GGGGGCGGAG CCTATGGAAA
5581 AACGCCAGCA ACGCGGCCTT TTTACGGTTC CTGGCCTTTT GCTGGCCTTT TGCTCACATG
5641 GCTCGACAGA TCT
```

FIG. 26 (continued)

(SEQ ID NO: 61) ICT1024 coding region: 947-3518

```
   1  TCGACTCGAG CGGCCGCATC GTGACTGACT GACGATCTGC CTCGCGCGTT TCGGTGATGA
  61  CGGTGAAAAC CTCTGACACA TGCAGCTCCC GGAGACGGTC ACAGCTTGTC TGTAAGCGGA
 121  TGCCGGGAGC AGACAAGCCC GTCAGGGCGC GTCAGCGGGT GTTGGCGGGT GTCGGGCGC
 181  AGCCATGACC CAGTCACGTA GCGATAGCGG AGTGTATAAT TCTTGAAGAC GAAAGGGCCT
 241  CGTGATACGC CTATTTTTAT AGGTTAATGT CATGATAATA ATGGTTTCTT AGACGTCAGG
 301  TGGCACTTTT CGGGGAAATG TGCGCGGAAC CCCTATTTGT TTATTTTTCT AAATACATTC
 361  AAATATGTAT CCGCTCATGA GACAATAACC CTGATAAATG CTTCAATAAT ATTGAAAAAG
 421  GAAGAGTATG AGTATTCAAC ATTTCCGTGT CGCCCTTATT CCCTTTTTTG CGGCATTTTG
 481  CCTTCCTGTT TTTGCTCACC CAGAAACGCT GGTGAAAGTA AAGATGCTG AAGATCAGTT
 541  GGGTGCACGA GTGGGTTACA TCGAACTGGA TCTCAACAGC GGTAAGATCC TTGAGAGTTT
 601  TCGCCCCGAA GAACGTTTTC CAATGATGAG CACTTTTAAA GTTCTGCTAT GTGGCGCGGT
 661  ATTATCCCGT GTTGACGCCG GGCAAGAGCA ACTCGGTCGC CGCATACACT ATTCTCAGAA
 721  TGACTTGGTT GAGTACTCAC CAGTCACAGA AAAGCATCTT ACGGATGGCA TGACAGTAAG
 781  AGAATTATGC AGTGCTGCCA TAACCATGAG TGATAACACT GCGGCCAACT TACTTCTGAC
 841  AACGATCGGA GGACCGAAGG AGCTAACCGC TTTTTTGCAC AACATGGGGG ATCATGTAAC
 901  TCGCCTTGAT CGTTGGGAAC CGGAGCTGAA TGAAGCCATA CCAAACGACG AGCGTGACAC
 961  CACGATGCCT GCAGCAATGG CAACAACGTT GCGCAAACTA TTAACTGGCG AACTACTTAC
1021  TCTAGCTTCC CGGCAACAAT TAATAGACTG GATGGAGGCG GATAAAGTTG CAGGACCACT
1081  TCTGCGCTCG GCCCTTCCGG CTGGCTGGTT TATTGCTGAT AAATCTGGAG CCGGTGAGCG
1141  TGGGTCTCGC GGTATCATTG CAGCACTGGG GCCAGATGGT AAGCCCTCCC GTATCGTAGT
1201  TATCTACACG ACGGGGAGTC AGGCAACTAT GGATGAACGA AATAGACAGA TCGCTGAGAT
1261  AGGTGCCTCA CTGATTAAGC ATTGGTAACT GTCAGACCAA GTTTACTCAT ATATACTTTA
1321  GATTGATTTA AAACTTCATT TTTAATTTAA AAGGATCTAG GTGAAGATCC TTTTTGATAA
1381  TCTCATGACC AAAATCCCTT AACGTGAGTT TTCGTTCCAC TGAGCGTCAG ACCCCGTAGA
1441  AAAGATCAAA GGATCTTCTT GAGATCCTTT TTTTCTGCGC GTAATCTGCT GCTTGCAAAC
1501  AAAAAAACCA CCGCTACCAG CGGTGGTTTG TTTGCCGGAT CAAGAGCTAC CAACTCTTTT
1561  TCCGAAGGTA ACTGGCTTCA GCAGAGCGCA GATACCAAAT ACTGTCCTTC TAGTGTAGCC
1621  GTAGTTAGGC CACCACTTCA AGAACTCTGT AGCACCGCCT ACATACCTCG CTCTGCTAAT
1681  CCTGTTACCA GTGGCTGCTG CCAGTGGCGA TAAGTCGTGT CTTACCGGGT TGGACTCAAG
1741  ACGATAGTTA CCGGATAAGG CGCAGCGGTC GGGCTGAACG GGGGGTTCGT GCACACAGCC
1801  CAGCTTGGAG CGAACGACCT ACACCGAACT GAGATACCTA CAGCGTGAGC TATGAGAAAG
1861  CGCCACGCTT CCCGAAGGGA GAAAGGCGGA CAGGTATCCG GTAAGCGGCA GGGTCGGAAC
1921  AGGAGAGCGC ACGAGGGAGC TTCCAGGGGG AAACGCCTGG TATCTTTATA GTCCTGTCGG
1981  GTTTCGCCAC CTCTGACTTG AGCGTCGATT TTTGTGATGC TCGTCAGGGG GCGGAGCCT
2041  ATGGAAAAAC GCCAGCAACG CGGCCTTTTT ACGGTTCCTG GCCTTTTGCT GGCCTTTTGC
2101  TCACATGTTC TTTCCTGCGT TATCCCCTGA TTCTGTGGAT AACCGTATTA CCGCCTTTGA
```

FIG. 27

```
2161  GTGAGCTGAT ACCGCTCGCC GCAGCCGAAC GACCGAGCGC AGCGAGTCAG TGAGCGAGGA
2221  AGCGGAAGAG CGCCTGATGC GGTATTTTCT CCTTACGCAT CTGTGCGGTA TTTCACACCG
2281  CATAAATTCC GACACCATCG AATGGTGCAA AACCTTTCGC GGTATGGCAT GATAGCGCCC
2341  GGAAGAGAGT CAATTCAGGG TGGTGAATGT GAAACCAGTA ACGTTATACG ATGTCGCAGA
2401  GTATGCCGGT GTCTCTTATC AGACCGTTTC CGCGTGGTG AACCAGGCCA GCCACGTTTC
2461  TGCGAAAACG CGGGAAAAAG TGGAAGCGGC GATGGCGGAG CTGAATTACA TTCCCAACCG
2521  CGTGGCACAA CAACTGGCGG GCAAACAGTC GTTGCTGATT GGCGTTGCCA CCTCCAGTCT
2581  GGCCCTGCAC GCGCCGTCGC AAATTGTCGC GGCGATTAAA TCTCGCGCCG ATCAACTGGG
2641  TGCCAGCGTG GTGGTGTCGA TGGTAGAACG AAGCGGCGTC GAAGCCTGTA AAGCGGCGGT
2701  GCACAATCTT CTCGCGCAAC GCGTCAGTGG GCTGATCATT AACTATCCGC TGGATGACCA
2761  GGATGCCATT GCTGTGGAAG CTGCCTGCAC TAATGTTCCG GCGTTATTTC TTGATGTCTC
2821  TGACCAGACA CCCATCAACA GTATTATTTT CTCCCATGAA GACGGTACGC GACTGGGCGT
2881  GGAGCATCTG GTCGCATTGG GTCACCAGCA AATCGCGCTG TTAGCGGGCC CATTAAGTTC
2941  TGTCTCGGCG CGTCTGCGTC TGGCTGGCTG GCATAAATAT CTCACTCGCA ATCAAATTCA
3001  GCCGATAGCG GAACGGGAAG GCGACTGGAG TGCCATGTCC GGTTTTCAAC AAACCATGCA
3061  AATGCTGAAT GAGGGCATCG TTCCCACTGC GATGCTGGTT GCCAACGATC AGATGGCGCT
3121  GGGCGCAATG CGCGCCATTA CCGAGTCCGG GCTGCGCGTT GGTGCGGATA TCTCGGTAGT
3181  GGGATACGAC GATACCGAAG ACAGCTCATG TTATATCCCG CCGTTAACCA CCATCAAACA
3241  GGATTTTCGC CTGCTGGGGC AAACCAGCGT GGACCGCTTG CTGCAACTCT CTCAGGGCCA
3301  GGCGGTGAAG GGCAATCAGC TGTTGCCCGT CTCACTGGTG AAAAGAAAAA CCACCCTGGC
3361  GCCCAATACG CAAACCGCCT CTCCCCGCGC GTTGGCCGAT TCATTAATGC AGCTGGCACG
3421  ACAGGTTTCC CGACTGGAAA GCGGGCAGTG AGCGCAACGC AATTAATGTG AGTTAGCTCA
3481  CTCATTAGGC ACCCCAGGCT TTACACTTTA TGCTTCCGGC TCGTATGTTG TGTGGAATTG
3541  TGAGCGGATA ACAATTTCAC ACAGGAAACA GCTATGACCA TGATTACGGA TTCACTGGCC
3601  GTCGTTTTAC AACGTCGTGA CTGGGAAAAC CCTGGCGTTA CCCAACTTAA TCGCCTTGCA
3661  GCACATCCCC CTTTCGCCAG CTGGCGTAAT AGCGAAGAGG CCCGCACCGA TCGCCCTTCC
3721  CAACAGTTGC GCAGCCTGAA TGGCGAATGG CGCTTTGCCT GGTTTCCGGC ACCAGAAGCG
3781  GTGCCGGAAA GCTGGCTGGA GTGCGATCTT CCTGAGGCCG ATACTGTCGT CGTCCCCTCA
3841  AACTGGCAGA TGCACGGTTA CGATGCGCCC ATCTACACCA ACGTAACCTA TCCCATTACG
3901  GTCAATCCGC CGTTTGTTCC CACGGAGAAT CCGACGGGTT GTTACTCGCT CACATTTAAT
3961  GTTGATGAAA GCTGGCTACA GGAAGGCCAG ACGCGAATTA TTTTTGATGG CGTTGGAATT
4021  AGCTTATCGA CTGCACGGTG CACCAATGCT TCTGGCGTCA GGCAGCCATC GGAAGCTGTG
4081  GTATGGCTGT GCAGGTCGTA ATCACTGCA TAATTCGTGT CGCTCAAGGC GCACTCCCGT
4141  TCTGGATAAT GTTTTTTGCG CCGACATCAT AACGGTTCTG GCAAATATTC TGAAATGAGC
4201  TGTTGACAAT TAATCATCGG CTCGTATAAT GTGTGGAATT GTGAGCGGAT AACAATTTCA
4261  CACAGGAAAC AGTATTCATG TCCCCTATAC TAGGTTATTG GAAAATTAAG GGCCTTGTGC
4321  AACCCACTCG ACTTCTTTTG GAATATCTTG AAGAAAAATA TGAAGAGCAT TTGTATGAGC
```

FIG. 27 (continued)

4381 GCGATGAAGG TGATAAATGG CGAAACAAAA AGTTTGAATT GGGTTTGGAG TTTCCCAATC
4441 TTCCTTATTA TATTGATGGT GATGTTAAAT TAACACAGTC TATGGCCATC ATACGTTATA
4501 TAGCTGACAA GCACAACATG TTGGGTGGTT GTCCAAAAGA GCGTGCAGAG ATTTCAATGC
4561 TTGAAGGAGC GGTTTTGGAT ATTAGATACG GTGTTTCGAG AATTGCATAT AGTAAAGACT
4621 TTGAAACTCT CAAAGTTGAT TTTCTTAGCA AGCTACCTGA AATGCTGAAA ATGTTCGAAG
4681 ATCGTTTATG TCATAAAACA TATTTAAATG GTGATCATGT AACCCATCCT GACTTCATGT
4741 TGTATGACGC TCTTGATGTT GTTTTATACA TGGACCCAAT GTGCCTGGAT GCGTTCCCAA
4801 AATTAGTTTG TTTTAAAAAA CGTATTGAAG CTATCCCACA AATTGATAAG TACTTGAAAT
4861 CCAGCAAGTA TATAGCATGG CCTTTGCAGG GCTGGCAAGC CACGTTTGGT GGTGGCGACC
4921 ATCCTCCAAA ATCGGATCTG ATCGAAGGTC GTGGGATCCC CAGG (SEQ ID NO: 62) ICT1024 N terminus 553 aa coding region: 947-2600

```
   1 AGCTTATCGA CTGCACGGTG CACCAATGCT TCTGGCGTCA GGCAGCCATC GGAAGCTGTG
  61 GTATGGCTGT GCAGGTCGTA AATCACTGCA TAATTCGTGT CGCTCAAGGC GCACTCCCGT
 121 TCTGGATAAT GTTTTTTGCG CCGACATCAT AACGGTTCTG GCAAATATTC TGAAATGAGC
 181 TGTTGACAAT TAATCATCGG CTCGTATAAT GTGTGGAATT GTGAGCGGAT AACAATTTCA
 241 CACAGGAAAC AGTATTCATG TCCCCTATAC TAGGTTATTG GAAAATTAAG GGCCTTGTGC
 301 AACCCACTCG ACTTCTTTTG GAATATCTTG AAGAAAAATA TGAAGAGCAT TTGTATGAGC
 361 GCGATGAAGG TGATAAATGG CGAAACAAAA AGTTTGAATT GGGTTTGGAG TTTCCCAATC
 421 TTCCTTATTA TATTGATGGT GATGTTAAAT TAACACAGTC TATGGCCATC ATACGTTATA
 481 TAGCTGACAA GCACAACATG TTGGGTGGTT GTCCAAAAGA GCGTGCAGAG ATTTCAATGC
 541 TTGAAGGAGC GGTTTTGGAT ATTAGATACG GTGTTTCGAG AATTGCATAT AGTAAAGACT
 601 TTGAAACTCT CAAAGTTGAT TTCTTAGCA AGCTACCTGA ATGCTGAAA ATGTTCGAAG
 661 ATCGTTTATG TCATAAAACA TATTTAAATG GTGATCATGT AACCCATCCT GACTTCATGT
 721 TGTATGACGC TCTTGATGTT GTTTTATACA TGGACCCAAT GTGCCTGGAT GCGTTCCCAA
 781 AATTAGTTTG TTTTAAAAAA CGTATTGAAG CTATCCCACA AATTGATAAG TACTTGAAAT
 841 CCAGCAAGTA TATAGCATGG CCTTTGCAGG GCTGGCAAGC CACGTTTGGT GGTGGCGACC
 901 ATCCTCCAAA ATCGGATCTG ATCGAAGGTC GTGGGATCCC CAGGAATTCC ATGAGTGAGG
 961 CCCGCAGGGA CAGCACGAGC AGCCTGCAGC GCAAGAAGCC ACCCTGGCTA AAGCTGGACA
1021 TTCCCTCTGC GGTGCCCCTG ACGGCAGAAG AGCCCAGCTT CCTGCAGCCC CTGAGGCGAC
1081 AGGCTTTCCT GAGGAGTGTG AGTATGCCAG CCGAGACAGC CCACATCTCT TCACCCCACC
1141 ATGAGCTCCG GCGGCCGGTG CTGCAACGCC AGACGTCCAT CACACAGACC ATCCGCAGGG
1201 GGACCGCCGA CTGGTTTGGA GTGAGCAAGG ACAGTGACAG CACCCAGAAA TGGCAGCGCA
1261 AGAGCATCCG TCACTGCAGC CAGCGCTACG GAAGCTGAA GCCCCAGGTC CTCCGGGAGC
1321 TGGACCTGCC CAGCCAGGAC AACGTGTCGC TGACCAGCAC CGAGACGCCA CCCCCACTCT
1381 ACGTGGGGCC ATGCCAGCTG GCATGCAGA AGATCATAGA CCCCCTGGCC CGTGGCCGTG
1441 CCTTCCGTGT GGCAGATGAC ACTGCGGAAG CCTGAGTGC CCCACACACT CCCGTCACGC
1501 CGGGTGCTGC CTCCCTCTGC TCCTTCTCCA GCTCCCGCTC AGGTTTCCAC CGGCTCCCGC
1561 GGCGGCGCAA GCGAGAGTCG GTGGCCAAGA TGAGCTTCCG GGCGGCCGCA GCGCTGATGA
1621 AAGGCCGCTC CGTTAGGGAT GGCACCTTTC GCCGGGCACG GCGTCGAAGC TTCACTCCAG
1681 CTAGCTTTCT GGAGGAGGAC ACAACTGATT TCCCCGATGA GCTGGACACA TCCTTCTTTG
1741 CCCGGGAAGG TATCCTCCAT GAAGAGCTGT CCACATACCC GGATGAAGTT TTCGAGTCCC
1801 CATCGGAGGC AGCGCTAAAG GACTGGGAGA AGGCACCGGA GCAGGCGGAC CTCACCGGCG
1861 GGGCCCTGGA CCGCAGCGAG CTTGAGCGCA GCCACCTGAT GCTGCCCTTG GAGCGAGGCT
1921 GGCGGAAGCA GAAGGAGGGC GCCGCAGCCC GCAGCCCAA GGTGCGGCTC GACAGGAGG
1981 TGGTGAGCAC CGCGGGGCCG CGACGGGGCC AGCGTATCGC GGTGCCGGTG CGCAAGCTCT
2041 TCGCCCGGGA GAAGCGGCCG TATGGGCTGG GCATGGTGGG ACGGCTCACC AACCGCACCT
2101 ACCGCAAGCG CATCGACAGC TTCGTCAAGC GCCAGATCGA GGACATGGAC GACCACAGGC
```

FIG. 28

```
2161  CCTTCTTCAC CTACTGGCTT ACCTTCGTGC ACTCGCTCGT CACCATCCTA GCCGTGTGCA
2221  TCTATGGCAT CGCGCCCGTG GGCTTCTCGC AGCATGAGAC GGTGGACTCG GTGCTGCGGA
2281  ACCGCGGGGT CTACGAGAAC GTCAAGTACG TGCAGCAGGA GAACTTCTGG ATCGGGCCCA
2341  GCTCGGAGGC CCTCATCCAC CTGGGCGCCA GTTTTCGCC CTGCATGCGC CAGGACCCGC
2401  AGGTGCACAG CTTCATTCGC TCGGCGCGCG AGCGCGAGAA GCACTCCGCC TGCTGCGTGC
2461  GCAACGACAG GTCGGGCTGC GTGCAGACCT CGGAGGAGGA GTGCTCGTCC ACGCTGGCAG
2521  TGTGGGTGAA GTGGCCCATC CATCCCAGCG CCCCAGAGCT TGCGGGCCAC AAGAGACAGT
2581  TTGGCTCTGT CTGCCACCAG GATCCCAGGT GAGTCGACTC GAGCGGCCGC ATCGTGACTG
2641  ACTGACGATC TGCCTCGCGC GTTTCGGTGA TGACGGTGAA AACCTCTGAC ACATGCAGCT
2701  CCCGGAGACG GTCACAGCTT GTCTGTAAGC GGATGCCGGG AGCAGACAAG CCCGTCAGGG
2761  CGCGTCAGCG GGTGTTGGCG GGTGTCGGGG CGCAGCCATG ACCCAGTCAC GTAGCGATAG
2821  CGGAGTGTAT AATTCTTGAA GACGAAAGGG CCTCGTGATA CGCCTATTTT TATAGGTTAA
2881  TGTCATGATA ATAATGGTTT CTTAGACGTC AGGTGGCACT TTTCGGGGAA ATGTGCGCGG
2941  AACCCCTATT TGTTTATTTT TCTAAATACA TTCAAATATG TATCCGCTCA TGAGACAATA
3001  ACCCTGATAA ATGCTTCAAT AATATTGAAA AAGGAAGAGT ATGAGTATTC AACATTTCCG
3061  TGTCGCCCTT ATTCCCTTTT TTGCGGCATT TTGCCTTCCT GTTTTTGCTC ACCCAGAAAC
3121  GCTGGTGAAA GTAAAAGATG CTGAAGATCA GTTGGGTGCA CGAGTGGGTT ACATCGAACT
3181  GGATCTCAAC AGCGGTAAGA TCCTTGAGAG TTTTCGCCCC GAAGAACGTT TTCCAATGAT
3241  GAGCACTTTT AAAGTTCTGC TATGTGGCGC GGTATTATCC CGTGTTGACG CCGGGCAAGA
3301  GCAACTCGGT CGCCGCATAC ACTATTCTCA GAATGACTTG GTTGAGTACT CACCAGTCAC
3361  AGAAAAGCAT CTTACGGATG GCATGACAGT AAGAGAATTA TGCAGTGCTG CCATAACCAT
3421  GAGTGATAAC ACTGCGGCCA ACTTACTTCT GACAACGATC GGAGGACCGA AGGAGCTAAC
3481  CGCTTTTTTG CACAACATGG GGGATCATGT AACTCGCCTT GATCGTTGGG AACCGGAGCT
3541  GAATGAAGCC ATACCAAACG ACGAGCGTGA CACCACGATG CCTGCAGCAA TGGCAACAAC
3601  GTTGCGCAAA CTATTAACTG GCGAACTACT TACTCTAGCT TCCCGGCAAC AATTAATAGA
3661  CTGGATGGAG GCGGATAAAG TTGCAGGACC ACTTCTGCGC TCGGCCCTTC CGGCTGGCTG
3721  GTTTATTGCT GATAAATCTG GAGCCGGTGA GCGTGGGTCT CGCGGTATCA TTGCAGCACT
3781  GGGGCCAGAT GGTAAGCCCT CCCGTATCGT AGTTATCTAC ACGACGGGGA GTCAGGCAAC
3841  TATGGATGAA CGAAATAGAC AGATCGCTGA GATAGGTGCC TCACTGATTA AGCATTGGTA
3901  ACTGTCAGAC CAAGTTTACT CATATATACT TTAGATTGAT TTAAAACTTC ATTTTTAATT
3961  TAAAAGGATC TAGGTGAAGA TCCTTTTTGA TAATCTCATG ACCAAAATCC CTTAACGTGA
4021  GTTTTCGTTC CACTGAGCGT CAGACCCCGT AGAAAAGATC AAAGGATCTT CTTGAGATCC
4081  TTTTTTTCTG CGCGTAATCT GCTGCTTGCA AACAAAAAAA CCACCGCTAC CAGCGGTGGT
4141  TTGTTTGCCG GATCAAGAGC TACCAACTCT TTTTCCGAAG GTAACTGGCT TCAGCAGAGC
4201  GCAGATACCA AATACTGTCC TTCTAGTGTA GCCGTAGTTA GGCCACCACT TCAAGAACTC
4261  TGTAGCACCG CCTACATACC TCGCTCTGCT AATCCTGTTA CCAGTGGCTG CTGCCAGTGG
4321  CGATAAGTCG TGTCTTACCG GGTTGGACTC AAGACGATAG TTACCGGATA AGGCGCAGCG
```

FIG. 28 (continued)

```
4381  GTCGGGCTGA ACGGGGGGTT CGTGCACACA GCCCAGCTTG GAGCGAACGA CCTACACCGA
4441  ACTGAGATAC CTACAGCGTG AGCTATGAGA AAGCGCCACG CTTCCCGAAG GGAGAAAGGC
4501  GGACAGGTAT CCGGTAAGCG GCAGGGTCGG AACAGGAGAG CGCACGAGGG AGCTTCCAGG
4561  GGGAAACGCC TGGTATCTTT ATAGTCCTGT CGGGTTTCGC CACCTCTGAC TTGAGCGTCG
4621  ATTTTTGTGA TGCTCGTCAG GGGGCGGAG CCTATGGAAA AACGCCAGCA ACGCGGCCTT
4681  TTTACGGTTC CTGGCCTTTT GCTGGCCTTT TGCTCACATG TTCTTTCCTG CGTTATCCCC
4741  TGATTCTGTG GATAACCGTA TTACCGCCTT TGAGTGAGCT GATACCGCTC GCCGCAGCCG
4801  AACGACCGAG CGCAGCGAGT CAGTGAGCGA GGAAGCGGAA GAGCGCCTGA TGCGGTATTT
4861  TCTCCTTACG CATCTGTGCG GTATTTCACA CCGCATAAAT TCCGACACCA TCGAATGGTG
4921  CAAAACCTTT CGCGGTATGG CATGATAGCG CCCGGAAGAG AGTCAATTCA GGGTGGTGAA
4981  TGTGAAACCA GTAACGTTAT ACGATGTCGC AGAGTATGCC GGTGTCTCTT ATCAGACCGT
5041  TTCCCGCGTG GTGAACCAGG CCAGCCACGT TTCTGCGAAA ACGCGGGAAA AAGTGGAAGC
5101  GGCGATGGCG GAGCTGAATT ACATTCCCAA CCGCGTGGCA CAACAACTGG CGGGCAAACA
5161  GTCGTTGCTG ATTGGCGTTG CCACCTCCAG TCTGGCCCTG CACGCGCCGT CGCAAATTGT
5221  CGCGGCGATT AAATCTCGCG CCGATCAACT GGGTGCCAGC GTGGTGGTGT CGATGGTAGA
5281  ACGAAGCGGC GTCGAAGCCT GTAAAGCGGC GGTGCACAAT CTTCTCGCGC AACGCGTCAG
5341  TGGGCTGATC ATTAACTATC CGCTGGATGA CCAGGATGCC ATTGCTGTGG AAGCTGCCTG
5401  CACTAATGTT CCGGCGTTAT TTCTTGATGT CTCTGACCAG ACACCCATCA ACAGTATTAT
5461  TTTCTCCCAT GAAGACGGTA CGCGACTGGG CGTGGAGCAT CTGGTCGCAT TGGGTCACCA
5521  GCAAATCGCG CTGTTAGCGG CCCATTAAG TTCTGTCTCG GCGCGTCTGC GTCTGGCTGG
5581  CTGGCATAAA TATCTCACTC GCAATCAAAT TCAGCCGATA GCGGAACGGG AAGGCGACTG
5641  GAGTGCCATG TCCGGTTTTC AACAAACCAT GCAAATGCTG AATGAGGGCA TCGTTCCCAC
5701  TGCGATGCTG GTTGCCAACG ATCAGATGGC GCTGGGCGCA ATGCGCGCCA TTACCGAGTC
5761  CGGGCTGCGC GTTGGTGCGG ATATCTCGGT AGTGGGATAC GACGATACCG AAGACAGCTC
5821  ATGTTATATC CCGCCGTTAA CCACCATCAA ACAGGATTTT CGCCTGCTGG GGCAAACCAG
5881  CGTGGACCGC TTGCTGCAAC TCTCTCAGGG CCAGGCGGTG AAGGGCAATC AGCTGTTGCC
5941  CGTCTCACTG GTGAAAAGAA AAACCACCCT GGCGCCCAAT ACGCAAACCG CCTCTCCCCG
6001  CGCGTTGGCC GATTCATTAA TGCAGCTGGC ACGACAGGTT TCCCGACTGG AAAGCGGGCA
6061  GTGAGCGCAA CGCAATTAAT GTGAGTTAGC TCACTCATTA GGCACCCCAG GCTTTACACT
6121  TTATGCTTCC GGCTCGTATG TTGTGTGGAA TTGTGAGCGG ATAACAATTT CACACAGGAA
6181  ACAGCTATGA CCATGATTAC GGATTCACTG GCCGTCGTTT TACAACGTCG TGACTGGGAA
6241  AACCCTGGCG TTACCCAACT TAATCGCCTT GCAGCACATC CCCCTTTCGC CAGCTGGCGT
```

```
6301 AATAGCGAAG AGGCCCGCAC CGATCGCCCT TCCCAACAGT TGCGCAGCCT GAATGGCGAA
6361 TGGCGCTTTG CCTGGTTTCC GGCACCAGAA GCGGTGCCGG AAAGCTGGCT GGAGTGCGAT
6421 CTTCCTGAGG CCGATACTGT CGTCGTCCCC TCAAACTGGC AGATGCACGG TTACGATGCG
6481 CCCATCTACA CCAACGTAAC CTATCCCATT ACGGTCAATC CGCCGTTTGT TCCCACGGAG
6541 AATCCGACGG GTTGTTACTC GCTCACATTT AATGTTGATG AAAGCTGGCT ACAGGAAGGC
6601 CAGACGCGAA TTATTTTTGA TGGCGTTGGA ATT
```

FIG. 28 (continued)

(SEQ ID NO:64) Coding region for the C terminus 375 aa: 945-2069

```
   1 AGCTTATCGA CTGCACGGTG CACCAATGCT TCTGGCGTCA GGCAGCCATC GGAAGCTGTG
  61 GTATGGCTGT GCAGGTCGTA ATCACTGCA TAATTCGTGT CGCTCAAGGC GCACTCCCGT
 121 TCTGGATAAT GTTTTTTGCG CCGACATCAT AACGGTTCTG GCAAATATTC TGAAATGAGC
 181 TGTTGACAAT TAATCATCGG CTCGTATAAT GTGTGGAATT GTGAGCGGAT AACAATTTCA
 241 CACAGGAAAC AGTATTCATG TCCCCTATAC TAGGTTATTG GAAAATTAAG GGCCTTGTGC
 301 AACCCACTCG ACTTCTTTTG GAATATCTTG AAGAAAAATA TGAAGAGCAT TTGTATGAGC
 361 GCGATGAAGG TGATAAATGG CGAAACAAAA AGTTTGAATT GGGTTTGGAG TTTCCCAATC
 421 TTCCTTATTA TATTGATGGT GATGTTAAAT TAACACAGTC TATGGCCATC ATACGTTATA
 481 TAGCTGACAA GCACAACATG TTGGGTGGTT GTCCAAAAGA GCGTGCAGAG ATTTCAATGC
 541 TTGAAGGAGC GGTTTTGGAT ATTAGATACG GTGTTTCGAG AATTGCATAT AGTAAAGACT
 601 TTGAAACTCT CAAAGTTGAT TTTCTTAGCA AGCTACCTGA AATGCTGAAA ATGTTCGAAG
 661 ATCGTTTATG TCATAAAACA TATTTAAATG GTGATCATGT AACCCATCCT GACTTCATGT
 721 TGTATGACGC TCTTGATGTT GTTTTATACA TGGACCCAAT GTGCCTGGAT GCGTTCCCAA
 781 AATTAGTTTG TTTTAAAAAA CGTATTGAAG CTATCCCACA AATTGATAAG TACTTGAAAT
 841 CCAGCAAGTA TATAGCATGG CCTTTGCAGG GCTGGCAAGC CACGTTTGGT GGTGGCGACC
 901 ATCCTCCAAA ATCGGATCTG ATCGAAGGTC GTGGGATCCC CAGGAATTCC CAGGTGCACA
 961 GCTTCATTCG CTCGGCGCGC GAGCGCGAGA AGCACTCCGC CTGCTGCGTG CGCAACGACA
1021 GGTCGGGCTG CGTGCAGACC TCGGAGGAGG AGTGCTCGTC CACGCTGGCA GTGTGGGTGA
1081 AGTGGCCCAT CCATCCCAGC GCCCCAGAGC TTGCGGGCCA CAAGAGACAG TTTGGCTCTG
1141 TCTGCCACCA GGATCCCAGG GTGTGTGATG AGCCCTCCTC CGAAGACCCT CATGAGTGGC
1201 CAGAAGACAT CACCAAGTGG CCGATCTGCA CCAAAAACAG CGCTGGGAAC CACACCAACC
1261 ATCCCCACAT GGACTGTGTC ATCACAGGAC GGCCCTGCTG CATTGGCACC AAGGGCAGGT
1321 GTGAGATCAC CTCCCGGGAG TACTGTGACT TCATGAGGGG CTACTTCCAT GAGGAGGCCA
1381 CGCTCTGCTC TCAGGTGCAC TGCATGGATG ATGTGTGTGG GCTCCTGCCT TTTCTCAACC
1441 CCGAGGTGCC TGACCAGTTC TACCGCCTGT GGCTATCCCT CTTCCTGCAC GCCGGGATCT
1501 TGCACTGCCT GGTGTCCATC TGCTTCCAGA TGACTGTCCT GCGGGACCTG GAGAAGCTGG
1561 CAGGCTGGCA CCGCATAGCC ATCATCTACC TGCTGAGTGG TGTCACCGGC AACCTGGCCA
1621 GTGCCATCTT CCTGCCATAC CGAGCAGAGG TGGGTCCTGC TGGCTCCCAG TTCGGCATCC
1681 TGGCCTGCCT CTTCGTGGAG CTCTTCCAGA GCTGGCAGAT CCTGGCGCGG CCCTGGCGTG
1741 CCTTCTTCAA GCTGCTGGCT GTGGTGCTCT TCCTCTTCAC CTTTGGGCTG CTGCCGTGGA
1801 TTGACAACTT TGCCCACATC TCGGGGTTCA TCAGTGGCCT CTTCCTCTCC TTCGCCTTCT
1861 TGCCCTACAT CAGCTTTGGC AAGTTCGACC TGTACCGGAA ACGCTGCCAG ATCATCATCT
1921 TTCAGGTGGT CTTCCTGGGC CTCCTGGCTG GCCTGGTGGT CCTCTTCTAC GTCTATCCTG
1981 TCCGCTGTGA GTGGTGTGAG TTCCTCACCT GCATCCCCTT CACTGACAAG TTCTGTGAGA
2041 GTACGAACTG GACGCTCAG CTCCACTGAG TCGACTCGAG CGGCCGCATC GTGACTGACT
2101 GACGATCTGC CTCGCGCGTT TCGGTGATGA CGGTGAAAAC CTCTGACACA TGCAGCTCCC
```

FIG. 29

```
2161  GGAGACGGTC ACAGCTTGTC TGTAAGCGGA TGCCGGGAGC AGACAAGCCC GTCAGGGCGC
2221  GTCAGCGGGT GTTGGCGGGT GTCGGGGCGC AGCCATGACC CAGTCACGTA GCGATAGCGG
2281  AGTGTATAAT TCTTGAAGAC GAAAGGGCCT CGTGATACGC CTATTTTTAT AGGTTAATGT
2341  CATGATAATA ATGGTTTCTT AGACGTCAGG TGGCACTTTT CGGGGAAATG TGCGCGGAAC
2401  CCCTATTTGT TTATTTTTCT AAATACATTC AAATATGTAT CCGCTCATGA GACAATAACC
2461  CTGATAAATG CTTCAATAAT ATTGAAAAAG GAAGAGTATG AGTATTCAAC ATTTCCGTGT
2521  CGCCCTTATT CCCTTTTTTG CGGCATTTTG CCTTCCTGTT TTTGCTCACC CAGAAACGCT
2581  GGTGAAAGTA AAAGATGCTG AAGATCAGTT GGGTGCACGA GTGGGTTACA TCGAACTGGA
2641  TCTCAACAGC GGTAAGATCC TTGAGAGTTT TCGCCCCGAA GAACGTTTTC CAATGATGAG
2701  CACTTTTAAA GTTCTGCTAT GTGGCGCGGT ATTATCCCGT GTTGACGCCG GGCAAGAGCA
2761  ACTCGGTCGC CGCATACACT ATTCTCAGAA TGACTTGGTT GAGTACTCAC CAGTCACAGA
2821  AAAGCATCTT ACGGATGGCA TGACAGTAAG AGAATTATGC AGTGCTGCCA TAACCATGAG
2881  TGATAACACT GCGGCCAACT TACTTCTGAC AACGATCGGA GGACCGAAGG AGCTAACCGC
2941  TTTTTTGCAC AACATGGGGG ATCATGTAAC TCGCCTTGAT CGTTGGGAAC CGGAGCTGAA
3001  TGAAGCCATA CCAAACGACG AGCGTGACAC CACGATGCCT GCAGCAATGG CAACAACGTT
3061  GCGCAAACTA TTAACTGGCG AACTACTTAC TCTAGCTTCC CGGCAACAAT TAATAGACTG
3121  GATGGAGGCG GATAAAGTTG CAGGACCACT TCTGCGCTCG GCCCTTCCGG CTGGCTGGTT
3181  TATTGCTGAT AAATCTGGAG CCGGTGAGCG TGGGTCTCGC GGTATCATTG CAGCACTGGG
3241  GCCAGATGGT AAGCCCTCCC GTATCGTAGT TATCTACACG ACGGGGAGTC AGGCAACTAT
3301  GGATGAACGA AATAGACAGA TCGCTGAGAT AGGTGCCTCA CTGATTAAGC ATTGGTAACT
3361  GTCAGACCAA GTTTACTCAT ATATACTTTA GATTGATTTA AAACTTCATT TTTAATTTAA
3421  AAGGATCTAG GTGAAGATCC TTTTTGATAA TCTCATGACC AAAATCCCTT AACGTGAGTT
3481  TTCGTTCCAC TGAGCGTCAG ACCCCGTAGA AAAGATCAAA GGATCTTCTT GAGATCCTTT
3541  TTTTCTGCGC GTAATCTGCT GCTTGCAAAC AAAAAAACCA CCGCTACCAG CGGTGGTTTG
3601  TTTGCCGGAT CAAGAGCTAC CAACTCTTTT TCCGAAGGTA ACTGGCTTCA GCAGAGCGCA
3661  GATACCAAAT ACTGTCCTTC TAGTGTAGCC GTAGTTAGGC CACCACTTCA AGAACTCTGT
3721  AGCACCGCCT ACATACCTCG CTCTGCTAAT CCTGTTACCA GTGGCTGCTG CCAGTGGCGA
3781  TAAGTCGTGT CTTACCGGGT TGGACTCAAG ACGATAGTTA CCGGATAAGG CGCAGCGGTC
3841  GGGCTGAACG GGGGGTTCGT GCACACAGCC CAGCTTGGAG CGAACGACCT ACACCGAACT
3901  GAGATACCTA CAGCGTGAGC TATGAGAAAG CGCCACGCTT CCCGAAGGGA GAAAGGCGGA
3961  CAGGTATCCG GTAAGCGGCA GGGTCGGAAC AGGAGAGCGC ACGAGGGAGC TTCCAGGGGG
4021  AAACGCCTGG TATCTTTATA GTCCTGTCGG GTTTCGCCAC CTCTGACTTG AGCGTCGATT
4081  TTTGTGATGC TCGTCAGGGG GCGGAGCCT ATGGAAAAAC GCCAGCAACG CGGCCTTTTT
4141  ACGGTTCCTG GCCTTTTGCT GGCCTTTGC TCACATGTTC TTTCCTGCGT TATCCCCTGA
4201  TTCTGTGGAT AACCGTATTA CCGCCTTTGA GTGAGCTGAT ACCGCTCGCC GCAGCCGAAC
4261  GACCGAGCGC AGCGAGTCAG TGAGCGAGGA AGCGGAAGAG CGCCTGATGC GGTATTTTCT
4321  CCTTACGCAT CTGTGCGGTA TTTCACACCG CATAAATTCC GACACCATCG AATGGTGCAA
```

FIG. 29 (continued)

```
4381 AACCTTTCGC GGTATGGCAT GATAGCGCCC GGAAGAGAGT CAATTCAGGG TGGTGAATGT
4441 GAAACCAGTA ACGTTATACG ATGTCGCAGA GTATGCCGGT GTCTCTTATC AGACCGTTTC
4501 CCGCGTGGTG AACCAGGCCA GCCACGTTTC TGCGAAAACG CGGGAAAAAG TGGAAGCGGC
4561 GATGGCGGAG CTGAATTACA TTCCCAACCG CGTGGCACAA CAACTGGCGG GCAAACAGTC
4621 GTTGCTGATT GGCGTTGCCA CCTCCAGTCT GGCCCTGCAC GCGCCGTCGC AAATTGTCGC
4681 GGCGATTAAA TCTCGCGCCG ATCAACTGGG TGCCAGCGTG GTGGTGTCGA TGGTAGAACG
4741 AAGCGGCGTC GAAGCCTGTA AAGCGGCGGT GCACAATCTT CTCGCGCAAC GCGTCAGTGG
4801 GCTGATCATT AACTATCCGC TGGATGACCA GGATGCCATT GCTGTGGAAG CTGCCTGCAC
4861 TAATGTTCCG GCGTTATTTC TTGATGTCTC TGACCAGACA CCCATCAACA GTATTATTTT
4921 CTCCCATGAA GACGGTACGC GACTGGGCGT GGAGCATCTG GTCGCATTGG GTCACCAGCA
4981 AATCGCGCTG TTAGCGGGCC CATTAAGTTC TGTCTCGGCG CGTCTGCGTC TGGCTGGCTG
5041 GCATAAATAT CTCACTCGCA ATCAAATTCA GCCGATAGCG AACGGGAAG GCGACTGGAG
5101 TGCCATGTCC GGTTTTCAAC AAACCATGCA AATGCTGAAT GAGGGCATCG TTCCCACTGC
5161 GATGCTGGTT GCCAACGATC AGATGGCGCT GGGCGCAATG CGCGCCATTA CCGAGTCCGG
5221 GCTGCGCGTT GGTGCGGATA TCTCGGTAGT GGGATACGAC GATACCGAAG ACAGCTCATG
5281 TTATATCCCG CCGTTAACCA CCATCAAACA GGATTTTCGC CTGCTGGGGC AAACCAGCGT
5341 GGACCGCTTG CTGCAACTCT CTCAGGGCCA GGCGGTGAAG GGCAATCAGC TGTTGCCCGT
5401 CTCACTGGTG AAAAGAAAAA CCACCCTGGC GCCCAATACG CAAACCGCCT CTCCCGCGC
5461 GTTGGCCGAT TCATTAATGC AGCTGGCACG ACAGGTTTCC CGACTGGAAA GCGGGCAGTG
5521 AGCGCAACGC AATTAATGTG AGTTAGCTCA CTCATTAGGC ACCCCAGGCT TTACACTTTA
5581 TGCTTCCGGC TCGTATGTTG TGTGGAATTG TGAGCGGATA ACAATTTCAC ACAGGAAACA
5641 GCTATGACCA TGATTACGGA TTCACTGGCC GTCGTTTTAC AACGTCGTGA CTGGGAAAAC
5701 CCTGGCGTTA CCCAACTTAA TCGCCTTGCA GCACATCCCC CTTTCGCCAG CTGGCGTAAT
5761 AGCGAAGAGG CCCGCACCGA TCGCCCTTCC CAACAGTTGC GCAGCCTGAA TGGCGAATGG
5821 CGCTTTGCCT GGTTTCCGGC ACCAGAAGCG GTGCCGGAAA GCTGGCTGGA GTGCGATCTT
5881 CCTGAGGCCG ATACTGTCGT CGTCCCCTCA AACTGGCAGA TGCACGGTTA CGATGCGCCC
5941 ATCTACACCA ACGTAACCTA TCCCATTACG GTCAATCCGC CGTTTGTTCC CACGGAGAAT
6001 CCGACGGGTT GTTACTCGCT CACATTTAAT GTTGATGAAA GCTGGCTACA GGAAGGCCAG
6061 ACGCGAATTA TTTTTGATGG CGTTGGAATT
```

FIG. 29 (continued)

(SEQ ID NO:66) ICT1024 coding region: 310-2879

```
   1 TAATACGACT CACTATAGGG GAATTGTGAG CGGATAACAA TTCCCCTCTA GACTTACAAT
  61 TTCCATTCGC CATTCAGGCT GCGCAACTGT TGGGAAGGGC GATCGGTACG GGCCTCTTCG
 121 CTATTACGCC AGCTTGCGAA CGGTGGGTGC GCTGCAAGGC GATTAAGTTG GGTAACGCCA
 181 GGATTCTCCC AGTCACGACG TTGTAAAACG ACGGCCAGCG AGAGATCTTG ATTGGCTAGC
 241 AGAATAATTT TGTTTAACTT TAAGAAGGAG ATATACCATG GCGATATCCC GGGAGCTCGT
 301 GGATCCGAAT TCCATGAGTG AGGCCCGCAG GGACAGCACG AGCAGCCTGC AGCGCAAGAA
 361 GCCACCCTGG CTAAAGCTGG ACATTCCCTC TGCGGTGCCC CTGACGGCAG AAGAGCCCAG
 421 CTTCCTGCAG CCCCTGAGGC GACAGGCTTT CCTGAGGAGT GTGAGTATGC CAGCCGAGAC
 481 AGCCCACATC TCTTCACCCC ACCATGAGCT CCGGCGGCCG GTGCTGCAAC GCCAGACGTC
 541 CATCACACAG ACCATCCGCA GGGGACCGC CGACTGGTTT GGAGTGAGCA AGGACAGTGA
 601 CAGCACCCAG AAATGGCAGC GCAAGAGCAT CCGTCACTGC AGCCAGCGCT ACGGGAAGCT
 661 GAAGCCCCAG GTCCTCCGGG AGCTGGACCT GCCCAGCCAG GACAACGTGT CGCTGACCAG
 721 CACCGAGACG CCACCCCCAC TCTACGTGGG GCCATGCCAG CTGGGCATGC AGAAGATCAT
 781 AGACCCCCTG GCCCGTGGCC GTGCCTTCCG TGTGGCAGAT GACACTGCGG AAGGCCTGAG
 841 TGCCCCACAC ACTCCCGTCA CGCCGGGTGC TGCCTCCCTC TGCTCCTTCT CCAGCTCCCG
 901 CTCAGGTTTC CACCGGCTCC CGCGGCGGCG CAAGCGAGAG TCGGTGGCCA AGATGAGCTT
 961 CCGGGCGGCC GCAGCGCTGA TGAAAGGCCG CTCCGTTAGG GATGGCACCT TTCGCCGGGC
1021 ACGGCGTCGA AGCTTCACTC CAGCTAGCTT TCTGGAGGAG GACACAACTG ATTTCCCCGA
1081 TGAGCTGGAC ACATCCTTCT TTGCCCGGGA AGGTATCCTC CATGAAGAGC TGTCCACATA
1141 CCCGGATGAA GTTTTCGAGT CCCCATCGGA GGCAGCGCTA AAGGACTGGG AGAAGGCACC
1201 GGAGCAGGCG GACCTCACCG GCGGGGCCCT GGACCGCAGC GAGCTTGAGC GCAGCCACCT
1261 GATGCTGCCC TTGGAGCGAG GCTGGCGGAA GCAGAAGGAG GGCGCCGCAG CCCCGCAGCC
1321 CAAGGTGCGG CTCCGACAGG AGGTGGTGAG CACCGCGGGG CCGCGACGGG GCCAGCGTAT
1381 CGCGGTGCCG GTGCGCAAGC TCTTCGCCCG GGAGAAGCGG CCGTATGGGC TGGGCATGGT
1441 GGGACGGCTC ACCAACCGCA CCTACCGCAA GCGCATCGAC AGCTTCGTCA AGCGCCAGAT
1501 CGAGGACATG GACGACCACA GGCCCTTCTT CACCTACTGG CTTACCTTCG TGCACTCGCT
1561 CGTCACCATC CTAGCCGTGT GCATCTATGG CATCGCGCCC GTGGGCTTCT CGCAGCATGA
1621 GACGGTGGAC TCGGTGCTGC GGAACCGCGG GGTCTACGAG AACGTCAAGT ACGTGCAGCA
1681 GGAGAACTTC TGGATCGGGC CCAGCTCGGA GGCCCTCATC CACCTGGGCG CCAAGTTTTC
1741 GCCCTGCATG CGCCAGGACC CGCAGGTGCA CAGCTTCATT CGCTCGGCGC GCGAGCGCGA
1801 GAAGCACTCC GCCTGCTGCG TGCGCAACGA CAGGTCGGGC TGCGTGCAGA CCTCGGAGGA
1861 GGAGTGCTCG TCCACGCTGG CAGTGTGGGT GAAGTGGCCC ATCCATCCCA GCGCCCCAGA
1921 GCTTGCGGGC CACAAGAGAC AGTTTGGCTC TGTCTGCCAC CAGGATCCCA GGGTGTGTGA
1981 TGAGCCCTCC TCCGAAGACC CTCATGAGTG GCCAGAAGAC ATCACCAAGT GGCCGATCTG
2041 CACCAAAAAC AGCGCTGGGA ACCACACCAA CCATCCCCAC ATGGACTGTG TCATCACAGG
2101 ACGGCCCTGC TGCATTGGCA CCAAGGGCAG GTGTGAGATC ACCTCCCGGG AGTACTGTGA
```

FIG. 30

```
2161 CTTCATGAGG GGCTACTTCC ATGAGGAGGC CACGCTCTGC TCTCAGGTGC ACTGCATGGA
2221 TGATGTGTGT GGGCTCCTGC CTTTTCTCAA CCCCGAGGTG CCTGACCAGT TCTACCGCCT
2281 GTGGCTATCC CTCTTCCTGC ACGCCGGGAT CTTGCACTGC CTGGTGTCCA TCTGCTTCCA
2341 GATGACTGTC CTGCGGGACC TGGAGAAGCT GGCAGGCTGG CACCGCATAG CCATCATCTA
2401 CCTGCTGAGT GGTGTCACCG GCAACCTGGC CAGTGCCATC TTCCTGCCAT ACCGAGCAGA
2461 GGTGGGTCCT GCTGGCTCCC AGTTCGGCAT CCTGGCCTGC CTCTTCGTGG AGCTCTTCCA
2521 GAGCTGGCAG ATCCTGGCGC GGCCCTGGCG TGCCTTCTTC AAGCTGCTGG CTGTGGTGCT
2581 CTTCCTCTTC ACCTTTGGGC TGCTGCCGTG GATTGACAAC TTTGCCCACA TCTCGGGGTT
2641 CATCAGTGGG CTCTTCCTCT CCTTCGCCTT CTTGCCCTAC ATCAGCTTTG GCAAGTTCGA
2701 CCTGTACCGG AAACGCTGCC AGATCATCAT CTTTCAGGTG GTCTTCCTGG GCCTCCTGGC
2761 TGGCCTGGTG GTCCTCTTCT ACGTCTATCC TGTCCGCTGT GAGTGGTGTG AGTTCCTCAC
2821 CTGCATCCCC TTCACTGACA AGTTCTGTGA GAAGTACGAA CTGGACGCTC AGCTCCACAT
2881 CGATACGCGT TCGAAGCTTG CGGCCGCACA GCTGTATACA CGTGCAAGCC AGCCAGAACT
2941 CGCTCCTGAA GACCCAGAGG ATCTCGAGCA CCACCACCAC CACCACTAAT GTTAATTAAG
3001 TTGGGCGTTG TAATCATAGT CATAATCAAT ACTCCTGACT GCGTTAGCAA TTTAACTGTG
3061 ATAAACTACC GCATTAAAGC TATTCGATGA TAAGCTGTCA AACATGATAA TTCTTGAAGA
3121 CGAAAGGGCC TAGGCTGATA AAACAGAATT TGCCTGGCGG CAGTAGCGCG GTGGTCCCAC
3181 CTGACCCCAT GCCGAACTCA GAAGTGAAAC GCCGTAGCGC CGATGGTAGT GTGGGGTCTC
3241 CCCATGCGAG AGTAGGGAAC TGCCAGGCAT CAAATAAAAC GAAAGGCTCA GTCGAAAGAC
3301 TGGGCCTTTC GTTTTATCTG TTGTTTGTCG GTGAACGCTC TCCTGAGTAG GACAAATCCG
3361 CCGGGAGCGG ATTTGAACGT TGCGAAGCAA CGGCCCGGAG GGTGGCGGGC AGGACGCCCG
3421 CCATAAACTG CCAGGCATCA AATTAAGCAG AAGGCCATCC TGACGGATGG CCTTTTTGCG
3481 TTTCTACAAA CTCTTTTGTT TATTTTTCTA AATACATTCA AATATGTATC CGCTGAGCAA
3541 TAACTAGCAT AACCCCTTGG GGCCTCTAAA CGGGTCTTGA GGGGTTTTTT GCTGAAAGGA
3601 GGAACTATAT CCGGATTGGC GAATGGGACG CGCCCTGTAG CGGCGCATTA AGCGCGGCGG
3661 GTGTGGTGGT TACGCGCAGC GTGACCGCTA CACTTGCCAG CGCCCTAGCG CCCGCTCCTT
3721 TCGCTTTCTT CCCTTCCTTT CTCGCCACGT TCGCCGGCTT TCCCCGTCAA GCTCTAAATC
3781 GGGGGCTCCC TTTAGGGTTC CGATTTAGTG CTTTACGGCA CCTCGACCCC AAAAAACTTG
3841 ATTAGGGTGA TGGTTCACGT AGTGGGCCAT CGCCCTGATA GACGGTTTTT CGCCCTTTGA
3901 CGTTGGAGTC CACGTTCTTT AATAGTGGAC TCTTGTTCCA AACTGGAACA ACACTCAACC
3961 CTATCTCGGT CTATTCTTTT GATTTATAAG GGATTTTGCC GATTTCGGCC TATTGGTTAA
4021 AAAATGAGCT GATTTAACAA AAATTTAACG CGAATTTTAA CAAAATATTA ACGTTTACAA
4081 TTTCTGGCGG CACGATGGCA TGAGATTATC AAAAAGGATC TTCACCTAGA TCCTTTTAAA
4141 TTAAAAATGA AGTTTTAAAT CAATCTAAAG TATATATGAG TAAACTTGGT CTGACAGTTA
4201 CCAATGCTTA ATCAGTGAGG CACCTATCTC AGCGATCTGT CTATTTCGTT CATCCATAGT
4261 TGCCTGACTC CCCGTCGTGT AGATAACTAC GATACGGGAG GGCTTACCAT CTGGCCCCAG
4321 TGCTGCAATG ATACCGCGAG ACCCACGCTC ACCGGCTCCA GATTTATCAG CAATAAACCA
```

FIG. 30 (continued)

```
4381 GCCAGCCGGA AGGGCCGAGC GCAGAAGTGG TCCTGCAACT TTATCCGCCT CCATCCAGTC
4441 TATTAATTGT TGCCGGGAAG CTAGAGTAAG TAGTTCGCCA GTTAATAGTT TGCGCAACGT
4501 TGTTGCCATT GCTACAGGCA TCGTGGTGTC ACGCTCGTCG TTTGGTATGG CTTCATTCAG
4561 CTCCGGTTCC CAACGATCAA GGCGAGTTAC ATGATCCCCC ATGTTGTGCA AAAAAGCGGT
4621 TAGCTCCTTC GGTCCTCCGA TCGTTGTCAG AAGTAAGTTG GCCGCAGTGT TATCACTCAT
4681 GGTTATGGCA GCACTGCATA ATTCTCTTAC TGTCATGCCA TCCGTAAGAT GCTTTTCTGT
4741 GACTGGTGAG TACTCAACCA AGTCATTCTG AGAATAGTGT ATGCGGCGAC CGAGTTGCTC
4801 TTGCCCGGCG TCAATACGGG ATAATACCGC GCCACATAGC AGAACTTTAA AAGTGCTCAT
4861 CATTGGAAAA CGTTCTTCGG GGCGAAAACT CTCAAGGATC TTACCGCTGT TGAGATCCAG
4921 TTCGATGTAA CCCACTCGTG CACCCAACTG ATCTTCAGCA TCTTTTACTT TCACCAGCGT
4981 TTCTGGGTGA GCAAAAACAG GAAGGCAAAA TGCCGCAAAA AAGGGAATAA GGGCGACACG
5041 GAAATGTTGA ATACTCATAC TCTTCCTTTT TCAATCATGA CCAAAATCCC TTAACGTGAG
5101 TTTTCGTTCC ACTGAGCGTC AGACCCCGTA GAAAAGATCA AAGGATCTTC TTGAGATCCT
5161 TTTTTTCTGC GCGTAATCTG CTGCTTGCAA ACAAAAAAAC CACCGCTACC AGCGGTGGTT
5221 TGTTTGCCGG ATCAAGAGCT ACCAACTCTT TTTCCGAAGG TAACTGGCTT CAGCAGAGCG
5281 CAGATACCAA ATACTGTCCT TCTAGTGTAG CCGTAGTTAG GCCACCACTT CAAGAACTCT
5341 GTAGCACCGC CTACATACCT CGCTCTGCTA ATCCTGTTAC CAGTGGCTGC TGCCAGTGGC
5401 GATAAGTCGT GTCTTACCGG GTTGGACTCA AGACGATAGT TACCGGATAA GGCGCAGCGG
5461 TCGGGCTGAA CGGGGGGTTC GTGCACACAG CCCAGCTTGG AGCGAACGAC CTACACCGAA
5521 CTGAGATACC TACAGCGTGA GCTATGAGAA AGCGCCACGC TTCCCGAAGG GAGAAAGGCG
5581 GACAGGTATC CGGTAAGCGG CAGGGTCGGA ACAGGAGAGC GCACGAGGGA GCTTCCAGGG
5641 GGAAACGCCT GGTATCTTTA TAGTCCTGTC GGGTTTCGCC ACCTCTGACT TGAGCGTCGA
5701 TTTTTGTGAT GCTCGTCAGG GGGGCGGAGC CTATGGAAAA ACGCCAGCAA CGCGGCCTTT
5761 TTACGGTTCC TGGCCTTTTG CTGGCCTTTT GCTCACATGT TCTTTCCTGC GTTATCCCCT
5821 GATTCTGTGG ATAACCGTAT TACCGCCTTT GAGTGAGCTG ATACCGCTCG CCGCAGCCGA
5881 ACGACCGAGC GCAGCGAGTC AGTGAGCGAG GAAGCCGGCG ATAATGGCCT GCTTCTCGCC
5941 GAAACGTTTG GTGGCGGGAC CAGTGACGAA GGCTTGAGCG AGGGCGTGCA AGATTCCGAA
6001 TACCGCAAGC GACAGGCCGA TCATCGTCGC GCTCCAGCGA AAGCGGTCCT CGCCGAAAAT
6061 GACCCAGAGC GCTGCCGGCA CCTGTCCTAC GAGTTGCATG ATAAAGAAGA CAGTCATAAG
6121 TGCGGCGACG ACCGGTGAAT TGTGAGCGCT CACAATTCTC GTGACATCAT AACGTCCCGC
6181 GAAAT
```

FIG. 30 (continued)

(SEQ ID NO:68) Coding region for the N terminus 400 aa of
ICT1024: 314-1515

```
   1 TAATACGACT CACTATAGGG GAATTGTGAG CGGATAACAA TTCCCCTCTA GACTTACAAT
  61 TTCCATTCGC CATTCAGGCT GCGCAACTGT TGGGAAGGGC GATCGGTACG GGCCTCTTCG
 121 CTATTACGCC AGCTTGCGAA CGGTGGGTGC GCTGCAAGGC GATTAAGTTG GGTAACGCCA
 181 GGATTCTCCC AGTCACGACG TTGTAAAACG ACGGCCAGCG AGAGATCTTG ATTGGCTAGC
 241 AGAATAATTT TGTTTAACTT TAAGAAGGAG ATATACCATG GCGATATCCC GGGAGCTCGT
 301 GGATCCGAAT TCCATGAGTG AGGCCCGCAG GGACAGCACG AGCAGCCTGC AGCGCAAGAA
 361 GCCACCCTGG CTAAAGCTGG ACATTCCCTC TGCGGTGCCC CTGACGGCAG AAGAGCCCAG
 421 CTTCCTGCAG CCCCTGAGGC GACAGGCTTT CCTGAGGAGT GTGAGTATGC CAGCCGAGAC
 481 AGCCCACATC TCTTCACCCC ACCATGAGCT CCGGCGGCCG GTGCTGCAAC GCCAGACGTC
 541 CATCACACAG ACCATCCGCA GGGGGACCGC CGACTGGTTT GGAGTGAGCA AGGACAGTGA
 601 CAGCACCCAG AAATGGCAGC GCAAGAGCAT CCGTCACTGC AGCCAGCGCT ACGGGAAGCT
 661 GAAGCCCCAG GTCCTCCGGG AGCTGGACCT GCCCAGCCAG GACAACGTGT CGCTGACCAG
 721 CACCGAGACG CCACCCCCAC TCTACGTGGG GCCATGCCAG CTGGGCATGC AGAAGATCAT
 781 AGACCCCCTG GCCCGTGGCC GTGCCTTCCG TGTGGCAGAT GACACTGCGG AAGGCCTGAG
 841 TGCCCCACAC ACTCCCGTCA CGCCGGGTGC TGCCTCCCTC TGCTCCTTCT CCAGCTCCCG
 901 CTCAGGTTTC CACCGGCTCC CGCGGCGGCG CAAGCGAGAG TCGGTGGCCA AGATGAGCTT
 961 CCGGGCGGCC GCAGCGCTGA TGAAAGGCCG CTCCGTTAGG GATGGCACCT TTCGCCGGGC
1021 ACGGCGTCGA AGCTTCACTC CAGCTAGCTT TCTGGAGGAG GACACAACTG ATTTCCCCGA
1081 TGAGCTGGAC ACATCCTTCT TTGCCCGGGA AGGTATCCTC CATGAAGAGC TGTCCACATA
1141 CCCCGGATGAA GTTTTCGAGT CCCCATCGGA GGCAGCGCTA AAGGACTGGG AGAAGGCACC
1201 GGAGCAGGCG GACCTCACCG GCGGGGCCCT GGACCGCAGC GAGCTTGAGC GCAGCCACCT
1261 GATGCTGCCC TTGGAGCGAG GCTGGCGGAA GCAGAAGGAG GGCGCCGCAG CCCCGCAGCC
1321 CAAGGTGCGG CTCCGACAGG AGGTGGTGAG CACCGCGGGG CCGCGACGGG GCCAGCGTAT
1381 CGCGGTGCCG GTGCGCAAGC TCTTCGCCCG GGAGAAGCGG CCGTATGGGC TGGGCATGGT
1441 GGGACGGCTC ACCAACCGCA CCTACCGCAA GCGCATCGAC AGCTTCGTCA AGCGCCAGAT
1501 CGAGGACATG GACATCGATA CGCGTTCGAA GCTTGCGGCC GCACAGCTGT ATACACGTGC
1561 AAGCCAGCCA GAACTCGCTC CTGAAGACCC AGAGGATCTC GAGCACCACC ACCACCACCA
1621 CTAATGTTAA TTAAGTTGGG CGTTGTAATC ATAGTCATAA TCAATACTCC TGACTGCGTT
1681 AGCAATTTAA CTGTGATAAA CTACCGCATT AAAGCTATTC GATGATAAGC TGTCAAACAT
1741 GATAATTCTT GAAGACGAAA GGGCCTAGGC TGATAAAACA GAATTTGCCT GGCGGCAGTA
1801 GCGCGGTGGT CCCACCTGAC CCCATGCCGA ACTCAGAAGT GAAACGCCGT AGCGCCGATG
1861 GTAGTGTGGG GTCTCCCCAT GCGAGAGTAG GGAACTGCCA GGCATCAAAT AAAACGAAAG
1921 GCTCAGTCGA AAGACTGGGC CTTTCGTTTT ATCTGTTGTT TGTCGGTGAA CGCTCTCCTG
1981 AGTAGGACAA ATCCGCCGGG AGCGGATTTG AACGTTGCGA AGCAACGGCC CGGAGGGTGG
2041 CGGGCAGGAC GCCCGCCATA AACTGCCAGG CATCAAATTA AGCAGAAGGC CATCCTGACG
```

FIG. 31

```
2101  GATGGCCTTT TTGCGTTTCT ACAAACTCTT TTGTTTATTT TTCTAAATAC ATTCAAATAT
2161  GTATCCGCTG AGCAATAACT AGCATAACCC CTTGGGGCCT CTAAACGGGT CTTGAGGGGT
2221  TTTTTGCTGA AAGGAGGAAC TATATCCGGA TTGGCGAATG GGACGCGCCC TGTAGCGGCG
2281  CATTAAGCGC GGCGGGTGTG GTGGTTACGC GCAGCGTGAC CGCTACACTT GCCAGCGCCC
2341  TAGCGCCCGC TCCTTTCGCT TTCTTCCCTT CCTTTCTCGC CACGTTCGCC GGCTTTCCCC
2401  GTCAAGCTCT AAATCGGGGG CTCCCTTTAG GGTTCCGATT TAGTGCTTTA CGGCACCTCG
2461  ACCCCAAAAA ACTTGATTAG GGTGATGGTT CACGTAGTGG GCCATCGCCC TGATAGACGG
2521  TTTTTCGCCC TTTGACGTTG GAGTCCACGT TCTTTAATAG TGGACTCTTG TTCCAAACTG
2581  GAACAACACT CAACCCTATC TCGGTCTATT CTTTTGATTT ATAAGGGATT TTGCCGATTT
2641  CGGCCTATTG GTTAAAAAAT GAGCTGATTT AACAAAAATT TAACGCGAAT TTTAACAAAA
2701  TATTAACGTT TACAATTTCT GGCGGCACGA TGGCATGAGA TTATCAAAAA GGATCTTCAC
2761  CTAGATCCTT TTAAATTAAA AATGAAGTTT TAAATCAATC TAAAGTATAT ATGAGTAAAC
2821  TTGGTCTGAC AGTTACCAAT GCTTAATCAG TGAGGCACCT ATCTCAGCGA TCTGTCTATT
2881  TCGTTCATCC ATAGTTGCCT GACTCCCCGT CGTGTAGATA ACTACGATAC GGGAGGGCTT
2941  ACCATCTGGC CCCAGTGCTG CAATGATACC GCGAGACCCA CGCTCACCGG CTCCAGATTT
3001  ATCAGCAATA AACCAGCCAG CCGGAAGGGC CGAGCGCAGA AGTGGTCCTG CAACTTTATC
3061  CGCCTCCATC CAGTCTATTA ATTGTTGCCG GGAAGCTAGA GTAAGTAGTT CGCCAGTTAA
3121  TAGTTTGCGC AACGTTGTTG CCATTGCTAC AGGCATCGTG GTGTCACGCT CGTCGTTTGG
3181  TATGGCTTCA TTCAGCTCCG GTTCCCAACG ATCAAGGCGA GTTACATGAT CCCCCATGTT
3241  GTGCAAAAAA GCGGTTAGCT CCTTCGGTCC TCCGATCGTT GTCAGAAGTA AGTTGGCCGC
3301  AGTGTTATCA CTCATGGTTA TGGCAGCACT GCATAATTCT CTTACTGTCA TGCCATCCGT
3361  AAGATGCTTT TCTGTGACTG GTGAGTACTC AACCAAGTCA TTCTGAGAAT AGTGTATGCG
3421  GCGACCGAGT TGCTCTTGCC CGGCGTCAAT ACGGGATAAT ACCGCGCCAC ATAGCAGAAC
3481  TTTAAAAGTG CTCATCATTG GAAAACGTTC TTCGGGGCGA AAACTCTCAA GGATCTTACC
3541  GCTGTTGAGA TCCAGTTCGA TGTAACCCAC TCGTGCACCC AACTGATCTT CAGCATCTTT
3601  TACTTTCACC AGCGTTTCTG GGTGAGCAAA AACAGGAAGG CAAAATGCCG CAAAAAAGGG
3661  AATAAGGGCG ACACGGAAAT GTTGAATACT CATACTCTTC CTTTTTCAAT CATGACCAAA
3721  ATCCCTTAAC GTGAGTTTTC GTTCCACTGA GCGTCAGACC CCGTAGAAAA GATCAAAGGA
3781  TCTTCTTGAG ATCCTTTTTT TCTGCGCGTA ATCTGCTGCT TGCAAACAAA AAAACCACCG
3841  CTACCAGCGG TGGTTTGTTT GCCGGATCAA GAGCTACCAA CTCTTTTTCC GAAGGTAACT
3901  GGCTTCAGCA GAGCGCAGAT ACCAAATACT GTCCTTCTAG TGTAGCCGTA GTTAGGCCAC
3961  CACTTCAAGA ACTCTGTAGC ACCGCCTACA TACCTCGCTC TGCTAATCCT GTTACCAGTG
4021  GCTGCTGCCA GTGGCGATAA GTCGTGTCTT ACCGGGTTGG ACTCAAGACG ATAGTTACCG
4081  GATAAGGCGC AGCGGTCGGG CTGAACGGGG GGTTCGTGCA CACAGCCCAG CTTGGAGCGA
4141  ACGACCTACA CCGAACTGAG ATACCTACAG CGTGAGCTAT GAGAAAGCGC CACGCTTCCC
4201  GAAGGGAGAA AGGCGGACAG GTATCCGGTA AGCGGCAGGG TCGGAACAGG AGAGCGCACG
4261  AGGGAGCTTC CAGGGGGAAA CGCCTGGTAT CTTTATAGTC CTGTCGGGTT TCGCCACCTC
```

FIG. 31 (continued)

```
4321  TGACTTGAGC GTCGATTTTT GTGATGCTCG TCAGGGGGGC GGAGCCTATG GAAAAACGCC
4381  AGCAACGCGG CCTTTTTACG GTTCCTGGCC TTTTGCTGGC CTTTTGCTCA CATGTTCTTT
4441  CCTGCGTTAT CCCCTGATTC TGTGGATAAC CGTATTACCG CCTTTGAGTG AGCTGATACC
4501  GCTCGCCGCA GCCGAACGAC CGAGCGCAGC GAGTCAGTGA GCGAGGAAGC CGGCGATAAT
4561  GGCCTGCTTC TCGCCGAAAC GTTTGGTGGC GGGACCAGTG ACGAAGGCTT GAGCGAGGGC
4621  GTGCAAGATT CCGAATACCG CAAGCGACAG GCCGATCATC GTCGCGCTCC AGCGAAAGCG
4681  GTCCTCGCCG AAAATGACCC AGAGCGCTGC CGGCACCTGT CCTACGAGTT GCATGATAAA
4741  GAAGACAGTC ATAAGTGCGG CGACGACCGG TGAATTGTGA GCGCTCACAA TTCTCGTGAC
4801  ATCATAACGT CCCGCGAAAT
```

FIG. 31 (continued)

(SEQ ID NO 69) Coding region for the C terminus 373 aa of
ICT1024: 308-1431

```
   1 TAATACGACT CACTATAGGG GAATTGTGAG CGGATAACAA TTCCCCTCTA GACTTACAAT
  61 TTCCATTCGC CATTCAGGCT GCGCAACTGT TGGGAAGGGC GATCGGTACG GGCCTCTTCG
 121 CTATTACGCC AGCTTGCGAA CGGTGGGTGC GCTGCAAGGC GATTAAGTTG GGTAACGCCA
 181 GGATTCTCCC AGTCACGACG TTGTAAAACG ACGGCCAGCG AGAGATCTTG ATTGGCTAGC
 241 AGAATAATTT TGTTTAACTT TAAGAAGGAG ATATACCATG GCGATATCCC GGGAGCTCGT
 301 GGATCCGAAT TCCCAGGTGC ACAGCTTCAT TCGCTCGGCG CGCGAGCGCG AGAAGCACTC
 361 CGCCTGCTGC GTGCGCAACG ACAGGTCGGG CTGCGTGCAG ACCTCGGAGG AGGAGTGCTC
 421 GTCCACGCTG GCAGTGTGGG TGAAGTGGCC CATCCATCCC AGCGCCCCAG AGCTTGCGGG
 481 CCACAAGAGA CAGTTTGGCT CTGTCTGCCA CCAGGATCCC AGGGTGTGTG ATGAGCCCTC
 541 CTCCGAAGAC CCTCATGAGT GGCCAGAAGA CATCACCAAG TGGCCGATCT GCACCAAAAA
 601 CAGCGCTGGG AACCACACCA CCATCCCCA CATGGACTGT GTCATCACAG GACGGCCCTG
 661 CTGCATTGGC ACCAAGGGCA GGTGTGAGAT CACCTCCCGG GAGTACTGTG ACTTCATGAG
 721 GGGCTACTTC CATGAGGAGG CCACGCTCTG CTCTCAGGTG CACTGCATGG ATGATGTGTG
 781 TGGGCTCCTG CCTTTTCTCA ACCCCGAGGT GCCTGACCAG TTCTACCGCC TGTGGCTATC
 841 CCTCTTCCTG CACGCCGGGA TCTTGCACTG CCTGGTGTCC ATCTGCTTCC AGATGACTGT
 901 CCTGCGGGAC CTGGAGAAGC TGGCAGGCTG GCACCGCATA GCCATCATCT ACCTGCTGAG
 961 TGGTGTCACC GGCAACCTGG CCAGTGCCAT CTTCCTGCCA TACCGAGCAG AGGTGGGTCC
1021 TGCTGGCTCC CAGTTCGGCA TCCTGGCCTG CCTCTTCGTG GAGCTCTTCC AGAGCTGGCA
1081 GATCCTGGCG CGGCCCTGGC GTGCCTTCTT CAAGCTGCTG GCTGTGGTGC TCTTCCTCTT
1141 CACCTTTGGG CTGCTGCCGT GGATTGACAA CTTTGCCCAC ATCTCGGGGT TCATCAGTGG
1201 CCTCTTCCTC TCCTTCGCCT TCTTGCCCTA CATCAGCTTT GGCAAGTTCG ACCTGTACCG
1261 GAAACGCTGC CAGATCATCA TCTTTCAGGT GGTCTTCCTG GGCCTCCTGG CTGGCCTGGT
1321 GGTCCTCTTC TACGTCTATC CTGTCCGCTG TGAGTGGTGT GAGTTCCTCA CCTGCATCCC
1381 CTTCACTGAC AAGTTCTGTG AGAAGTACGA ACTGGACGCT CAGCTCCACA TCGATACGCG
1441 TTCGAAGCTT GCGGCCGCAC AGCTGTATAC ACGTGCAAGC CAGCCAGAAC TCGCTCCTGA
1501 AGACCCAGAG GATCTCGAGC ACCACCACCA CCACCACTAA TGTTAATTAA GTTGGGCGTT
1561 GTAATCATAG TCATAATCAA TACTCCTGAC TGCGTTAGCA ATTTAACTGT GATAAACTAC
1621 CGCATTAAAG CTATTCGATG ATAAGCTGTC AAACATGATA ATTCTTGAAG ACGAAAGGGC
1681 CTAGGCTGAT AAAACAGAAT TTGCCTGGCG GCAGTAGCGC GGTGGTCCCA CCTGACCCCA
1741 TGCCGAACTC AGAAGTGAAA CGCCGTAGCG CCGATGGTAG TGTGGGGTCT CCCCATGCGA
1801 GAGTAGGGAA CTGCCAGGCA TCAAATAAAA CGAAAGGCTC AGTCGAAAGA CTGGGCCTTT
1861 CGTTTTATCT GTTGTTTGTC GGTGAACGCT CTCCTGAGTA GGACAAATCC GCCGGGAGCG
1921 GATTTGAACG TTGCGAAGCA ACGGCCCGGA GGGTGGCGGG CAGGACGCCC GCCATAAACT
1981 GCCAGGCATC AAATTAAGCA GAAGGCCATC CTGACGGATG GCCTTTTTGC GTTTCTACAA
2041 ACTCTTTTGT TTATTTTTCT AAATACATTC AAATATGTAT CCGCTGAGCA ATAACTAGCA
```

FIG. 32

```
2101  TAACCCCTTG GGGCCTCTAA ACGGGTCTTG AGGGGTTTTT TGCTGAAAGG AGGAACTATA
2161  TCCGGATTGG CGAATGGGAC GCGCCCTGTA GCGGCGCATT AAGCGCGGCG GGTGTGGTGG
2221  TTACGCGCAG CGTGACCGCT ACACTTGCCA GCGCCCTAGC GCCCGCTCCT TTCGCTTTCT
2281  TCCCTTCCTT TCTCGCCACG TTCGCCGGCT TTCCCCGTCA AGCTCTAAAT CGGGGGCTCC
2341  CTTTAGGGTT CCGATTTAGT GCTTTACGGC ACCTCGACCC CAAAAAACTT GATTAGGGTG
2401  ATGGTTCACG TAGTGGGCCA TCGCCCTGAT AGACGGTTTT TCGCCCTTTG ACGTTGGAGT
2461  CCACGTTCTT TAATAGTGGA CTCTTGTTCC AAACTGGAAC AACACTCAAC CCTATCTCGG
2521  TCTATTCTTT TGATTTATAA GGGATTTTGC CGATTTCGGC CTATTGGTTA AAAAATGAGC
2581  TGATTTAACA AAAATTTAAC GCGAATTTTA ACAAAATATT AACGTTTACA ATTTCTGGCG
2641  GCACGATGGC ATGAGATTAT CAAAAGGAT CTTCACCTAG ATCCTTTTAA ATTAAAAATG
2701  AAGTTTTAAA TCAATCTAAA GTATATATGA GTAAACTTGG TCTGACAGTT ACCAATGCTT
2761  AATCAGTGAG GCACCTATCT CAGCGATCTG TCTATTTCGT TCATCCATAG TTGCCTGACT
2821  CCCCGTCGTG TAGATAACTA CGATACGGGA GGGCTTACCA TCTGGCCCCA GTGCTGCAAT
2881  GATACCGCGA GACCCACGCT CACCGGCTCC AGATTTATCA GCAATAAACC AGCCAGCCGG
2941  AAGGGCCGAG CGCAGAAGTG GTCCTGCAAC TTTATCCGCC TCCATCCAGT CTATTAATTG
3001  TTGCCGGGAA GCTAGAGTAA GTAGTTCGCC AGTTAATAGT TTGCGCAACG TTGTTGCCAT
3061  TGCTACAGGC ATCGTGGTGT CACGCTCGTC GTTTGGTATG GCTTCATTCA GCTCCGGTTC
3121  CCAACGATCA AGGCGAGTTA CATGATCCCC CATGTTGTGC AAAAAAGCGG TTAGCTCCTT
3181  CGGTCCTCCG ATCGTTGTCA GAAGTAAGTT GGCCGCAGTG TTATCACTCA TGGTTATGGC
3241  AGCACTGCAT AATTCTCTTA CTGTCATGCC ATCCGTAAGA TGCTTTTCTG TGACTGGTGA
3301  GTACTCAACC AAGTCATTCT GAGAATAGTG TATGCGGCGA CCGAGTTGCT CTTGCCCGGC
3361  GTCAATACGG GATAATACCG CGCCACATAG CAGAACTTTA AAAGTGCTCA TCATTGGAAA
3421  ACGTTCTTCG GGGCGAAAAC TCTCAAGGAT CTTACCGCTG TTGAGATCCA GTTCGATGTA
3481  ACCCACTCGT GCACCCAACT GATCTTCAGC ATCTTTTACT TTCACCAGCG TTTCTGGGTG
3541  AGCAAAAACA GGAAGGCAAA ATGCCGCAAA AAAGGGAATA AGGGCGACAC GGAAATGTTG
3601  AATACTCATA CTCTTCCTTT TTCAATCATG ACCAAAATCC CTTAACGTGA GTTTTCGTTC
3661  CACTGAGCGT CAGACCCCGT AGAAAAGATC AAAGGATCTT CTTGAGATCC TTTTTTTCTG
3721  CGCGTAATCT GCTGCTTGCA AACAAAAAAA CCACCGCTAC CAGCGGTGGT TTGTTTGCCG
3781  GATCAAGAGC TACCAACTCT TTTTCCGAAG GTAACTGGCT TCAGCAGAGC GCAGATACCA
3841  AATACTGTCC TTCTAGTGTA GCCGTAGTTA GGCCACCACT TCAAGAACTC TGTAGCACCG
3901  CCTACATACC TCGCTCTGCT AATCCTGTTA CCAGTGGCTG CTGCCAGTGG CGATAAGTCG
3961  TGTCTTACCG GGTTGGACTC AAGACGATAG TTACCGGATA AGGCGCAGCG GTCGGGCTGA
4021  ACGGGGGGTT CGTGCACACA GCCCAGCTTG GAGCGAACGA CCTACACCGA ACTGAGATAC
4081  CTACAGCGTG AGCTATGAGA AAGCGCCACG CTTCCCGAAG GGAGAAAGGC GGACAGGTAT
4141  CCGGTAAGCG GCAGGGTCGG AACAGGAGAG CGCACGAGGG AGCTTCCAGG GGGAAACGCC
4201  TGGTATCTTT ATAGTCCTGT CGGGTTTCGC CACCTCTGAC TTGAGCGTCG ATTTTTGTGA
4261  TGCTCGTCAG GGGGGCGGAG CCTATGGAAA AACGCCAGCA ACGCGGCCTT TTTACGGTTC
```

FIG. 32 (continued)

```
4321 CTGGCCTTTT GCTGGCCTTT TGCTCACATG TTCTTTCCTG CGTTATCCCC TGATTCTGTG
4381 GATAACCGTA TTACCGCCTT TGAGTGAGCT GATACCGCTC GCCGCAGCCG AACGACCGAG
4441 CGCAGCGAGT CAGTGAGCGA GGAAGCCGGC GATAATGGCC TGCTTCTCGC CGAAACGTTT
4501 GGTGGCGGGA CCAGTGACGA AGGCTTGAGC GAGGGCGTGC AAGATTCCGA ATACCGCAAG
4561 CGACAGGCCG ATCATCGTCG CGCTCCAGCG AAAGCGGTCC TCGCCGAAAA TGACCCAGAG
4621 CGCTGCCGGC ACCTGTCCTA CGAGTTGCAT GATAAAGAAG ACAGTCATAA GTGCGGCGAC
4681 GACCGGTGAA TTGTGAGCGC TCACAATTCT CGTGACATCA TAACGTCCCG CGAAAT
```

FIG. 32 (continued)

| USER PARAMETERS AND SCORING INFORMATION ||
|---|---|
| METHOD SELECTED TO LIMIT NUMBER OF RESULTS | EXPLICIT NUMBER |
| NUMBER OF RESULTS REQUESTED | 20 |
| HLA MOLECULE TYPE SELECTED | A_0201 |
| LENGTH SELECTED FOR SUBSEQUENCES TO BE SCORED | 9 |
| ECHOING MODE SELECTED FOR INPUT SEQUENCE | Y |
| ECHOING FORMAT | NUMBERED LINES |
| LENGTH OF USER'S INPUT PEPTIDE SEQUENCE | 803 |
| NUMBER OF SUBSEQUENCE SCORES CALCULATED | 795 |
| NUMBER OF TOP-SCORING SUBSEQUENCES REPORTED BACK IN SCORING OUTPUT TABLE | 20 |

| SCORING RESULTS ||||
|---|---|---|---|
| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) |
| 1 | 425 | MMPKYLNFV | 1080.239 |
| 2 | 410 | KLYVRRVFI | 642.660 |
| 3 | 557 | RLLKKGYEV | 257.342 |
| 4 | 203 | FLVADKVIV | 131.175 |
| 5 | 144 | LLHVTDTGV | 118.238 |
| 6 | 547 | KEAESSPFV | 106.738 |
| 7 | 639 | RLTESPCAL | 87.586 |
| 8 | 381 | VTFKSILFV | 76.863 |
| 9 | 3 | ALWVLGLCC | 41.234 |
| 10 | 6 | VLGLCCVLL | 36.316 |
| 11 | 189 | SELIGQFGV | 29.023 |
| 12 | 741 | RMLRLSLNI | 27.879 |
| 13 | 451 | LQQHKLLKV | 27.573 |
| 14 | 280 | YVWSSKTET | 24.895 |
| 15 | 259 | LELDTIKNL | 24.638 |
| 16 | 417 | FITDDFHDM | 24.478 |
| 17 | 467 | KTLDMIKKI | 17.695 |
| 18 | 463 | KLVRKTLDM | 17.388 |
| 19 | 429 | YLNFVKGVV | 17.053 |
| 20 | 197 | VGPYSAFLV | 16.564 |

FIG. 33

SUGGESTED MODELS FOR TRANSMEMBRANE TOPOLOGY FOR ICT1025

---> STRONGLY prefered model: N-terminus inside
2 strong transmembrane helices, total score : 2962
from  to length score orientation
1    3   19 (17)  2034 i-o
2  191 212 (22)   928 o-i ---> alternative model
2 strong transmembrane helices, total score : 2607
from  to length score orientation
1    3   19 (17)  1929 o-i
2  191 213 (23)   678 i-o

FIG. 34

"DAS" - TRANSMEMBRANE PREDICTION SERVER ICT 1025

POTENTIAL TRANSMEMBRANE SEGMENTS

| START | STOP | LENGTH~ | CUTOFF |
|-------|------|---------|--------|
| 6 | 18 | 13 ~ | 1.7* |
| 7 | 17 | 11 ~ | 2.2 |
| 195 | 209 | 15 ~ | 1.7* |
| 197 | 206 | 10 ~ | 2.2 |
| 247 | 248 | 2 ~ | 1.7 |
| 384 | 390 | 7 ~ | 1.7 |
| 710 | 723 | 14 ~ | 1.7 |
| 713 | 719 | 7 ~ | 2.2* |

FIG. 35

SCREENING OF ICT1025 mAb FOR SURFACE BINDING ACTIVITIES IN COLON TUMOR CELLS

```
                       SEQUENCE LISTING

<160> NUMBER OF SEQ ID NOS: 111

<210> SEQ ID NO 1
<211> LENGTH: 1934
<212> TYPE: DNA
<213> ORGANISM: Homo sapiens

<400> SEQUENCE: 1 agaacccgc ggggtctgag cagcccagcg tgcccattcc agcgcccgcg tccccgcagc      60
atgccgcgcc cccgcctgct ggccgcgctg tgcggcgcgc tgctctgcgc ccccagcctc     120
ctcgtcgccc tggatatctg ttccaaaaac ccctgccaca cggtggttt atgcgaggag     180 atttcccaag aagtgcgagg agatgtcttc ccctcgtaca cctgcacgtg ccttaagggc     240
tacgcgggca accactgtga cgaaatgt gtcgagccac tgggcatgga gaatgggaac     300
attgccaact cacagatcgc cgcctcatct gtgcgtgtga ccttcttggg tttgcagcat     360
tgggtcccgg agctggcccg cctgaaccgc gcaggcatgg tcaatgcctg gacacccagc     420
agcaatgacg ataacccctg gatccaggtg aacctgctgc ggaggatgtg ggtaacaggt     480
gtggtgacgc agggtgccag ccgcttggcc agtcatgagt acctgaaggc cttcaaggtg     540
gcctacagcc ttaatggaca cgaattcgat ttcatccatg atgttaataa aaacacaag     600 gagtttgtgg gtaactggaa caaaaacgcg gtgcatgtca acctgtttga daccccctgtg     660 gaggctcagt acgtgagatt gtaccccacg agctgccaca cggcctgcac tctgcgcttt     720
gagctactgg gctgtgagct gaacggatgc gccaatcccc tgggcctgaa gaataacagc     780
atccctgaca gcagatcac ggcctccagc agctacaaga cctggggctt gcatctcttc     840
agctggaacc cctcctatgc acggctggac aagcagggca acttcaacgc ctgggttgcg     900
gggagctacg gtaacgatca gtggctgcag gtggacctgg gctcctcgaa ggaggtgaca     960
ggcatcatca cccagggggc ccgtaacttt ggctctgtcc agtttgtggc atcctacaag    1020
gttgcctaca gtaatgacag tgcgaactgg actgagtacc aggaccccag gactggcagc    1080
agtaagatct cccctggcaa ctgggacaac cactcccaca gaagaacctt gtttgagacg    1140
cccatcctgg ctcgctatgt gcgcatcctg cctgtagcct ggcacaaccg catcgccctg    1200
cgcctggagc tgctgggctg ttagtggcca cctgccaccc ccaggtcttc ctgctttcca    1260
tgggcccgct gcctcttggc ttctcagccc cttttaaatca ccatagggct ggggactggg    1320
gaaggggagg gtgttcagag gcagcaccac cacacagtca cccctccctc cctcttccc    1380 accctccacc tctcacgggc cctgcccag cccctaagcc ccgtccccta acccccagtc    1440
ctcactgtcc tgttttctta ggcactgagg gatctgagta ggtctgggat ggacaggaaa    1500
```

-continued

```
gggcaaagta gggcgtgtgg tttccctgcc cctgtccgga ccgccgatcc caggtgcgtg   1560
tgtctctgtc tctcctagcc cctctctcac acatcacatt cccatggtgg cctcaagaaa   1620
ggcccggaag ccccaggctg agataacag cctcttgccc gtcggccctg cgtcggccct    1680
ggggtaccat gtgccacaac tgctgtggcc ccctgtcccc aagacacttc cccttgtctc   1740
cctggttgcc tctcttgccc cttgtcctga agcccagcga cacagaaggg ggtgggcgg    1800 gtctatgggg agaaagggag cgaggtcaga ggagccggca tgggttggca gggtgggcgt   1860
ttggggccct catgctggct tttcacccca gaggacacag gcagcttcca aaatatattt   1920
atcttcttca cggg                                                    1934
```

<210> SEQ ID NO 2
<211> LENGTH: 387
<212> TYPE: PRT
<213> ORGANISM: Homo sapiens

<400> SEQUENCE: 2

```
Met Pro Arg Pro Arg Leu Leu Ala Ala Leu Cys Gly Ala Leu Leu Cys
 1               5                   10                  15

Ala Pro Ser Leu Leu Val Ala Leu Asp Ile Cys Ser Lys Asn Pro Cys
                20                  25                  30

His Asn Gly Gly Leu Cys Glu Glu Ile Ser Gln Glu Val Arg Gly Asp
            35                  40                  45

Val Phe Pro Ser Tyr Thr Cys Thr Cys Leu Lys Gly Tyr Ala Gly Asn
        50                  55                  60

His Cys Glu Thr Lys Cys Val Glu Pro Leu Gly Met Glu Asn Gly Asn
 65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
        275                 280                 285
```

| | | | | | | | | | | |
|---|---|---|---|---|---|---|---|---|---|---|
|Leu|Gln|Val|Asp|Leu|Gly|Ser|Ser|Lys|Glu|Val|Thr|Gly|Ile|Ile|Thr|
| |290| | | |295| | | |300| |

Gln Gly Ala Arg Asn Phe Gly Ser Val Gln Phe Val Ala Ser Tyr Lys
305             310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
            340                 345                 350

His Lys Lys Asn Leu Phe Glu Thr Pro Ile Leu Ala Arg Tyr Val Arg
        355                 360                 365

Ile Leu Pro Val Ala Trp His Asn Arg Ile Ala Leu Arg Leu Glu Leu
    370                 375                 380

Leu Gly Cys
385

<210> SEQ ID NO 3
<211> LENGTH: 1164
<212> TYPE: DNA
<213> ORGANISM: Homo sapiens

<400> SEQUENCE: 3

```
atgccgcgcc cccgcctgct ggccgcgctg tgcggcgcgc tgctctgcgc ccccagcctc      60
ctcgtcgccc tggatatctg ttccaaaaac ccctgccaca acggtggttt atgcgaggag     120
atttcccaag aagtgcgagg agatgtcttc ccctcgtaca cctgcacgtg ccttaagggc     180
tacgcgggca accactgtga gacgaaatgt gtcgagccac tgggcatgga gaatgggaac     240
attgccaact cacagatcgc cgcctcatct gtgcgtgtga ccttcttggg tttgcagcat     300
tgggtcccgg agctggcccg cctgaaccgc gcaggcatgg tcaatgcctg acacccagc      360
agcaatgacg ataacccctg gatccaggtg aacctgctgc ggaggatgtg ggtaacaggt     420
gtggtgacgc agggtgccag ccgcttggcc agtcatgagt acctgaaggc cttcaaggtg     480
gcctacagcc ttaatggaca cgaattcgat ttcatccatg atgttaataa aaaacacaag     540
gagtttgtgg gtaactggaa caaaaacgcg gtgcatgtca acctgtttga dcccctgtg     600
gaggctcagt acgtgagatt gtaccccacg agctgccaca cggcctgcac tctgcgcttt     660
gagctactgg gctgtgagct gaacggatgc gccaatcccc tgggcctgaa gaataacagc     720
atccctgaca gcagatcac ggcctccagc agctacaaga cctggggctt gcatctcttc     780
agctggaacc cctcctatgc acggctggac aagcagggca acttcaacgc ctgggttgcg     840
gggagctacg gtaacgatca gtggctgcag gtggacctgg gctcctcgaa ggaggtgaca     900
ggcatcatca cccaggggcc ccgtaacttt ggctctgtcc agtttgtggc atcctacaag     960
gttgcctaca gtaatgacag tgcgaactgg actgagtacc aggaccccag gactggcagc    1020
agtaagatct ccctggcaa ctgggacaac cactcccaca gaagaactt gtttgagacg    1080
cccatcctgg ctcgctatgt gcgcatcctg cctgtagcct ggcacaaccg catcgccctg    1140
cgcctggagc tgctgggctg ttag                                            1164
```

<210> SEQ ID NO 4
<211> LENGTH: 2036
<212> TYPE: DNA
<213> ORGANISM: Homo sapiens

<400> SEQUENCE: 4

```
agaactcagc cagtttcttg cttccgtgcc cctggttctc ctccccatcg agcccacccc       60
```

-continued

```
tcctttccca ccttcagtca ccctagtga actgccccag cgatctctgc tgtgcttgac    120
cccgagggtc ttccaccctc gccctgaccc tggacactgc ccagcttggc ccccatcct    180
gctcctggca caatgccctc tagccagcca accttccctc ccccaaccct ggggccgccc    240
cagggttcct gcgcactgcc tgttcctcct gggtgtcact ggcagccctg tccttcctag    300
agggactgga acctaattct cctgaggctg agggagggtg gagggtctca aggcaacgct    360
ggccccacga cggagtgcca ggagcactaa cagtacccc agcttgcttt cctcctccct    420
ccttttatt ttcaagttcc ttttatttc tccttgcgta acaaccttct tcccttctgc    480
accactgccc gtaccttac ccgccccgcc acctccttgc tacccactc ttgaaaccac    540
agctgttggc agggtcccca gctcatgcca gcctcatctc ctttcttgct agccccaaa    600
gggcctccag gcaacatggg gggcccagtc agagagccgg cactctcagt tgccctctgg    660
ttgagttggg gggcagctct gggggccgtg gcttgtgcca tggctctgct gacccaacaa    720
acagagctgc agagcctcag gagagaggtg agccggctgc aggggacagg aggcccctcc    780
cagaatgggg aagggtatcc ctggcagagt ctcccggagc agagttccga tgccctggaa    840
gcctgggaga gtggggagag atcccggaaa aggagagcag tgctcaccca aaaacagaag    900
aatgactccg atgtgacaga ggtgatgtgg caaccagctc ttaggcgtgg agaggcta    960
caggcccaag gatatggtgt ccgaatccag gatgctggag tttatctgct gtatagccag   1020
gtcctgtttc aagacgtgac tttcaccatg ggtcaggtgg tgtctcgaga aggccaagga   1080
aggcaggaga ctctattccg atgtataaga agtatgccct cccacccgga ccgggcctac   1140
aacagctgct atagcgcagg tgtcttccat ttacaccaag gggatattct gagtgtcata   1200
attccccggg caagggcgaa acttaacctc tctccacatg gaaccttcct ggggtttgtg   1260
aaactgtgat tgtgttataa aaagtggctc ccagcttgga agaccagggt gggtacatac   1320
tggagacagc caagagctga gtatataaag gagagggaat gtgcaggaac agaggcgtct   1380
tcctgggttt ggctccccgt tcctcacttt tccctttca ttcccacccc ctagactttg    1440
attttacgga tatcttgctt ctgttcccca tggagctccg aattcttgcg tgtgtgtaga   1500
tgagggcgg gggacgggcg ccaggcattg tccagacctg gtcggggccc actgaagca    1560
tccagaacag caccaccatc tagcggccgc tcgagggaag cacccgccgg ttggccgaag   1620
tccacgaagc cgccctctgc tagggaaaac ccctggttct ccatgccaca cctctctcca   1680
ggtgccctct gcctcttcac cccacaagaa gccttatcct acgtccttct ctccatctat   1740
cggaccccag tttccatcac tatctccaga gatgtagcta ttatgcgccc gtctacaggg   1800
ggtgcccgac gatgacggtg ccttcgcagt caaattactc ttcgggtccc aaggtttggc   1860
tttcacgcgc tccattgccc cggcgtggca ggccattcca agcccttccg ggctggaact   1920
ggtgtcggag gagcctcggg tgtatcgtac gccctggtgt tggtgttgcc tcactcctct   1980
gagctcttct ttctgatcaa gcccctgctta aagttaaata aatagaatg aatgat        2036
```

<210> SEQ ID NO 5
<211> LENGTH: 250
<212> TYPE: PRT
<213> ORGANISM: Homo sapiens

<400> SEQUENCE: 5

```
Met Pro Ala Ser Ser Pro Phe Leu Leu Ala Pro Lys Gly Pro Pro Gly
  1               5                  10                  15

Asn Met Gly Gly Pro Val Arg Glu Pro Ala Leu Ser Val Ala Leu Trp
             20                  25                  30
```

```
Leu Ser Trp Gly Ala Ala Leu Gly Ala Val Ala Cys Ala Met Ala Leu
         35                  40                  45
Leu Thr Gln Gln Thr Glu Leu Gln Ser Leu Arg Arg Glu Val Ser Arg
     50                  55                  60
Leu Gln Gly Thr Gly Gly Pro Ser Gln Asn Gly Glu Gly Tyr Pro Trp
 65                  70                  75                  80
Gln Ser Leu Pro Glu Gln Ser Ser Asp Ala Leu Glu Ala Trp Glu Asn
                 85                  90                  95
Gly Glu Arg Ser Arg Lys Arg Ala Val Leu Thr Gln Lys Gln Lys
                100                 105                 110
Lys Gln His Ser Val Leu His Leu Val Pro Ile Asn Ala Thr Ser Lys
            115                 120                 125
Asp Asp Ser Asp Val Thr Glu Val Met Trp Gln Pro Ala Leu Arg Arg
        130                 135                 140
Gly Arg Gly Leu Gln Ala Gln Gly Tyr Gly Val Arg Ile Gln Asp Ala
145                 150                 155                 160
Gly Val Tyr Leu Leu Tyr Ser Gln Val Leu Phe Gln Asp Val Thr Phe
                165                 170                 175
Thr Met Gly Gln Val Val Ser Arg Glu Gly Gln Gly Arg Gln Glu Thr
            180                 185                 190
Leu Phe Arg Cys Ile Arg Ser Met Pro Ser His Pro Asp Arg Ala Tyr
        195                 200                 205
Asn Ser Cys Tyr Ser Ala Gly Val Phe His Leu His Gln Gly Asp Ile
    210                 215                 220
Leu Ser Val Ile Ile Pro Arg Ala Arg Ala Lys Leu Asn Leu Ser Pro
225                 230                 235                 240
His Gly Thr Phe Leu Gly Phe Val Lys Leu
                245                 250

<210> SEQ ID NO 6
<211> LENGTH: 2241
<212> TYPE: DNA
<213> ORGANISM: Homo sapiens

<400> SEQUENCE: 6
cacatggttt aagaagcatc attatggctt ttgtgtgttt tggtgtgtgt ggctgtgaag      60
cctcaggaat ttagtttaag cttctgaaaa gcccaccaat atgtatttag aattctgttg     120
tcccatatct tagtcatctc aatgtttctc atttctaact ttaaaacatg tcaattaaaa     180
aaattcagta tatcattaat ttcgtctaaa atgtcacata aatctctgac ataatttggt     240
ttttaaacaa taaccaataa tttggtttta tttatgtgat gagaataaca actggtattt     300
attgtctata cttatgcaat tttatagatg gagttttaac attgaatgcg gagaacacta     360
attatgccta tcaagttcca aacttccata atgtgaaat ctgtctacta tcttttccaa     420
aagaatccca gtttcaacgc cacatgaggg atcacgagcg aaatgacaag ccacatcgat     480
gtgaccagtg ccccaaaca tttaatgttg aattcaacct gacacttcat aaatgcaccc     540
acagcgggga agatcctacc tgccctgtgt gtaacaagaa attctccaga gtggctagtc     600
tcaaagcgca tattatgcta catgaaaagg aagagaatct catctgttct gagtgtgggg     660
gtgagtttac tctgcagagt cagctggccg tgcacatgga ggagcaccgc caggagctgg     720
ctggaacccg gcagcatgcc tgcaaggcct gcaagaaaga gttcgagacc tcctcggagc     780
tgaaggaaca catgaagact cattacaaaa ttagggtatc aagtacaagg tcttataacc     840
```

-continued

```
ggaatatcga cagaagtgga ttcacgtatt cgtgtccgca ctgtggaaag acgtttcaaa    900
agccaagcca gttaacgcga cacattagga tacacacagg tgaaaggccg ttcaaatgta    960
gtgaatgtgg aaaggctttt aaccagaagg gggcactgca gacccacatg atcaagcaca   1020
caggtgaaaa accccatgcc tgtgccttct gtcctgccgc cttctctcag aaagggaatc   1080
ttcagtcgca cgtgcagcga gtccactcag aggtcaagaa tggtcctacc tataactgta   1140
cagaatgtag ttgtgtattt aaaagtttag gcagcttaaa cacgcatatc agcaagatgc   1200
atatgggtgg ccacagaat tcaacaagtt ctacagagac tgctcatgtt ttaacggcca   1260
cacttttca gacgttacct cttcaacaga cggaagccca agccacgtcg gcctcaagcc   1320
agccgagctc ccaggcggtg agcgacgtca tccagcagct cctggagctc tcagagccgg   1380
cgccggtgga gtcgggggcag tccccgcagc ctgggcagca gctgagcatc acagtgggca   1440
tcaaccagga cattttacag caagccttag aaaacagtgg gctgtcttca attccagctg   1500
cagcacatcc taatgactcc tgccatgcca agacctctgc accacacgct caaaacccag   1560
atgtttccag cgtttcaaat gagcagacgg accccacaga cgcagagcaa gaaaaagaac   1620
aggaaagccc ggagaaactg gataaaaaaa aaaaaaaag ggccacatgt gctcgagctg   1680
caggtcgcgg ccgctagact agtctagaga aaaaacctcc cacacctccc cctgaacctg   1740
aaacataaaa tgaatgcaat tgttgttgtt aacttgttta ttgcagctta taatggttac   1800
aaataaagca atagcatcac aaatttcaca aataaagcat ttttttcact gcattctagt   1860
tgtggtttgt ccaaactcat caatgtatct tatcatgtct ggatccccgg gtaccgagct   1920
cgaattaatt cctcttccgc ttcctcgctc actgactcgc tgcgctcggt cgttcggctg   1980
cggcgagcgg tatcagctca ctcaaaggcg gtaatacggt tatccacaga atcagggat   2040
aacgcaggaa agaacatgtg agcaaaaggc cagcaaaagg ccaggaaccg taaaaaggcc   2100
gcgttgctgg cgttttttcca taggctccgc ccccctgacg agcatcacaa aaatcgacgc   2160
tcaagtcaga ggtggcgaaac cccgacagga ctataaagat accaggcgtt cccccctgga   2220
agctccctcg tgcgctctcc t                                              2241
```

<210> SEQ ID NO 7
<211> LENGTH: 472
<212> TYPE: PRT
<213> ORGANISM: Homo sapiens

<400> SEQUENCE: 7

```
Met Arg Ile Thr Thr Gly Ile Tyr Cys Leu Tyr Leu Cys Asn Phe Ile
 1               5                   10                  15

Asp Gly Val Leu Thr Leu Asn Ala Glu Asn Thr Asn Tyr Ala Tyr Gln
            20                  25                  30

Val Pro Asn Phe His Lys Cys Glu Ile Cys Leu Leu Ser Phe Pro Lys
        35                  40                  45

Glu Ser Gln Phe Gln Arg His Met Arg Asp His Glu Arg Asn Asp Lys
    50                  55                  60

Pro His Arg Cys Asp Gln Cys Pro Gln Thr Phe Asn Val Glu Phe Asn
65                  70                  75                  80

Leu Thr Leu His Lys Cys Thr His Ser Gly Glu Asp Pro Thr Cys Pro
                85                  90                  95

Val Cys Asn Lys Lys Phe Ser Arg Val Ala Ser Leu Lys Ala His Ile
            100                 105                 110

Met Leu His Glu Lys Glu Glu Asn Leu Ile Cys Ser Glu Cys Gly Gly
        115                 120                 125
```

```
Glu Phe Thr Leu Gln Ser Gln Leu Ala Val His Met Glu Glu His Arg
            130                 135                 140

Gln Glu Leu Ala Gly Thr Arg Gln His Ala Cys Lys Ala Cys Lys Lys
145                 150                 155                 160

Glu Phe Glu Thr Ser Ser Glu Leu Lys Glu His Met Lys Thr His Tyr
                165                 170                 175

Lys Ile Arg Val Ser Ser Thr Arg Ser Tyr Asn Arg Asn Ile Asp Arg
            180                 185                 190

Ser Gly Phe Thr Tyr Ser Cys Pro His Cys Gly Lys Thr Phe Gln Lys
        195                 200                 205

Pro Ser Gln Leu Thr Arg His Ile Arg Ile His Thr Gly Glu Arg Pro
    210                 215                 220

Phe Lys Cys Ser Glu Cys Gly Lys Ala Phe Asn Gln Lys Gly Ala Leu
225                 230                 235                 240

Gln Thr His Met Ile Lys His Thr Gly Glu Lys Pro His Ala Cys Ala
                245                 250                 255

Phe Cys Pro Ala Ala Phe Ser Gln Lys Gly Asn Leu Gln Ser His Val
            260                 265                 270

Gln Arg Val His Ser Glu Val Lys Asn Gly Pro Thr Tyr Asn Cys Thr
        275                 280                 285

Glu Cys Ser Cys Val Phe Lys Ser Leu Gly Ser Leu Asn Thr His Ile
    290                 295                 300

Ser Lys Met His Met Gly Gly Pro Gln Asn Ser Thr Ser Ser Thr Glu
305                 310                 315                 320

Thr Ala His Val Leu Thr Ala Thr Leu Phe Gln Thr Leu Pro Leu Gln
                325                 330                 335

Gln Thr Glu Ala Gln Ala Thr Ser Ala Ser Gln Pro Ser Ser Gln
            340                 345                 350

Ala Val Ser Asp Val Ile Gln Gln Leu Leu Glu Leu Ser Glu Pro Ala
        355                 360                 365

Pro Val Glu Ser Gly Gln Ser Pro Gln Pro Gly Gln Gln Leu Ser Ile
    370                 375                 380

Thr Val Gly Ile Asn Gln Asp Ile Leu Gln Gln Ala Leu Glu Asn Ser
385                 390                 395                 400

Gly Leu Ser Ser Ile Pro Ala Ala Ala His Pro Asn Asp Ser Cys His
                405                 410                 415

Ala Lys Thr Ser Ala Pro His Ala Gln Asn Pro Asp Val Ser Ser Val
            420                 425                 430

Ser Asn Glu Gln Thr Asp Pro Thr Asp Ala Glu Gln Glu Lys Glu Gln
        435                 440                 445

Glu Ser Pro Glu Lys Leu Asp Lys Lys Lys Lys Arg Ala Thr Cys
    450                 455                 460

Ala Arg Ala Ala Gly Arg Gly Arg
465                 470

<210> SEQ ID NO 8
<211> LENGTH: 1419
<212> TYPE: DNA
<213> ORGANISM: Homo sapiens

<400> SEQUENCE: 8
atgagaataa caactggtat ttattgtcta tacttatgca attttataga tggagtttta      60
acattgaatg cggagaacac taattatgcc tatcaagttc caaacttcca taatgtgaa     120
```

```
atctgtctac tatctttcc aaaagaatcc cagtttcaac gccacatgag ggatcacgag      180
cgaaatgaca agccacatcg atgtgaccag tgcccccaaa catttaatgt tgaattcaac     240
ctgacacttc ataaatgcac ccacagcggg gaagatccta cctgccctgt gtgtaacaag     300
aaattctcca gagtggctag tctcaaagcg catattatgc tacatgaaaa ggaagagaat     360
ctcatctgtt ctgagtgtgg gggtgagttt actctgcaga gtcagctggc cgtgcacatg     420
gaggagcacc gccaggagct ggctggaacc cggcagcatg cctgcaaggc ctgcaagaaa     480
gagttcgaga cctcctcgga gctgaaggaa cacatgaaga ctcattacaa aattagggta     540
tcaagtacaa ggtcttataa ccggaatatc gacagaagtg gattcacgta ttcgtgtccg     600
cactgtggaa agacgtttca aaagccaagc cagttaacgc gacacattag gatacacaca     660
ggtgaaaggc cgttcaaatg tagtgaatgt ggaaaggctt ttaaccagaa gggggcactg     720
cagacccaca tgatcaagca cacaggtgaa aaaccccatg cctgtgcctt ctgtcctgcc     780
gccttctctc agaaagggaa tcttcagtcg cacgtgcagc gagtccactc agaggtcaag     840
aatggtccta cctataactg tacagaatgt agttgtgtat ttaaaagttt aggcagctta     900
aacacgcata tcagcaagat gcatatgggt gggccacaga attcaacaag ttctacagag     960
actgctcatg ttttaacggc cacactttt cagacgttac ctcttcaaca gacggaagcc    1020
caagccacgt cggcctcaag ccagccgagc tcccaggcgg tgagcgacgt catccagcag    1080
ctcctggagc tctcagagcc ggcgccggtg gagtcggggc agtccccgca gcctgggcag    1140
cagctgagca tcacagtggg catcaaccag gacattttac agcaagcctt agaaaacagt    1200
gggctgtctt caattccagc tgcagcacat cctaatgact cctgccatgc caagacctct    1260
gcaccacacg ctcaaaaccc agatgtttcc agcgtttcaa atgagcagac ggaccccaca    1320
gacgcagagc aagaaaaaga acaggaaagc ccggagaaac tggataaaaa aaaaaaaaaa    1380
agggccacat gtgctcgagc tgcaggtcgc ggccgctag                           1419
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aacccctgcc acaacggtgg t                                                21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
aaccccugcc acaacggugg u                                                21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 11
aaccactgtg agacgaaatg t                                              21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
aaccacugug agacgaaaug u                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aactgcccca gcgatctctg c                                              21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
aacugcccca gcgaucucug c                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aacctaattc tcctgaggct g                                              21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
aaccuaauuc uccugaggcu g                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
```
aatgcggaga acactaatta t                                                  21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aaugcggaga acacuaauua u                                                  21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aatgacaagc cacatcgatg t                                                  21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aaugacaagc cacaucgaug u                                                  21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aagctggaca ttccctctgc g                                                  21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aagagcccag cttcctgcag c                                                  21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

-continued

```
aactgttgag gagcccatgg a                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aatctgatga tgaagctgca g                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aagagcccag cttcctgcag c                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aagctggaca ttccctctgc g                                              21

<210> SEQ ID NO 27
<211> LENGTH: 152
<212> TYPE: PRT
<213> ORGANISM: Homo sapiens

<400> SEQUENCE: 27

Ala Leu Arg Asn Trp Gln Val Tyr Arg Leu Val Thr Tyr Ile Phe Val
  1               5                  10                  15

Tyr Glu Asn Pro Ile Ser Leu Leu Cys Gly Ala Ile Ile Ile Trp Arg
             20                  25                  30

Phe Ala Gly Asn Phe Glu Arg Thr Val Gly Thr Val Arg His Cys Phe
         35                  40                  45

Phe Thr Val Ile Phe Ala Ile Phe Ser Ala Ile Ile Phe Leu Ser Phe
     50                  55                  60

Glu Ala Val Ser Ser Leu Ser Lys Leu Gly Glu Val Glu Asp Ala Arg
 65                  70                  75                  80

Gly Phe Thr Pro Val Ala Phe Ala Met Leu Gly Val Thr Thr Val Arg
                 85                  90                  95

Ser Arg Met Arg Arg Ala Leu Val Phe Gly Met Val Val Pro Ser Val
            100                 105                 110

Leu Val Pro Trp Leu Leu Leu Gly Ala Ser Trp Leu Ile Pro Gln Thr
        115                 120                 125

Ser Phe Leu Ser Asn Val Cys Gly Leu Ser Ile Gly Leu Ala Tyr Ala
    130                 135                 140

His Leu Leu Leu Phe His Arg Pro
145                 150
```

<210> SEQ ID NO 28
<211> LENGTH: 152
<212> TYPE: PRT
<213> ORGANISM: Saccharomyces cerevisiae

<400> SEQUENCE: 28

```
Leu Leu Gln Lys Arg Gln Leu Tyr Glu Ile Ile Thr Tyr Val Thr Leu
 1               5                   10                  15

His Leu Ser Met Leu His Ile Val Phe Asn Phe Val Ser Leu Leu Pro
            20                  25                  30

Ala Met Ser Gln Phe Glu Lys Lys Gln Gly Thr Leu Ala Cys Ile Leu
        35                  40                  45

Val Thr Val Ile Pro Tyr Thr Leu Phe Pro Gly Ile Met His Leu Ile
    50                  55                  60

Val Tyr His Phe Phe Leu Arg Lys Asp Tyr Val Ser Ile Ala Gly Leu
 65                  70                  75                  80

Ser Gly Trp Ala Phe Ala Phe Ile Ser Ala Ser Cys Val His Ser Pro
                85                  90                  95

Gln Arg Leu Ile Ser Phe Phe Asn Leu Phe Ser Ile Pro Ala Tyr Cys
            100                 105                 110

Phe Pro Ile Ile Tyr Leu Ile Met Thr Thr Ile Leu Val Pro Lys Ala
        115                 120                 125

Ser Phe Ile Gly His Ala Ser Gly Ala Val Met Gly Tyr Cys Thr Pro
130                 135                 140

Phe Met Leu Gly Ser Ile Pro Leu
145                 150
```

<210> SEQ ID NO 29
<211> LENGTH: 145
<212> TYPE: PRT
<213> ORGANISM: Schizosaccharomyces pombe

<400> SEQUENCE: 29

```
Pro Arg Ser Leu Glu Gly Leu Arg Gly Ile Val Phe Ala Pro Phe Leu
 1               5                   10                  15

His Ala Asp Phe Gly His Leu Ile Ala Asn Ser Val Pro Phe Val Val
            20                  25                  30

Leu Ala Trp Leu Val Met Leu Gln Glu Val Ser Asp Phe Trp Ile Val
        35                  40                  45

Thr Ile Ile Thr Met Val Val Gly Gly Leu Gly Val Trp Leu Ile Ala
    50                  55                  60

Pro Pro Asn Thr Val Thr Val Gly Ala Ser Ile Leu Ile Phe Gly Tyr
 65                  70                  75                  80

Leu Gly Phe Leu Leu Phe Arg Gly Trp Phe Gln Lys Asn Leu Ala Ser
                85                  90                  95

Ile Val Leu Ser Ile Val Val Leu Val Leu Tyr Gly Ser Ala Leu Trp
            100                 105                 110

Gly Leu Leu Pro Gly Arg Ala Gly Val Ser Trp Gln Gly His Leu Phe
        115                 120                 125

Gly Phe Ile Gly Gly Ala Ile Ala Ala Trp Leu Ile Ala Arg Glu Lys
130                 135                 140

His
145
```

<210> SEQ ID NO 30
<211> LENGTH: 145

```
<212> TYPE: PRT
<213> ORGANISM: Saccharomyces cerevisiae

<400> SEQUENCE: 30

Ser Lys Ser Asn Ala Arg Pro Val Val Ala Ile Gly Asp Ser Asp Ile
1               5                   10                  15

Tyr Ser Tyr Arg Leu Trp Ser Phe Phe Cys Gln Trp Ile Asn Thr Ile
            20                  25                  30

Phe Cys Trp Ser Asn Arg Arg Pro Leu Gly Leu Thr Pro Phe Leu
        35                  40                  45

Leu Leu Tyr Val Leu Ser Gly Val Met Gly Asn Ala Phe Thr Phe Trp
    50                  55                  60

Leu Thr Pro Glu Thr Val Ala Ala Gly Ala Ser Thr Ser Leu Phe Gly
65              70                  75                  80

Leu Phe Ala Ala Ile Val Val Leu Ser Phe Leu Gly Lys Asn Gln Ala
                85                  90                  95

Leu Lys Asp Leu Gly Lys Ser Tyr Gln Thr Leu Ile Val Val Asn Leu
            100                 105                 110

Leu Met Asn Leu Phe Met Pro Asn Val Ser Met Ala Gly His Ile Gly
        115                 120                 125

Gly Val Val Gly Gly Ala Leu Leu Ser Ile Val Phe Pro Thr Lys Met
    130                 135                 140

Arg
145

<210> SEQ ID NO 31
<211> LENGTH: 156
<212> TYPE: PRT
<213> ORGANISM: Homo sapiens

<400> SEQUENCE: 31

Pro Glu Lys Arg Glu Ala Trp Arg Phe Ile Ser Tyr Met Leu Val
1               5                   10                  15

His Ala Gly Val Gln His Ile Leu Gly Asn Leu Cys Met Gln Leu Val
            20                  25                  30

Leu Gly Ile Pro Leu Glu Met Val His Lys Gly Leu Arg Val Gly Leu
        35                  40                  45

Val Tyr Leu Ala Gly Val Ile Ala Gly Ser Leu Ala Ser Ser Ile Phe
    50                  55                  60

Asp Pro Leu Arg Tyr Leu Val Gly Ala Ser Gly Val Tyr Ala Leu
65              70                  75                  80

Met Gly Gly Tyr Phe Met Asn Val Leu Val Asn Phe Gln Glu Met Ile
                85                  90                  95

Pro Ala Phe Gly Ile Phe Arg Leu Leu Ile Ile Leu Ile Ile Val
            100                 105                 110

Leu Asp Met Gly Phe Ala Leu Tyr Arg Arg Phe Phe Val Pro Glu Asp
        115                 120                 125

Gly Ser Pro Val Ser Phe Ala Ala His Ile Ala Gly Gly Phe Ala Gly
    130                 135                 140

Met Ser Ile Gly Tyr Thr Val Phe Ser Cys Phe Asp
145                 150                 155

<210> SEQ ID NO 32
<211> LENGTH: 145
<212> TYPE: PRT
<213> ORGANISM: Escherichia coli
```

<400> SEQUENCE: 32

```
Pro Thr Leu Lys Phe Glu Phe Trp Arg Tyr Phe Thr His Ala Leu Met
 1               5                  10                  15

His Phe Ser Leu Met His Ile Leu Phe Asn Leu Leu Trp Trp Trp Tyr
             20                  25                  30

Leu Gly Gly Ala Val Glu Lys Arg Leu Gly Ser Gly Lys Leu Ile Val
         35                  40                  45

Ile Arg Ser Ile Ser Ala Leu Leu Ser Gly Tyr Val Gln Gln Lys Phe
     50                  55                  60

Ser Gly Pro Trp Phe Gly Gly Leu Ser Gly Val Val Tyr Ala Leu Met
 65                  70                  75                  80

Gly Tyr Val Trp Leu Arg Gly Glu Arg Asp Pro Gln Ser Gly Ile Tyr
                 85                  90                  95

Leu Gln Arg Gly Leu Ile Ile Phe Ala Leu Ile Trp Ile Val Ala Gly
                100                 105                 110

Trp Phe Asp Leu Phe Gly Met Ser Met Ala Asn Gly Ala His Ile Ala
            115                 120                 125

Gly Leu Ala Val Gly Leu Ala Met Ala Phe Val Asp Ser Leu Asn Ala
    130                 135                 140

Arg
145
```

<210> SEQ ID NO 33
<211> LENGTH: 157
<212> TYPE: PRT
<213> ORGANISM: Homo sapiens

<400> SEQUENCE: 33

```
Ser Asn Pro Ala Ser Lys Val Leu Cys Ser Pro Met Leu Leu Ser Thr
 1               5                  10                  15

Phe Ser His Phe Ser Leu Phe His Met Ala Ala Asn Met Tyr Val Leu
             20                  25                  30

Trp Ser Phe Ser Ser Ser Ile Val Asn Ile Leu Gly Gln Glu Gln Phe
         35                  40                  45

Met Ala Val Tyr Leu Ser Ala Gly Val Ile Ser Asn Phe Val Ser Tyr
     50                  55                  60

Leu Gly Lys Val Ala Thr Gly Arg Tyr Gly Pro Ser Leu Gly Ala Ser
 65                  70                  75                  80

Gly Ala Ile Met Thr Val Leu Ala Ala Val Cys Thr Lys Ile Pro Glu
                 85                  90                  95

Gly Arg Leu Ala Ile Ile Phe Leu Pro Met Phe Thr Phe Thr Ala Gly
                100                 105                 110

Asn Ala Leu Lys Ala Ile Ile Ala Met Asp Thr Ala Gly Met Ile Leu
            115                 120                 125

Gly Trp Lys Phe Phe Asp His Ala Ala His Leu Gly Gly Ala Leu Phe
    130                 135                 140

Gly Ile Trp Tyr Val Thr Tyr Gly His Glu Leu Ile Trp
145                 150                 155
```

<210> SEQ ID NO 34
<211> LENGTH: 142
<212> TYPE: PRT
<213> ORGANISM: Sulfolobus solfataricus

<400> SEQUENCE: 34

```
Tyr Leu Val Ile Lys Gly Tyr Tyr Ser Glu Leu Phe Thr Ser Ile Phe
```

```
                1               5              10              15
Ile Thr Asn Ser Phe Val Asp Phe Ile Phe Asn Phe Ile Ser Leu Tyr
                        20                  25                  30

Val Ile Tyr Leu Ile Phe Gly Ser Arg Ala Gly Lys His Glu Tyr Gly
                35                  40                  45

Ile Phe Ile Leu Ala Gly Ile Leu Gly Asn Leu Leu Thr Val Ile Phe
                    50                  55                  60

Tyr Ser Pro Phe Thr Leu Ser Ser Gly Ala Ser Gly Gly Ile Phe Gly
 65                      70                  75                  80

Leu Leu Ser Tyr Tyr Thr Phe Tyr Asp Phe Lys Lys Asp Asn Leu
                    85                  90                  95

Gly Val Tyr Gly Leu Val Phe Leu Val Ser Val Phe Gly Val Ser Asp
                100                 105                 110

Leu Ile Phe Pro Asn Val Asn Val Val Ala His Ile Gly Gly Ile Leu
                115                 120                 125

Gly Gly Ile Met Tyr Ala Val Val Tyr Tyr Leu Ile Arg Ser
                130                 135                 140
```

<210> SEQ ID NO 35
<211> LENGTH: 156
<212> TYPE: PRT
<213> ORGANISM: Arabidopsis thaliana

<400> SEQUENCE: 35

```
Ile Phe Lys His Lys Asp Leu Lys Arg Leu Phe Leu Ser Ala Phe Tyr
 1               5                  10                  15

His Val Asn Glu Pro His Leu Val Tyr Asn Met Met Ser Leu Leu Trp
                20                  25                  30

Lys Gly Ile Lys Leu Glu Thr Ser Met Gly Ser Ser Glu Phe Ala Ser
            35                  40                  45

Met Val Phe Thr Leu Ile Gly Met Ser Gln Val Thr Leu Leu Leu
         50                  55                  60

Ala Lys Ser Leu Leu Leu Leu Phe Asp Tyr Asp Arg Ala Tyr Tyr Asn
 65                  70                  75                  80

Glu Tyr Ala Val Gly Phe Ser Gly Val Leu Phe Ala Met Lys Val Val
                85                  90                  95

Leu Asn Ser Gln Ala Glu Asp Tyr Ser Ser Val Tyr Gly Ile Leu Val
                100                 105                 110

Pro Thr Lys Tyr Ala Ala Trp Ala Glu Leu Ile Leu Val Gln Met Phe
                115                 120                 125

Val Pro Asn Ala Ser Phe Leu Gly His Leu Gly Gly Ile Leu Ala Gly
                130                 135                 140

Ile Ile Tyr Leu Lys Leu Lys Gly Ser Tyr Ser Gly
145                 150                 155
```

<210> SEQ ID NO 36
<211> LENGTH: 10
<212> TYPE: DNA
<213> ORGANISM: Homo sapiens

<400> SEQUENCE: 36
tggccaataa                                                      10

<210> SEQ ID NO 37
<211> LENGTH: 854
<212> TYPE: PRT
<213> ORGANISM: Homo sapiens

<400> SEQUENCE: 37

```
Met Ser Glu Ala Arg Arg Asp Ser Thr Ser Ser Leu Gln Arg Lys Lys
1               5                   10                  15

Pro Pro Trp Leu Lys Leu Asp Ile Pro Ser Ala Val Pro Leu Thr Ala
            20                  25                  30

Glu Glu Pro Ser Phe Leu Gln Pro Leu Arg Arg Gln Ala Phe Leu Arg
        35                  40                  45

Ser Val Ser Met Pro Ala Glu Thr Ala His Ile Ser Ser Pro His His
    50                  55                  60

Glu Leu Arg Arg Pro Val Leu Gln Arg Gln Thr Ser Ile Thr Gln Thr
65                  70                  75                  80

Ile Arg Arg Gly Thr Ala Asp Trp Phe Gly Val Ser Lys Asp Ser Asp
                85                  90                  95

Ser Thr Gln Lys Trp Gln Arg Lys Ser Ile Arg His Cys Ser Gln Arg
            100                 105                 110

Tyr Gly Lys Leu Lys Pro Gln Val Leu Arg Glu Leu Asp Leu Pro Ser
        115                 120                 125

Gln Asp Asn Val Ser Leu Thr Ser Thr Glu Thr Pro Pro Leu Tyr
    130                 135                 140

Val Gly Pro Cys Gln Leu Gly Met Gln Lys Ile Ile Asp Pro Leu Ala
145                 150                 155                 160

Arg Gly Arg Ala Phe Arg Val Ala Asp Asp Thr Ala Glu Gly Leu Ser
                165                 170                 175

Ala Pro His Thr Pro Val Thr Pro Gly Ala Ala Ser Leu Cys Ser Phe
            180                 185                 190

Ser Ser Ser Arg Ser Gly Phe His Arg Leu Pro Arg Arg Arg Lys Arg
            195                 200                 205

Glu Ser Val Ala Lys Met Ser Phe Arg Ala Ala Ala Leu Met Lys
    210                 215                 220

Gly Arg Ser Val Arg Asp Gly Thr Phe Arg Arg Ala Arg Ser Phe
225                 230                 235                 240

Thr Pro Ala Ser Phe Leu Glu Glu Asp Thr Thr Asp Phe Pro Asp Glu
                245                 250                 255

Leu Asp Thr Ser Phe Phe Ala Arg Glu Gly Ile Leu His Glu Glu Leu
            260                 265                 270

Ser Thr Tyr Pro Asp Glu Val Phe Glu Ser Pro Ser Glu Ala Ala Leu
        275                 280                 285

Lys Asp Trp Glu Lys Ala Pro Glu Gln Ala Asp Leu Thr Gly Gly Ala
    290                 295                 300

Leu Asp Arg Ser Glu Leu Glu Arg Ser His Leu Met Leu Pro Leu Glu
305                 310                 315                 320

Arg Gly Trp Arg Lys Gln Lys Glu Gly Ala Ala Pro Gln Pro Lys
                325                 330                 335

Val Arg Leu Arg Gln Glu Val Val Ser Thr Ala Gly Pro Arg Arg Gly
            340                 345                 350

Gln Arg Ile Ala Val Pro Val Lys Leu Phe Ala Arg Glu Lys Arg
        355                 360                 365

Pro Tyr Gly Leu Gly Met Val Gly Arg Leu Thr Asn Arg Thr Tyr Arg
        370                 375                 380

Lys Arg Ile Asp Ser Phe Val Lys Arg Gln Ile Glu Asp Met Asp Asp
385                 390                 395                 400

His Arg Pro Phe Phe Thr Tyr Trp Leu Thr Phe Val His Ser Leu Val
```

-continued

```
                405                 410                 415
Thr Ile Leu Ala Val Cys Ile Tyr Gly Ile Ala Pro Val Gly Phe Ser
            420                 425                 430
Gln His Glu Thr Val Asp Ser Val Leu Arg Asn Arg Gly Val Tyr Glu
        435                 440                 445
Asn Val Lys Tyr Val Gln Gln Glu Asn Phe Trp Ile Gly Pro Ser Ser
    450                 455                 460
Glu Ala Leu Ile His Leu Gly Ala Lys Phe Ser Pro Cys Met Arg Gln
465                 470                 475                 480
Asp Pro Gln Val His Ser Phe Ile Arg Ser Ala Arg Glu Arg Glu Lys
                485                 490                 495
His Ser Ala Cys Cys Val Arg Asn Asp Arg Ser Gly Cys Val Gln Thr
            500                 505                 510
Ser Glu Glu Glu Cys Ser Ser Thr Leu Ala Val Trp Val Lys Trp Pro
        515                 520                 525
Ile His Pro Ser Ala Pro Glu Leu Ala Gly His Lys Arg Gln Phe Gly
    530                 535                 540
Ser Val Cys His Gln Asp Pro Arg Val Cys Asp Glu Pro Ser Ser Glu
545                 550                 555                 560
Asp Pro His Glu Trp Pro Glu Asp Ile Thr Lys Trp Pro Ile Cys Thr
                565                 570                 575
Lys Asn Ser Ala Gly Asn His Thr Asn His Pro His Met Asp Cys Val
            580                 585                 590
Ile Thr Gly Arg Pro Cys Cys Ile Gly Thr Lys Gly Arg Cys Glu Ile
        595                 600                 605
Thr Ser Arg Glu Tyr Cys Asp Phe Met Arg Gly Tyr Phe His Glu Glu
    610                 615                 620
Ala Thr Leu Cys Ser Gln Val His Cys Met Asp Asp Val Cys Gly Leu
625                 630                 635                 640
Leu Pro Phe Leu Asn Pro Glu Val Pro Asp Gln Phe Tyr Arg Leu Trp
                645                 650                 655
Leu Ser Leu Phe Leu His Ala Gly Ile Leu His Cys Leu Val Ser Ile
            660                 665                 670
Cys Phe Gln Met Thr Val Leu Arg Asp Leu Glu Lys Leu Ala Gly Trp
        675                 680                 685
His Arg Ile Ala Ile Ile Tyr Leu Leu Ser Gly Val Thr Gly Asn Leu
    690                 695                 700
Ala Ser Ala Ile Phe Leu Pro Tyr Arg Ala Glu Val Gly Pro Ala Gly
705                 710                 715                 720
Ser Gln Phe Gly Ile Leu Ala Cys Leu Phe Val Glu Leu Phe Gln Ser
                725                 730                 735
Trp Gln Ile Leu Ala Arg Pro Trp Arg Ala Phe Phe Lys Leu Leu Ala
            740                 745                 750
Val Val Leu Phe Leu Phe Thr Phe Gly Leu Leu Pro Trp Ile Asp Asn
        755                 760                 765
Phe Ala His Ile Ser Gly Phe Ile Ser Gly Leu Phe Leu Ser Phe Ala
    770                 775                 780
Phe Leu Pro Tyr Ile Ser Phe Gly Lys Phe Asp Leu Tyr Arg Lys Arg
785                 790                 795                 800
Cys Gln Ile Ile Ile Phe Gln Val Val Phe Leu Gly Leu Leu Ala Gly
                805                 810                 815
Leu Val Val Leu Phe Tyr Val Tyr Pro Val Arg Cys Glu Trp Cys Glu
            820                 825                 830
```

```
Phe Leu Thr Cys Ile Pro Phe Thr Asp Lys Phe Cys Glu Lys Tyr Glu
        835                 840                 845

Leu Asp Ala Gln Leu His
    850

<210> SEQ ID NO 38
<211> LENGTH: 292
<212> TYPE: PRT
<213> ORGANISM: Homo sapiens

<400> SEQUENCE: 38

Met Asn Leu Asn Met Gly Arg Glu Met Lys Glu Leu Glu Glu Glu
 1               5                  10                  15

Glu Lys Met Arg Glu Asp Gly Gly Lys Asp Arg Ala Lys Ser Lys
            20                  25                  30

Lys Val His Arg Ile Val Ser Lys Trp Met Leu Pro Glu Lys Ser Arg
            35                  40                  45

Gly Thr Tyr Leu Glu Arg Ala Asn Cys Phe Pro Pro Val Phe Ile
        50                  55                  60

Ile Ser Ile Ser Leu Ala Glu Leu Ala Val Phe Ile Tyr Tyr Ala Val
 65                  70                  75                  80

Trp Lys Pro Gln Lys Gln Trp Ile Thr Leu Asp Thr Gly Ile Leu Glu
                85                  90                  95

Ser Pro Phe Ile Tyr Ser Pro Glu Lys Arg Glu Glu Ala Trp Arg Phe
            100                 105                 110

Ile Ser Tyr Met Leu Val His Ala Gly Val Gln His Ile Leu Gly Asn
        115                 120                 125

Leu Cys Met Gln Leu Val Leu Gly Ile Pro Leu Glu Met Val His Lys
    130                 135                 140

Gly Leu Arg Val Gly Leu Val Tyr Leu Ala Gly Val Ile Ala Gly Ser
145                 150                 155                 160

Leu Ala Ser Ser Ile Phe Asp Pro Leu Arg Tyr Leu Val Gly Ala Ser
                165                 170                 175

Gly Gly Val Tyr Ala Leu Met Gly Gly Tyr Phe Met Asn Val Leu Val
            180                 185                 190

Asn Phe Gln Glu Met Ile Pro Ala Phe Gly Ile Phe Arg Leu Leu Ile
        195                 200                 205

Ile Ile Leu Ile Ile Val Leu Asp Met Gly Phe Ala Leu Tyr Arg Arg
    210                 215                 220

Phe Phe Val Pro Glu Asp Gly Ser Pro Val Ser Phe Ala Ala His Ile
225                 230                 235                 240

Ala Gly Gly Phe Ala Gly Met Ser Ile Gly Tyr Thr Val Phe Ser Cys
                245                 250                 255

Phe Asp Lys Ala Leu Leu Lys Asp Pro Arg Phe Trp Ile Ala Ile Ala
            260                 265                 270

Ala Tyr Leu Ala Cys Val Leu Phe Ala Val Phe Phe Asn Ile Phe Leu
        275                 280                 285

Ser Pro Ala Asn
    290

<210> SEQ ID NO 39
<211> LENGTH: 619
<212> TYPE: PRT
<213> ORGANISM: Homo sapiens

<400> SEQUENCE: 39
```

```
Met Ser Val Ala His Met Ser Leu Gln Ala Ala Ala Leu Leu Lys
  1               5                  10                  15

Gly Arg Ser Val Leu Asp Ala Thr Gly Gln Arg Cys Arg Val Val Lys
                 20                  25                  30

Arg Ser Phe Ala Phe Pro Ser Phe Leu Glu Glu Asp Val Val Asp Gly
             35                  40                  45

Ala Asp Thr Phe Asp Ser Ser Phe Phe Ser Lys Glu Glu Met Ser Ser
         50                  55                  60

Met Pro Asp Asp Val Phe Glu Ser Pro Pro Leu Ser Ala Ser Tyr Phe
 65                  70                  75                  80

Arg Gly Ile Pro His Ser Ala Ser Pro Val Ser Pro Asp Gly Val Gln
                 85                  90                  95

Ile Pro Leu Lys Glu Tyr Gly Arg Ala Pro Val Pro Gly Pro Arg Arg
             100                 105                 110

Gly Lys Arg Ile Ala Ser Lys Val Lys His Phe Ala Phe Asp Arg Lys
             115                 120                 125

Lys Arg His Tyr Gly Leu Gly Val Val Gly Asn Trp Leu Asn Arg Ser
 130                 135                 140

Tyr Arg Arg Ser Ile Ser Ser Thr Val Gln Arg Gln Leu Glu Ser Phe
145                 150                 155                 160

Asp Ser His Arg Pro Tyr Phe Thr Tyr Trp Leu Thr Phe Val His Val
                 165                 170                 175

Ile Ile Thr Leu Leu Val Ile Cys Thr Tyr Gly Ile Ala Pro Val Gly
             180                 185                 190

Phe Ala Gln His Val Thr Thr Gln Leu Val Leu Arg Asn Lys Gly Val
             195                 200                 205

Tyr Glu Ser Val Lys Tyr Ile Gln Gln Glu Asn Phe Trp Val Gly Pro
210                 215                 220

Ser Ser Ile Asp Leu Ile His Leu Gly Ala Lys Phe Ser Pro Cys Ile
225                 230                 235                 240

Arg Lys Asp Gly Gln Ile Glu Gln Leu Val Leu Arg Glu Arg Asp Leu
             245                 250                 255

Glu Arg Asp Ser Gly Cys Cys Val Gln Asn Asp His Ser Gly Cys Ile
             260                 265                 270

Gln Thr Gln Arg Lys Asp Cys Ser Glu Thr Leu Ala Thr Phe Val Lys
             275                 280                 285

Trp Gln Asp Asp Thr Gly Pro Pro Met Asp Lys Ser Asp Leu Gly Gln
290                 295                 300

Lys Arg Thr Ser Gly Ala Val Cys His Gln Asp Pro Arg Thr Cys Glu
305                 310                 315                 320

Glu Pro Ala Ser Ser Gly Ala His Ile Trp Pro Asp Asp Ile Thr Lys
                 325                 330                 335

Trp Pro Ile Cys Thr Glu Gln Ala Arg Ser Asn His Thr Gly Phe Leu
             340                 345                 350

His Met Asp Cys Glu Ile Lys Gly Arg Pro Cys Cys Ile Gly Thr Lys
             355                 360                 365

Gly Ser Cys Glu Ile Thr Thr Arg Glu Tyr Cys Glu Phe Met His Gly
             370                 375                 380

Tyr Phe His Glu Glu Ala Thr Leu Cys Ser Gln Val His Cys Leu Asp
385                 390                 395                 400

Lys Val Cys Gly Leu Leu Pro Phe Leu Asn Pro Glu Val Pro Asp Gln
                 405                 410                 415
```

```
Phe Tyr Arg Leu Trp Leu Ser Leu Phe Leu His Ala Gly Val Val His
            420             425             430

Cys Leu Val Ser Val Val Phe Gln Met Thr Ile Leu Arg Asp Leu Glu
            435             440             445

Lys Leu Ala Gly Trp His Arg Ile Ala Ile Phe Ile Leu Ser Gly
450             455             460

Ile Thr Gly Asn Leu Ala Ser Ala Ile Phe Leu Pro Tyr Arg Ala Glu
465             470             475             480

Val Gly Pro Ala Gly Ser Gln Phe Gly Leu Leu Ala Cys Leu Phe Val
            485             490             495

Glu Leu Phe Gln Ser Trp Pro Leu Leu Glu Arg Pro Trp Lys Ala Phe
            500             505             510

Leu Asn Leu Ser Ala Ile Val Leu Phe Leu Phe Ile Cys Gly Leu Leu
            515             520             525

Pro Trp Ile Asp Asn Ile Ala His Ile Phe Gly Phe Leu Ser Gly Leu
            530             535             540

Leu Leu Ala Phe Ala Phe Leu Pro Tyr Ile Thr Phe Gly Thr Ser Asp
545             550             555             560

Lys Tyr Arg Lys Arg Ala Leu Ile Leu Val Ser Leu Leu Ala Phe Ala
            565             570             575

Gly Leu Phe Ala Ala Leu Val Leu Trp Leu Tyr Ile Tyr Pro Ile Asn
            580             585             590

Trp Pro Trp Ile Glu His Leu Thr Cys Phe Pro Phe Thr Ser Arg Phe
            595             600             605

Cys Glu Lys Tyr Glu Leu Asp Gln Val Leu His
610             615

<210> SEQ ID NO 40
<211> LENGTH: 404
<212> TYPE: PRT
<213> ORGANISM: Homo sapiens

<400> SEQUENCE: 40

Met Gly Glu His Pro Ser Pro Gly Pro Ala Val Ala Ala Cys Ala Glu
1               5               10              15

Ala Glu Arg Ile Glu Glu Leu Glu Pro Glu Ala Glu Glu Arg Leu Pro
            20              25              30

Ala Ala Pro Glu Asp His Trp Lys Val Leu Phe Asp Gln Phe Asp Pro
        35              40              45

Gly Asn Thr Gly Tyr Ile Ser Thr Gly Lys Phe Arg Ser Leu Leu Glu
    50              55              60

Ser His Ser Ser Lys Leu Asp Pro His Lys Arg Glu Val Leu Leu Ala
65              70              75              80

Leu Ala Asp Ser His Ala Asp Gly Gln Ile Gly Tyr Gln Asp Phe Val
            85              90              95

Ser Leu Met Ser Asn Lys Arg Ser Asn Ser Phe Arg Gln Ala Ile Leu
            100             105             110

Gln Gly Asn Arg Arg Leu Ser Ser Lys Ala Leu Leu Glu Glu Lys Gly
            115             120             125

Leu Ser Leu Ser Gln Arg Leu Ile Arg His Val Ala Tyr Glu Thr Leu
            130             135             140

Pro Arg Glu Ile Asp Arg Lys Trp Tyr Tyr Asp Ser Tyr Thr Cys Cys
145             150             155             160

Pro Pro Pro Trp Phe Met Ile Thr Val Thr Leu Leu Glu Val Ala Phe
            165             170             175
```

```
Phe Leu Tyr Asn Gly Val Ser Leu Gly Gln Phe Val Leu Gln Val Thr
                180                 185                 190

His Pro Arg Tyr Leu Lys Asn Ser Leu Val Tyr His Pro Gln Leu Arg
            195                 200                 205

Ala Gln Val Trp Arg Tyr Leu Thr Tyr Ile Phe Met His Ala Gly Ile
        210                 215                 220

Glu His Leu Gly Leu Asn Val Leu Gln Leu Leu Val Gly Val Pro
225                 230                 235                 240

Leu Glu Met Val His Gly Ala Thr Arg Ile Gly Leu Val Tyr Val Ala
                245                 250                 255

Gly Val Val Ala Gly Ser Leu Ala Val Ser Val Ala Asp Met Thr Ala
                260                 265                 270

Pro Val Gly Ser Ser Gly Val Tyr Ala Leu Val Ser Ala His
            275                 280                 285

Leu Ala Asn Ile Val Met Asn Trp Ser Gly Met Lys Cys Gln Phe Lys
            290                 295                 300

Leu Leu Arg Met Ala Val Ala Leu Ile Cys Met Ser Met Glu Phe Gly
305                 310                 315                 320

Arg Ala Val Trp Leu Arg Phe His Pro Ser Ala Tyr Pro Cys Pro
                325                 330                 335

His Pro Ser Phe Val Ala His Leu Gly Gly Val Ala Val Gly Ile Thr
            340                 345                 350

Leu Gly Val Val Val Leu Arg Asn Tyr Glu Gln Arg Leu Gln Asp Gln
                355                 360                 365

Ser Leu Trp Trp Ile Phe Val Ala Met Tyr Thr Val Phe Val Leu Phe
            370                 375                 380

Ala Val Phe Trp Asn Ile Phe Ala Tyr Thr Leu Leu Asp Leu Lys Leu
385                 390                 395                 400

Pro Pro Pro Pro

<210> SEQ ID NO 41
<211> LENGTH: 379
<212> TYPE: PRT
<213> ORGANISM: Homo sapiens

<400> SEQUENCE: 41

Met Ala Trp Arg Gly Trp Ala Gln Arg Gly Trp Gly Cys Gly Gln Ala
  1               5                  10                  15

Trp Gly Ala Ser Val Gly Gly Arg Ser Cys Glu Glu Leu Thr Ala Val
             20                  25                  30

Leu Thr Pro Pro Gln Leu Leu Gly Arg Arg Phe Asn Phe Phe Ile Gln
         35                  40                  45

Gln Lys Cys Gly Phe Arg Lys Ala Pro Arg Lys Val Glu Pro Arg Arg
    50                  55                  60

Ser Asp Pro Gly Thr Ser Gly Glu Ala Tyr Lys Arg Ser Ala Leu Ile
 65                  70                  75                  80

Pro Pro Val Glu Glu Thr Val Phe Tyr Pro Ser Pro Tyr Pro Ile Arg
                 85                  90                  95

Ser Leu Ile Lys Pro Leu Phe Phe Thr Val Gly Phe Thr Gly Cys Ala
            100                 105                 110

Phe Gly Ser Ala Ala Ile Trp Gln Tyr Glu Ser Leu Lys Ser Arg Val
        115                 120                 125

Gln Ser Tyr Phe Asp Gly Ile Lys Ala Asp Trp Leu Asp Ser Ile Arg
    130                 135                 140
```

```
Pro Gln Lys Glu Gly Asp Phe Arg Lys Glu Ile Asn Lys Trp Trp Asn
145                 150                 155                 160

Asn Leu Ser Asp Gly Gln Arg Thr Val Thr Gly Ile Ile Ala Ala Asn
                165                 170                 175

Val Leu Val Phe Cys Leu Trp Arg Val Pro Ser Leu Gln Arg Thr Met
            180                 185                 190

Ile Arg Tyr Phe Thr Ser Asn Pro Ala Ser Lys Val Leu Cys Ser Pro
        195                 200                 205

Met Leu Leu Ser Thr Phe Ser His Phe Ser Leu Phe His Met Ala Ala
    210                 215                 220

Asn Met Tyr Val Leu Trp Ser Phe Ser Ser Ile Val Asn Ile Leu
225                 230                 235                 240

Gly Gln Glu Gln Phe Met Ala Val Tyr Leu Ser Ala Gly Val Ile Ser
                245                 250                 255

Asn Phe Val Ser Tyr Leu Gly Lys Val Ala Thr Gly Arg Tyr Gly Pro
            260                 265                 270

Ser Leu Gly Ala Ser Gly Ala Ile Met Thr Val Leu Ala Ala Val Cys
        275                 280                 285

Thr Lys Ile Pro Glu Gly Arg Leu Ala Ile Ile Phe Leu Pro Met Phe
290                 295                 300

Thr Phe Thr Ala Gly Asn Ala Leu Lys Ala Ile Ala Met Asp Thr
305                 310                 315                 320

Ala Gly Met Ile Leu Gly Trp Lys Phe Phe Asp His Ala Ala His Leu
                325                 330                 335

Gly Gly Ala Leu Phe Gly Ile Trp Tyr Val Thr Tyr Gly His Glu Leu
            340                 345                 350

Ile Trp Lys Asn Arg Glu Pro Leu Val Lys Ile Trp His Glu Ile Arg
        355                 360                 365

Thr Asn Gly Pro Lys Lys Gly Gly Ser Lys
    370                 375

<210> SEQ ID NO 42
<211> LENGTH: 315
<212> TYPE: PRT
<213> ORGANISM: Homo sapiens

<400> SEQUENCE: 42

Met Gln Arg Arg Ser Arg Gly Ile Asn Thr Gly Leu Ile Leu Leu Leu
1               5                   10                  15

Ser Gln Ile Phe His Val Gly Ile Asn Asn Ile Pro Pro Val Thr Leu
            20                  25                  30

Ala Thr Leu Ala Leu Asn Ile Trp Phe Phe Leu Asn Pro Gln Lys Pro
        35                  40                  45

Leu Tyr Ser Ser Cys Leu Ser Val Glu Lys Cys Tyr Gln Gln Lys Asp
    50                  55                  60

Trp Gln Arg Leu Leu Leu Ser Pro Leu His Ala Asp Asp Trp His
65                  70                  75                  80

Leu Tyr Phe Asn Met Ala Ser Met Leu Trp Lys Gly Ile Asn Leu Glu
                85                  90                  95

Arg Arg Leu Gly Ser Arg Trp Phe Ala Tyr Val Ile Thr Ala Phe Ser
            100                 105                 110

Val Leu Thr Gly Val Val Tyr Leu Leu Leu Gln Phe Ala Val Ala Glu
        115                 120                 125

Phe Met Asp Glu Pro Asp Phe Lys Arg Ser Cys Ala Val Gly Phe Ser
```

```
                130                 135                 140
Gly Val Leu Phe Ala Leu Lys Val Leu Asn Asn His Tyr Cys Pro Gly
145                 150                 155                 160

Gly Phe Val Asn Ile Leu Gly Phe Pro Val Pro Asn Arg Phe Ala Cys
                165                 170                 175

Trp Val Glu Leu Val Ala Ile His Leu Phe Ser Pro Gly Thr Ser Phe
                180                 185                 190

Ala Gly His Leu Ala Gly Ile Leu Val Gly Leu Met Tyr Thr Gln Gly
                195                 200                 205

Pro Leu Lys Lys Ile Met Glu Ala Cys Ala Gly Gly Phe Ser Ser Ser
210                 215                 220

Val Gly Tyr Pro Gly Arg Gln Tyr Tyr Phe Asn Ser Ser Gly Ser Ser
225                 230                 235                 240

Gly Tyr Gln Asp Tyr Tyr Pro His Gly Arg Pro Asp His Tyr Glu Glu
                245                 250                 255

Ala Pro Arg Asn Tyr Asp Thr Tyr Thr Ala Gly Leu Ser Glu Glu Glu
                260                 265                 270

Gln Leu Glu Arg Ala Leu Gln Ala Ser Leu Trp Asp Arg Gly Asn Thr
                275                 280                 285

Arg Asn Ser Pro Pro Tyr Gly Phe His Leu Ser Pro Glu Glu Met
290                 295                 300

Arg Arg Gln Arg Leu His Arg Phe Asp Ser Gln
305                 310                 315

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Leu Ser Ala Pro His Thr Pro Val
 1                5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Met Gln Lys Ile Ile Asp Pro Leu
 1                5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Met Ser Phe Arg Ala Ala Ala Ala
 1                5

<210> SEQ ID NO 46
```

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Thr Ala Glu Glu Pro Ser Phe Leu
 1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Gln His Glu Thr Val Asp Ser Val
 1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Val Tyr Glu Asn Val Lys Tyr Val
 1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Val Gln Gln Glu Asn Phe Trp Ile
 1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Leu Pro Phe Leu Asn Pro Glu Val
 1               5

<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

-continued

```
Arg Gly Arg Ala Phe Arg Val Ala Asp Asp Thr Ala Glu Gly Leu Ser
 1               5                  10                  15

Ala Pro His Thr Pro Val Thr Pro Gly Ala Ala Ser Leu Cys
            20                  25                  30
```

<210> SEQ ID NO 52
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Val Lys Tyr Val Gln Gln Glu Asn Phe Trp Ile Gly Pro Ser Ser Glu
 1               5                  10                  15

Ala Leu Ile His Leu Gly Ala Lys Phe Ser Pro Cys Met Arg
            20                  25                  30
```

<210> SEQ ID NO 53
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Pro Val Arg Cys Glu Trp Cys Glu Phe Leu Thr Cys Ile Pro Phe Thr
 1               5                  10                  15

Asp Lys Phe Cys Glu Lys Tyr Glu Leu Asp Ala Gln Leu His
            20                  25                  30
```

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
caggaattcc atgagtgagg cccgcagg                                       28

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ccctgggatc ctggtggcag acagag                                         26

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ccggcgtcga ctcagtggag ctgagcgtc                                      29

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
caccaggatc ccagggtgtg tgatga                                          26

<210> SEQ ID NO 58
<211> LENGTH: 6559
<212> TYPE: DNA
<213> ORGANISM: Homo sapiens

<400> SEQUENCE: 58
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgcccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg ccccctattg acgtcaatga     420
cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaataaccc     660
cgccccgttg acgcaaatgg gcggtaggcg tgtacggtgg gaggtctata taagcagagc     720
tcgtttagtg aaccgtcaga tcactagaag ctttattgcg gtagtttatc acagttaaat     780
tgctaacgca gtcagtgctt ctgacacaac agtctcgaac ttaagctgca gaagttggtc     840
gtgaggcact gggcaggtaa gtatcaaggt tacaagacag gtttaaggag accaatagaa     900
actgggcttg tcgagacaga aagactcttg cgtttctgat aggcaccta ttggtcttac     960 tgacatccac tttgcctttc tctccacagg tgtccactcc cagttcaatt acagctctta    1020
aggctagagt acttaatacg actcactata ggctagcctc gagaattcca tgagtgaggc    1080
ccgcagggac agcacgagca gcctgcagcg caagaagcca ccctggctaa agctggacat    1140
tccctctgcg gtgcccctga cggcagaaga gcccagcttc ctgcagcccc tgaggcgaca    1200
ggctttcctg aggagtgtga gtatgccagc cgagacagcc cacatctctt caccccacca    1260
tgagctccgg cggccggtgc tgcaacgcca gacgtccatc acacagacca tccgcagggg    1320
gaccgccgac tggtttggag tgagcaagga cagtgacagc acccagaaat ggcagcgcaa    1380
gagcatccgt cactgcagcc agcgctacgg gaagctgaag ccccaggtcc tcgggagct    1440 ggacctgccc agccaggaca acgtgtcgct gaccagcacc gagacgccac ccccactcta    1500
cgtggggcca tgccagctgg gcatgcagaa gatcatagac cccctggccc gtggccgtgc    1560
cttccgtgtg gcagatgaca ctgcggaagg cctgagtgcc ccacacactc ccgtcacgcc    1620
gggtgctgcc tccctctgct ccttctccag ctcccgctca ggtttccacc ggctcccgcg    1680
gcggcgcaag cgagagtcgg tggccaagat gagcttccgg gcggccgcag cgctgatgaa    1740

```
aggccgctcc gttagggatg gcacctttcg ccgggcacgg cgtcgaagct tcactccagc   1800
tagctttctg gaggaggaca caactgattt ccccgatgag ctggacacat ccttctttgc   1860 ccggaaggt atcctccatg aagagctgtc cacatacccg gatgaagttt tcgagtcccc   1920
atcggaggca gcgctaaagg actgggagaa ggcaccggag caggcggacc tcaccggcgg   1980
ggccctggac cgcagcgagc ttgagcgcag ccacctgatg ctgcccttgg agcgaggctg   2040
gcggaagcag aaggagggcg ccgcagcccc gcagcccaag gtgcggctcc gacaggaggt   2100
ggtgagcacc gcggggccgc gacggggcca gcgtatcgcg gtgccggtgc gcaagctctt   2160
cgcccgggag aagcggccgt atgggctggg catggtggga cggctcacca accgcaccta   2220
ccgcaagcgc atcgacagct tcgtcaagcg ccagatcgag gacatggacg accacaggcc   2280
cttcttcacc tactggctta ccttcgtgca ctcgctcgtc accatcctag ccgtgtgcat   2340
ctatggcatc gcgcccgtgg gcttctcgca gcatgagacg gtggactcgg tgctgcggaa   2400
ccgcggggtc tacgagaacg tcaagtacgt gcagcaggag aacttctgga tcgggcccag   2460
ctcggaggcc ctcatccacc tgggcgccaa gttttcgccc tgcatgcgcc aggacccgca   2520
ggtgcacagc ttcattcgct cggcgcgcga gcgcagaag cactccgcct gctgcgtgcg   2580
caacgacagg tcgggctgcg tgcagacctc ggaggaggag tgctcgtcca cgctggcagt   2640
gtgggtgaag tggcccatcc atcccagcgc cccagagctt gcgggccaca agagacagtt   2700
tggctctgtc tgccaccagg atcccagggt gtgtgatgag ccctcctccg aagaccctca   2760
tgagtggcca gaagacatca ccaagtggcc gatctgcacc aaaaacagcg ctgggaacca   2820
caccaaccat ccccacatgg actgtgtcat cacaggacgg ccctgctgca ttggcaccaa   2880
gggcaggtgt gagatcacct cccgggagta ctgtgacttc atgaggggct acttccatga   2940
ggaggccacg ctctgctctc aggtgcactg catggatgat gtgtgtgggc tcctgccttt   3000
tctcaacccc gaggtgcctg accagttcta ccgcctgtgg ctatccctct tcctgcacgc   3060
cgggatcttg cactgcctgg tgtccatctg cttccagatg actgtcctgc gggacctgga   3120
gaagctggca ggctggcacc gcatagccat catctacctg ctgagtggtg tcaccggcaa   3180
cctggccagt gccatcttcc tgccataccg agcagaggtg ggtcctgctg gctcccagtt   3240
cggcatcctg gcctgcctct tcgtggagct cttccagagc tggcagatcc tggcgcggcc   3300
ctggcgtgcc ttcttcaagc tgctggctgt ggtgctcttc ctcttcacct ttgggctgct   3360
gccgtggatt gacaactttg cccacatctc ggggttcatc agtggcctct tcctctcctt   3420
cgccttcttg ccctacatca gctttggcaa gttcgacctg taccggaaac gctgccagat   3480
catcatcttt caggtggtct tcctgggcct cctggctggc ctggtggtcc tcttctacgt   3540
ctatcctgtc cgctgtgagt ggtgtgagtt cctcacctgc atccccttca ctgacaagtt   3600
ctgtgagaag tacgaactgg acgctcagct ccactgagtc gacccgggcg gccgcttcga   3660
gcagacatga taagatacat tgatgagttt ggacaaacca caactagaat gcagtgaaaa   3720
aaatgcttta tttgtgaaat ttgtgatgct attgctttat tgtaaccat tataagctgc   3780 aataaacaag ttaacaacaa caattgcatt cattttatgt ttcaggttca ggggggagatg   3840 tgggaggttt tttaaagcaa gtaaaacctc tacaaatgtg gtaaaatcga taaggatccg   3900
ggctggcgta atagcgaaga ggcccgcacc gatcgccctt cccaacagtt gcgcagcctg   3960
aatggcgaat ggacgcgccc tgtagcggcg cattaagcgc ggcgggtgtg gtggttacgc   4020
gcagcgtgac cgctacactt gccagcgccc tagcgcccgc tcctttcgct ttcttccctt   4080
cctttctcgc cacgttcgcc ggctttcccc gtcaagctct aaatcggggg ctcccttag   4140
```

```
ggttccgatt tagagcttta cggcacctcg accgcaaaaa acttgatttg ggtgatggtt    4200
cacgtagtgg gccatcgccc tgatagacgg ttttttcgccc tttgacgttg gagtccacgt    4260
tctttaatag tggactcttg ttccaaactg gaacaacact caaccctatc tcggtctatt    4320
cttttgattt ataagggatt ttgccgattt cggcctattg gttaaaaaat gagctgattt    4380
aacaaatatt taacgcgaat tttaacaaaa tattaacgtt tacaatttcg cctgatgcgg    4440
tattttctcc ttacgcatct gtgcggtatt tcacaccgca tatggtgcac tctcagtaca    4500
atctgctctg atgccgcata gttaagccag ccccgacacc cgccaacacc cgctgacgcg    4560
ccctgacggg cttgtctgct cccggcatcc gcttacagac aagctgtgac cgtctccggg    4620
agctgcatgt gtcagaggtt ttcaccgtca tcaccgaaac gcgcgagacg aaagggcctc    4680
gtgatacgcc tatttttata ggttaatgtc atgataataa tggtttctta cgtcaggt    4740 ggcacttttc ggggaaatgt gcgcggaacc cctatttgtt tattttttcta aatacattca    4800 aatatgtatc cgctcatgag acaataaccc tgataaatgc ttcaataata ttgaaaaagg    4860
aagagtatga gtattcaaca tttccgtgtc gcccttattc cctttttgc ggcattttgc    4920 cttcctgttt ttgctcaccc agaaacgctg gtgaaagtaa aagatgctga agatcagttg    4980
ggtgcacgag tgggttacat cgaactggat ctcaacagcg gtaagatcct tgagagtttt    5040
cgccccgaag aacgttttcc aatgatgagc acttttaaag ttctgctatg tggcgcggta    5100
ttatcccgta ttgacgccgg gcaagagcaa ctcggtcgcc gcatacacta ttctcagaat    5160
gacttggttg agtactcacc agtcacagaa aagcatctta cggatggcat gacagtaaga    5220
gaattatgca gtgctgccat aaccatgagt gataacactg cggccaactt acttctgaca    5280
acgatcggag gaccgaagga gctaaccgct ttttttgcaca acatggggga tcatgtaact    5340
cgccttgatc gttgggaacc ggagctgaat gaagccatac caaacgacga gcgtgacacc    5400
acgatgcctg tagcaatggc aacaacgttg cgcaaactat taactggcga actacttact    5460
ctagcttccc ggcaacaatt aatagactgg atggaggcgg ataaagttgc aggaccactt    5520
ctgcgctcgg cccttccggc tggctggttt attgctgata atctggagc cggtgagcgt    5580 gggtctcgcg gtatcattgc agcactgggg ccagatggta agccctcccg tatcgtagtt    5640
atctacacga cggggagtca ggcaactatg gatgaacgaa atagacagat cgctgagata    5700
ggtgcctcac tgattaagca ttggtaactg tcagaccaag tttactcata tatactttag    5760
attgatttaa aacttcattt ttaatttaaa aggatctagg tgaagatcct ttttgataat    5820
ctcatgacca aaatccctta acgtgagttt tcgttccact gagcgtcaga ccccgtagaa    5880
aagatcaaag gatcttcttg agatcctttt tttctgcgcg taatctgctg cttgcaaaca    5940
aaaaaaccac cgctaccagc ggtggtttgt ttgccggatc aagagctacc aactcttttt    6000
ccgaaggtaa ctggcttcag cagagcgcag ataccaaata ctgtccttct agtgtagccg    6060
tagttaggcc accacttcaa gaactctgta gcaccgccta catcctcgc tctgctaatc    6120 ctgttaccag tggctgctgc cagtggcgat aagtcgtgtc ttaccgggtt ggactcaaga    6180
cgatagttac cggataaggc gcagcggtcg ggctgaacgg ggggttcgtg cacacagccc    6240
agcttggagc gaacgaccta caccgaactg agatacctac agcgtgagct atgagaaagc    6300
gccacgcttc ccgaagggag aaaggcggac aggtatccgg taagcggcag gtcggaaca    6360 ggagagcgca cgagggagct tccagggga acgcctggt atctttatag tcctgtcggg    6420
tttcgccacc tctgacttga gcgtcgattt ttgtgatgct cgtcaggggg gcggagccta    6480
```

```
tggaaaaacg ccagcaacgc ggccttttta cggttcctgg ccttttgctg gcctttttgct    6540 cacatggctc gacagatct                                                  6559

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccctggtcga ctcacctggg atcctggtg                                         29

<210> SEQ ID NO 60
<211> LENGTH: 5653
<212> TYPE: DNA
<213> ORGANISM: Homo sapiens

<400> SEQUENCE: 60
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccccctattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca gtctccacc ccattgacgt     600 caatgggagt ttgttttggc accaaaatca acgggacttt ccaaaatgtc gtaataaccc     660
cgccccgttg acgcaaatgg gcggtaggcg tgtacggtgg gaggtctata taagcagagc     720
tcgtttagtg aaccgtcaga tcactagaag ctttattgcg gtagtttatc acagttaaat     780
tgctaacgca gtcagtgctt ctgacacaac agtctcgaac ttaagctgca gaagttggtc     840
gtgaggcact gggcaggtaa gtatcaaggt tacaagacag gtttaaggag accaatagaa     900
actgggcttg tcgagacaga gaagactctt gcgtttctga taggcaccta ttggtcttac     960
tgacatccac tttgcctttc tctccacagg tgtccactcc cagttcaatt acagctctta    1020
aggctagagt acttaatacg actcactata ggctagcctc gagaattcca tgagtgaggc    1080
ccgcagggac agcacgagca gcctgcagcg caagaagcca ccctggctaa agctggacat    1140
tccctctgcg gtgccctga cggcagaaga gcccagcttc ctgcagcccc tgaggcgaca    1200
ggctttcctg aggagtgtga gtatgccagc cgagacagcc cacatctctt caccccacca    1260
tgagctccgg cggccggtgc tgcaacgcca gacgtccatc acacagacca tccgcagggg    1320
gaccgccgac tggtttggag tgagcaagga cagtgacagc acccagaaat ggcagcgcaa    1380
gagcatccgt cactgcagcc agcgctacgg gaagctgaag ccccaggtcc tccgggagct    1440
ggacctgccc agccaggaca acgtgtcgct gaccagcacc gagacgccac ccccactcta    1500
cgtgggccca tgccagctgg gcatgcagaa gatcatagac cccctggccc gtggccgtgc    1560
cttccgtgtg gcagatgaca ctgcggaagg cctgagtgcc ccacacactc ccgtcacgcc    1620
```

-continued

```
gggtgctgcc tccctctgct ccttctccag ctcccgctca ggtttccacc ggctcccgcg    1680
gcggcgcaag cgagagtcgg tggccaagat gagcttccgg gcggccgcag cgctgatgaa    1740
aggccgctcc gttagggatg gcacctttcg ccgggcacgg cgtcgaagct tcactccagc    1800
tagctttctg gaggaggaca caactgattt ccccgatgag ctggacacat ccttctttgc    1860
ccgggaaggt atcctccatg aagagctgtc cacatacccg gatgaagttt tcgagtcccc    1920
atcggaggca gcgctaaagg actgggagaa ggcaccggag caggcggacc tcaccggcgg    1980
ggccctggac cgcagcgagc ttgagcgcag ccacctgatg ctgcccttgg agcgaggctg    2040
gcggaagcag aaggagggcg ccgcagcccc gcagcccaag gtgcggctcc gacaggaggt    2100
ggtgagcacc gcggggccgc gacggggcca gcgtatcgcg gtgccggtgc gcaagctctt    2160
cgcccgggag aagcggccgt atgggctggg catggtggga cggctcacca accgcaccta    2220
ccgcaagcgc atcgacagct tcgtcaagcg ccagatcgag gacatggacg accacaggcc    2280
cttcttcacc tactggctta ccttcgtgca ctcgctcgtc accatcctag ccgtgtgcat    2340
ctatggcatc gcgcccgtgg gcttctcgca gcatgagacg gtggactcgg tgctgcggaa    2400
ccgcggggtc tacgagaacg tcaagtacgt gcagcaggaa aacttctgga tcgggcccag    2460
ctcggaggcc ctcatccacc tgggcgccaa gttttcgccc tgcatgcgcc aggacccgca    2520
ggtgcacagc ttcattcgct cggcgcgcga gcgcgagaag cactccgcct gctgcgtgcg    2580
caacgacagg tcgggctgcg tgcagacctc ggaggaggag tgctcgtcca cgctggcagt    2640
gtgggtgaag tggcccatcc atcccagcgc cccagagctt gcgggccaca agagacagtt    2700
tggctctgtc tgccaccagg atcccaggtg agtcgacccg ggcggccgct tcgagcagac    2760
atgataagat acattgatga gtttggacaa accacaacta gaatgcagtg aaaaaaatgc    2820
tttatttgtg aaatttgtga tgctattgct ttatttgtaa ccattataag ctgcaataaa    2880
caagttaaca acaacaattg cattcatttt atgtttcagg ttcaggggga gatgtgggag    2940 gtttttttaaa gcaagtaaaa cctctacaaa tgtggtaaaa tcgataagga tccgggctgg    3000
cgtaatagcg aagaggcccg caccgatcgc ccttcccaac agttgcgcag cctgaatggc    3060
gaatggacgc gccctgtagc ggcgcattaa gcgcggcggg tgtggtggtt acgcgcagcg    3120
tgaccgctac acttgccagc gccctagcgc ccgctccttt cgctttcttc ccttcctttc    3180
tcgccacgtt cgccggcttt ccccgtcaag ctctaaatcg ggggctccct ttagggttcc    3240
gatttagagc tttacggcac ctcgaccgca aaaaacttga tttgggtgat ggttcacgta    3300
gtgggccatc gccctgatag acggtttttc gccctttgac gttggagtcc acgttcttta    3360
atagtggact cttgttccaa actggaacaa cactcaaccc tatctcggtc tattcttttg    3420
atttataagg gattttgccg atttcggcct attggttaaa aaatgagctg atttaacaaa    3480
tatttaacgc gaattttaac aaaatattaa cgtttacaat ttcgcctgat gcggtatttt    3540
ctccttacgc atctgtgcgg tatttcacac cgcatatggt gcactctcag tacaatctgc    3600
tctgatgccg catagttaag ccagccccga cacccgccaa cacccgctga cgcgccctga    3660
cgggcttgtc tgctcccggc atccgcttac agacaagctg tgaccgtctc cgggagctgc    3720
atgtgtcaga ggttttcacc gtcatcaccg aaacgcgcga acgaaaggg cctcgtgata    3780 cgcctatttt tataggttaa tgtcatgata ataatggttt cttagacgtc aggtggcact    3840
tttcggggaa atgtgcgcgg aacccctatt tgtttatttt tctaaataca ttcaaatatg    3900
tatccgctca tgagacaata accctgataa atgcttcaat aatattgaaa aggaagagt    3960 atgagtattc aacatttccg tgtcgccctt attcccttt ttgcggcatt ttgccttcct    4020
```

```
gtttttgctc acccagaaac gctggtgaaa gtaaaagatg ctgaagatca gttgggtgca    4080
cgagtgggtt acatcgaact ggatctcaac agcggtaaga tccttgagag ttttcgcccc    4140
gaagaacgtt ttccaatgat gagcactttt aaagttctgc tatgtggcgc ggtattatcc    4200
cgtattgacg ccgggcaaga gcaactcggt cgccgcatac actattctca gaatgacttg    4260
gttgagtact caccagtcac agaaaagcat cttacggatg gcatgacagt aagagaatta    4320
tgcagtgctg ccataaccat gagtgataac actgcggcca acttacttct gacaacgatc    4380
ggaggaccga aggagctaac cgcttttttg cacaacatgg gggatcatgt aactcgcctt    4440
gatcgttggg aaccggagct gaatgaagcc ataccaaacg acgagcgtga caccacgatg    4500
cctgtagcaa tggcaacaac gttgcgcaaa ctattaactg gcgaactact tactctagct    4560
tcccggcaac aattaataga ctggatggag gcggataaag ttgcaggacc acttctgcgc    4620
tcggcccttc cggctggctg gtttattgct gataaatctg gagccggtga gcgtgggtct    4680
cgcggtatca ttgcagcact ggggccagat ggtaagccct cccgtatcgt agttatctac    4740
acgacgggga gtcaggcaac tatggatgaa cgaaatagac agatcgctga gataggtgcc    4800
tcactgatta agcattggta actgtcagac caagtttact catatatact ttagattgat    4860
ttaaaacttc attttttaatt taaaaggatc taggtgaaga tcctttttga taatctcatg    4920
accaaaatcc cttaacgtga gttttcgttc cactgagcgt cagaccccgt agaaaagatc    4980
aaaggatctt cttgagatcc ttttttttctg cgcgtaatct gctgcttgca acaaaaaaaa    5040
ccaccgctac cagcggtggt ttgtttgccg gatcaagagc taccaactct ttttccgaag    5100
gtaactggct tcagcagagc gcagatacca aatactgtcc ttctagtgta gccgtagtta    5160
ggccaccact tcaagaactc tgtagcaccg cctacatacc tcgctctgct aatcctgtta    5220
ccagtggctg ctgccagtgg cgataagtcg tgtcttaccg ggttggactc aagacgatag    5280
ttaccggata aggcgcagcg gtcgggctga acggggggtt cgtgcacaca gcccagcttg    5340
gagcgaacga cctacaccga actgagatac ctacagcgtg agctatgaga aagcgccacg    5400
cttcccgaag ggagaaaggc ggacaggtat ccggtaagcg gcagggtcgg aacaggagag    5460
cgcacgaggg agcttccagg gggaaacgcc tggtatcttt atagtcctgt cgggtttcgc    5520
cacctctgac ttgagcgtcg atttttgtga tgctcgtcag gggggcggag cctatggaaa    5580
aacgccagca acgcggcctt tttacggttc ctggccttttt gctggccttt tgctcacatg    5640
gctcgacaga tct                                                       5653

<210> SEQ ID NO 61
<211> LENGTH: 4964
<212> TYPE: DNA
<213> ORGANISM: Homo sapiens

<400> SEQUENCE: 61
tcgactcgag cggccgcatc gtgactgact gacgatctgc ctcgcgcgtt tcggtgatga      60
cggtgaaaac ctctgacaca tgcagctccc ggagacggtc acagcttgtc tgtaagcgga     120
tgccgggagc agacaagccc gtcagggcgc gtcagcgggt gttggcgggt gtcggggcgc     180
agccatgacc cagtcacgta gcgatagcgg agtgtataat tcttgaagac gaaagggcct     240
cgtgatacgc ctatttttat aggttaatgt catgataata atggtttctt agacgtcagg     300
tggcactttt cggggaaatg tgcgcggaac ccctatttgt ttatttttct aaatacattc     360
aaatatgtat ccgctcatga gacaataacc ctgataaatg cttcaataat attgaaaaag     420
```

-continued

```
gaagagtatg agtattcaac atttccgtgt cgcccttatt cccttttttg cggcattttg    480
ccttcctgtt tttgctcacc cagaaacgct ggtgaaagta aaagatgctg aagatcagtt    540
gggtgcacga gtgggttaca tcgaactgga tctcaacagc ggtaagatcc ttgagagttt    600
tcgccccgaa gaacgttttc caatgatgag cacttttaaa gttctgctat gtggcgcggt    660
attatcccgt gttgacgccg ggcaagagca actcggtcgc cgcatacact attctcagaa    720
tgacttggtt gagtactcac cagtcacaga aaagcatctt acggatggca tgacagtaag    780
agaattatgc agtgctgcca taaccatgag tgataacact gcggccaact tacttctgac    840
aacgatcgga ggaccgaagg agctaaccgc ttttttgcac aacatggggg atcatgtaac    900
tcgccttgat cgttgggaac cggagctgaa tgaagccata ccaaacgacg agcgtgacac    960
cacgatgcct gcagcaatgg caacaacgtt gcgcaaacta ttaactggcg aactacttac   1020
tctagcttcc cggcaacaat taatagactg gatggaggcg gataaagttg caggaccact   1080
tctgcgctcg gcccttccgg ctggctggtt tattgctgat aaatctggag ccggtgagcg   1140
tgggtctcgc ggtatcattg cagcactggg gccagatggt aagccctccc gtatcgtagt   1200
tatctacacg acggggagtc aggcaactat ggatgaacga aatagacaga tcgctgagat   1260
aggtgcctca ctgattaagc attggtaact gtcagaccaa gtttactcat atatacttta   1320
gattgattta aaacttcatt tttaatttaa aaggatctag gtgaagatcc ttttgataa    1380 tctcatgacc aaaatccctt aacgtgagtt ttcgttccac tgagcgtcag accccgtaga   1440
aaagatcaaa ggatcttctt gagatccttt ttttctgcgc gtaatctgct gcttgcaaac   1500
aaaaaaacca ccgctaccag cggtggtttg tttgccggat caagagctac caactctttt   1560
tccgaaggta actggcttca gcagagcgca gataccaaat actgtccttc tagtgtagcc   1620
gtagttaggc caccacttca agaactctgt agcaccgcct acatacctcg ctctgctaat   1680
cctgttacca gtggctgctg ccagtggcga taagtcgtgt cttaccgggt tggactcaag   1740
acgatagtta ccggataagg cgcagcggtc gggctgaacg gggggttcgt gcacacagcc   1800
cagcttggag cgaacgacct acaccgaact gagatacccta cagcgtgagc tatgagaaag   1860
cgccacgctt cccgaaggga gaaaggcgga caggtatccg gtaagcggca gggtcggaac   1920
aggagagcgc acgagggagc ttccagggg aaacgcctgg tatctttata gtcctgtcgg   1980
gtttcgccac ctctgacttg agcgtcgatt tttgtgatgc tcgtcagggg gcggagcct    2040 atggaaaaac gccagcaacg cggccttttt acggttcctg gccttttgct ggccttttgc   2100
tcacatgttc tttcctgcgt tatccctga ttctgtggat aaccgtatta ccgcctttga    2160
gtgagctgat accgctcgcc gcagccgaac gaccgagcgc agcgagtcag tgagcgagga   2220
agcggaagag cgcctgatgc ggtatttct ccttacgcat ctgtgcggta tttcacaccg    2280
cataaattcc gacaccatcg aatggtgcaa aacctttcgc ggtatggcat gatagcgccc   2340
ggaagagagt caattcaggg tggtgaatgt gaaaccagta acgttatacg atgtcgcaga   2400
gtatgccggt gtctcttatc agaccgtttc ccgcgtggtg aaccaggcca gccacgtttc   2460
tgcgaaaacg cgggaaaaag tggaagcggc gatggcggag ctgaattaca ttcccaaccg   2520
cgtggcacaa caactggcgg gcaaacagtc gttgctgatt ggcgttgcca cctccagtct   2580
ggccctgcac gcgccgtcgc aaattgtcgc ggcgattaaa tctcgcgccg atcaactggg   2640
tgccagcgtg gtggtgtcga tggtagaacg aagcggcgtc gaagcctgta aagcggcgt    2700 gcacaatctt ctcgcgcaac gcgtcagtgg gctgatcatt aactatccgc tggatgacca   2760
ggatgccatt gctgtggaag ctgcctgcac taatgttccg gcgttatttc ttgatgtctc   2820
```

```
tgaccagaca cccatcaaca gtattatttt ctcccatgaa gacggtacgc gactgggcgt    2880
ggagcatctg gtcgcattgg gtcaccagca aatcgcgctg ttagcgggcc cattaagttc    2940
tgtctcggcg cgtctgcgtc tggctggctg gcataaatat ctcactcgca atcaaattca    3000
gccgatagcg gaacgggaag gcgactggag tgccatgtcc ggttttcaac aaaccatgca    3060
aatgctgaat gagggcatcg ttcccactgc gatgctggtt gccaacgatc agatggcgct    3120
gggcgcaatg cgcgccatta ccgagtccgg gctgcgcgtt ggtgcggata tctcggtagt    3180
gggatacgac gataccgaag acagctcatg ttatatcccg ccgttaacca ccatcaaaca    3240
ggattttcgc ctgctggggc aaaccagcgt ggaccgcttg ctgcaactct ctcagggcca    3300
ggcggtgaag ggcaatcagc tgttgcccgt ctcactggtg aaaagaaaaa ccaccctggc    3360
gcccaatacg caaaccgcct ctccccgcgc gttggccgat tcattaatgc agctggcacg    3420
acaggtttcc cgactggaaa gcgggcagtg agcgcaacgc aattaatgtg agttagctca    3480
ctcattaggc accccaggct ttacacttta tgcttccggc tcgtatgttg tgtggaattg    3540
tgagcggata caatttcac acaggaaaca gctatgacca tgattacgga ttcactggcc    3600
gtcgttttac aacgtcgtga ctgggaaaac cctggcgtta cccaacttaa tcgccttgca    3660
gcacatcccc ctttcgccag ctggcgtaat agcgaagagg cccgcaccga tcgcccttcc    3720
caacagttgc gcagcctgaa tggcgaatgg cgctttgcct ggtttccggc accagaagcg    3780
gtgccggaaa gctggctgga gtgcgatctt cctgaggccg atactgtcgt cgtccctca    3840
aactggcaga tgcacggtta cgatgcgccc atctacacca acgtaaccta tcccattacg    3900
gtcaatccgc cgtttgttcc cacggagaat ccgacgggtt gttactcgct cacatttaat    3960
gttgatgaaa gctggctaca ggaaggccag acgcgaatta ttttttgatgg cgttggaatt    4020
agcttatcga ctgcacggtg caccaatgct tctggcgtca ggcagccatc ggaagctgtg    4080
gtatggctgt gcaggtcgta aatcactgca taattcgtgt cgctcaaggc gcactcccgt    4140
tctggataat gttttttgcg ccgacatcat aacggttctg gcaaatattc tgaaatgagc    4200
tgttgacaat taatcatcgg ctcgtataat gtgtggaatt gtgagcggat aacaatttca    4260
cacaggaaac agtattcatg tccctatac taggttattg gaaaattaag ggccttgtgc    4320
aacccactcg acttcttttg gaatatcttg aagaaaaata tgaagagcat ttgtatgagc    4380
gcgatgaagg tgataaatgg cgaaacaaaa agtttgaatt gggtttggag tttcccaatc    4440
ttccttatta tattgatggt gatgttaaat taacacagtc tatggccatc atacgttata    4500
tagctgacaa gcacaacatg ttgggtggtt gtccaaaaga gcgtgcagag atttcaatgc    4560
ttgaaggagc ggtttttggat attagatacg gtgtttcgag aattgcatat agtaaagact    4620
ttgaaactct caaagttgat tttcttagca agctacctga aatgctgaaa atgttcgaag    4680
atcgtttatg tcataaaaca tatttaaatg gtgatcatgt aacccatcct gacttcatgt    4740
tgtatgacgc tcttgatgtt gttttataca tggacccaat gtgcctggat gcgttcccaa    4800
aattagtttg ttttaaaaaa cgtattgaag ctatcccaca aattgataag tacttgaaat    4860
ccagcaagta tatagcatgg cctttgcagg gctggcaagc cacgtttggt ggtggcgacc    4920
atcctccaaa atcggatctg atcgaaggtc gtgggatccc cagg                    4964
```

<210> SEQ ID NO 62
<211> LENGTH: 6633
<212> TYPE: DNA
<213> ORGANISM: Homo sapiens

<400> SEQUENCE: 62

```
agcttatcga ctgcacggtg caccaatgct tctggcgtca ggcagccatc ggaagctgtg      60
gtatggctgt gcaggtcgta aatcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattcatg tccctatac taggttattg gaaaattaag ggccttgtgc      300
aacccactcg acttcttttg gaatatcttg aagaaaaata tgaagagcat ttgtatgagc     360
gcgatgaagg tgataaatgg cgaaacaaaa gtttgaattt gggtttggag tttcccaatc     420
ttccttatta tattgatggt gatgttaaat taacacagtc tatggccatc atacgttata     480
tagctgacaa gcacaacatg ttgggtggtt gtccaaaaga gcgtgcagag atttcaatgc     540
ttgaaggagc ggttttggat attagatacg gtgtttcgag aattgcatat agtaaagact     600
ttgaaactct caaagttgat tttcttagca agctacctga aatgctgaaa atgttcgaag     660
atcgtttatg tcataaaaca tatttaaatg gtgatcatgt aacccatcct gacttcatgt     720
tgtatgacgc tcttgatgtt gttttataca tggacccaat gtgcctggat gcgttcccaa     780
aattagtttg ttttaaaaaa cgtattgaag ctatcccaca aattgataag tacttgaaat     840
ccagcaagta tatagcatgg cctttgcagg gctggcaagc cacgtttggt ggtggcgacc     900
atcctccaaa atcggatctg atcgaaggtc gtgggatccc caggaattcc atgagtgagg     960
cccgcaggga cagcacgagc agcctgcagc gcaagaagcc accctggcta aagctggaca    1020
ttccctctgc ggtgcccctg acggcagaag agcccagctt cctgcagccc ctgaggcgac    1080
aggctttcct gaggagtgtg agtatgccag ccgagacagc ccacatctct tcacccacc     1140
atgagctccg gcggccggtg ctgcaacgcc agacgtccat cacacagacc atccgcaggg    1200
ggaccgccga ctggtttgga gtgagcaagg acagtgacag cacccagaaa tggcagcgca    1260
agagcatccg tcactgcagc cagcgctacg ggaagctgaa gccccaggtc ctccgggagc    1320
tggacctgcc cagccaggac aacgtgtcgc tgaccagcac cgagacgcca ccccactct     1380
acgtggggcc atgccagctg ggcatgcaga agatcataga ccccctggcc cgtggccgtg    1440
ccttccgtgt ggcagatgac actgcggaag gcctgagtgc cccacacact cccgtcacgc    1500
cgggtgctgc ctccctctgc tccttctcca gctcccgctc aggtttccac cggctcccgc    1560
ggcggcgcaa gcgagagtcg gtggccaaga tgagcttccg ggcggccgca gcgctgatga    1620
aaggccgctc cgttagggat ggcacctttc gccgggcacg gcgtcgaagc ttcactccag    1680
ctagctttct ggaggaggac acaactgatt tccccgatga gctggacaca tccttctttg    1740
cccgggaagg tatcctccat gaagagctgt ccacataccc ggatgaagtt ttcgagtccc    1800
catcggaggc agcgctaaag gactgggaga aggcaccgga gcaggcggac ctcaccggcg    1860
gggccctgga ccgcagcgag cttgagcgca gccacctgat gctgcccttg agcgaggct     1920
ggcggaagca aaggagggc gccgcagccc cgcagcccaa ggtgcggctc gacaggagg      1980
tggtgagcac cgcggggccg cgacgggcc agcgtatcgc ggtgccggtg cgcaagctct    2040
tcgcccggga gaagcggccg tatgggctgg gcatggtggg acggctcacc aaccgcacct    2100
accgcaagcg catcgacagc ttcgtcaagc gccagatcga ggacatggac gaccacaggc    2160
ccttcttcac ctactggctt accttcgtgc actcgctcgt caccatccta gccgtgtgca    2220
tctatggcat cgcgccgtg ggcttctcgc agcatgagac ggtggactcg gtgctgcgga    2280
accgcggggt ctacgagaac gtcaagtacg tgcagcagga gaacttctgg atcgggccca    2340
```

-continued

```
gctcggaggc cctcatccac ctgggcgcca agttttcgcc ctgcatgcgc caggacccgc    2400
aggtgcacag cttcattcgc tcggcgcgcg agcgcgagaa gcactccgcc tgctgcgtgc    2460
gcaacgacag gtcgggctgc gtgcagacct cggaggagga gtgctcgtcc acgctggcag    2520
tgtgggtgaa gtggcccatc catcccagcg ccccagagct tgcgggccac aagagacagt    2580
ttggctctgt ctgccaccag gatcccaggt gagtcgactc gagcggccgc atcgtgactg    2640
actgacgatc tgcctcgcgc gtttcggtga tgacggtgaa aacctctgac acatgcagct    2700
cccggagacg gtcacagctt gtctgtaagc ggatgccggg agcagacaag cccgtcaggg    2760
cgcgtcagcg ggtgttggcg ggtgtcgggg cgcagccatg acccagtcac gtagcgatag    2820
cggagtgtat aattcttgaa gacgaaaggg cctcgtgata cgcctatttt tataggttaa    2880
tgtcatgata ataatggttt cttagacgtc aggtggcact tttcggggaa atgtgcgcgg    2940 aaccccctatt tgtttatttt tctaaataca ttcaaatatg tatccgctca tgagacaata    3000
accctgataa atgcttcaat aatattgaaa aaggaagagt atgagtattc aacatttccg    3060
tgtcgccctt attccctttt ttgcggcatt ttgccttcct gttttttgctc acccagaaac    3120 gctggtgaaa gtaaaagatg ctgaagatca gttgggtgca cgagtgggtt acatcgaact    3180
ggatctcaac agcggtaaga tccttgagag ttttcgcccc gaagaacgtt ttccaatgat    3240
gagcactttt aaagttctgc tatgtggcgc ggtattatcc cgtgttgacg ccgggcaaga    3300
gcaactcggt cgccgcatac actattctca gaatgacttg gttgagtact caccagtcac    3360
agaaaagcat cttacggatg gcatgacagt aagagaatta tgcagtgctg ccataaccat    3420
gagtgataac actgcggcca acttacttct gacaacgatc ggaggaccga aggagctaac    3480
cgcttttttg cacaacatgg gggatcatgt aactcgcctt gatcgttggg aaccggagct    3540
gaatgaagcc ataccaaacg acgagcgtga caccacgatg cctgcagcaa tggcaacaac    3600
gttgcgcaaa ctattaactg gcgaactact tactctagct tcccggcaac aattaataga    3660
ctggatggag gcggataaag ttgcaggacc acttctgcgc tcggcccttc cggctggctg    3720
gtttattgct gataaatctg gagccggtga gcgtgggtct cgcggtatca ttgcagcact    3780
ggggccagat ggtaagccct cccgtatcgt agttatctac acgacgggga gtcaggcaac    3840 tatgatgaa cgaaatagac agatcgctga gataggtgcc tcactgatta gcattggta    3900 actgtcagac caagtttact catatatact ttagattgat ttaaaacttc atttttaatt    3960
taaaaggatc taggtgaaga tcctttttga atctcatg accaaaatcc cttaacgtga    4020
gttttcgttc cactgagcgt cagaccccgt agaaaagatc aaaggatctt cttgagatcc    4080 ttttttctg cgcgtaatct gctgcttgca acaaaaaaa ccaccgctac cagcggtggt    4140
ttgtttgccg gatcaagagc taccaactct ttttccgaag gtaactggct tcagcagagc    4200
gcagatacca aatactgtcc ttctagtgta gccgtagtta ggccaccact tcaagaactc    4260
tgtagcaccg cctacatacc tcgctctgct aatcctgtta ccagtggctg ctgccagtgg    4320
cgataagtcg tgtcttaccg ggttggactc aagacgatag ttaccggata aggcgcagcg    4380
gtcgggctga cgggggggtt cgtgcacaca gcccagcttg gagcgaacga cctacaccga    4440
actgagatac ctacagcgtg agctatgaga aagcgccacg cttcccgaag ggagaaaggc    4500
ggacaggtat ccggtaagcg gcagggtcgg aacaggagag cgcacgaggg agcttccagg    4560
gggaaacgcc tggtatcttt atagtcctgt cgggtttcgc cacctctgac ttgagcgtcg    4620
atttttgtga tgctcgtcag ggggggcggag cctatggaaa aacgccagca acgcggcctt    4680
```

```
tttacggttc ctggcctttt gctggccttt tgctcacatg ttctttcctg cgttatcccc    4740
tgattctgtg gataaccgta ttaccgcctt tgagtgagct gataccgctc gccgcagccg    4800
aacgaccgag cgcagcgagt cagtgagcga ggaagcggaa gagcgcctga tgcggtattt    4860
tctccttacg catctgtgcg gtatttcaca ccgcataaat tccgacacca tcgaatggtg    4920 caaaacctt cgcggtatgg catgatagcg cccggaagag agtcaattca gggtggtgaa    4980
tgtgaaacca gtaacgttat acgatgtcgc agagtatgcc ggtgtctctt atcagaccgt    5040
ttcccgcgtg gtgaaccagg ccagccacgt ttctgcgaaa acgcgggaaa agtggaagc    5100 ggcgatggcg gagctgaatt acattcccaa ccgcgtggca caacaactgg cgggcaaaca    5160
gtcgttgctg attggcgttg ccacctccag tctggccctg cacgcgccgt cgcaaattgt    5220
cgcggcgatt aaatctcgcg ccgatcaact gggtgccagc gtggtggtgt cgatggtaga    5280
acgaagcggc gtcgaagcct gtaaagcggc ggtgcacaat cttctcgcgc aacgcgtcag    5340
tgggctgatc attaactatc cgctggatga ccaggatgcc attgctgtgg aagctgcctg    5400
cactaatgtt ccggcgttat tcttgatgt ctctgaccag acacccatca acagtattat    5460
tttctcccat gaagacggta cgcgactggg cgtggagcat ctggtcgcat gggtcacca    5520 gcaaatcgcg ctgttagcgg gcccattaag ttctgtctcg gcgcgtctgc gtctggctgg    5580
ctggcataaa tatctcactc gcaatcaaat tcagccgata gcggaacggg aaggcgactg    5640
gagtgccatg tccggttttc aacaaaccat gcaaatgctg aatgagggca tcgttcccac    5700
tgcgatgctg gttgccaacg atcagatggc gctgggcgca atgcgcgcca ttaccgagtc    5760
cgggctgcgc gttggtgcgg atatctcggt agtgggatac gacgataccg aagacagctc    5820
atgttatatc ccgccgttaa ccaccatcaa acaggatttt cgcctgctgg ggcaaaccag    5880
cgtggaccgc ttgctgcaac tctctcaggg ccaggcggtg aagggcaatc agctgttgcc    5940
cgtctcactg gtgaaaagaa aaaccaccct ggcgcccaat acgcaaaccg cctctccccg    6000
cgcgttggcc gattcattaa tgcagctggc acgacaggtt tcccgactgg aaagcgggca    6060
gtgagcgcaa cgcaattaat gtgagttagc tcactcatta ggcacccag ctttacact    6120 ttatgcttcc ggctcgtatg ttgtgtggaa ttgtgagcgg ataacaattt cacacaggaa    6180
acagctatga ccatgattac ggattcactg gccgtcgttt tacaacgtcg tgactgggaa    6240
aaccctggcg ttacccaact taatcgcctt gcagcacatc cccctttcgc cagctggcgt    6300
aatagcgaag aggcccgcac cgatcgccct tcccaacagt tgcgcagcct gaatggcgaa    6360
tggcgctttg cctggtttcc ggcaccagaa gcggtgccgg aaagctggct ggagtgcgat    6420
cttcctgagg ccgatactgt cgtcgtcccc tcaaactggc agatgcacgg ttacgatgcg    6480
cccatctaca ccaacgtaac ctatcccatt acggtcaatc cgccgtttgt tcccacggag    6540
aatccgacgg gttgttactc gctcacattt aatgttgatg aaagctggct acaggaaggc    6600
cagacgcgaa ttatttttga tggcgttgga att                                 6633
```

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cccaggaatt cccaggtgca cagcttcatt                                       30

<210> SEQ ID NO 64
<211> LENGTH: 6090
<212> TYPE: DNA
<213> ORGANISM: Homo sapiens

<400> SEQUENCE: 64

| | | | | | |
|---|---|---|---|---|---|
| agcttatcga | ctgcacggtg | caccaatgct | tctggcgtca | ggcagccatc | ggaagctgtg | 60 |
| gtatggctgt | gcaggtcgta | aatcactgca | taattcgtgt | cgctcaaggc | gcactcccgt | 120 |
| tctggataat | gttttttgcg | ccgacatcat | aacggttctg | gcaaatattc | tgaaatgagc | 180 |
| tgttgacaat | taatcatcgg | ctcgtataat | gtgtggaatt | gtgagcggat | aacaatttca | 240 |
| cacaggaaac | agtattcatg | tcccctatac | taggttattg | gaaaattaag | ggccttgtgc | 300 |
| aacccactcg | acttctttg | gaatatcttg | aagaaaaata | tgaagagcat | ttgtatgagc | 360 |
| gcgatgaagg | tgataaatgg | cgaaacaaaa | agtttgaatt | gggtttggag | tttcccaatc | 420 |
| ttccttatta | tattgatggt | gatgttaaat | taacacagtc | tatggccatc | atacgttata | 480 |
| tagctgacaa | gcacaacatg | ttgggtggtt | gtccaaaaga | gcgtgcagag | atttcaatgc | 540 |
| ttgaaggagc | ggttttggat | attagatacg | gtgtttcgag | aattgcatat | agtaaagact | 600 |
| ttgaaactct | caaagttgat | tttcttagca | agctacctga | aatgctgaaa | atgttcgaag | 660 |
| atcgtttatg | tcataaaaca | tatttaaatg | gtgatcatgt | aacccatcct | gacttcatgt | 720 |
| tgtatgacgc | tcttgatgtt | gttttataca | tggacccaat | gtgcctggat | gcgttcccaa | 780 |
| aattagtttg | ttttaaaaaa | cgtattgaag | ctatcccaca | aattgataag | tacttgaaat | 840 |
| ccagcaagta | tatagcatgg | cctttgcagg | gctggcaagc | cacgtttggt | ggtggcgacc | 900 |
| atcctccaaa | atcggatctg | atcgaaggtc | gtgggatccc | caggaattcc | caggtgcaca | 960 |
| gcttcattcg | ctcggcgcgc | gagcgcgaga | agcactccgc | ctgctgcgtg | cgcaacgaca | 1020 |
| ggtcgggctg | cgtgcagacc | tcggaggagg | agtgctcgtc | cacgctggca | gtgtgggtga | 1080 |
| agtggcccat | ccatcccagc | gccccagagc | ttgcgggcca | aagagacag | tttggctctg | 1140 |
| tctgccacca | ggatcccagg | gtgtgtgatg | agccctcctc | cgaagaccct | catgagtggc | 1200 |
| cagaagacat | caccaagtgg | ccgatctgca | ccaaaaacag | cgctgggaac | cacaccaacc | 1260 |
| atccccacat | ggactgtgtc | atcacaggac | ggccctgctg | cattggcacc | aagggcaggt | 1320 |
| gtgagatcac | ctcccgggag | tactgtgact | tcatgagggg | ctacttccat | gaggaggcca | 1380 |
| cgctctgctc | tcaggtgcac | tgcatggatg | atgtgtgtgg | gctcctgcct | tttctcaacc | 1440 |
| ccgaggtgcc | tgaccagttc | taccgcctgt | ggctatccct | cttcctgcac | gccgggatct | 1500 |
| tgcactgcct | ggtgtccatc | tgcttccaga | tgactgtcct | gcgggacctg | gagaagctgg | 1560 |
| caggctggca | ccgcatagcc | atcatctacc | tgctgagtgg | tgtcaccggc | aacctggcca | 1620 |
| gtgccatctt | cctgccatac | cgagcagagg | tgggtcctgc | tggctcccag | ttcggcatcc | 1680 |
| tggcctgcct | cttcgtggag | ctcttccaga | gctggcagat | cctggcgcgg | ccctggcgtg | 1740 |
| ccttcttcaa | gctgctggct | gtggtgctct | tcctcttcac | ctttgggctg | ctgccgtgga | 1800 |
| ttgacaactt | tgcccacatc | tcggggttca | tcagtgcct | cttcctctcc | ttcgccttct | 1860 |
| tgccctacat | cagctttggc | aagttcgacc | tgtaccggaa | acgctgccag | atcatcatct | 1920 |
| ttcaggtggt | cttcctgggc | ctcctggctg | gcctggtggt | cctcttctac | gtctatcctg | 1980 |
| tccgctgtga | gtggtgtgag | ttcctcacct | gcatccccc | cactgacaag | ttctgtgaga | 2040 |
| agtacgaact | ggacgctcag | ctccactgag | tcgactcgag | cggccgcatc | gtgactgact | 2100 |
| gacgatctgc | ctcgcgcgtt | tcggtgatga | cggtgaaaac | ctctgacaca | tgcagctccc | 2160 |

```
ggagacggtc acagcttgtc tgtaagcgga tgccgggagc agacaagccc gtcagggcgc    2220
gtcagcgggt gttggcgggt gtcggggcgc agccatgacc cagtcacgta gcgatagcgg    2280
agtgtataat tcttgaagac gaaagggcct cgtgatacgc ctattttat aggttaatgt     2340 catgataata atggtttctt agacgtcagg tggcactttt cggggaaatg tgcgcggaac    2400
ccctatttgt ttattttct aaatacattc aaatatgtat ccgctcatga acaataacc     2460 ctgataaatg cttcaataat attgaaaaag gaagagtatg agtattcaac atttccgtgt    2520
cgcccttatt ccctttttg cggcattttg ccttcctgtt tttgctcacc cagaaacgct    2580
ggtgaaagta aaagatgctg aagatcagtt gggtgcacga gtgggttaca tcgaactgga    2640
tctcaacagc ggtaagatcc ttgagagttt cgccccgaa gaacgttttc caatgatgag    2700
cacttttaaa gttctgctat gtggcgcggt attatcccgt gttgacgccg gcaagagca    2760 actcggtcgc cgcatacact attctcagaa tgacttggtt gagtactcac cagtcacaga    2820
aaagcatctt acggatggca tgacagtaag agaattatgc agtgctgcca taaccatgag    2880
tgataacact gcggccaact tacttctgac aacgatcgga ggaccgaagg agctaaccgc    2940
ttttttgcac aacatggggg atcatgtaac tcgccttgat cgttgggaac cggagctgaa    3000
tgaagccata ccaaacgacg agcgtgacac cacgatgcct gcagcaatgg caacaacgtt    3060
gcgcaaacta ttaactggcg aactacttac tctagcttcc cggcaacaat taatagactg    3120
gatggaggcg gataaagttg caggaccact tctgcgctcg gcccttccgg ctggctggtt    3180
tattgctgat aaatctggag ccggtgagcg tgggtctcgc ggtatcattg cagcactggg    3240
gccagatggt aagccctccc gtatcgtagt tatctacacg acggggagtc aggcaactat    3300
ggatgaacga aatagacaga tcgctgagat aggtgcctca ctgattaagc attggtaact    3360
gtcagaccaa gtttactcat atatacttta gattgattta aaacttcatt tttaatttaa    3420
aaggatctag gtgaagatcc tttttgataa tctcatgacc aaaatccctt aacgtgagtt    3480
ttcgttccac tgagcgtcag accccgtaga aaagatcaaa ggatcttctt gagatccttt    3540
ttttctgcgc gtaatctgct gcttgcaaac aaaaaaacca ccgctaccag cggtggtttg    3600
tttgccggat caagagctac caactctttt tccgaaggta actggcttca gcagagcgca    3660
gataccaaat actgtccttc tagtgtagcc gtagttaggc caccacttca agaactctgt    3720
agcaccgcct acatacctcg ctctgctaat cctgttacca gtggctgctg ccagtggcga    3780
taagtcgtgt cttaccgggt tggactcaag acgatagtta ccggataagg cgcagcggtc    3840
gggctgaacg gggggttcgt gcacacagcc cagcttggag cgaacgacct acaccgaact    3900 gagatacccta cagcgtgagc tatgagaaag cgccacgctt cccgaaggga aaaggcgga    3960 caggtatccg gtaagcggca gggtcggaac aggagagcgc acgagggagc ttccaggggg    4020
aaacgcctgg tatctttata gtcctgtcgg gtttcgccac ctctgacttg agcgtcgatt    4080
tttgtgatgc tcgtcagggg ggcggagcct atggaaaaac gccagcaacg cggcctttt    4140 acggttcctg gccttttgct ggccttttgc tcacatgttc tttcctgcgt tatcccctga    4200
ttctgtggat aaccgtatta ccgcctttga gtgagctgat accgctcgcc gcagccgaac    4260
gaccgagcgc agcgagtcag tgagcgagga agcggaagag cgcctgatgc ggtattttct    4320
ccttacgcat ctgtgcggta tttcacaccg cataaattcc gacaccatcg aatggtgcaa    4380
aacctttcgc ggtatggcat gatagcgccc ggaagagagt caattcaggg tggtgaatgt    4440
gaaaccagta acgttatacg atgtcgcaga gtatgccggt gtctcttatc agaccgtttc    4500
```

-continued

```
ccgcgtggtg aaccaggcca gccacgtttc tgcgaaaacg cgggaaaaag tggaagcggc    4560
gatggcggag ctgaattaca ttcccaaccg cgtggcacaa caactggcgg gcaaacagtc    4620
gttgctgatt ggcgttgcca cctccagtct ggccctgcac gcgccgtcgc aaattgtcgc    4680
ggcgattaaa tctcgcgccg atcaactggg tgccagcgtg gtggtgtcga tggtagaacg    4740
aagcggcgtc gaagcctgta aagcggcggt gcacaatctt ctcgcgcaac gcgtcagtgg    4800
gctgatcatt aactatccgc tggatgacca ggatgccatt gctgtggaag ctgcctgcac    4860
taatgttccg gcgttatttc ttgatgtctc tgaccagaca cccatcaaca gtattatttt    4920
ctcccatgaa gacggtacgc gactgggcgt ggagcatctg gtcgcattgg gtcaccagca    4980
aatcgcgctg ttagcgggcc cattaagttc tgtctcggcg cgtctgcgtc tggctggctg    5040 gcataaaatat ctcactcgca atcaaattca gccgatagcg gaacgggaag gcgactggag   5100
tgccatgtcc ggttttcaac aaaccatgca aatgctgaat gagggcatcg ttcccactgc    5160
gatgctggtt gccaacgatc agatggcgct gggcgcaatg cgcgccatta ccgagtccgg    5220
gctgcgcgtt ggtgcggata tctcggtagt gggatacgac gataccgaag acagctcatg    5280
ttatatcccg ccgttaacca ccatcaaaca ggattttcgc ctgctggggc aaaccagcgt    5340
ggaccgcttg ctgcaactct ctcagggcca ggcggtgaag ggcaatcagc tgttgcccgt    5400
ctcactggta aaaagaaaaa ccaccctggc gcccaatacg caaaccgcct ctccccgcgc    5460
gttggccgat tcattaatgc agctggcacg acaggtttcc cgactggaaa gcgggcagtg    5520
agcgcaacgc aattaatgtg agttagctca ctcattaggc accccaggct ttacactttá    5580 tgcttccggc tcgtatgttg tgtggaattg tgagcggata acaatttcac acaggaaaca    5640
gctatgacca tgattacgga ttcactggcc gtcgttttac aacgtcgtga ctgggaaaac    5700
cctggcgtta cccaacttaa tcgccttgca gcacatcccc ctttcgccag ctggcgtaat    5760
agcgaagagg cccgcaccga tcgcccttcc caacagttgc gcagcctgaa tggcgaatgg    5820
cgctttgcct ggtttccggc accagaagcg gtgccggaaa gctggctgga gtgcgatctt    5880
cctgaggccg atactgtcgt cgtcccctca aactggcaga tgcacggtta cgatgcgccc    5940
atctacacca acgtaaccta tcccattacg gtcaatccgc cgtttgttcc cacggagaat    6000
ccgacgggtt gttactcgct cacatttaat gttgatgaaa gctggctaca ggaaggccag    6060
acgcgaatta ttttttgatgg cgttggaatt                                   6090
```

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 65

```
cgcggcatcg atgtggagct gagcgtccag                                      30
```

<210> SEQ ID NO 66
<211> LENGTH: 6185
<212> TYPE: DNA
<213> ORGANISM: Homo sapiens

<400> SEQUENCE: 66

```
taatacgact cactataggg gaattgtgag cggataacaa ttcccctcta gacttacaat      60
ttccattcgc cattcaggct gcgcaactgt tgggaagggc gatcggtacg ggcctcttcg     120
```

```
ctattacgcc agcttgcgaa cggtgggtgc gctgcaaggc gattaagttg ggtaacgcca      180
ggattctccc agtcacgacg ttgtaaaacg acggccagca gagatcttg attggctagc      240 agaataattt tgtttaactt taagaaggag atataccatg gcgatatccc gggagctcgt      300
ggatccgaat tccatgagtg aggcccgcag ggacagcacg agcagcctgc agcgcaagaa      360
gccaccctgg ctaaagctgg acattccctc tgcggtgccc ctgacggcag aagagcccag      420
cttcctgcag cccctgaggc gacaggcttt cctgaggagt gtgagtatgc cagccgagac      480
agcccacatc tcttcacccc accatgagct ccggcggccg tgctgcaac gccagacgtc      540 catcacacag accatccgca gggggaccgc cgactggttt ggagtgagca aggacagtga      600
cagcacccag aaatggcagc gcaagagcat ccgtcactgc agccagcgct acgggaagct      660 gaagcccag gtcctccggg agctggacct gcccagccag acaacgtgt cgctgaccag       720 caccgagacg ccaccccac tctacgtggg gccatgccag ctgggcatgc agaagatcat      780
agaccccctg gcccgtggcc gtgccttccg tgtggcagat gacactgcgg aaggcctgag      840
tgccccacac actcccgtca cgccgggtgc tgcctccctc tgctccttct ccagctcccg      900
ctcaggtttc caccggctcc cgcggcgcg caagcgagag tcggtggcca agatgagctt      960
ccgggcggcc gcagcgctga tgaaaggccg ctccgttagg gatggcacct ttcgccgggc     1020
acggcgtcga agcttcactc cagctagctt tctggaggag gacacaactg atttccccga     1080
tgagctggac acatccttct ttgcccggga aggtatcctc catgaagagc tgtccacata     1140
cccggatgaa gttttcgagt ccccatcgga ggcagcgcta aaggactggg agaaggcacc     1200
ggagcaggcg gacctcaccg gcggggccct ggaccgcagc gagcttgagc gcagccacct     1260
gatgctgccc ttggagcgag gctggcggaa gcagaaggag ggcgccgcag ccccgcagcc     1320
caaggtgcgg ctccgacagg aggtggtgag caccgcgggg ccgcgacggg gccagcgtat     1380
cgcggtgccg gtgcgcaagc tcttcgcccg ggagaagcgg ccgtatgggc tgggcatggt     1440
gggacggctc accaaccgca cctaccgcaa gcgcatcgac agcttcgtca agcgccagat     1500
cgaggacatg gacgaccaca ggcccttctt cacctactgg cttaccttcg tgcactcgct     1560
cgtcaccatc ctagccgtgt gcatctatgg catcgcgccc gtgggcttct cgcagcatga     1620
gacggtggac tcggtgctgc ggaaccgcgg ggtctacgag aacgtcaagt acgtgcagca     1680
ggagaacttc tggatcgggc ccagctcgga ggccctcatc cacctgggcg ccaagttttc     1740
gccctgcatg cgccaggacc cgcaggtgca cagcttcatt cgctcggcgc gcgagcgcga     1800
gaagcactcc gcctgctgcg tgcgcaacga caggtcgggc tgcgtgcaga cctcggagga     1860
ggagtgctcg tccacgctgg cagtgtgggt gaagtggccc atccatccca gcgcccaga     1920 gcttgcgggc cacaagagac agtttggctc tgtctgccac caggatccca gggtgtgtga     1980
tgagccctcc tccgaagacc tcatgagtg ccagaagac atcaccaagt ggccgatctg      2040
caccaaaaac agcgctggga accacaccaa ccatccccac atggactgtg tcatcacagg     2100
acggccctgc tgcattggca ccaagggcag gtgtgagatc acctcccggg agtactgtga     2160
cttcatgagg ggctacttcc atgaggaggc cacgctctgc tctcaggtgc actgcatgga     2220
tgatgtgtgt gggctcctgc ttttctcaa ccccgaggtg cctgaccagt ctaccgcct       2280 gtggctatcc ctcttcctgc acgcggat cttgcactgc ctggtgtcca tctgcttcca      2340
gatgactgtc ctgcgggacc tggagaagct ggcaggctgg caccgcatag ccatcatcta     2400
cctgctgagt ggtgtcaccg gcaacctggc cagtgccatc ttcctgccat accgagcaga     2460
ggtgggtcct gctggctccc agttcggcat cctggcctgc ctcttcgtgg agctcttcca     2520
```

```
gagctggcag atcctggcgc ggccctggcg tgccttcttc aagctgctgg ctgtggtgct   2580
cttcctcttc acctttgggc tgctgccgtg gattgacaac tttgcccaca tctcggggtt   2640
catcagtggc ctcttcctct ccttcgcctt cttgccctac atcagctttg caagttcga    2700 cctgtaccgg aaacgctgcc agatcatcat ctttcaggtg gtcttcctgg gcctcctggc   2760
tggcctggtg gtcctcttct acgtctatcc tgtccgctgt gagtggtgtg agttcctcac   2820
ctgcatcccc ttcactgaca gttctgtga gaagtacgaa ctggacgctc agctccacat   2880
cgatacgcgt tcgaagcttg cggccgcaca gctgtataca cgtgcaagcc agccagaact   2940
cgctcctgaa gacccagagg atctcgagca ccaccaccac caccactaat gttaattaag   3000
ttgggcgttg taatcatagt cataatcaat actcctgact gcgttagcaa tttaactgtg   3060
ataaactacc gcattaaagc tattcgatga taagctgtca acatgataa ttcttgaaga    3120 cgaaagggcc taggctgata aaacagaatt gcctggcgg cagtagcgcg gtggtcccac    3180
ctgaccccat gccgaactca gaagtgaaac gccgtagcgc cgatggtagt gtggggtctc   3240
cccatgcgag agtagggaac tgccaggcat caaataaaac gaaaggctca gtcgaaagac   3300
tgggcctttc gttttatctg ttgtttgtcg gtgaacgctc tcctgagtag gacaaatccg   3360
ccgggagcgg atttgaacgt tgcgaagcaa cggcccggag ggtggcgggc aggacgcccg   3420
ccataaactg ccaggcatca aattaagcag aaggccatcc tgacggatgg ccttttttgcg   3480 tttctacaaa ctcttttgtt tattttttcta aatacattca aatatgtatc cgctgagcaa   3540
taactagcat aaccccttgg ggcctctaaa cgggtcttga ggggttttttt gctgaaagga   3600 ggaactatat ccggattggc gaatgggacg cgccctgtag cggcgcatta agcgcggcgg   3660
gtgtggtggt tacgcgcagc gtgaccgcta cacttgccag cgccctagcg cccgctcctt   3720
tcgctttctt cccttccttt ctcgccacgt tcgccggctt tccccgtcaa gctctaaatc   3780 ggggggctccc tttagggttc cgatttagtg ctttacggca cctcgacccc aaaaaacttg   3840
attagggtga tggttcacgt agtgggccat cgccctgata acggttttt cgccctttga    3900 cgttggagtc cacgttcttt aatagtggac tcttgttcca aactggaaca acactcaacc   3960
ctatctcggt ctattctttt gatttataag ggattttgcc gatttcggcc tattggttaa   4020
aaaatgagct gatttaacaa aaatttaacg cgaattttaa caaaatatta cgtttacaa    4080 tttctggcgg cacgatggca tgagattatc aaaaaggatc ttcacctaga tccttttaaa   4140
ttaaaaatga gttttaaat caatctaaag tatatatgag taaacttggt ctgacagtta    4200
ccaatgctta atcagtgagg cacctatctc agcgatctgt ctatttcgtt catccatagt   4260
tgcctgactc cccgtcgtgt agataactac gatacgggag gcttaccat ctggccccag    4320 tgctgcaatg ataccgcgag acccacgctc accggctcca gatttatcag caataaacca   4380
gccagccgga agggccgagc gcagaagtgg tcctgcaact ttatccgcct ccatccagtc   4440
tattaattgt tgccgggaag ctagagtaag tagttcgcca gttaatagtt tgcgcaacgt   4500
tgttgccatt gctacaggca tcgtggtgtc acgctcgtcg tttggtatgg cttcattcag   4560
ctccggttcc caacgatcaa ggcgagttac atgatccccc atgttgtgca aaaaagcggt   4620
tagctccttc ggtcctccga tcgttgtcag aagtaagttg gccgcagtgt tatcactcat   4680
ggttatggca gcactgcata attctcttac tgtcatgcca tccgtaagat gcttttctgt   4740
gactggtgag tactcaacca agtcattctg agaatagtgt atgcggcgac cgagttgctc   4800
ttgcccggcg tcaatacggg ataataccgc gccacatagc agaactttaa aagtgctcat   4860
```

```
cattggaaaa cgttcttcgg ggcgaaaact ctcaaggatc ttaccgctgt tgagatccag    4920
ttcgatgtaa cccactcgtg cacccaactg atcttcagca tcttttactt tcaccagcgt    4980
ttctgggtga gcaaaaacag gaaggcaaaa tgccgcaaaa aagggaataa gggcgacacg    5040
gaaatgttga atactcatac tcttcctttt tcaatcatga ccaaaatccc ttaacgtgag    5100
ttttcgttcc actgagcgtc agaccccgta gaaaagatca aaggatcttc ttgagatcct    5160
ttttttctgc gcgtaatctg ctgcttgcaa acaaaaaaac caccgctacc agcggtggtt    5220
tgtttgccgg atcaagagct accaactctt tttccgaagg taactggctt cagcagagcg    5280
cagataccaa atactgtcct tctagtgtag ccgtagttag gccaccactt caagaactct    5340
gtagcaccgc ctacatacct cgctctgcta atcctgttac cagtggctgc tgccagtggc    5400
gataagtcgt gtcttaccgg gttggactca agacgatagt taccggataa ggcgcagcgg    5460
tcgggctgaa cggggggttc gtgcacacag cccagcttgg agcgaacgac ctacaccgaa    5520
ctgagatacc tacagcgtga gctatgagaa agcgccacgc ttcccgaagg agaaaggcg     5580 gacaggtatc cggtaagcgg cagggtcgga acaggagagc gcacgaggga gcttccaggg    5640
ggaaacgcct ggtatcttta tagtcctgtc gggtttcgcc acctctgact tgagcgtcga    5700
tttttgtgat gctcgtcagg gggcggagc ctatggaaaa acgccagcaa cgcggccttt     5760
ttacggttcc tggccttttg ctggcctttt gctcacatgt tctttcctgc gttatcccct    5820
gattctgtgg ataaccgtat taccgccttt gagtgagctg ataccgctcg ccgcagccga    5880
acgaccgagc gcagcgagtc agtgagcgag gaagccggcg ataatggcct gcttctcgcc    5940
gaaacgtttg gtggcgggac cagtgacgaa ggcttgagcg agggcgtgca agattccgaa    6000
taccgcaagc gacaggccga tcatcgtcgc gctccagcga aagcggtcct cgccgaaaat    6060
gacccagagc gctgccggca cctgtcctac gagttgcatg ataaagaaga cagtcataag    6120
tgcggcgacg accggtgaat tgtgagcgct cacaattctc gtgacatcat aacgtcccgc    6180
gaaat                                                                6185

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cgcggcatcg atgtccatgt cctcgatctg                                        30

<210> SEQ ID NO 68
<211> LENGTH: 4820
<212> TYPE: DNA
<213> ORGANISM: Homo sapiens

<400> SEQUENCE: 68
taatacgact cactataggg gaattgtgag cggataacaa ttcccctcta gacttacaat        60
ttccattcgc cattcaggct gcgcaactgt tgggaagggc gatcggtacg ggcctcttcg       120
ctattacgcc agcttgcgaa cggtgggtgc gctgcaaggc gattaagttg ggtaacgcca       180
ggattctccc agtcacgacg ttgtaaaacg acggccagcg agagatcttg attggctagc       240
agaataattt tgtttaactt taagaaggag atataccatg gcgatatccc gggagctcgt       300
ggatccgaat tccatgagtg aggcccgcag ggacagcacg agcagcctgc agcgcaagaa       360
```

```
gccaccctgg ctaaagctgg acattccctc tgcggtgccc ctgacggcag aagagcccag    420
cttcctgcag cccctgaggc gacaggcttt cctgaggagt gtgagtatgc cagccgagac    480
agcccacatc tcttcacccc accatgagct ccggcggccg tgctgcaac gccagacgtc     540 catcacacag accatccgca gggggaccgc cgactggttt ggagtgagca aggacagtga    600
cagcacccag aaatggcagc gcaagagcat ccgtcactgc agccagcgct acgggaagct    660 gaagcccag gtcctccggg agctggacct gcccagccag acaacgtgt cgctgaccag      720 caccgagacg ccaccccac tctacgtggg gccatgccag ctgggcatgc agaagatcat     780 agacccctg gcccgtggcc gtgccttccg tgtggcagat gacactgcgg aaggcctgag     840
tgccccacac actcccgtca cgccgggtgc tgcctccctc tgctccttct ccagctcccg    900
ctcaggtttc caccggctcc cgcggcgcg caagcgagag tcggtggcca agatgagctt     960
ccgggcggcc gcagcgctga tgaaaggccg ctccgttagg gatggcacct ttcgccgggc   1020
acggcgtcga agcttcactc cagctagctt tctggaggag acacaactg atttccccga    1080 tgagctggac acatccttct ttgcccggga aggtatcctc catgaagagc tgtccacata   1140
cccggatgaa gttttcgagt ccccatcgga ggcagcgcta aaggactggg agaaggcacc   1200
ggagcaggcg gacctcaccg gcggggccct ggaccgcagc gagcttgagc gcagccacct   1260
gatgctgccc ttggagcgag gctggcggaa gcagaaggag ggcgccgcag ccccgcagcc   1320
caaggtgcgg ctccgacagg aggtggtgag caccgcgggg ccgcgacggg gccagcgtat   1380
cgcggtgccg gtgcgcaagc tcttcgcccg ggagaagcgg ccgtatgggc tgggcatggt   1440
gggacggctc accaaccgca cctaccgcaa gcgcatcgac agcttcgtca gcgccagat    1500 cgaggacatg gacatcgata cgcgttcgaa gcttgcggcc gcacagctgt atacacgtgc   1560
aagccagcca gaactcgctc ctgaagaccc agaggatctc gagcaccacc accaccacca   1620
ctaatgttaa ttaagttggg cgttgtaatc atagtcataa tcaatactcc tgactgcgtt   1680
agcaatttaa ctgtgataaa ctaccgcatt aaagctattc gatgataagc tgtcaaacat   1740
gataattctt gaagacgaaa gggcctaggc tgataaaaca gaatttgcct ggcggcagta   1800
gcgcggtggt cccacctgac cccatgccga actcagaagt gaaacgccgt agcgccgatg   1860
gtagtgtggg gtctccccat gcgagagtag ggaactgcca ggcatcaaat aaaacgaaag   1920
gctcagtcga aagactgggc ctttcgtttt atctgttgtt tgtcggtgaa cgctctcctg   1980
agtaggacaa atccgccggg agcggatttg aacgttgcga agcaacggcc cggagggtgg   2040
cgggcaggac gcccgccata aactgccagg catcaaatta agcagaaggc catcctgacg   2100
gatggccttt ttgcgtttct acaaactctt tgtttatttt tctaaatac attcaaatat     2160 gtatccgctg agcaataact agcataaccc cttgggcct ctaaacgggt cttgaggggt    2220 ttttgctga aggaggaac tatatccgga ttggcgaatg gacgcgccc tgtagcggcg      2280 cattaagcgc ggcgggtgtg gtggttacgc gcagcgtgac cgctacactt gccagcgccc    2340
tagcgcccgc tcctttcgct ttcttccctt cctttctcgc cacgttcgcc ggctttcccc    2400
gtcaagctct aaatcggggg ctccctttag ggttccgatt tagtgcttta cggcacctcg    2460
accccaaaaa acttgattag ggtgatggtt cacgtagtgg gccatcgccc tgatagacgg    2520
tttttcgccc tttgacgttg gagtccacgt tctttaatag tggactcttg ttccaaactg    2580
gaacaacact caaccctatc tcggtctatt cttttgattt ataagggatt ttgccgattt    2640
cggcctattg gttaaaaaat gagctgattt aacaaaaatt taacgcgaat tttaacaaaa    2700
tattaacgtt tacaatttct ggcggcacga tggcatgaga ttatcaaaaa ggatcttcac    2760
```

-continued

```
ctagatccttt taaattaaa aatgaagttt taaatcaatc taaagtatat atgagtaaac   2820
ttggtctgac agttaccaat gcttaatcag tgaggcacct atctcagcga tctgtctatt   2880
tcgttcatcc atagttgcct gactccccgt cgtgtagata actacgatac gggagggctt   2940
accatctggc cccagtgctg caatgatacc gcgagaccca cgctcaccgg ctccagattt   3000
atcagcaata aaccagccag ccggaagggc cgagcgcaga agtggtcctg caactttatc   3060
cgcctccatc cagtctatta attgttgccg ggaagctaga gtaagtagtt cgccagttaa   3120
tagtttgcgc aacgttgttg ccattgctac aggcatcgtg gtgtcacgct cgtcgtttgg   3180
tatggcttca ttcagctccg gttcccaacg atcaaggcga gttacatgat cccccatgtt   3240
gtgcaaaaaa gcggttagct ccttcggtcc tccgatcgtt gtcagaagta agttggccgc   3300
agtgttatca ctcatggtta tggcagcact gcataattct cttactgtca tgccatccgt   3360
aagatgcttt tctgtgactg gtgagtactc aaccaagtca ttctgagaat agtgtatgcg   3420
gcgaccgagt tgctcttgcc cggcgtcaat acgggataat accgcgccac atagcagaac   3480
tttaaaagtg ctcatcattg gaaaacgttc ttcggggcga aaactctcaa ggatcttacc   3540
gctgttgaga tccagttcga tgtaacccac tcgtgcaccc aactgatctt cagcatcttt   3600
tactttcacc agcgtttctg ggtgagcaaa aacaggaagg caaaatgccg caaaaaaggg   3660
aataagggcg acacggaaat gttgaatact catactcttc ctttttcaat catgaccaaa   3720
atcccttaac gtgagttttc gttccactga gcgtcagacc ccgtagaaaa gatcaaagga   3780
tcttcttgag atcctttttt tctgcgcgta atctgctgct tgcaaacaaa aaaaccaccg   3840
ctaccagcgg tggtttgttt gccggatcaa gagctaccaa ctcttttttcc gaaggtaact   3900
ggcttcagca gagcgcagat accaaatact gtccttctag tgtagccgta gttaggccac   3960
cacttcaaga actctgtagc accgcctaca tacctcgctc tgctaatcct gttaccagtg   4020
gctgctgcca gtggcgataa gtcgtgtctt accgggttgg actcaagacg atagttaccg   4080
gataaggcgc agcggtcggg ctgaacgggg ggttcgtgca cacagcccag cttggagcga   4140
acgacctaca ccgaactgag atacctacag cgtgagctat gagaaagcgc cacgcttccc   4200
gaagggagaa aggcggacag gtatccggta agcggcaggg tcggaacagg agagcgcacg   4260
agggagcttc caggggggaaa cgcctggtat ctttatagtc ctgtcgggtt tcgccacctc   4320
tgacttgagc gtcgattttt gtgatgctcg tcagggggc ggagcctatg gaaaaacgcc   4380
agcaacgcgg cctttttacg gttcctggcc ttttgctggc cttttgctca catgttcttt   4440
cctgcgttat cccctgattc tgtggataac cgtattaccg cctttgagtg agctgatacc   4500
gctcgccgca gccgaacgac cgagcgcagc gagtcagtga gcgaggaagc cggcgataat   4560
ggcctgcttc tcgccgaaac gtttggtggc gggaccagtg acgaaggctt gagcgagggc   4620
gtgcaagatt ccgaataccg caagcgacag gccgatcatc gtcgcgctcc agcgaaagcg   4680
gtcctcgccg aaaatgaccc agagcgctgc cggcacctgt cctacgagtt gcatgataaa   4740
gaagacagtc ataagtgcgg cgacgaccgg tgaattgtga gcgctcacaa ttctcgtgac   4800
atcataacgt cccgcgaaat                                                4820
```

<210> SEQ ID NO 69
<211> LENGTH: 4736
<212> TYPE: DNA
<213> ORGANISM: Homo sapiens

<400> SEQUENCE: 69

```
taatacgact cactataggg gaattgtgag cggataacaa ttccctctcta gacttacaat    60
ttccattcgc cattcaggct gcgcaactgt tgggaagggc gatcggtacg ggcctcttcg   120
ctattacgcc agcttgcgaa cggtgggtgc gctgcaaggc gattaagttg ggtaacgcca   180
ggattctccc agtcacgacg ttgtaaaacg acggccagcg agagatcttg attggctagc   240
agaataattt tgtttaactt taagaaggag atataccatg gcgatatccc gggagctcgt   300
ggatccgaat tcccaggtgc acagcttcat tcgctcggcg cgcgagcgcg agaagcactc   360
cgcctgctgc gtgcgcaacg acaggtcggg ctgcgtgcag acctcggagg aggagtgctc   420
gtccacgctg gcagtgtggg tgaagtggcc catccatccc agcgcccag agcttgcggg    480
ccacaagaga cagtttggct ctgtctgcca ccaggatccc agggtgtgtg atgagccctc   540
ctccgaagac cctcatgagt ggccagaaga catcaccaag tggccgatct gcaccaaaaa   600
cagcgctggg aaccacacca accatcccca catggactgt gtcatcacag acggccctg    660
ctgcattggc accaagggca ggtgtgagat cacctcccgg gagtactgtg acttcatgag   720
gggctacttc catgaggagg ccacgctctg ctctcaggtg cactgcatgg atgatgtgtg   780
tgggctcctg ccttttctca accccgaggt gcctgaccag ttctaccgcc tgtggctatc   840
cctcttcctg cacgccggga tcttgcactg cctggtgtcc atctgcttcc agatgactgt   900
cctgcgggac ctggagaagc tggcaggctg gcaccgcata gccatcatct acctgctgag   960
tggtgtcacc ggcaacctgg ccagtgccat cttcctgcca taccgagcag aggtgggtcc  1020
tgctggctcc cagttcggca tcctggcctg cctcttcgtg gagctcttcc agagctggca  1080
gatcctggcg cggccctggc gtgccttctt caagctgctg gctgtggtgc tcttcctctt  1140
cacctttggg ctgctgccgt ggattgacaa ctttgcccac atctcggggt tcatcagtgg  1200
cctcttcctc tccttcgcct tcttgcccta catcagcttt ggcaagttcg acctgtaccg  1260
gaaacgctgc cagatcatca tctttcaggt ggtcttcctg ggcctcctgg ctggcctggt  1320
ggtcctcttc tacgtctatc ctgtccgctg tgagtggtgt gagttcctca cctgcatccc  1380
cttcactgac aagttctgtg agaagtacga actggacgct cagctccaca tcgatacgcg  1440
ttcgaagctt gcggccgcac agctgtatac acgtgcaagc cagccagaac tcgctcctga  1500
agacccagag gatctcgagc accaccacca ccaccactaa tgttaattaa gttgggcgtt  1560
gtaatcatag tcataatcaa tactcctgac tgcgttagca atttaactgt gataaactac  1620
cgcattaaag ctattcgatg ataagctgtc aaacatgata attcttgaag acgaaagggc  1680
ctaggctgat aaaacagaat ttgcctggcg gcagtagcgc ggtggtccca cctgacccca  1740
tgccgaactc agaagtgaaa cgccgtagcg ccgatggtag tgtggggtct cccatgcga   1800
gagtagggaa ctgccaggca tcaaataaaa cgaaaggctc agtcgaaaga ctgggccttt  1860
cgttttatct gttgtttgtc ggtgaacgct ctcctgagta ggacaaatcc gccggagcg   1920
gatttgaacg ttgcgaagca acggcccgga gggtggcggg caggacgccc gccataaact  1980
gccaggcatc aaattaagca gaaggccatc ctgacggatg cctttttgc gtttctacaa   2040
actctttgt tatttttct aaatacattc aaatatgtat ccgctgagca ataactagca   2100
taacccttg gggcctctaa acgggtcttg aggggttttt tgctgaaagg aggaactata   2160
tccggattgg cgaatgggac gcgccctgta gcggcgcatt aagcgcggcg ggtgtggtgg  2220
ttacgcgcag cgtgaccgct acacttgcca gcgccctagc gcccgctcct ttcgctttct  2280
tcccttcctt tctcgccacg ttcgccggct tccccgtcca agctctaaat cgggggctcc  2340
ctttagggtt ccgatttagt gctttacggc acctcgaccc caaaaaactt gattagggtg  2400
```

```
atggttcacg tagtgggcca tcgccctgat agacggtttt tcgcccttttg acgttggagt    2460
ccacgttctt taatagtgga ctcttgttcc aaactggaac aacactcaac cctatctcgg    2520
tctattctt  tgatttataa gggattttgc cgatttcggc ctattggtta aaaaatgagc    2580
tgatttaaca aaaatttaac gcgaatttta acaaaatatt aacgtttaca atttctggcg    2640
gcacgatggc atgagattat caaaaaggat cttcacctag atccttttaa attaaaaatg    2700
aagttttaaa tcaatctaaa gtatatatga gtaaacttgg tctgacagtt accaatgctt    2760
aatcagtgag gcacctatct cagcgatctg tctatttcgt tcatccatag ttgcctgact    2820
ccccgtcgtg tagataacta cgatacggga gggcttacca tctgcccca  gtgctgcaat    2880
gataccgcga gacccacgct caccggctcc agatttatca gcaataaacc agccagccgg    2940
aagggccgag cgcagaagtg gtcctgcaac tttatccgcc tccatccagt ctattaattg    3000
ttgccgggaa gctagagtaa gtagttcgcc agttaatagt ttgcgcaacg ttgttgccat    3060
tgctacaggc atcgtggtgt cacgctcgtc gtttggtatg gcttcattca gctccggttc    3120
ccaacgatca aggcgagtta catgatcccc catgttgtgc aaaaaagcgg ttagctcctt    3180
cggtcctccg atcgttgtca gaagtaagtt ggccgcagtg ttatcactca tggttatggc    3240
agcactgcat aattctctta ctgtcatgcc atccgtaaga tgcttttctg tgactggtga    3300
gtactcaacc aagtcattct gagaatagtg tatgcggcga ccgagttgct cttgcccggc    3360
gtcaatacgg gataataccg cgccacatag cagaacttta aaagtgctca tcattggaaa    3420
acgttcttcg gggcgaaaac tctcaaggat cttaccgctg ttgagatcca gttcgatgta    3480
acccactcgt gcacccaact gatcttcagc atcttttact ttcaccagcg tttctgggtg    3540
agcaaaaaca ggaaggcaaa atgccgcaaa aaagggaata agggcgacac ggaaatgttg    3600
aatactcata ctcttccttt ttcaatcatg accaaaatcc cttaacgtga gttttcgttc    3660
cactgagcgt cagaccccgt agaaaagatc aaaggatctt cttgagatcc ttttttttctg    3720
cgcgtaatct gctgcttgca acaaaaaaa  ccaccgctac cagcggtggt ttgtttgccg    3780
gatcaagagc taccaactct ttttccgaag gtaactggct tcagcagagc gcagatacca    3840
aatactgtcc ttctagtgta gccgtagtta ggccaccact tcaagaactc tgtagcaccg    3900
cctacatacc tcgctctgct aatcctgtta ccagtggctg ctgccagtgg cgataagtcg    3960
tgtcttaccg ggttggactc aagacgatag ttaccggata aggcgcagcg gtcgggctga    4020
acggggggtt cgtgcacaca gcccagcttg gagcgaacga cctacaccga actgagatac    4080
ctacagcgtg agctatgaga aagcgccacg cttcccgaag ggagaaaggc ggacaggtat    4140
ccggtaagcg gcagggtcgg aacaggagag cgcacgaggg agcttccagg gggaaacgcc    4200
tggtatcttt atagtcctgt cgggtttcgc cacctctgac ttgagcgtcg attttttgtga   4260
tgctcgtcag gggggcggag cctatggaaa aacgccagca acgcggcctt tttacggttc    4320
ctggcctttt gctggccttt tgctcacatg ttctttcctg cgttatcccc tgattctgtg    4380
gataaccgta ttaccgcctt tgagtgagct gataccgctc gccgcagccg aacgaccgag    4440
cgcagcgagt cagtgagcga ggaagccggc gataatggcc tgcttctcgc cgaaacgttt    4500
ggtggcggga ccagtgacga aggcttgagc gagggcgtgc aagattccga ataccgcaag    4560
cgacaggccg atcatcgtcg cgctccagcg aaagcggtcc tcgccgaaaa tgacccagag    4620
cgctgccggc acctgtccta cgagttgcat gataaagaag acagtcataa gtgcggcgac    4680
gaccggtgaa ttgtgagcgc tcacaattct cgtgacatca taacgtcccg cgaaat        4736
```

<210> SEQ ID NO 70

<400> SEQUENCE: 70

000

<210> SEQ ID NO 71

<400> SEQUENCE: 71

000

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aatctgatga tgaagctgca g                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aactgttgag gagcccatgg a                                              21

<210> SEQ ID NO 74

<400> SEQUENCE: 74

000

<210> SEQ ID NO 75

<400> SEQUENCE: 75

000

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Leu Trp Val Leu Gly Leu Cys Cys
 1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

```
Val Leu Gly Leu Cys Cys Val Leu Leu
 1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Leu His Val Thr Asp Thr Gly Val
 1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Glu Leu Ile Gly Gln Phe Gly Val
 1               5

<210> SEQ ID NO 80
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Asp Asp Glu Val Asp Val Asp Gly Thr Val Glu Glu Asp Leu Gly
 1               5                  10                  15

Lys Ser Arg Glu Gly Ser Arg Thr Asp Asp Glu Val Val Gln
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Ala Phe Leu Val Ala Asp Lys Val Ile Val Thr Ser Lys His Asn
 1               5                  10                  15

Asn Asp Thr Gln His Ile Trp Glu Ser Asp Ser Asn Glu Phe
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Glu Lys Thr Lys Glu Ser Arg Glu Ala Val Glu Lys Glu Phe Glu
 1               5                  10                  15
```

```
Pro Leu Leu Asn Trp Met Lys Asp Lys Ala Leu Lys Asp Lys
            20                  25                  30

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met Met Pro Lys Tyr Leu Asn Phe Val
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 84

Lys Leu Tyr Val Arg Arg Val Phe Ile
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Leu Leu Lys Lys Gly Tyr Glu Val
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Phe Leu Val Ala Asp Lys Val Ile Val
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Leu His Val Thr Asp Thr Gly Val
1               5

<210> SEQ ID NO 88
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 88

Lys Glu Ala Glu Ser Ser Pro Phe Val
 1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Leu Thr Glu Ser Pro Cys Ala Leu
 1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Thr Phe Lys Ser Ile Leu Phe Val
 1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Leu Trp Val Leu Gly Leu Cys Cys
 1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Leu Gly Leu Cys Cys Val Leu Leu
 1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Glu Leu Ile Gly Gln Phe Gly Val
 1               5
```

```
<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Met Leu Arg Leu Ser Leu Asn Ile
 1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Gln Gln His Lys Leu Leu Lys Val
 1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Val Trp Ser Ser Lys Thr Glu Thr
 1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Glu Leu Asp Thr Ile Lys Asn Leu
 1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Phe Ile Thr Asp Asp Phe His Asp Met
 1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99
```

```
Lys Thr Leu Asp Met Ile Lys Lys Ile
  1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Leu Val Arg Lys Thr Leu Asp Met
  1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Tyr Leu Asn Phe Val Lys Gly Val Val
  1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Val Gly Phe Tyr Ser Ala Phe Leu Val
  1               5

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Lys Asp Glu Leu
  1

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 104

Gly Ala Ser Gly Gly
  1               5

<210> SEQ ID NO 105
<211> LENGTH: 5
<212> TYPE: PRT
<213> ORGANISM: Artificial Sequence
```

<220> FEATURE:
<223> OTHER INFORMATION: Description of Artificial Sequence: Synthetic
      peptide motif

<400> SEQUENCE: 105

Gly Asp Ser Gly Gly
1               5

<210> SEQ ID NO 106
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Trp Leu Thr Phe Val His Ser Leu Val Thr Ile Leu Ala Val Cys Ile
1               5                   10                  15

Tyr Gly Ile Ala Pro Val Gly
            20

<210> SEQ ID NO 107
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Trp Leu Ser Leu Phe Leu His Ala Gly Ile Leu His Cys Leu Val
1               5                   10                  15

Ser Ile Cys Phe Gln Met Thr
            20

<210> SEQ ID NO 108
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Ser Gly Val Thr Gly Asn Leu Ala Ser Ala Ile Phe Leu Pro Tyr
1               5                   10                  15

Arg Ala Glu Val Gly Pro Ala
            20

<210> SEQ ID NO 109
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Trp Arg Ala Phe Phe Lys Leu Leu Ala Val Val Leu Phe Leu Phe Thr
1               5                   10                  15

Phe Gly Leu Leu Pro Trp Ile
            20

<210> SEQ ID NO 110

-continued

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ile Ser Gly Phe Ile Ser Gly Leu Phe Leu Ser Phe Ala Phe Leu Pro
1               5                   10                  15

Tyr Ile Ser Phe Gly Lys
            20

<210> SEQ ID NO 111
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Ile Ile Ile Phe Gln Val Val Phe Leu Gly Leu Leu Ala Gly Leu
1               5                   10                  15

Val Val Leu Phe Tyr Val Tyr
            20
```

TARGETS FOR TUMOR GROWTH INHIBITION

This application is a national stage application under 35 U.S.C. § 371 of International Application PCT/US04/10059, filed Apr. 1, 2004, which claims priority from U.S. Provisional Application 60/489,504, filed Jul. 24, 2003 and from U.S. Provisional Application 60/458,948, filed Apr. 1, 2003.

FIELD OF THE INVENTION

The present invention relates to methods for treating diseases by manipulating activity or expression of validated cancer drug targets, where the targets have been validated by methods manipulating target gene expression in animal disease models. More specifically, the invention relates to up-regulation, silencing, inhibition and/or down-regulation of targets such as ICT1024, ICT1025, ICT1030, ICTB1031 and ICBT1003 that are validated using siRNA. The invention pertains to methods that are useful in treating cancers and/or inhibiting tumor growth by enhancing expression of a gene that is validated as target ICT1030 for protein, peptide and gene therapy drug modalities, or by RNA interference to silence and/or down-regulate genes that are validated as targets ICT1024, ICT1025, ICT1031 and ICT1003, for antibody, small molecule and other inhibitor drug modalities.

BACKGROUND OF THE INVENTION

Cancer or pre-cancerous growth generally refers to malignant tumors, rather than benign tumors. Benign tumor cells are similar to normal, surrounding cells. Treatment becomes necessary only when the tumors grow large enough to interfere with other organs. Malignant tumors, by contrast, grow faster than benign tumors, and they penetrate and destroy local tissues. Some malignant tumors may spread throughout the body via blood or the lymphatic system. The unpredictable and uncontrolled growth makes malignant cancers dangerous, and fatal in many cases. These tumors are not morphologically typical of the original tissue and are not encapsulated. Malignant tumors commonly recur after surgical removal.

Many human diseases are a result of proliferative cellular pathologies. Cancer or pre-cancerous growth is frequently a consequence of proliferative cellular pathologies and generally refers to malignant tumors, rather than benign tumors. Benign tumor cells are similar to normal, surrounding cells. Treatment becomes necessary only when the tumors grow large enough to interfere with other organs. Malignant tumors, by contrast, grow faster than benign tumors, and they penetrate and destroy local tissues. Some malignant tumors may spread throughout the body via blood or the lymphatic system, and their unpredictable and uncontrolled growth makes malignant cancers dangerous, and fatal in many cases. Such tumors are not morphologically typical of the original tissue and are not encapsulated. Malignant tumors commonly recur after surgical removal. Accordingly, treatment of proliferative diseases ordinarily targets proliferative cellular activities such as occur in malignant cancers or malignant tumors with a goal to intervene in the proliferative processes.

The inhibition or prevention of malignant growth is most effective at the early stage of the cancer development. It is important, therefore, to identify and validate molecular targets that play a role in proliferative processes and their induction and, in malignant diseases in particular, early signs of tumor formation. A particular goal is to determine potent tumor growth or gene expression suppression elements or agents associated therewith. The development of such tumor growth and/or gene expression and therapeutic elements or agents involves an understanding of the genetic control mechanisms for cell division and differentiation, particularly in connection with tumorigenesis. Unfortunately, the number of established protein targets that are suitable for intervention in proliferative disease is limiting. Of the small number of established targets, such as growth factors like EGF and its receptor, few, if any, permit adequate intervention in proliferative diseases such as malignant cancer and psoriasis.

Moreover, it has proven difficult to identify better targets for intervention in cellular proliferative pathologies. Large numbers of genes and proteins exist within the human genome and many of these genes and proteins, as well as post-translationally modified forms of the proteins, correlate with cellular proliferative pathologies. Of these many genes, proteins, and post-translationally modified proteins, only a few specific factors can be targeted to effectively intervene in cellular proliferative pathologies. Therefore, identification of these specific factors is needed. In addition to a need to identify specific genes, proteins, and post-translationally modified proteins to target to intervene in proliferative cellular pathologies, another problem is a need to confirm that the targeted factor indeed provides effective intervention within the active pathology within active pathological tissues. Unfortunately, proliferation of cells in cell culture conditions shows many factors can be targeted but most ultimately do not prove effective as intervention targets in active pathological tissues. Consequently, accurate identification of targets for effective intervention in proliferative cellular pathologies requires study of active pathological tissues such as in animal models of human disease.

Accordingly, treatment ordinarily targets malignant cancers or malignant tumors. The intervention of malignant growth is most effective at the early stage of the cancer development. It is thus exceedingly important to identify and validate a target for early signs of tumor formation and to determine potent tumor growth or gene expression suppression elements or agents associated therewith. The development of such tumor growth and/or gene expression and therapeutic elements or agents involves an understanding of the genetic control mechanisms for cell division and differentiation, particularly in connection with tumorigenesis.

RNA interference (RNAi) is a post-transcriptional process where the double-stranded RNA (dsRNA) inhibits gene expression in a sequence specific fashion. The RNAi process occurs in at least two steps: in first step, the longer dsRNA is cleaved by an endogenous ribonuclease into shorter, less than 100-, 50-, 30-, 23-, or 21-nucleotide-long dsRNAs, termed "small interfering RNAs" or siRNAs. In second step, the smaller siRNAs mediate the degradation of the target mRNA molecule. This RNAi effect can be achieved by introducing either longer dsRNA or shorter siRNA to the target sequence within cells. It is also demonstrated that RNAi effect can be achieved by introducing plasmids that generate dsRNA complementary to target gene.

The RNAi have been sucessfully used in gene function determination in Drosophila (Kennerdell et al. (2000) Nature Biotech 18: 896-898; Worby et al. (2001) *Sci STKE* Aug. 14, 2001 (95):PL1; Schmid et al. (2002) *Trends Neurosci* 25(2): 71-74; Hammond et al. (2000). Nature, 404: 293-298), C. elegans (Tabara et al. (1998) Science 282: 430-431; Kamath et al. (2000) Genome Biology 2: 2.1-2.10; Grishok et al. (2000) Science 287: 2494-2497), and Zebrafish (Kennerdell et al. (2000) *Nature Biotech* 18: 896-898). In those model organisms, it has been reported that both the chemically synthesized shorter siRNA or in vitro transcribed longer dsRNA can effectively inhibit target gene expression. There are increasing reports on successfully achieved RNAi effects in non-human mammalian and human cell cultures (Manche et al. (1992). *Mol. Cell. Biol.* 12:5238-5248; Minks et al. (1979). *J. Biol. Chem.* 254:10180-10183; Yang et al. (2001) *Mol. Cell. Biol.* 21(22):7807-7816; Paddison et al. (2002). *Proc. Natl. Acad. Sci.* USA 99(3):1443-1448; Elbashir et al. (2001) *Genes Dev* 15(2):188-200; Elbashir et al. (2001) *Nature* 411: 494-498; Caplen et al. (2001) *Proc. Natl. Acad. Sci.* USA 98: 9746-9747; Holen et al. (2002) *Nucleic Acids Research* 30(8): 1757-1766; Elbashir et al. (2001) *EMBO J* 20: 6877-6888; Jarvis et al. (2001) *TechNotes* 8(5): 3-5; Brown et al. (2002) *TechNotes* 9(1): 3-5; Brummelkamp et al. (2002) *Science* 296:550-553; Lee et al. (2002) *Nature Biotechnol.* 20:500-505; Miyagishi et al. (2002) *Nature Biotechnol.* 20:497-500; Paddison et al. (2002) *Genes & Dev.* 16:948-958; Paul et al. (2002) *Nature Biotechnol.* 20:505-508; Sui et al. (2002) *Proc. Natl. Acad. Sci.* USA 99(6):5515-5520; Yu et al. (2002) *Proc. Natl. Acad. Sci.* USA 99(9):6047-6052).

EGFR-RP (Validated Target ICT1024): Homo sapiens Epithelial growth factor receptor-related protein, EGFR-RP or EGFR-RS is published GenBank accession nos. are AK026010, NM_022450, BC014425, AK056708 and M99624.

All eukaryotic cells contain elaborate systems of internal membranes which set up various membrane-enclosed compartments within the cell. The plasma membrane serves as the interface between the machinery in the interior of the cell and the extracellular fluid (ECF) that bathes all cells. Cell membranes are built from lipids and proteins. The lipids in the plasma membrane are chiefly phospholipids like phosphatidyl ethanolamine and cholesterol. Phospholipids are amphiphilic with the hydrocarbon tail of the molecule being hydrophobic; its polar head hydrophilic. As the plasma membrane faces watery solutions on both sides, its phospholipids accommodate this by forming a phospholipid bilayer with the hydrophobic tails facing each other. Many of the proteins associated with the plasma membrane are tightly bound to it. Some are attached to lipids in the bilayer, and others are transmembrane proteins —the polypeptide chain actually traverses the lipid bilayer.

All membrane proteins have a specific upside-down or right-side-up orientation in the bilayer. Some proteins are anchored to the membrane by ionic interactions between residues with positively charged side chains and negatively charged lipid head groups since biological membranes tend to have a net negative charge. Other proteins are anchored by post-synthetic attachment of a hydrocarbon chain such as myristoyl, palmitoyl, farnesyl or gerenyl-gerenyl, or a lipid such as glycosylphosphatidylinositol (GPI) which confines them in regions close to their protein partners. Other proteins are anchored to the surface by ionic contacts. The term monotopic or peripheral membrane protein refers to proteins that have a fairly shallow penetration of the membrane surface. Many peripheral proteins can be released from the membrane by increasing the ionic strength of the solution. A second category of membrane proteins is integral or transmembrane bitopic or multitopic proteins. These proteins can only be released from the membrane by bilayer disruption with detergents.

Many transmembrane proteins that are structurally related are also functionally related. For example, the EGF (epidermal growth factor receptor) and the insulin receptor fall into a family of growth factor receptors which have very large disulfide-rich extracellular and a tyrosine kinase intracellular domains connected by a single-transmembrane helix. Most members of this family are monomers and binding of ligand induces dimerization and activation of the intracellular tyrosine kinase domain. The insulin receptor is a dimer in its non-ligand bound state and it is possible that in this case the binding of insulin changes the intersubunit orientation of the monomers, allowing for activation.

Another important family of transmembrane proteins is the seven transmembrane family of G proteins (guanine nucleotide binding proteins) coupled receptors. These receptors are the most abundant class of receptors in mammalian cells and mediate an extremely diverse range of signals into the cell, from light (rhodopsin) to neurotransmitters (muscarinic or adrenergic receptors) to sex-related signals (oxytocin). Although their ligand activators are diverse, these receptors all couple to G proteins to transduce their signal. Structurally, they are similar in having seven transmembrane loops in a defined topology. In contrast to the growth factor receptor family, these proteins have relatively small extramembrane loops.

Integral membrane proteins that transport species such as nutrients and ions must be able to shield their ligands from the surrounding hydrocarbon interior. Thus, these proteins are much larger than the signal transduction proteins mentioned above, and often contain several subunits. An example of this class is the 12 membrane spanning family belonging to transporters, such as GLUT1 and antibiotics. A newly identified family of integral membrane proteins, Rhomboid family, is exemplified by the rhomboid (RHO) protein from Drosophila melanogaster, a developmental regulator involved in epidermal growth factor (EGF)-dependent signaling pathways (1, 2, 3). Not only were homologs of rhomboid detected in prokaryotes and eukaryotes, but the pattern of sequence conservation in this family appeared uncharacteristic of nonenzymatic membrane proteins, such as transporters (4, 5). Specifically, several polar amino-acid residues are conserved in nearly all members of the rhomboid family, suggesting the possibility of an enzymatic activity. As three of these conserved residues were histidines, it appears that rhomboid-family proteins may function as metal-dependent membrane proteases (5, 6). Recently, however, it has been shown that RHO cleaves a transmembrane helix (TMH) in the membrane-bound precursor of the TGFα-like growth factor Spitz, enabling the released Spitz to activate the EGF receptor, and that a conserved serine and a conserved histidine in RHO are essential for this cleavage (7, 8). Thus, it appears that rhomboid-family proteins are a distinct group of intramembrane serine proteases. Altogether, the genome of Drosophila encodes seven RHO paralogs (now designated RHO 1-7, with the original rhomboid becoming RHO-1), at least three of which are involved in distinct EGF-dependent pathways, apparently through proteolytic activation of diverse ligands of the EGF receptor.

One human gene sharing homology with multiple cDNA sequences (Accession No. AK026010, NM_022450, Z69719, AK056708, BC014425, M99624) has been annotated as an ortholog of mouse epidermal growth factor receptor related sequence (EGFR-RS), hypothetical protein similar to epidermal growth factor receptor-related protein, human epidermal growth factor receptor-related gene, and lately human rhomboid family 1. The cDNA sequences AK026010, BC014425 and NM_022450 encode the same 855 amino acid protein (Accession No. BAB15318, AAH14425 and AAA02490). However, the biological activity of this protein presently is unknown.

TRA1 (Validated Target ICT1025): Homo sapiens Tumor rejection antigen, TRA1 or heat shock protein gp96 or grp94 is published with GenBank accession nos. NM_003299, AK025459, BC009195, AY040226, X15187 and AF087988. See also, U.S. Publication Nos. 2003/0215874; 2003/0054996; and 2002/0160496.

One of the targets selected with Efficacy-First, tumor rejection antigen-1 (TRA-1), was found to have increased expression in tumors induced to accelerated growth. TRA-1, also known as glucose-regulated protein 94 (grp94), gp96, endoplasmiin precursor and other names, was first described as a molecular chaperone [Hartl FU. (1996) Molecular chaperones in cellular protein folding. *Nature* 381(6583):571-9] with important roles in endoplasmic reticulum related to nuclear signaling, protein folding, sorting and secretion [Nicchitta, C. V. (1998): Biochemical, cell biological and immunological issues surrounding the endoplasmic reticulum chaperone GRP94/gp96. *Current Opinion in Immunology*, 10:103-109.]. In addition, it exerts a specific protection against Ca2+ depletion stress and is involved in antigen presentation [Tamura, Y. P. Peng, K. Liu, M. Daou, P. K. Srivastava, 1997: Immunotherapy of tumors with autologous tumor-derived heat shock protein preparation. *Science*, 278: 117-120]. Furthermore, it also has an important role in tumorigencity [Udono H, Levey D L, Srivastava P K. (1994) Cellular requirements for tumor-specific immunity elicited by heat shock proteins: tumor rejection antigen gp96 primes CD8=T cells in vivo. *Pro Natl Acad Sci USA* 91: 3077-3081.]. Menoret et al. [Menoret A, Meflah K, Le Pendu J. (1994) Expression of the 100 kDa glucose-regulated protein (GRP100/endoplasmin) is associated with tumorigenicity in a model of rat colon adenocarcinoma. *Int J Cancer* 56: 400-405] reported that there was an overexpression of TRA-1 in a model of rat colon adenocarcinoma. Gazit et al. [Gadi Gazit, Jun lu, Amy S. Lee. (1999) De-regulation of GRP stress protein expression in human breast cancer cell lines. *Breast Cancer Research and Treatment* 54: 135-146.] found out there was a 3-5 fold increase in the level of TRA-1 protein was observed in five human breast cancer lines as compared to the normal human mammary lines. Cai et al. [Cai J W, Henderson B W, Shen J W, et al (1993) Induction of glucose-regulated proteins during growth of murine tumor. *J Cell Physiol* 154; 229-237] found through studies during growth of tumors that the level of the TRA-1 is increased, correlating with the size of the tumor. Elevated level of TRA-1 has been implicated to protect neoplastic cells and tumors against cytotoxic T-lymphocyte mediated cytotoxicity and protected tissues culture cells against adverse physiological conditions [Sugawara S, Takeda K, Lee A, et al. (1993) Suppression of stress protein GRP78 induction in tumor B/C10ME eliminates resistance to cell mediated cytotoxicity. *Cancer Research.* 53: 6001-6005]. Public domain databases reveal that TRA-1 is overexpressed in many human cancer tissues including prostate, mammary, brain, stomach, and soft tissue tumors. Overexpression, antisense and ribozyme approaches in tissue culture system directly showed that TRA-1 could protect cells against cell death [Little E, Ramakrishnan M, Roy B, et al. (1994) The glucose-regulated proteins (GRP78 and GRP94): Functions, gene regulation, and applications. *Crit Rev Eukaryot Gene Expr* 4: 1-18, Garrido C, Gurbuxani S, Ravagnan L, Kroemer G. (2001). Heat shock proteins: endogenous modulators of apoptotic cell death. Biochem *Biophys Res Commun.* 286(3):433-42., Ramachandra K. Reddy, et al. (1999). The endoplasmic reticulum chaperone glycoprotein GRP94 with Ca2+-binding and antiapoptotic properties is a novel proteolytic target of calpain during etoposide-induced apoptosis. *J Biol. Chem* 274: 28476-28483]. These anti-apoptosis effects of TRA-1 are associated with induction in neoplastic cells and may lead to cancer progression and chemotherapy resistance. Although normally confined to the ER, TRA-1 has been shown to escape to KDEL (SEQ ID NO: 103)-mediated retention system in several cell types. For instance, a significant fraction of TRA-1 is secreted to the extracellular space by hepatocytes and exocrine pancreatic cells, via the normal secretory pathway. In several tumor cell lines TRA- 1 is detectable as an outer surface protein [Altmeyer A, Maki R G, Feldweg A M, Heike M, Protopopov V P, Masur S K, Srivastava P K (1996). Tumor-specific cell surface expression of the-KDEL (SEQ ID NO: 103) containing, endoplasmic reticular heat shock protein gp96. *Int. J Cancer* 22;69(4):340-9.].

TRA-1 has been shown to chaperone a broad array of peptides, including those derived from normal proteins as well as from foreign and altered proteins present in cancer or virus-infected cells. Thus, tumor-derived TRA-1 carries tumor antigenic peptides, and its preparations from virus-infected cells carry viral epitopes. Although TRA-1 is normally intracellular, necrotic cells release TRA-1 peptide complexes, which are taken up by scavenging antigen-presenting cells. Presentation of the peptides on the surface of these cells leads to stimulation of T lymphocytes and a pro-inflammatory response.

Complexes of TRA-1 with peptides, whether isolated from cells or reconstituted in vitro, have been demonstrated to serve as effective vaccines, producing anti-tumor immune responses in animals and in man [Tamura, Y. P. Peng, K. Liu, M. Daou, P. K. Srivastava, 1997: Immunotherapy of tumors with autologous tumor-derived heat shock protein preparation. *Science,* 278:117-120.]. Oncophage is a vaccine made from individual patients' tumors. Patients have surgery to remove part or all of the cancerous tissue, and a portion of this tissue is shipped overnight to Antigenics' manufacturing facility in Massachusetts. The Oncophage clinical studies in several cancers including pancreatic, melanoma, kidney, colorectal, gastric, and non-Hodgkin's lymphoma have yielded very promising results. Their analysis provides a strong indication that antigen presentation by TRA-1 can induce an immune response in patients and clinical responses. With melanoma or colorectal cancer in one study, 10 out of 39 melanoma patients responded clinically to Oncophage treatment, including two patients whose cancer disappeared completely for more than two years. Of the 24 melanoma patients who were evaluated for immune response, 10 demonstrated increased antimelanoma T-cell activity. In colorectal cancer patients, a T-cell response was observed in 17 out of 29 patients, and seemed to be correlated with survival. The mechanism by which Oncophage induces immune response in melanoma and colorectal cancer was determined to be the sam-—confirming a wealth of preclinical and early clinical data demonstrating that this mechanism is virtually identical in all cancers and species tested to date.

MFGE8 (Validated Target ICT1030): Homo sapiens milk fat globule-EGF factor 8 protein (MFGE8) or breast epithelial BA46 antigen is published under GenBank accession nos. is NM_005928 and BC003610. U.S. Pat. No. 6,339,066 B1 describes aspects of MFGE8 related molecules such as 'protein kinase C-eta' (PKC-η).

TNFSF13 (Validated Target ICT1031): Homo sapiens Tumor necrosis factor ligand super family member 13 (TNFSF13) is published GenBank accession nos. are AK090698 and O75888. Several international patent applications describe aspects of TNFSF13 related molecules such as APRIL (A proliferation-inducing ligand), TALL-2 (TNF-and APOL-related leukocyte expressed ligand 2), and TRDL- 1 (TNF-related death ligand-1) (see, for example, WO 99/12965 and WO 01/60397).

ZFP236 (Validated Target ICT1003): Homo sapiens zinc finger protein 236 (ZFP236) is published under GenBank accession no. AK000847.

SUMMARY OF THE INVENTION

The invention provides methods for treating diseases, such as cancers, by up-regulation, silencing, or down-regulation of a validated target gene expression, by nucleic acid interaction, by introducing RNA interference or other agents, such as antibodies, soluble receptors, small molecule inhibitors, and the like, to modulate activity of a validated drug target, and as a result inhibit tumor growth.

One aspect of the invention provides methods for treating a disease, for example, a cancer or a precancerous growth, in a mammal associated with undesirable expression of a target ICT1030 gene, comprising applying a nucleic acid composition that interacts with the target ICT1030 DNA or RNA, wherein the nucleic acid composition is capable of enhancing expression of the target ICT1030 gene when introduced into a tissue of the mammal.

According to another aspect of the invention, nucleic acid molecules are introduced into tissues, including breast tissue, colon tissue, prostate tissue, skin tissue, bone tissue, parotid gland tissue, pancreatic tissue, kidney tissue, uterine cervix tissue, lung tissue, lymph node tissue, or ovarian tissue, wherein the nucleic acid molecule is a decoy molecule, a decoy DNA, a double stranded DNA, a single-stranded DNA, a complexed DNA, an encapsulated DNA, a viral DNA, a plasmid DNA, a naked RNA, an encapsulated RNA, a viral RNA, a double stranded RNA, a molecule capable of enhancing expression of the target ICT1030 gene, or combinations thereof.

In the another aspect, the invention provides methods for inhibiting cancer or precancerous growth in a mammalian tissue, comprising contacting the tissue with an enhancer that interacts with the target ICT1030 DNA or RNA and thereby enhances the target ICT1030 gene expression.

In the another aspect, the invention provides methods for inhibiting cancer or precancerous growth in a mammalian tissue, comprising contacting the tissue with an enhancer that interacts with the target ICT1030 peptide and thereby enhances the target ICT1030 gene expression, wherein the tissue is breast tissue, colon tissue, prostate tissue, skin tissue, bone tissue, parotid gland tissue, pancreatic tissue, kidney tissue, uterine cervix tissue, lymph node tissue, or ovarian tissue, wherein the enhancer is a nucleic acid molecule, a decoy molecule, a decoy DNA, a double stranded DNA, a single-stranded DNA, a complexed DNA, an encapsulated DNA, a viral DNA, a plasmid DNA, a naked RNA, an encapsulated RNA, a viral RNA, a double stranded RNA, a molecule capable of enhancing the target ICT1030 or combinations thereof.

Another aspect of the invention provides methods of administering nucleic acid to a patient in need thereof, wherein the nucleic acid molecule is delivered in the form of a naked oligonucleotide or a vector, wherein the nucleic acid interacts with the target ICT1030 gene.

Yet another aspect of the invention provides methods of administering nucleic acid to a patient in need thereof, wherein the nucleic acid molecule is delivered in the form of a naked oligonucleotide or a vector, wherein the nucleic acid interacts with the target ICT1030 gene, wherein the nucleic acid is delivered as a vector, wherein the vector is a plasmid, cosmid, bacteriophage, or a virus, for example, a retrovirus or an adenovirus based vector.

Still another aspect of the invention provides methods of enhancing in vivo expression of a gene by administering a vector to a patient in need thereof, wherein the vector containing target ICT1030 gene, wherein the nucleic acid interacts with the target ICT1030 gene expression, wherein the nucleic acid enhances the target ICT1030 gene expression in a mammalian cell, for example, a human cell.

According an aspect of the invention, the target ICT1030 gene, as described herein, comprises a polynucleotide selected from the group consisting of: a) a polynucleotide encoding the polypeptide set forth in SEQ ID NO:2; b) a polynucleotide set forth in SEQ ID NO:1; and SEQ ID NO:3; or c) a polynucleotide having at least about 90% sequence identity to the polynucleotide of a) or b).

In another aspect, the invention provides methods for treating a disease, for example, a cancer or a precancerous growth, in a mammal associated with undesirable expression of a target ICT 1024 or ICT 1025 or ICT 1003 or ICT1031 gene, comprising applying a nucleic acid composition containing an inhibitor that interacts with the target ICT 1024 or ICT 1025 or ICT 1003 or ICT1031 DNA or RNA, wherein the nucleic acid composition is capable of reducing expression of the target ICT 1024 or ICT 1025 or ICT 1003 or ICT1031 gene when introduced into a tissue of the mammal.

According to another aspect of the invention, nucleic acid molecules are introduced into tissues, including breast tissue, colon tissue, prostate tissue, skin tissue, bone tissue, parotid gland tissue, pancreatic tissue, kidney tissue, uterine cervix tissue, lung tissue, lymph node tissue, or ovarian tissue.

According to another aspect, the invention provides methods for treating a disease, for example, a cancer or a precancerous growth, in a mammal, comprising applying a nucleic acid composition containing an inhibitor that interacts with the target ICT 1024 or ICT 1025 or ICT 1003 or ICT1031 DNA or RNA, wherein the inhibitor is a siRNA, an RNAi, a shRNA, an antisense RNA, an antisense DNA, a decoy molecule, a decoy DNA, a double stranded DNA, a single-stranded DNA, a complexed DNA, an encapsulated DNA, a viral DNA, a plasmid DNA, a naked RNA, an encapsulated RNA, a viral RNA, a double stranded RNA, a molecule capable of generating RNA interference, or combinations thereof.

In another aspect, the invention provides methods for inhibiting cancer or precancerous growth in a mammalian tissue, comprising contacting the tissue with an inhibitor that interacts with a target ICT 1024 or ICT 1025 or ICT 1003 or ICT1031 protein, DNA or RNA and thereby reduces target ICT 1024 or ICT 1025 or ICT 1003 or ICT1031 activity or gene expression.

Yet in another aspect, the invention provides methods for inhibiting cancer or precancerous growth in a mammalian tissue, wherein the tissue is a breast tissue, colon tissue, prostate tissue, skin tissue, bone tissue, parotid gland tissue, pancreatic tissue, kidney tissue, uterine cervix tissue, lung tissue, lymph node tissue, or ovarian tissue.

Still in another aspect, the invention provides methods for inhibiting cancer or precancerous growth in a mammalian tissue, comprising contacting the tissue with an inhibitor, wherein the inhibitor is a siRNA, an RNAi, a shRNA, an antisense RNA, an antisense DNA, a decoy molecule, a decoy DNA, a double stranded DNA, a single-stranded DNA, a complexed DNA, an encapsulated DNA, a viral DNA, a plasmid DNA, a naked RNA, an encapsulated RNA, a viral RNA, a double stranded RNA, a molecule capable of generating RNA interference, or combinations thereof.

According an aspect of the invention, the target ICT1031 gene, as described herein, comprises a polynucleotide selected from the group consisting of: a) a polynucleotide encoding the polypeptide set forth in SEQ ID NO:5; b) a polynucleotide set forth in SEQ ID NO:4; and c) a polynucleotide having at least about 90% sequence identity to the polynucleotide of a) or b).

According an aspect of the invention, the target ICT1003 gene, as described herein, comprises a polynucleotide selected from the group consisting of: a) a polynucleotide encoding the polypeptide set forth in SEQ ID NO:7; b) a polynucleotide set forth in SEQ ID NO:6 or SEQ ID NO:8; and c) a polynucleotide having at least about 90% sequence identity to the polynucleotide of a) or b).

In another aspect, the invention provides methods of administering siRNA to a patient in need thereof, wherein the siRNA molecule is delivered in the form of an oligonucleotide in a naked form or in a formulation or a vector, wherein the siRNA interacts with a target ICT 1024 or ICT 1025 or ICT 1003 or ICT1031 gene or a target ICT 1024 or ICT 1025 or ICT 1003 or ICT1031 MRNA transcript, wherein the siRNA is delivered as a vector, wherein the vector is a plasmid, cosmid, bacteriophage, or a virus, for example, a retrovirus or an adenovirus based vector.

Another aspect of the inventions provides methods of blocking in vivo expression of a target ICT 1024 or ICT 1025 or ICT 1003 or ICT1031 gene by administering a vector to a patient in need thereof, wherein the vector containing a target ICT 1024 or ICT 1025 or ICT 1003 or ICT1031 siRNA, wherein the siRNA interferes with target ICT 1024 or ICT 1025 or ICT 1003 or ICT1031 gene expression, for example, the siRNA causes post-transcriptional silencing of the target ICT 1024 or ICT 1025 or ICT 1003 or ICT1031 gene in a mammalian cell such as a human cell.

In another aspect, the invention provides methods for treating a disease, for example, a cancer or a precancerous growth, in a mammal associated with undesirable expression of a target ICT 1024 or ICT 1025 or ICT 1003 or ICT1031 gene, comprising applying a nucleic acid composition containing an inhibitor that interacts with the target ICT 1024 or ICT 1025 or ICT 1003 or ICT1031 DNA or RNA, wherein the nucleic acid composition is capable of reducing expression of the target ICT 1024 or ICT 1025 or ICT 1003 or ICT1031 gene when introduced into a tissue of the mammal.

According to another aspect, the invention provides methods for treating a disease, for example, a cancer or a precancerous growth, in a mammal, comprising applying a nucleic acid composition containing an inhibitor that interacts with the target ICT1003 DNA or RNA, wherein the inhibitor is a siRNA, an RNAi, a shRNA, an antisense RNA, an antisense DNA, a decoy molecule, a decoy DNA, a double stranded DNA, a single-stranded DNA, a complexed DNA, an encapsulated DNA, a viral DNA, a plasmid DNA, a naked RNA, an encapsulated RNA, a viral RNA, a double stranded RNA, a molecule capable of generating RNA interference, or combinations thereof.

BRIEF DESCRIPTION OF THE DRAWINGS

FIG. 1 shows that the targets identified by the Efficacy-First Discovery™ method are different from those identified using a conventional approach. Expression changes of the targets are due to perturbation of delivered genes and disease process dynamic. They are better fit for drug discovery.

FIG. 2 indicates that among a total of 156 selected targets, 111 were known based on UniGene database annotations and 45 were unknown novel targets. Within the known targets, 87% are tumor related. If the same ratio holds the truth, we expect more then 35 targets are novel tumor targets. In addition, the hits also belong to several tumorigenesis pathways.

FIG. 12 shows that ICT1024 protein has significant structural homology to other rhomboid proteins from various organisms, such as yeast, bacteria and plant. (SEQ ID NOs: 27-35, respectively in order of appearance)

FIG. 13 shows that ICT1024 is a novel human protein and only shares structural homology with other human rhomboid proteins in the C-terminal domain. (SEQ ID NO: 37 (ICT1024); SEQ ID NO:38 (HRhomboid 2); SEQ ID NO:39

(HRhomboid 3); SEQ ID NO:40 (HRhomboid 4); SEQ ID NO:41 (HRhomboid 5) and SEQ ID NO:42 (HRhomboid 6).

Figure 14:
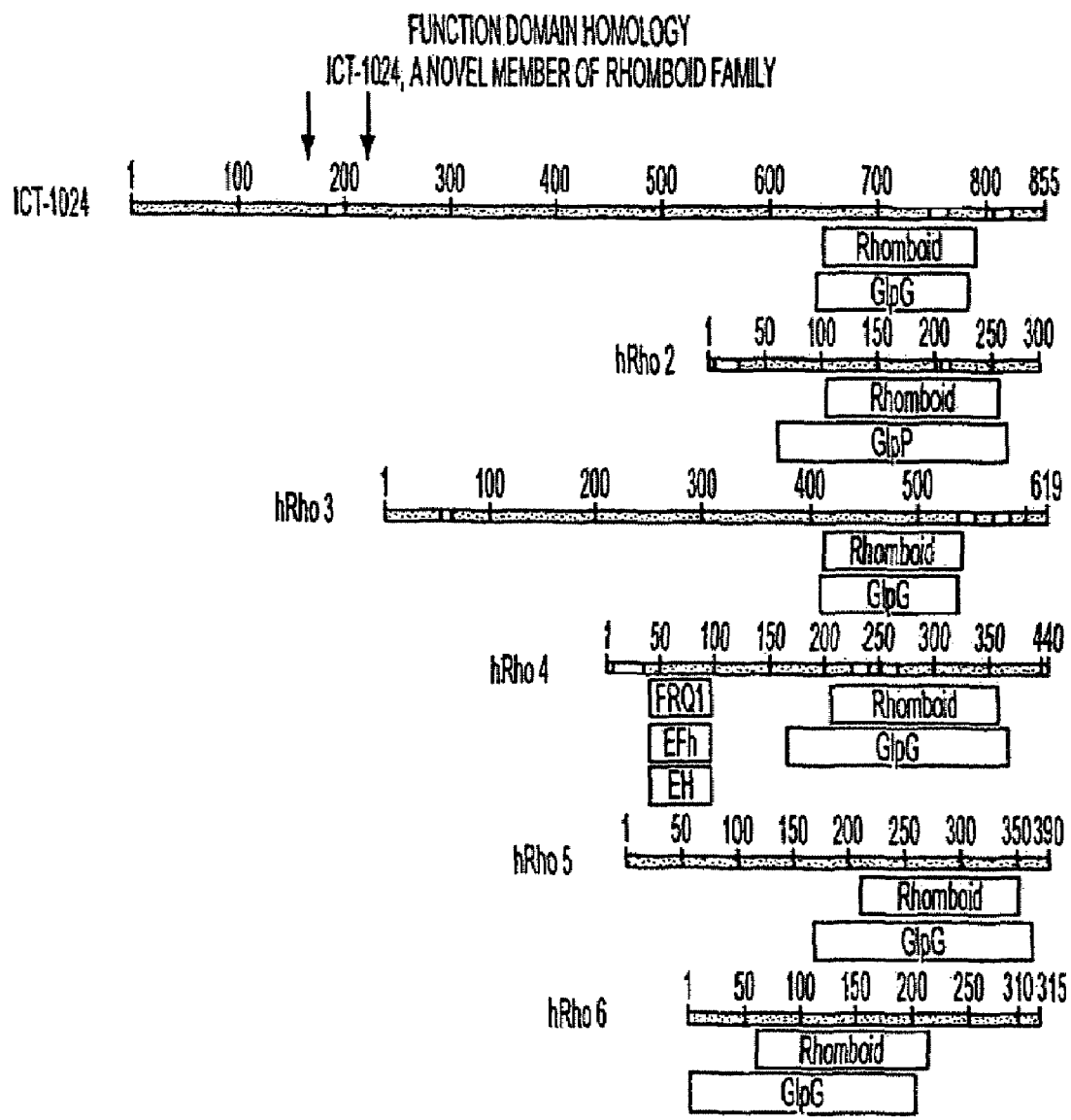

FIG. 14 shows that ICT1024 does not share DNA or protein sequence homology with other human rhomboid proteins. The siRNA targeted sequences is uniquely designed for ICT1024 protein.

Figure 15:
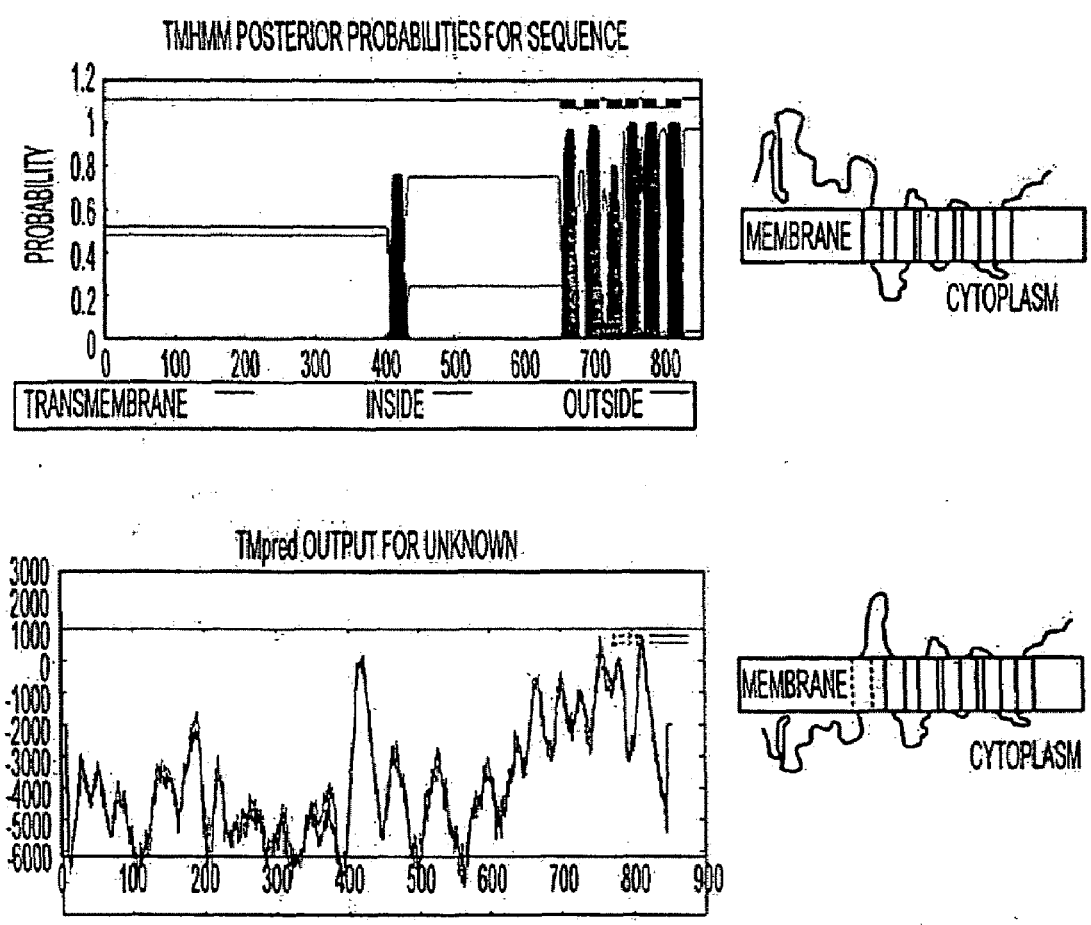

FIG. 15 shows that the cellular location and topology predication of ICT1024 protein based on multiple hydrophobicity analyses. At least 6 transmembrane domains were predicted with one additionally questioned 7th domains. However, the N-terminal portion of the protein has a large region (1-400 or 1-590 AA) of peptide exposed outside the membrane, and at least part of this region located in extracellular environment.

Figure 16:
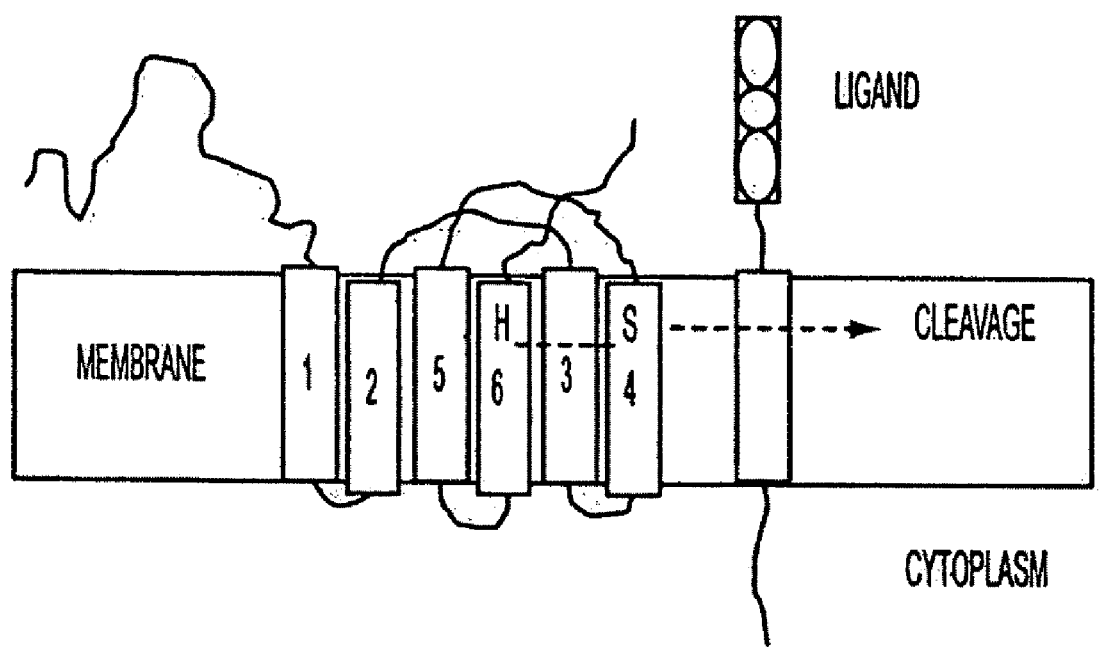

FIG. 16 shows that the potential proteinase activity for activation of EGF related factors, based on the discussion about the role of rhomboid protein function in the insect models. The histidine and serine protease activity is able to cleavage intramembranely the transmembrane domain of EGF like factors, resulting release of these ligands to activate the corresponding pathways.

Figure 17:
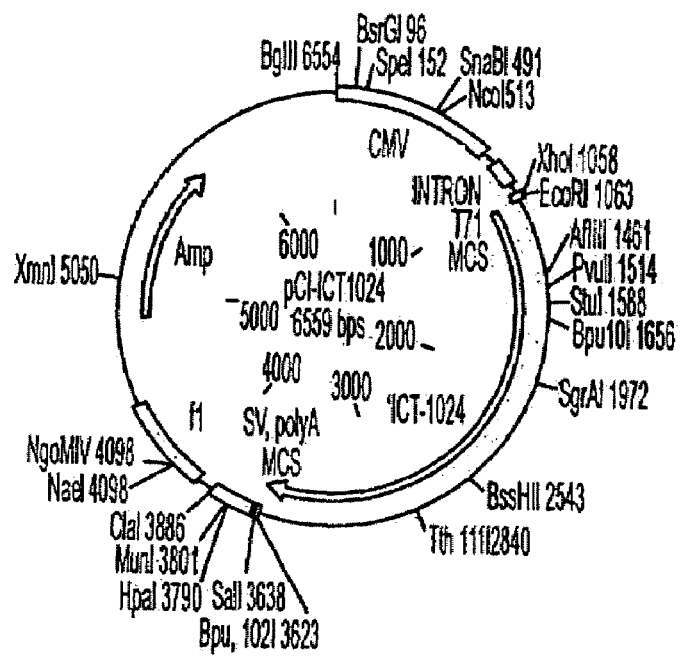

FIG. 17 shows a plasmid construct pCI-ICT1024 containing full-length cDNA encoding ICT1024 with CMV promoter driven expression cassette. Transfection of this plasmid into MDA-MD-435 cells resulted in highly expressed ICT1024 protein.

Figure 18:
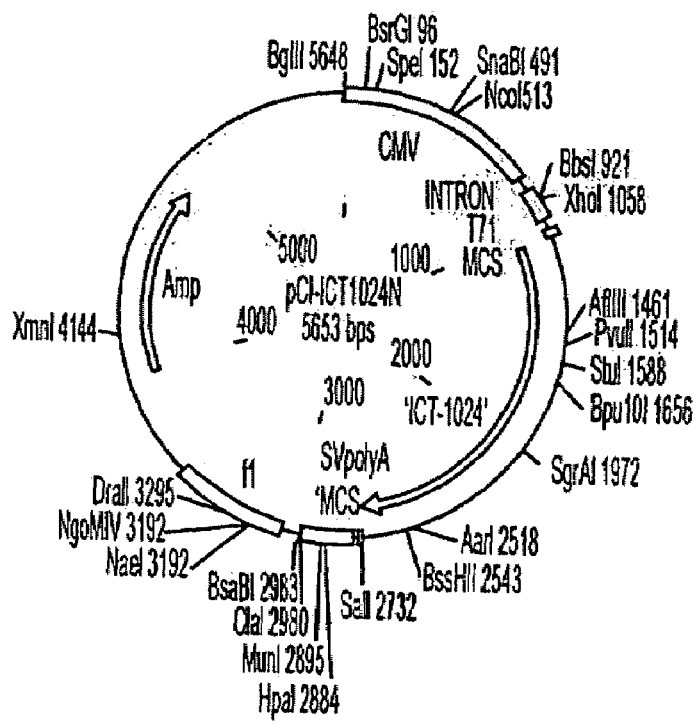

FIG. 18 shows a plasmid construct pCI-ICT1024N containing a cDNA fragment of ICT1024 encoding the N-terminal domain. Transfection of this plasmid, which contains a CMV promoter driven expression cassette into MDA-MD-435 cells results in highly expressed ICT1024 protein fragment.

Figure 19:
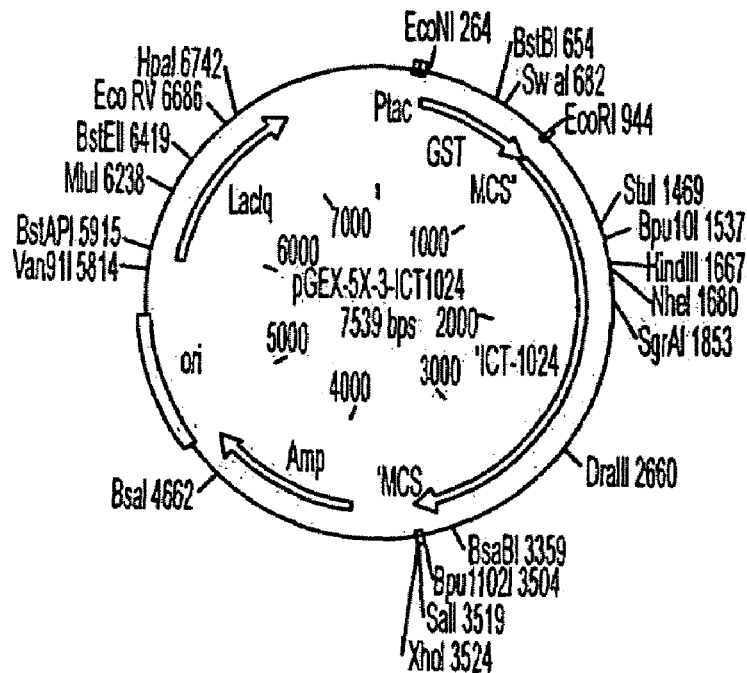

FIG. 19 shows the plasmid construct pGEX-5X-3-ICT1024 we built containing full-length cDNA of ICT1024 encoding ICT1024 protein. Transfection of this plasmid with prokaryotic promoter driven expression cassette into bacteria cells resulted in highly expressed ICT1024 protein.

Figure 20:
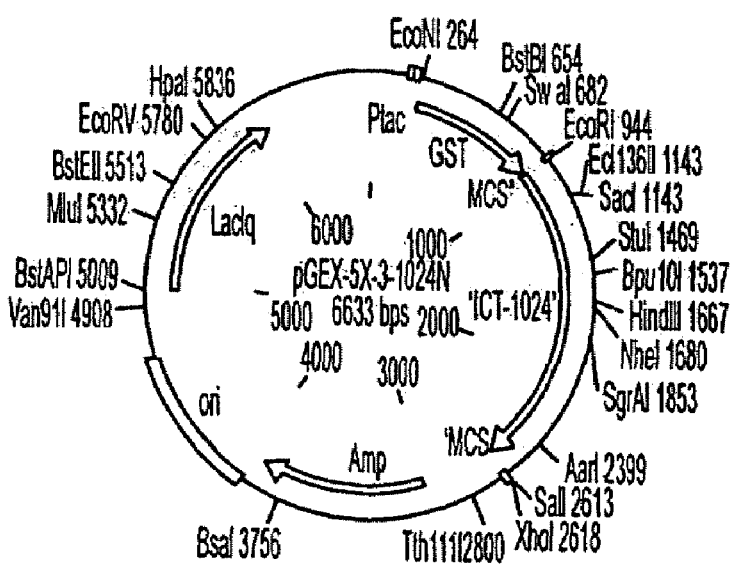

FIG. 20 shows the plasmid construct pGEX-5X-3-1024N we built containing cDNA fragment of ICT1024 encoding ICT1024 protein N-terminal domain. Transfection of this plasmid with prokaryotic promoter driven expression cassette into bacteria cells resulted in highly expressed ICT1024 protein fragment.

Figure 21:
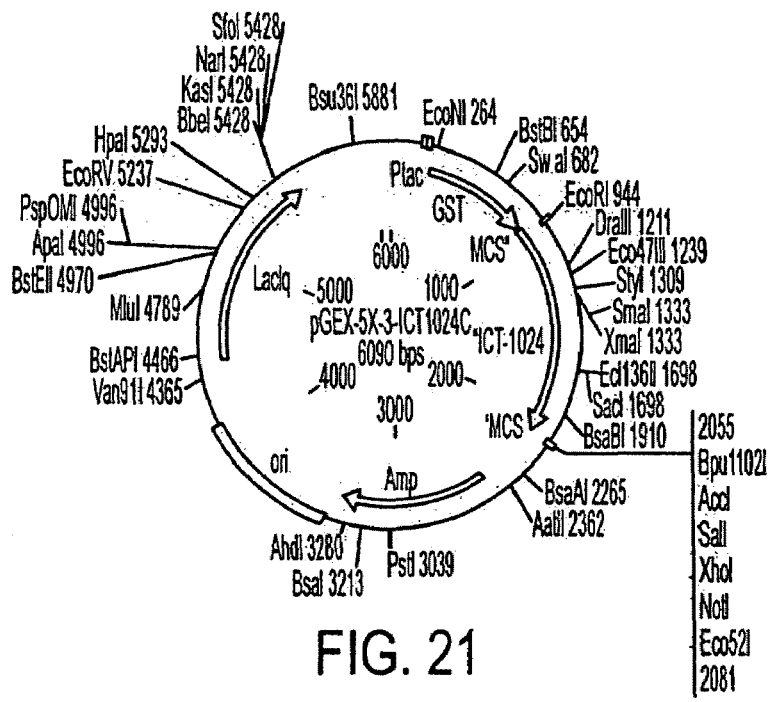

FIG. 21 shows the plasmid construct pGEX-5X-3-ICT1024C we built containing cDNA fragment of ICT1024 encoding ICT1024 protein C-terminal domain. Transfection of this plasmid with prokaryotic promoter driven expression cassette into bacteria cells resulted in highly expressed ICT1024 protein fragment.

Figure 22:
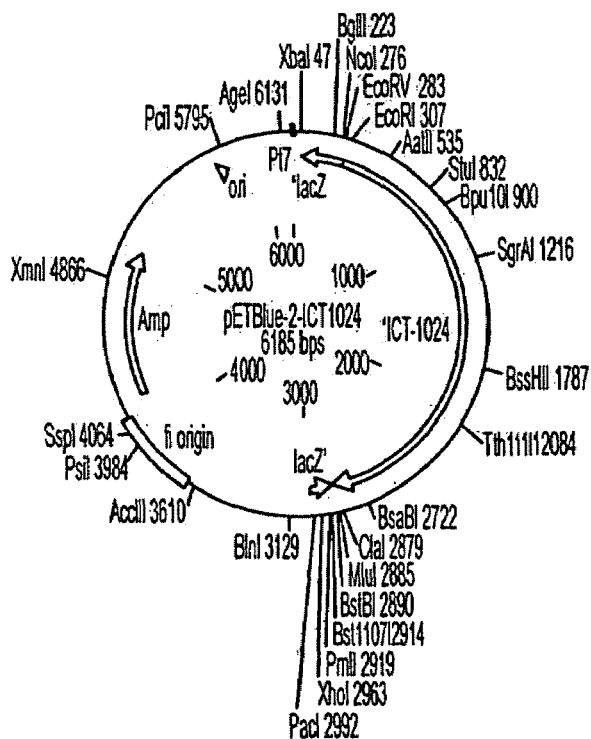

FIG. 22 shows the plasmid construct pETBlue-2-ICT1024 we built containing full-length cDNA of ICT1024 encoding ICT1024 protein. Transfection of this plasmid with prokaryotic promoter driven expression cassette into bacteria cells resulted in highly expressed ICT1024 protein.

Figure 23:
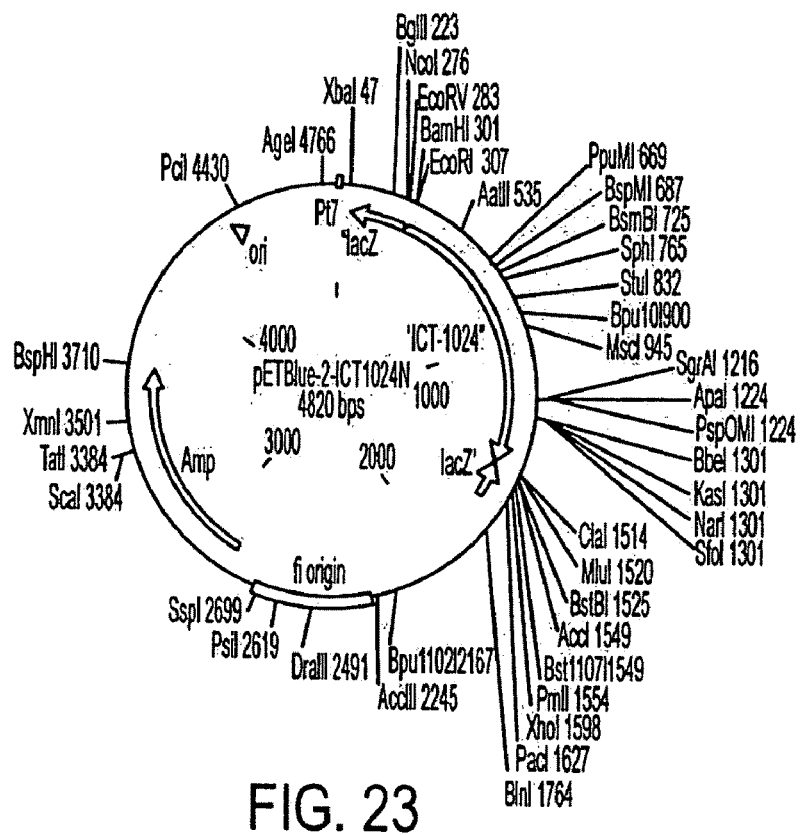

FIG. 23 shows the plasmid construct pETBlue-2-ICT1024N containing cDNA fragment of ICT1024 encoding ICT1024 protein N-terminal domain. Transfection of this plasmid with prokaryotic promoter driven expression cassette into bacteria cells resulted in highly expressed ICT1024 protein fragment.

Figure 24:
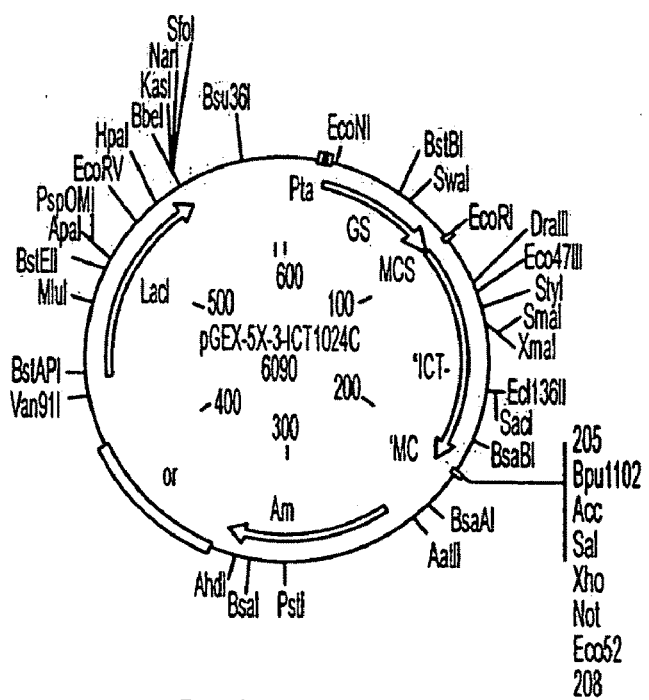

FIG. 24 shows the plasmid construct we built containing cDNA fragment of ICT1024 encoding ICT1024 protein C-terminal domain. Transfection of this plasmid with prokaryotic promoter driven expression cassette into bacteria cells resulted in highly expressed ICT1024 protein fragment.

FIG. 25 is the confirmed sequence of ICT1024 protein coding region 1670-3637 (SEQ ID NO:58).

FIG. 26 (SEQ ID NO:60) is the sequence of the N TERMINUS 553 AA CODING REGION: 1070-2731 of ICT1024

FIG. 27, (SEQ ID NO:61) is the sequence of the ICT1024 coding region: 947-3518

FIG. 28, (SEQ ID NO:62) is the sequence of the ICT1024 N terminus 553 aa coding region:, 947-2600

FIG. 29, (SEQ ID NO:64) is the sequence of the ICT1024 coding region for the C terminus 375 aa:, 945-2069

FIG. 30, (SEQ ID NO:66) is the sequence of the ICT1024 coding region, 310-2879

FIG. 31, (SEQ ID NO:68) is the sequence of the coding region for the N terminus 400 aa of ICT1024, 314-1515

FIG. 32, (SEQ ID NO:69) Coding region for the C terminus 373 aa of ICT1024: 308-1431

FIG. 33 shows HLa peptide motif search results (SEQ ID NOS 83-102, respectively in order of appearance).

FIG. 34 shows suggested models for transmembrane biology of ICT 1025.

FIG. 35 shows predicted transmembrane segments of ICT 1025.

Figure 36:
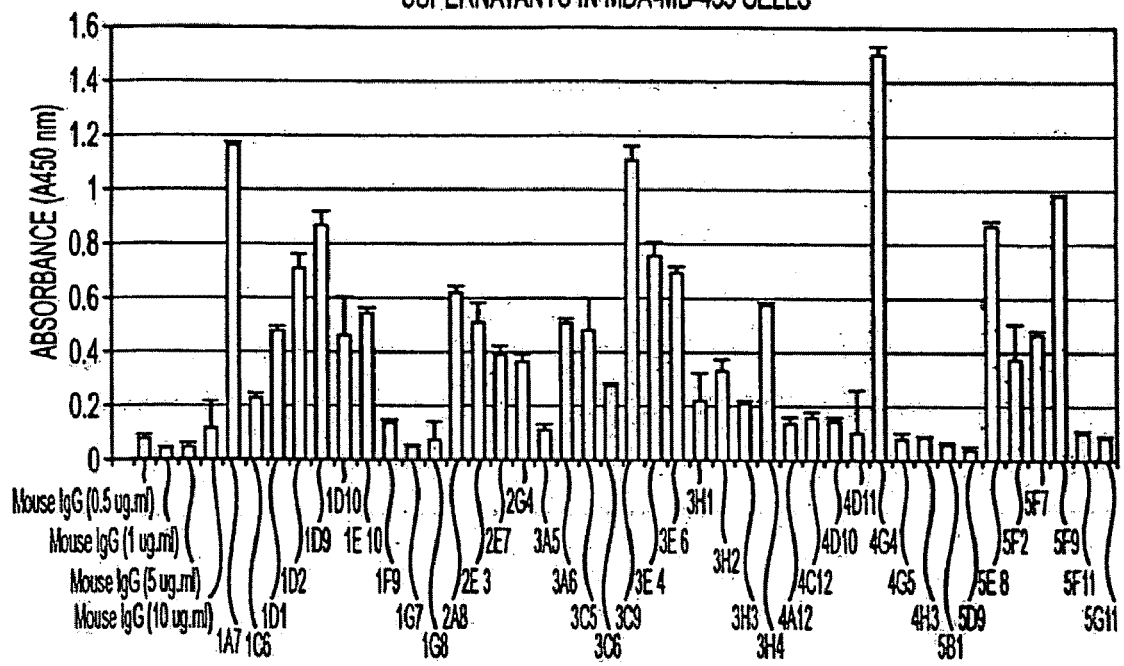

FIG. 36 shows screening of ICT 1025 mAB for surface binding activities in breast tumor cells.

Figure 37:
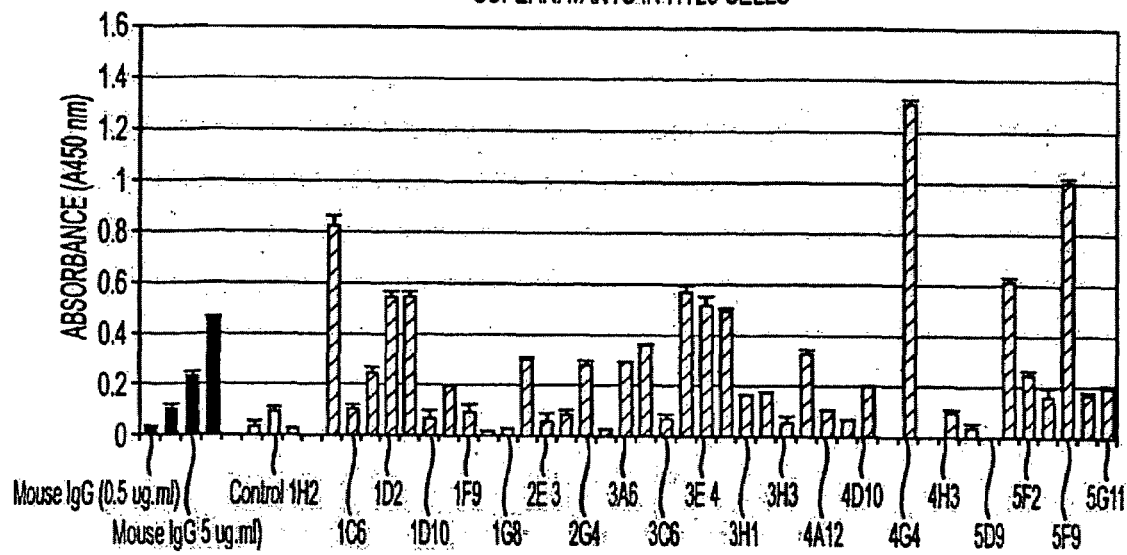

FIG. 37 shows screening of ICT1025 mAB for surface binding activities in colon tumor cells.

Figure 38:
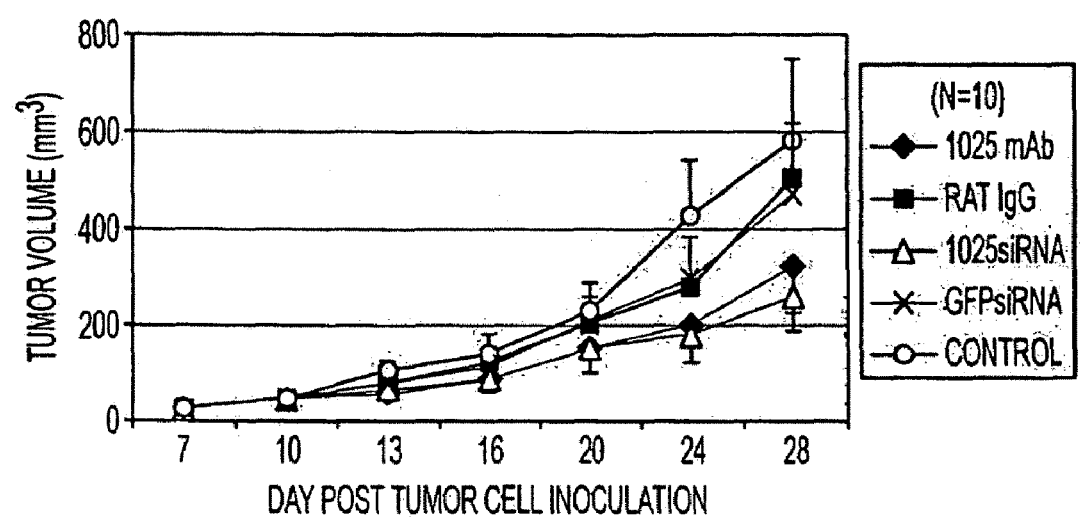

FIG. 38 shows inhibition of tumorigenesis and tumor growth by treating tumor cells with antibody or siRNA prior to inoculation.

DESCRIPTION OF THE INVENTION

The present invention provides validated targets for inhibition of tumor growth, disease progression and methods and compositions for the inhibition and treatment of tumors and cancers, for example, breast cancer, colon cancer, prostate cancer, skin cancer, bone cancer, parotid gland cancer, pancreatic cancer, kidney cancer, uterine cervix cancer, lymph node cancer, or ovarian cancer, in mammals, for example, humans. The invention is based on the findings of novel targets, such as ICT1024, ICT1025, ICT1030, ICT1031, and ICT1003. ICT1030 and/or ICT1031 and/or ICT1003 and/or ICT1024 and/or ICT1025 can thus be used as targets for therapy; and, they also can be used to identify compounds useful in the diagnosis, prevention, and therapy of tumors and cancers (for example, breast cancer, colon cancer, prostate cancer, skin cancer, bone cancer, parotid gland cancer, pancreatic cancer, kidney cancer, uterine cervix cancer, lymph node cancer, ovarian cancer, or lung cancer.

The targets ICT1024, ICT1025, ICT1030, ICT1031, and ICT1003, as disclosed herein, are validated by a method of validating drug targets that determines the targets control tumor progression and thus justify anti-tumor drug discovery (see, U.S. Provisional Application No. 60/326,422 and WO03/063765, incorporated herein by reference). This unique and proprietary Tumor Target Discrimination Method validates targets directly in animal tumor models through transgene over-expression and eliminates targets lacking disease control. The method reduces the need for protein generation, antibodies, and/or transgenic animals—all costly and slow, while providing clear and definitive evidence that targets actually control the disease. Moreover, the method provides valuable information that may be lost with methods that rely solely on cell-culture and miss the complex interactions of multiple cell types that result in disease pathology.

The platform technology (see, International Application No. WO 0147496 incorporated by reference), as described above, is a powerful tool for validation of genes that are under-expressed in tumor tissue. However, a technology platform to achieve gene silencing is highly desired for validation of genes that are over-expressed in tumor tissue. Recently, double stranded RNA has been demonstrated to induce gene specific silencing by a phenomenon called RNA interference (RNAi). Although the mechanism of RNAi is still not completely understood, overwhelming early results suggested that this RNAi effect may be achieved in various cell types including mammalian species. A double stranded RNA targeted against MRNA results in the degradation of the target mRNA causing the silencing of the corresponding gene. Large double stranded RNA is cleaved into smaller fragments, for example, fragments of 21-23 nucleotides long, by a RNase III like activity involving an enzyme Dicer. These shorter fragments known as siRNA (small interfering RNA) are believed to mediate the cleavage of mRNA. The RNAi mechanism for down regulation of gene expression has been studied in C. elegans and other lower organisms, its effectiveness in mammalian cells has been demonstrated. Recently, the RNAi effect is demonstrated in mouse using the firefly luciferase gene reporter system (Worby et al. (2001) *Sci STKE* Aug. 14, 2001(95):PL1).

Our unique PolyTran™ technology (see, International Application No. WO 0147496) enables direct administration of plasmids into tumor. This provides strong tumor expression and activity of candidate target proteins in the tumor.

Definitions

In general, a "gene" is a region on the genome that is capable of being transcribed to an RNA that either has a regulatory function, a catalytic function; and/or encodes a protein. An eukaryotic gene typically has introns and exons, which may organize to produce different RNA splice variants that encode alternative versions of a mature protein. The skilled artisan will appreciate that the present invention encompasses all endogenous gene that may be found, including splice variants, allelic variants and transcripts that occur because of alternative promoter sites or alternative poly-adenylation sites. The endogenous gene, as described herein, also can be a mutated endogenous gene, and that the mutation can be in the coding or regulatory regions.

A "target gene" refers to a differentially expressed gene in which modulation of the level of gene expression or of gene product activity prevents and/or ameliorates disease progression, for example, a tumor growth. Thus, compounds that modulate the expression of a target gene, the target genes, or the activity of a target gene product can be used in the diagnosis, treatment or prevention of a disease. In particular, target genes in the present invention includes endogenous genes and their variants, as described herein.

A full-length gene or RNA therefore encompasses any naturally occurring splice variants, allelic variants, other alternative transcripts, splice variants generated by recombinant technologies which bear the same function as the naturally occurring variants, and the resulting RNA molecules. A fragment of a gene can be any portion from the gene, which may or may not represent a functional domain, for example, a catalytic domain, a DNA binding domain, etc. A fragment may preferably include nucleotide sequences that encode for at least 16 contiguous amino acids, more preferably at least 25 contiguous amino acids, and most preferably at least about 30, 40, 50, 60, 65, 70, 75 or more contiguous amino acids or any integer thereabout or therebetween. A structural gene is a DNA sequence that is transcribed into messenger RNA (mRNA) which is then translated into a sequence of amino acids characteristic of a specific polypeptide.

"Complementary DNA" (cDNA), often referred to as "copy DNA", is a single-stranded DNA molecule that is formed from an mRNA template by the enzyme reverse transcriptase. Typically, a primer complementary to portions of the mRNA is employed for the initiation of reverse transcription. Those skilled in the art also use the term "cDNA" to refer to a double-stranded DNA molecule that comprises such a single-stranded DNA molecule and its complement DNA strand.

"Gene expression" refers to the biosynthesis of a gene product. For example, in the case of a structural gene, gene expression involves transcription of the structural gene into mRNA and the translation of mRNA into one or more polypeptides.

The term "operably associated" is used to describe the connection between regulatory elements and a gene or its coding region. That is, gene expression is typically placed under the control of certain regulatory elements, including constitutive or inducible promoters, tissue-specific regulatory elements, and enhancers. Such a gene or coding region is the to be "operably linked to" or "operatively linked to" or "operably associated with" the regulatory elements, meaning that the gene or coding region is controlled or influenced by the regulatory element.

"Sequence homology" is used to describe the sequence relationships between two or more nucleic acids, polynucleotides, proteins, or polypeptides, and is understood in the context of and in conjunction with the terms including: (a) reference sequence, (b) comparison window, (c) sequence identity, (d) percentage of sequence identity, and (e) substantial identity or "homologous."

(a) A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

(b) A "comparison window" includes reference to a contiguous and specified segment of a polynucleotide sequence, wherein the polynucleotide sequence may be compared to a reference sequence and wherein the portion of the polynucleotide sequence in the comparison window may comprise additions, substitutions, or deletions (i.e., gaps) compared to the reference sequence (which does not comprise additions, substitutions, or deletions) for optimal alignment of the two sequences. Generally, the comparison window is at least 20 contiguous nucleotides in length, and optionally can be 30, 40, 50, 100, or longer. Those of skill in the art understand that to avoid a misleadingly high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.*, 2: 482, 1981; by the homology alignment algorithm of Needleman and Wunsch, *J. Mol. Biol.*, 48: 443, 1970; by the search for similarity method of Pearson and Lipman, *Proc. Natl. Acad. Sci. USA*, 8: 2444, 1988; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 7 Science Dr., Madison, Wis., USA; the CLUSTAL program is well described by Higgins and Sharp, Gene, 73: 237-244, 1988; Corpet, et al., Nucleic Acids Research, 16:881-90, 1988; Huang, et al., Computer Applications in the Biosciences, 8:1-6, 1992; and Pearson, et al., Methods in Molecular Biology, 24:7-331, 1994. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York, 1995. New versions of the above programs or new programs altogether will undoubtedly become available in the future, and can be used with the present invention.

Unless otherwise stated, sequence identity/similarity values provided herein refer to the value obtained using the BLAST 2.0 suite of programs, or their successors, using default parameters. Altschul et al., *Nucleic Acids Res*, 2:3389-3402, 1997. It is to be understood that default settings of these parameters can be readily changed as needed in the future.

As those ordinary skilled in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163, 1993) and XNU (Claverie and States, *Comput. Chem.*, 17:191-1, 1993) low-complexity filters can be employed alone or in combination.

(c) "Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins it is recognized that residue positions which are not identical often differ by conservative amino acid substitutions, where amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences which differ by such conservative substitutions are said to have sequence similarity. Approaches for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers and Miller, *Computer Applic. Biol. Sci.*, 4: 11-17, 1988, for example, as implemented in the program PC/GENE (Intelligenetics, Mountain View, Calif., USA).

(d) "Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" or "homologous" in their various grammatical forms means that a polynucleotide comprises a sequence that has a desired identity, for example, at least 60% identity, preferably at least 70% sequence identity, more preferably at least 80%, still more preferably at least 90% and even more preferably at least 95%, 96%, 97%, 98%, 99% or 100% identity, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and even more preferably at least 95%, 96%, 97%, 98%, 99% or 100%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, for example, when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid, although such cross-reactivity is not required for two polypeptides to be deemed substantially identical.

(e) (ii) The terms "substantial identity" or "homologous" in their various grammatical forms in the context of a peptide indicates that a peptide comprises a sequence that has a desired identity, for example, at least 60% identity, preferably at least 70% sequence identity to a reference sequence, more preferably 80%, still more preferably 85%, even more preferably at least 90% or 95%, 96%, 97%, 98%, 99% or 100% sequence identity to the reference sequence over a specified comparison window. Preferably, optimal alignment is conducted using the homology alignment algorithm of Needleman and Wunsch, *J. Mol. Biol.*, 48:443, 1970. An indication that two peptide sequences are substantially identical is that one peptide is immunologically reactive with antibodies raised against the second peptide, although such cross-reactivity is not required for two polypeptides to be deemed substantially identical. Thus, a peptide is substantially identical to a second peptide, for example, where the two peptides differ only by a conservative substitution. Peptides which are "substantially similar" share sequences as noted above except that residue positions which are not identical may differ by conservative amino acid changes. Conservative substitutions typically include, but are not limited to, substitutions within the following groups: glycine and alanine; valine, isoleucine, and leucine; aspartic acid and glutamic acid; asparagine and glutamine; serine and threonine; lysine and arginine; and phenylalanine and tyrosine, and others as known to the skilled person.

The term "antisense RNA" refers to in eukaryotes, RNA polymerase catalyzes the transcription of a structural gene to produce mRNA. A DNA molecule can be designed to contain an RNA polymerase template in which the RNA transcript has a sequence that is complementary to that of a preferred mRNA. The RNA transcript is termed an "antisense RNA." Antisense RNA molecules can inhibit mRNA expression (for example, Rylova et al., *Cancer Res,* 62(3):801-8, 2002; Shim et al., *Int. J. Cancer,* 94(1):6-15, 2001).

The term "antisense DNA" or "DNA decoy" or "decoy molecule" means with respect to a first nucleic acid molecule, a second DNA molecule or a second chimeric nucleic acid molecule that is created with a sequence, which is a complementary sequence or homologous to the complementary sequence of the first molecule or portions thereof, is referred to as the antisense DNA or DNA decoy or decoy molecule of the first molecule. The term "decoy molecule" also includes a nucleic molecule, which may be single or double stranded, that comprises DNA or PNA (peptide nucleic acid) (Mischiati et al., *Int. J. Mol. Med.,* 9(6):633-9, 2002), and that contains a sequence of a protein binding site, preferably a binding site for a regulatory protein and more preferably a binding site for a transcription factor. Applications of antisense nucleic acid molecules, including antisense DNA and decoy DNA molecules are known in the art, for example, Morishita et al., *Ann. N Y Acad. Sci.,* 947:294-301, 2001; Andratschke et al., *Anticancer Res,* 21:(5)3541-3550, 2001.

"siRNA" refers to small interfering RNAs, which also include short hairpin RNA ("shRNA") (Paddison et al., *Genes & Dev.* 16: 948-958, 2002), that are capable of causing interference (as described herein for RNAi) and can cause post-transcriptional silencing of specific genes in cells, for example, mammalian cells (including human cells) and in the body, for example, mammalian bodies (including humans). The phenomenon of RNA interference (RNAi) is described and discussed in Bass, *Nature,* 411:428-29, 2001; Elbashir et al., *Nature,* 411:494-98, 2001; and Fire et al., *Nature,* 391: 806-11, 1998, wherein methods of making interfering RNA also are discussed. Exemplary siRNAs according to the invention could have up to 29 bps, 25 bps, 22 bps, 21 bps, 20 bps, 15 bps, 10 bps, 5 bps or any integer thereabout or therebetween.

A "stabilized RNAi", "siRNA" or a "shRNA" as described herein, is protected against degradation by exonucleases, including RNase, for example, using a nucleotide analogue that is modified at the 3' position of the ribose sugar (for example, by including a substituted or unsubstituted alkyl, alkoxy, alkenyl, alkenyloxy, alkynyl or alkynyloxy group as defined above). The RNAi, siRNA or a shRNA also can be stabilized against degradation at the 3' end by exonucleases by including a 3'-3'-linked dinucleotide structure (Ortigao et al., *Antisense Research and Development* 2:129-146 (1992)) and/or two modified phospho bonds, such as two phosphorothioate bonds.

The RNA molecules used in the electroporation method, as described herein, can be stabilized RNAs. The RNAs of the instant invention include isolated RNAi, siRNA, mRNA or antisense RNA molecule and glyceraldehyde-3-phosphate dehydrogenase (GAPDH) polypeptide or a portion thereof which is capable of binding a target gene motif. A peptide derived from GAPDH is known to bind to and stabilize RNA and may be useful in the stabilization of therapeutic siRNA/RNAi/shRNA molecules in a cell.

The term "cancer" refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells.

The term "tumor" refers to all neoplastic cell growth and proliferation, whether malignant or benign, and all precancerous and cancerous cells and tissues.

The term "precancerous" refers to cells or tissues having characteristics relating to changes that may lead to malignancy or cancer. Examples include adenomatous growths in tissues, or conditions, for example, dysplastic nevus syndrome, a precursor to malignant melanoma of the skin. Examples also include, abnormal neoplastic, in addition to dysplastic nevus syndromes, polyposis syndromes, prostatic dysplasia, and other such neoplasms, whether the precancerous lesions are clinically identifiable or not.

The term "complexed DNA" include a DNA molecule complexed or combined with another molecule, for example, a carbohydrate, for example, a sugar, that a sugar-DNA complex is formed. Such complex, for example, a sugar complexed DNA can enhance or support efficient gene delivery via receptor, for example, glucose can be complexed with DNA and delivered to a cell via receptor, such as mannose receptor.

"Encapsulated nucleic acids", including encapsulated DNA or encapsulated RNA, refer to nucleic acid molecules in microsphere or microparticle and coated with materials that are relatively non-immunogenic and subject to selective enzymatic degradation, for example, synthesized microspheres or microparticles by the complex coacervation of materials, for example, gelatin and chondroitin sulfate (see, for example, U.S. Pat. No. 6,410,517). Encapsulated nucleic acids in a microsphere or a microparticle are encapsulated in such a way that it retains its ability to induce expression of its coding sequence (see, for example, U.S. Pat. No. 6,406,719).

"Inhibitors" refers to molecules that inhibit and/or block an identified function. Any molecule having potential to inhibit and/or block an identified function can be a "test molecule," as described herein. For example, referring to oncogenic function or anti-apoptotic activity of ICT1024, ICT1025, ICT1031 or ICT1003, such molecules may be identified using in vitro and in vivo assays of ICT1024, ICT1025, ICT1031 or ICT1003, respectively. Inhibitors are compounds that partially or totally block ICT1024, ICT1025 and/or ICT1031 and/or ICT1003 activity, decrease, prevent, or delay their activation, or desensitize its cellular response. This may be accomplished by binding to ICT1024, ICT1025, ICT1031, or ICT1003 proteins directly or via other intermediate molecules. An antagonist or an antibody that blocks ICT1024, ICT1025 and/or ICT1031 and/or ICT1003 activity, including inhibition of oncogenic function or anti-apoptotic activity of ICT1024, ICT1025, ICT1031 and/or ICT1003, is considered to be such an inhibitor. Inhibitors according to the instant invention is: a siRNA, an RNAi, a shRNA, an antisense RNA, an antisense DNA, a decoy molecule, a decoy DNA, a double stranded DNA, a single-stranded DNA, a complexed DNA, an encapsulated DNA, a viral DNA, a plasmid DNA, a naked RNA, an encapsulated RNA, a viral RNA, a double stranded RNA, a molecule capable of generating RNA interference, or combinations thereof. The group of inhibitors of this invention also includes genetically modified versions of ICT1024, ICT1025, ICT1030, ICT1031, or ICT1003, for example, versions with altered activity. The group thus is inclusive of the naturally occurring protein as well as synthetic ligands, antagonists, agonists, antibodies, small chemical molecules and the like.

"Assays for inhibitors" refer to experimental procedures including, for example, expressing ICT1024, ICT1025, ICT1031, or ICT1003 in vitro, in cells, applying putative inhibitor compounds, and then determining the functional effects on ICT1024, ICT1025, ICT1031, or ICT1003 activity or transcription, as described above. Samples that contain or are suspected of containing ICT1024, ICT1025, ICT1031, or ICT1003 are treated with a potential inhibitor. The extent of inhibition or change is examined by comparing the activity measurement from the samples of interest to control samples. A threshold level is established to assess inhibition. For example, inhibition of a ICT1024, ICT1025, ICT1031, or ICT1003 polypeptide is considered achieved when the ICT1024, ICT1025, ICT1031, or ICT1003 activity value relative to the control is 80% or lower.

ICT1030: The term "ICT1030" refers to validated target ICT1030, which includes MFGE8 (Accession No. NM_005928, BC003610), related molecules or consensus, nucleic acid (DNA and RNA) or protein (or polypeptide), and can include their polymorphic variants, alleles, mutants, and interspecies homologs that have (i) substantial nucleotide sequence homology (for example, at least 60% identity, preferably at least 70% sequence identity, more preferably at least 80%, still more preferably at least 90% and even more preferably at least 95%) with the nucleotide sequence of the GenBank Accession No. NM_005928 (protein ID. NP_005919.1), Homo sapiens milk fat globule-EGF factor 8 protein (MFGE8) (protein ID. NP_005919.1); or (ii) at least 65% sequence homology with the amino acid sequence of the GenBank protein_id NP_005919.1 (ICT1030); or (iii) substantial nucleotide sequence homology (for example, at least 60% identity, preferably at least 70% sequence identity to a reference sequence, more preferably 80%, still more preferably 85%, even more preferably at least 90% or 95%) with the nucleotide sequence as set forth in SEQ ID NO:1 or SEQ ID NO:3; or (iv) substantial sequence homology with the encoded amino acid sequence (for example, SEQ ID NO:2).

ICT1030 polynucleotides or polypeptides are typically from a mammal including, but not limited to, human, rat, mouse, hamster, cow, pig, horse, sheep, or any mammal. A "ICT1030 polynucleotide" and a "ICT1030 polypeptide," may be either naturally occurring, recombinant, or synthetic (for example, via chemical synthesis).

MFGE8 DNA sequence contains 1934 base pairs (see SEQ ID NO:1), ICT1030 coding sequence contains 1164 base pairs (see SEQ ID NO:3), encoding a protein of 387 amino acids (see SEQ ID NO:2).

According to an aspect of the present invention, it has been determined that the target ICT1030, for example, MFGE8, is a novel target, a tumor suppressor, in mammalian tissues, including breast tissue, colon tissue, prostate tissue, skin tissue, bone tissue, parotid gland tissue, pancreatic tissue, kidney tissue, uterine cervix tissue, lymph node tissue, and ovarian tissue. Human chromosome region 15q25 is one of the novel targets identified that is validated as a tumor suppressor. Therefore, the tumor-suppressing gene(s) located on chromosome region 15q25 can play an important role in the cancer therapy, including breast, colon, prostate, skin, bone, parotid gland, pancreatic, kidney, uterine cervix, lymph node, and ovarian cancers.

ICT1031: The term "ICT1031" refers to validated target ICT1031, which includes TNFSF13 (Accession Nos. AK090698 and O75888), related molecules such as APRIL, TALL-2 and TRDL-1, or consensus, nucleic acid (DNA and RNA) or protein (or polypeptide), and can include their polymorphic variants, alleles, mutants, and interspecies homologs that have (i) substantial nucleotide sequence homology (for example, at least 60% identity, preferably at least 70% sequence identity, more preferably at least 80%, still more preferably at least 90% and even more preferably at least 95%) with the nucleotide sequence of the Accession No. AK090698, Homo sapiens TNFSF13 (Accession Nos. AK090698 and O75888); or (ii) at least 65% sequence homology with the amino acid sequence of the Accession No. O75888 (TNFSF13); or (iii) substantial nucleotide sequence homology (for example, at least 60% identity, preferably at least 70% sequence identity to a reference sequence, more preferably 80%, still more preferably 85%, even more preferably at least 90% or 95%) with the nucleotide sequence as set forth in SEQ ID NO:4; or (iv) substantial sequence homology with the encoded amino acid sequence (for example, SEQ ID NO:5).

ICT1031 polynucleotides or polypeptides are typically from a mammal including, but not limited to, human, rat, mouse, hamster, cow, pig, horse, sheep, or any mammal. A "ICT1031 polynucleotide" and a "ICT1031 polypeptide," may be either naturally occurring, recombinant, or synthetic (for example, via chemical synthesis).

TNFSF13 DNA sequence (Accession No. AK090698) contains 2036 base pairs (see SEQ ID NO:4) and TNFSF13 encoding protein (Accession No. O75888) contains 250 amino acids (see SEQ ID NO:5).

According to an aspect of the present invention, it has been determined that the target ICT1031, for example, TNFSF13, is a novel target for tumor growth inhibition in mammalian tissues, including breast tissue, colon tissue, esophagus tissue, and ovarian tissue. Therefore, inhibition of tumor-promoting target ICT1031 can play an important role in the cancer therapy, including breast, colon, esophagus, and ovarian cancers.

ICT1003: The term "ICT1003" refers to validated target ICT1003, which includes ZFP236 (Accession Nos. AK000847), related molecules, or consensus, nucleic acid (DNA and RNA) or protein (or polypeptide), and can include their polymorphic variants, alleles, mutants, and interspecies homologs that have (i) substantial nucleotide sequence homology (for example, at least 60% identity, preferably at least 70% sequence identity, more preferably at least 80%, still more preferably at least 90% and even more preferably at least 95%) with the nucleotide sequence of the GenBank Accession No. AK000847, novel Homo sapiens zinc finger protein 236 (GenBank Accession No. AK000847.1); or (ii) at least 65% sequence homology with the amino acid sequence of the protein_id BAA91398.1 (ICTB1003); or (iii) substantial nucleotide sequence homology (for example, at least 60% identity, preferably at least 70% sequence identity to a reference sequence, more preferably 80%, still more preferably 85%, even more preferably at least 90% or 95%) with the nucleotide sequence as set forth in SEQ ID NO:6 or SEQ ID NO:8; or (iv) substantial sequence homology with the encoded amino acid sequence (for example, SEQ ID NO:7).

ICT1003 polynucleotides or polypeptides are typically from a mammal including, but not limited to, human, rat, mouse, hamster, cow, pig, horse, sheep, or any mammal. A "ICT1003 polynucleotide" and a "ICT1003 polypeptide," may be either naturally occurring, recombinant, or synthetic (for example, via chemical synthesis).

ZFP236 DNA sequence contains 2241 base pairs (see SEQ ID NO:6), ZFP236 coding sequence contains 1419 base pairs (see SEQ ID NO:8), encoding a protein of 472 amino acids (see SEQ ID NO:7).

According to an aspect of the present invention, it has been determined that the target ICT1003, for example, ZFP236, is a novel target for tumor growth inhibition in mammalian tissues, including breast tissue, colon tissue, lung tissue, and ovarian tissue. Therefore, inhibition of tumor-promoting target ICT1003 can play an important role in the cancer therapy, including breast, colon, lung and ovarian cancers.

ICT1024: The term "ICT1024" refers to validated target ICT1024, the gene and protein EGF-AP. The was identified first using a process called Efficacy-First™ discovery (described in PCT/US02/31554, which is hereby incorporated by reference in its entirety). Briefly, human breast tumor carcinoma cells, MDA-MB-435, were inoculated subcutaneously into mouse breast fat pads. When the xenograft tumors grew up to 200 mm3 in volume, plasmids expressing basic Fibroblast Growth Factors (FGF-2) were intratumorally delivered repeatedly. The treated tumor demonstrated much faster growth than the untreated tumor.

Figure 7:
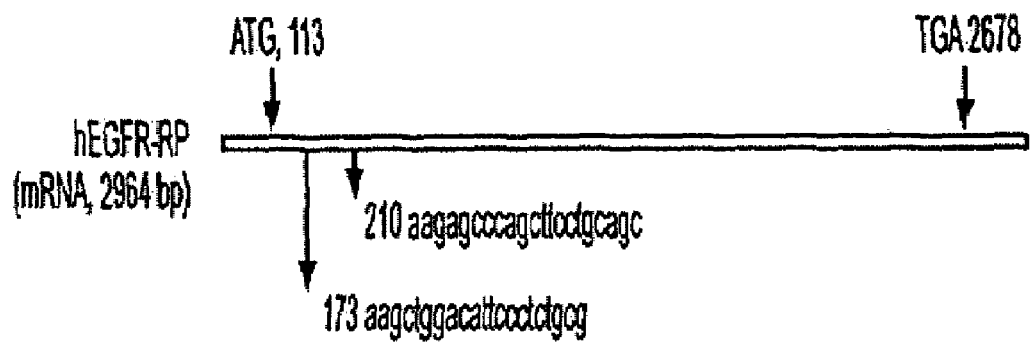
FIG. 7 shows that the ICT1024 siRNA Design: two 21 nt sequences from ICT1024 were selected as the targets for RNAi-mediated knockdown of ICT1024 gene expression. (SEQ ID NO: 25 and SEQ ID NO: 26)
Figure 8:
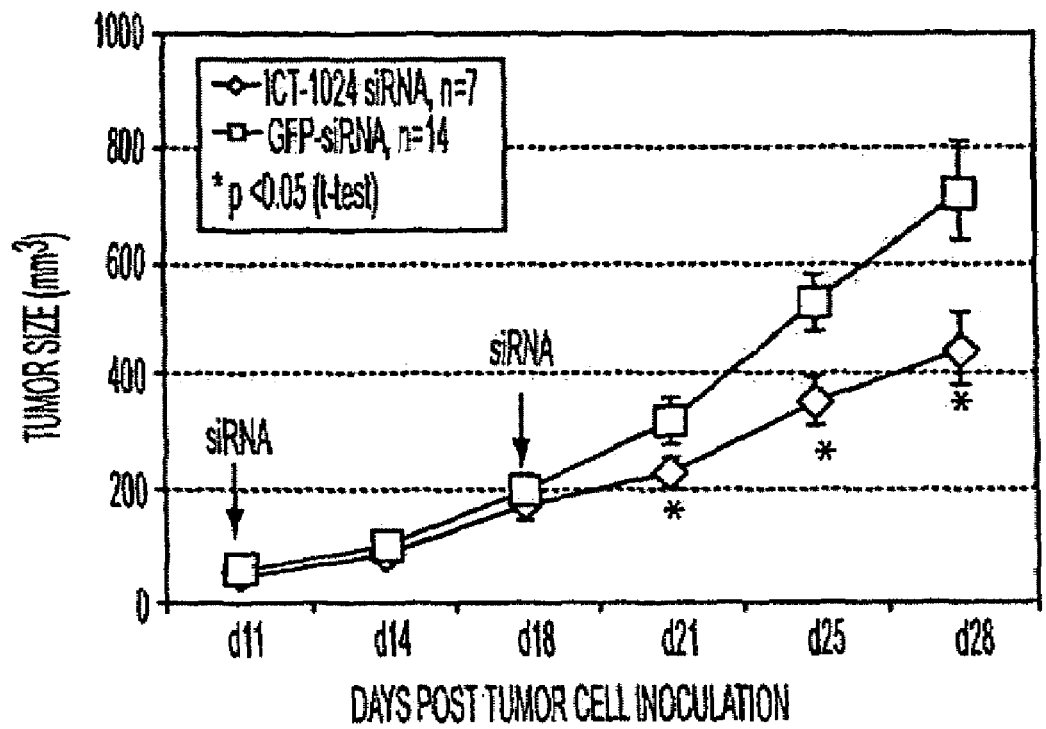
FIG. 8 shows that ICT1024 siRNA duplexes inhibit growth of MDA-MB-435 cell formed xenograft tumor on nude mice.
Figure 9:
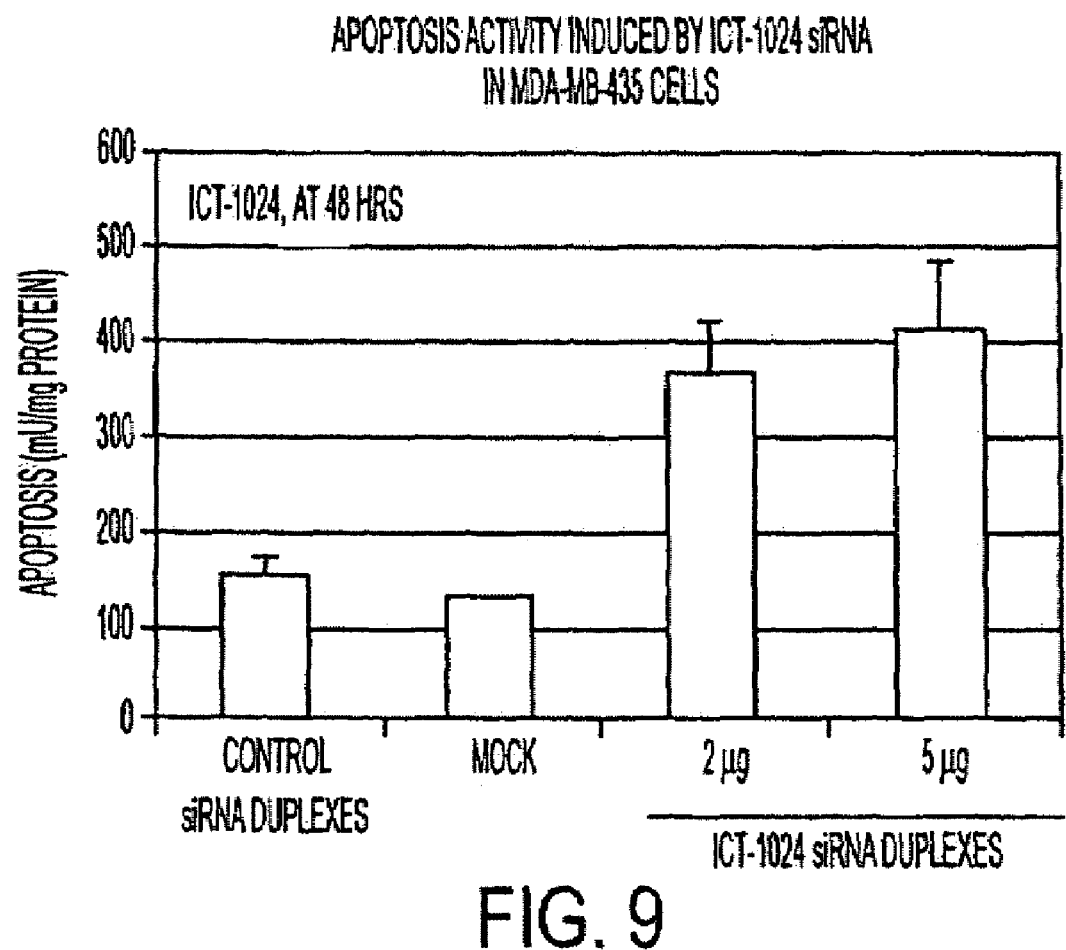
FIG. 9 shows that ICT1024 siRNA duplexes induce apoptosis activity in a MDA-MB-435 cell culture assay.

Tumor tissues was obtained and used to isolate total RNA for microarray analysis (Affymetrix, U133). One of the highly un- or down-regulated genes (about 1% of the total probes on the U133 chip), ICT1024, demonstrated significant up-regulated expression with signal from 585 (control group expression level), to 1208 (treated group expression level). This gene was therefore selected for the next level of target validation with a method called Disease-Control™ validation, using an siRNA based in vivo knockdown in the same xenograft tumor model. Two siRNA duplexes, 21 base pair each (FIG. 7) (SEQ ID NO: 25 and 26), were designed targeting this ICT1024 gene, specific to the sequence of AK026010, NM_022450 and M99624, in the coding region (aagctggacattccctctgcg (SEQ ID NO: 26), aagagcccagcttcct-gcagc (SEQ ID NO: 25)). Then the two siRNA duplexes were delivered intratumorally three times. The siRNA-mediated knockdown of ICT1024 gene expression resulted in tumor growth inhibition (FIG. 8). The further analysis in a cell culture based study demonstrated that knocking down ICT1024 gene expression in the tumor cell MDA-MB-435, induced a remarkable increase of the apoptosis activity (FIG. 9). Based on these results, ICT1024 was selected for further evaluation as a therapeutic target.

After this identification and validation of the biological function of this gene in cell culture and in a xenograft tumor model, a series of analyses of ICT1024 gene expression profile searches were conducted through both public domain databases and the GeneLogic Express Analysis. The results from the analyses further demonstrated the biological function and its relevance to the disease status, particularly in the area of tumor growth, tumor cell apoptosis and tumor metastasis.

Figure 10:
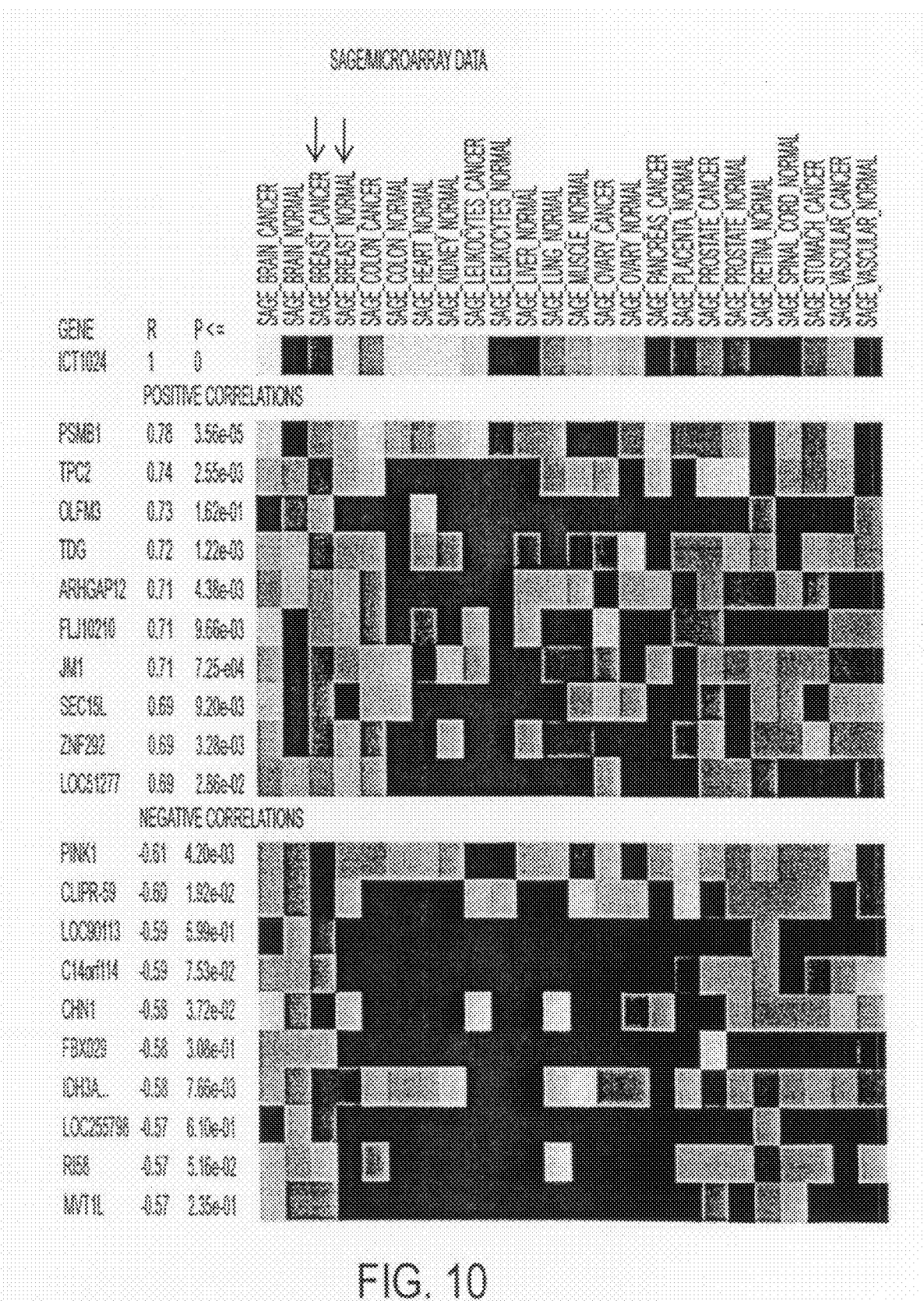
FIG. 10 shows that expression of ICT1024 in breast tumor tissue has significantly positive correlation with other breast cancer genes and other cancer genes, based on the SAGE/microarray analysis.

ICT1024 gene is highly expressed in various tumor samples. In addition to the observation from the Efficacy-First™ study that ICT1024 was up-regulated in bFGF treated xenograft tumor formed by inoculation of human breast carcinoma cell, MDA-MB-435 (there is some evidences that this cell line may be from melanoma rather than breast carcinoma), it was found out that ICT1024 is significantly up-regulated in tumor tissue, especially in breast carcinoma tissue samples, from three different analyses. Those analyses were provide online from SAGE Genie databases of NCBI's CANCER GENOME ANATOMY PROJECT. The first analysis is from a SAGE digital Northern (see Table I) (SEQ ID NO:36) that demonstrated a very clearly up-regulated ICT1024 expression in metastatic breast carcinoma tissues. From the same analysis, the up-regulation of ICT1024 gene expression was also observed in stomach cancer, prostate adenocarcinoma, brain glioblastoma and other tumor types. The second analysis is from Monochromatic SAGE/cDNA Virtual Northern (see Table II). In terms of all tissue types, the ICT1024 has been identified as highly up-regulated genes from both EST data set and SAGE data set. In the mammary gland tumor tissue, this gene was significantly up regulated in the SAGE dataset. Brain and prostate are other tissue types showed significant up regulated gene expression in tumor tissues than in the normal tissues. The third analysis is from Two Dimensional Array Display (see FIG. 10). ICT1024 expressions is correlated with the expressions of a group of tumorigenic genes in the breast tumor tissues.

Figure 11:
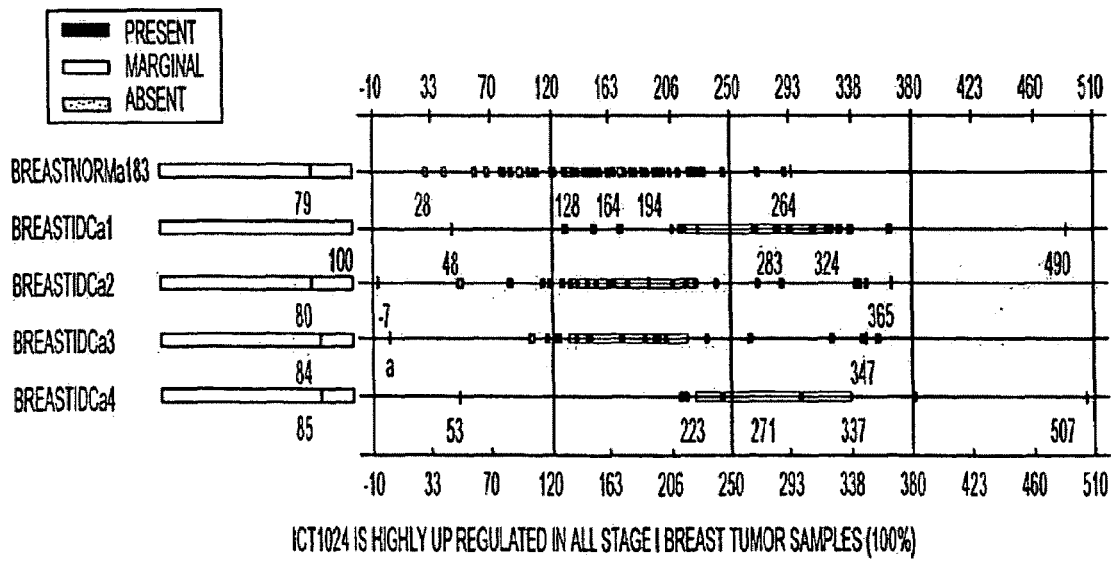
FIG. 11 shows that ICT1024 is highly up regulated in all Stage I Breast Tumor samples (100%), based on Gene Logic GeneExpress analysis.

Using Gene Logic's GeneExpress analysis, we found out that not only was ICT1024 up-regulated in the breast tumor tissues, but also was much more up-regulated in the tissues from the stage I tumors than those from other stages of the tumors (FIG. 11). This finding indicates that ICT1024 is actively involved in the early stage of tumor growth.

Through the literature search, ICT1024 was found to have a positive correlation with expression of PSMB1, Proteosome Beta Subunit 1. Proteosome is a multicatalytic proteinase complex and it is able to cleave peptides in a ubiquitin-dependent process. The Ubiquitin-mediated degradation of critical regulators is currently a well-recognized anticancer target Another positive correlation with RAP1 expression was also been observed. RAP1 is Ras-associated protein-1 and is involved in activation of the Ras oncogene.

ICT1025: The term "ICT1025" refers to validated target ICT1025. The inventors identified the gene and protein, TRA-1, first using a process called Efficacy-First™ discovery (described in PCT/US02/31554, which is hereby incorporated by reference in its entirety). Briefly, human breast tumor carcinoma cells, MDA-MB-435, were inoculated subcutaneously into mouse breast fat pads. When the xenograft tumors grew up to 200 mm3 in volume, plasmids expressing basic Fibroblast Growth Factors (FGF-2) were intratumorally delivered repeatedly. The treated tumor demonstrated much faster growth than the untreated tumor.

Tumor tissues was obtained and used to isolate total RNA for microarray analysis (Affymetrix, U133). One of the highly un- or down-regulated genes (about 1% of the total probes on the U133 chip), ICT1025, demonstrated significant up-regulated expression with signal from 279 (control group expression level), to 412 (treated group expression level). This gene (Accession No. AK025852, NM_003299 and BC009195) was therefore selected for the next level of target validation with a method called Disease-Control™ validation, using an siRNA based in vivo knockdown in the same xenograft tumor model. Two siRNA duplexes, 21 base pair each, were designed targeting this ICT1025 gene, specific to the sequence in the coding regions of aactgttgaggagcccatgga (started at nt 966) (SEQ ID NO: 23) and aatctgatgatgaagctg-cag (started at nt 1008) (SEQ ID NO: 24). Then the two siRNA duplexes were delivered intratumorally three times. The siRNA-mediated knockdown of ICT1025 gene expression resulted in tumor growth inhibition. The further analysis in a cell culture based study demonstrated that knocking down ICT1025 gene expression in the tumor cells MDA-MB-435, HT29 induced remarkable increases of the apoptosis activity and decrease of cell proliferation. Based on these results, ICT1025 was selected for further evaluation as a therapeutic target.

After this identification and validation of the biological function of this gene in cell culture and in a xenograft tumor model, a series of ICT1025 gene expression profile searches were conducted through both public domain databases and the GeneLogic Express Analysis. The results from the analyses further demonstrated the biological function and its relevance to the disease status, particularly in the areas of tumor growth, tumor cell apoptosis and tumor metastasis.

TRA-1s downregulation by siRNA delivery specifically inhibiting its expression has demonstrated that its expression has a "Disease-Controlling" role in proliferative diseases. By using siRNA-mediated knockdown of TRA-1 expression in the xenograft tumor model it was found that tumor growth rate is inhibited when TRA-1 expression is inhibited. We further found out that knocking down the expression of this protein in several breast tumor cell lines induced significant increase of the apoptotic activity. This finding was further verified when the cells were treated with the monoclonal antibody specifically against this protein. During the process to define the subcellular location of this protein in the breast tumor cells, we found that not only this protein are cell surface membrane bound but also has substantial potion located extracellularly.

Given our findings, one hypothesis for the promising autologous protocol clinical results is that administration of the isolated TRA-1 complex induces antibodies toward TRA-1 itself, not just the autologous patient specific peptides, and contributes substantially to tumor inhibition, or potentially is the major mechanism of activity. Using cell surface biotinylation technique, we observed that existence of TRA-1 proteins in the outer surface of the MDA-MB-435 and MCF-7 breast cancer cells. To explore the biological relevance of the cell surface localization of TRA-1 from breast cancer cells, we examined the mAb on cell apoptosis and proliferation. When the cells were treated with a TRA-1 monoclonal antibody, increase of apoptosis activity and inhibition of cell proliferation were observed. These results strongly suggest an involvement of cell surface TRA-1 in apoptosis and cell proliferation signal pathway. Therefore, TRA-1 inhibitors, including siRNA agent to reduce its expression and antibodies to bind it and inhibit its activity, provide novel and effective treatments for breast cancer, other malignancies, and many proliferative diseases. Success of mAb therapy inhibiting TRA-1 will have broad applications and will be clinical feasible.

The invention provides methods and compositions for inhibiting or blocking the biological activity of ICT1025 protein. Therapeutic methods and compositions for treatment of cancer, autoimmune disease and other diseases also are provided. More specifically, the invention provides methods and compositions that permit down-regulation of the production and activity of ICT1025 at the nucleic acid and/or protein level, and that allow deactivation, inhibition, blocking, or down-regulation of biochemical functions of this protein. The inhibition can be achieved, for example, by down-regulating transcription or translation of the protein; by degrading mRNA encoding the protein, by degrading the protein, by blocking and/or deactivating RNA and by inhibiting protein function. The invention provides inhibitors of ICT1025 including, but nor limited to, antibodies, mRNA sequence specific inhibitors, such as siRNA and antisense, peptide antagonists, and small molecule protease inhibitors. The invention also provides methods for generating these inhibitors, and for using one or more inhibitors to achieve a desired biological function, such as treatment and prevention of neoplastic, immunological and/or infectious diseases. In particular, the invention provides immunoglobulin agents, including antibodies and antibody fragments, and methods of using these agents for the treatment and diagnosis of disease. The content of the provisional application Ser. No. 60/458,948 is hereby incorporated by reference in its entirety.

DNA and Protein Sequence Homology Analyses

ICT 1024: There are three full-length cDNA sequences: NM_022450, BC014425 and AK026010, which code for the same protein. The protein contains 855 amino acids and has a molecular weight of about 130 kD.

Using BLAST search for homology of DNA sequences, we found about 325 homologous sequences in human, murine, rattus and fugu, etc. However, only a very few human homologues were found. There is only one cDNA sequence (AK056708) has very high homology with the above three cDNAs, but a short stretch of mutated sequence, which may caused by cloning artifact. Therefore, the protein coding region was disrupted. Other partial cDNA sequences and chromosome sequences were also found. The cDNA was originally named in the NCBI nucleotide database as EGFR related sequence (EGFR-RS), or EGFR related protein (EGFR-RP) before Apr. 22 of 2003. Currently the cDNA has been named as Homo sapiens rhomboid family 1.

We further analyzed the protein sequence of ICT1024. This 855 AA protein has several domain signatures identified by Conserved Domain Architecture Retrieval Tool from NCBI database. One of the major domain structure is a region covering about 146 AA. This domain has been recognized as the conservative region of the Rhomboid family. This family contains integral membrane proteins that are related to Drosophila rhomboid protein. Members of this family are found in bacteria and eukaryotes. Rhomboid promotes the cleavage of the membrane-anchored TGF-alpha-like growth factor Spitz, allowing it to activate the Drosophila EGF receptor (4, 5, 6, 7). Analysis suggests that Rhomboid-1 is a novel intramembrane serine protease that directly cleaves Spitz. These proteins contain three strongly conserved histidines in the putative transmembrane regions that may be involved in the peptidase function. We first compared the ICT1024 rhomboid domain with a group of rhomboid proteins from various organism (FIG. 12). Although the framework of the ICT1024 rhomboid domain is quite similar to those from other organisms, the sequences are very different. In comparison of the ICT1024 rhomboid domain with other human rhomboid like proteins (FIG. 13), the sequence of ICT1024 is very different from others. In addition, the ICT1024 specific siRNA duplexes used in both in vitro and in vivo validations target regions that are quite different from any of those human rhomboid proteins (FIG. 14).

We also analyzed the hydrophobicity of ICT1024 protein and its potential trans-membrane location. Multiple prediction program have been applied, including SOSUI model (Table III (SEQ ID NOS 106-111, respectively in order of appearance)), TMHMM Model and TMpred Models (FIG. 15). From those analyses, it seems that ICT1024 is a integral membrane protein with multiple transmembrane domains and intracellular domains and extracellular domains. Whatever methods used for the predication of the protein location and topology, this protein has been demonstrated with a long N-terminal domain outside the membrane. This N-terminal domain would either be outside of cell or inside the cytoplasm. There are other regions of this protein also exposed to the outside of the cell or cytoplasm. The membrane protein, ICT1024, has a proteinase activity for activation of EGF-EGF receptor pathway and, based on the discoveries described herein, is a very attractive target for therapeutic development of various modalities of drugs, including monoclonal antibody, siRNA inhibitor, peptide antagonist and small molecular inhibitors, etc. A suitable monoclonal antibody will bind to either the extracellular or intracellular domain of the protein and block function of the protein.

ICT 1025

As mentioned in the Background section, there are three full-length cDNA sequences: NM_003299, AK025459 and BC009195, which code for the same protein. The protein contains 803 amino acids.

Using BLAST search for homology of DNA sequences, we found about many homologous sequences in human, murine, rattus and fugu, etc. However, only a very few human homologues were found. There is only one cDNA sequence (AK025459) has very high homology with the above three cDNAs, but a short stretch of mutated sequence, which may caused by cloning art fact. Therefore, the protein coding region was disrupted. Other partial cDNA sequences and chromosome sequences were also found. The cDNA was originally named in the NCBI nucleotide database as Tumor Rejection Protein 1 (TRA-1).

We also analyzed the hydrophobicity of ICT1025 protein and its potential trans-membrane location. Multiple prediction programs including DAS model and TMpred Model were used for the analyses (FIG. 17). Whatever methods used for the predication of the protein location and topology, this protein has been demonstrated with several transmembrane domains. This N-terminal domain would be either outside of cell or inside the cytoplasm. There are other regions of this protein also exposed to the outside of the cell or cytoplasm. The membrane presentation of ICT1025 may play very important roles in tumorigenesis and tumor antigen presenting. Therefore, ICT1025 is a very attractive target for therapeutic development of various modalities of drugs, including monoclonal antibody, siRNA inhibitor, peptide antagonist and small molecular inhibitors, etc. A suitable monoclonal antibody will bind to either the extracellular or intracellular domain of the protein and block finction of the protein.

The Role in Tumor Metastasis and Growth

ICT1024

The protein ICT1024 apparently plays a key role in tumor metastasis and tumor growth, through its activation of the EGF-EGFR pathway, and other proteinase functions and the additional unknown functions. We have evidence to demonstrate that this gene is up-regulated in fast growing tumor from a xenograft tumor model study treated with bFGF expression vector. This gene is up-regulated in mRNA level in tumor tissues, from breast cancer, prostate cancer, brain cancer and other types of cancers, based on the SAGE virtual and digital northern analyses. This gene has also been shown to be up-regulated using Gene Logic's GeneExpresse analysis. When the gene expression was knockdown with ICT-1024 specific siRNA duplexes in the growing xenograft tumors, the tumor growth was significantly inhibited (FIG. 8).

Apoptosis (programmed cell death) is a form of cellular suicide that typically includes plasma membrane blebbing, cellular volume contraction, and nuclear condensation, and culminates in the activation of endogenous endonucleases that degrade cellular DNA. The well-defined loss of specific cells is crucial during embryonic development and organogenesis. In addition to its physiological roles, apoptosis also occurs in many types of cancer cells when they are exposed to various chemotherapeutic drugs, including antimetabolites, deoxynucleotide synthesis inhibitors, DNA topoisomerase inhibitors, anti-microtubule agents, alkylating agents, and endoplasmic reticulum (ER) stressors. Interestingly enough, when we knockdown ICT-1024 expression in MDA-MB-435 cells transfected with the specific siRNA duplexes, the apoptosis activity was dramatically increased, as tested with a TUNEL assay, in which terminal deoxynucleotidyl transferase (TdT) catalyzes the incorporation of bromo-deoxyuridine (BrdU) residues into the fragmenting nuclear DNA at the 3'-hydroxyl ends by nicked end labeling.

The specific ICT1024 gene silencing by siRNA duplexes has been verified by RT-PCR. This finding suggested that ICT-1024 plays a crucial role in regulation of tumor cell apoptosis. Other evidence tends to show that the EGF-EGFR is sufficient to activate the major signaling pathways leading to cell proliferation and survival, and EGFR signaling is sufficient to suppress apoptosis induced by serum withdrawal (12).

Malignant tumors grow out of control due to the highly expressed and activated growth factors, EGF, PDGF and VEGF, etc. They penetrate and destroy local tissues and spread throughout the body via blood or the lymphatic system. These tumors are not morphologically typical of the original tissue and are not encapsulated. Malignant tumors commonly recur after surgical removal. Accordingly, treatment ordinarily targets malignant cancers or malignant tumors. The intervention of malignant growth is most effective at the early stage of the cancer development. It is important, therefore, to identify and validate a target for early signs of tumor formation and to determine potent tumor growth or gene expression suppression elements or agents associated therewith. The development of such tumor growth and/or gene expression and therapeutic elements or agents involves an understanding of the genetic control mechanisms for cell division and differentiation, particularly in connection with tumorigenesis.

Based on the GeneExpress analysis, which is based on thousands of clinical samples of tumor tissues and normal tissues, we found that ICT1024 has significantly up-regulated expression in Stage 1 tumor samples (FIG. 11). The signals from Affymetrix array U133 for the Stage 1 tumor samples are much higher (283) than those from the normal tissues (165). All Stage 1 tumor samples showed significant up-regulation of ICT1024 gene expression. Accordingly, ICT1024 is useful as a marker for early cancer diagnosis. It is also very useful for cancer treatment when this gene is specifically knocked down.

In the *Drosophila* cell, the polytopic membrane protein Rhomboid-1 promotes the cleavage of the membrane-anchored TGFalpha-like growth factor Spitz, allowing it to activate the *Drosophila* EGF receptor. Until now, the mechanism of this key signaling regulator has remained obscure, but this analysis suggests that Rhomboid-1 is a novel intramembrane serine protease that directly cleaves Spitz. In accordance with the putative Rhomboid active site being in the membrane bilayer, Spitz is cleaved within its transmembrane domain, and thus is the first example of a growth factor activated by regulated intramembrane proteolysis. Rhomboid-1 is conserved throughout evolution from archaea to humans, and these results show that a human Rhomboid promotes Spitz cleavage by a similar mechanism. This growth factor activation mechanism may therefore be widespread (6). Although Rhomboid-1 does not contain any obvious sequence homology domains, it has the characteristics of a serine protease (7). Four of its six essential residues parallel the residues required for a serine protease catalytic triad charge-relay system and an oxyanion stabilization site (consisting of a glycine two residues away from the active serine, and the serine itself; G215 and S217). These are the two active site determinants of serine proteases, and these four essential residues account for all of the amino acids known to participate directly in the serine protease catalytic mechanism (5) These residues are absolutely conserved in all Rhomboids, and their mutation to even very similar residues (i.e., G215A, S217T, and S217C) abolishes Rhomboid-1 activity. These are hallmarks of active site residues. (3) The location of the essential residues is highly suggestive of a serine protease active site; both G215 and S217 occur in the conserved GASGG motif (SEQ ID NO: 104), which is remarkably similar to the conserved GDSGG motif (SEQ ID NO: 105) surrounding the active serine of 200 different serine proteases. Furthermore, the essential residues N169 and H281 occur at the same height in their transmembrane domains (TMDs) as the GASGG motif (SEQ ID NO: 104), consistent with the proposal that they associate with S217 to generate a catalytic triad. Finally, Spitz processing is directly inhibited by the specific serine protease inhibitors DCI and TPCK, and Rhomboid-1 itself becomes limiting in their presence, suggesting that Rhomboid-1 is their direct target and thus the serine protease responsible for Spitz cleavage. The suggested model is presented in FIG. 16.

Because of our understanding about this gene and its encoded protein, and its potential function in human cell, we designate this gene as EGF Activation Protein (EGF-AP). We also conclude that EGF-AP is an attractive cancer target for anti-tumor therapeutic development. Inhibitors, such as DNA binding protein, RNA binding protein, siRNA or other types of RNAi, antisense, ribozyme and DNAzyme, etc., that are able to block the ICT1024 protein production, are effective for treating diseases associated with increased ICT1024 expression. In addition, these diseases also may be treated using inhibitors, such as monoclonal antibodies, polyclonal antibodies, single chain antibodies, intrabodies, protein antagonists, small molecule protease inhibitors or other types of inhibitors, will be effective blockers of ICT1024 protein functions. We have also recognized that this ICT1024 protein may represent a novel class of drug targets useful for treatment of cancer and other diseases.

REFERENCES

1 Sturtevant M A, Roark M, Bier E: The *Drosophila* rhomboid gene mediates the localized formation of wing veins and interacts genetically with components of the EGF-R signaling pathway. *Genes Dev* 1993, 7:961-973.
2 Sturtevant M A, Roark M, O'Neill J W, Biehs B, Colley N, Bier E: The *Drosophila* rhomboid protein is concentrated in patches at the apical cell surface. *Dev Biol* 1996, 174:298-309.
3 Guichard A, Biehs B, Sturtevant M A, Wickline L, Chacko J, Howard K, Bier E: rhomboid and Star interact synergistically to promote EGFR/MAPK signaling during *Drosophila* wing vein development. *Development* 1999, 126:2663-2676.
4 Mushegian A R, Koonin E V: Sequence analysis of eukaryotic developmental proteins: ancient and novel domains. *Genetics* 1996, 144:817-828.
5 Pellegrini L, Passer B J, Canelles M, Lefterov I, Ganjei J K, Fowlkes B J, Koonin E V, D'Adamio L: PAMP and PARL, two novel putative metalloproteases interacting with the COOH-terminus of Presenilin-1 and -2. *J Alzheiiners Dis* 2001, 3:181-190.
6 Urban S, Lee J R, Freeman M: *Drosophila rhomboid-1* defines a family of putative intramembrane serine proteases. *Cell* 2001, 107:173-182.
7 Klambt C: EGF receptor signaling: roles of star and rhomboid revealed. *Curr Biol* 2002, 12:R21-R23.
8 Guichard A, Roark M, Ronshaugen M, Bier E: brother of rhomboid, a rhomboid-related gene expressed during early *Drosophila* oogenesis, promotes EGF-R/MAPK signaling. *Dev Biol* 2000, 226:255-266.
9 Wasserman J D, Urban S, Freeman M: A family of rhomboid-like genes: *Drosophila rhomboid*-1 and roughoid/ rhomboid-3 cooperate to activate EGF receptor ignaling. *Genes Dev* 2000, 14:1651-1663.
10 Brown M S, Ye J, Rawson R B, Goldstein J L: Regulated intramembrane proteolysis: a control mechanism conserved from bacteria to humans. *Cell* 2000, 100:391-398.
11 Urban S, Freeman M: Intramembrane proteolysis controls diverse signaling pathways throughout evolution. *Curr Opin Genet Dev* 2002, 12:512-518.
12 Wang Y, Pennock S, Chen X, Wang Z. 2002:Endosomal signaling of epidermal growth factor receptor stimulates signal transduction pathways leading to cell survival. *Mol Cell Biol*. 2002 Oct;22(20):7279-90.
13 Patrick Lu, Frank Xie et al. U.S. Application No. 60/458,948 Targets for Tumor Treatment

ICT1025

The protein ICT1025 apparently plays a key role in tumor metastasis and tumor growth, through its multiple roles as inhibitor of apoptosis, activator of proliferation and up-regulation of multiple drug resistant genes. We have evidence to demonstrate that this gene is up-regulated in fast growing tumor from a xenograft tumor model study treated with bFGF expression vector. This gene is up-regulated in mRNA level in tumor tissues, from breast cancer, prostate cancer, brain cancer and other types of cancers, based on the SAGE virtual and digital northern analyses. This gene has also been shown to be up-regulated using Gene Logic's GeneExpresse analysis. When the gene expression was knockdown with ICT1025 specific siRNA duplexes in the growing xenograft tumors, the tumor growth was significantly inhibited.

Apoptosis (programmed cell death) is a form of cellular suicide that typically includes plasma membrane blebbing, cellular volume contraction, and nuclear condensation, and culminates in the activation of endogenous endonucleases that degrade cellular DNA. The well-defined loss of specific cells is crucial during embryonic development and organogenesis. In addition to its physiological roles, apoptosis also occurs in many types of cancer cells when they are exposed to various chemotherapeutic drugs, including antimetabolites, deoxynucleotide synthesis inhibitors, DNA topoisomerase inhibitors, anti-microtubule agents, alkylating agents, and endoplasmic reticulum (ER) stressors. Interestingly enough, when we knockdown ICT1025 expression in MDA-MB-435 cells and HT-29 cells, transfected with the specific siRNA duplexes, the apoptosis activity was dramatically increased, as tested with a TUNEL assay, in which terminal deoxynucleotidyl transferase (TdT) catalyzes the incorporation of bromo-deoxyuridine (BrdU) residues into the fragmenting nuclear DNA at the 3'-hydroxyl ends by nicked end labeling. The specific ICT1025 gene silencing by siRNA duplexes has been verified by RT-PCR. This finding suggested that ICT1025 plays a crucial role in regulation of tumor cell apoptosis. Other evidence tends to show that the ICT1025 is sufficient to activate the major signaling pathways leading to cell proliferation and survival.

Methods of Treating Cellular Proliferative Diseases Using Inhibitors to Block ICT1024 and ICT1025 Protein Production RNAi, antisense, ribozyme and other nucleic acid therapeutics can be used to inhibit expression of ICT 1003 and ICT-1024 and ICT 1025 and ICT 1031 in patients suffering diseases with cellular proliferation. For example, an ICT 1003 or ICT-1024 or ICT 1025 or ICT 1031 antisense strand (either RNA or DNA) is directly introduced into the cells in a form that is capable of binding to the mRNA transcripts. Alternatively, a vector containing a sequence which once within the target cells, is transcribed into the appropriate antisense mRNA, may be administered. Antisense nucleic acids which hybridize to target mRNA decrease or inhibit production of the polypeptide product encoded by a gene by associating with the normally single-stranded mRNA transcript, thereby interfering with translation and thus, expression of the protein. For example, DNA containing a promoter, e.g., a tissue-specific or tumor specific promoter, is operably linked to a DNA sequence (an antisense template), which is transcribed into an antisense RNA. By "operably linked" is meant that a coding sequence and a regulatory sequence(s) (i.e., a promoter) are connected in such a way as to permit gene expression when the appropriate molecules (e.g., transcriptional activator proteins) are bound to the regulatory sequence(s).

Oligonucleotides complementary to various portions of ICT 1003 or ICT-1024 or ICT 1025 or ICT1031 can be determined in vitro for their ability to decrease production of ICT 1003 or ICT-1024 or ICT 1025 or ICT1031 in human cells (e.g., using the FOCUS hepatocellular carcinoma (HCC) cell line) according to standard methods. A reduction in ICT 1003 or ICT-1024 or ICT 1025 or ICT1031 gene product in cells contacted with the candidate antisense composition compared to cells cultured in the absence of the candidate composition is detected using ICT 1003 or ICT-1024 or ICT 1025 or ICT1031-specific antibodies or other detection strategies. Sequences which decrease production of ICT 1003 or ICT-1024 or ICT 1025 or ICT1031 in in vitro cell-based or cell-free assays are then be tested in vivo in rats or mice to confirm decreased ICT 1003 or ICT-1024 or ICT 1025 or ICT1031 production in animals with malignant neoplasms.

Antisense therapy is carried out by administering to a patient an antisense nucleic acid by standard vectors and/or gene delivery systems. Suitable gene delivery systems may include liposomes, polymers, receptor-mediated delivery systems, naked DNA, and viral vectors such as herpes viruses, retroviruses, adenoviruses and adeno-associated viruses, among others. A therapeutic nucleic acid composition is formulated in a pharmaceutically acceptable carrier. The therapeutic composition may also include a gene delivery system as described above. Pharmaceutically acceptable carriers are biologically compatible vehicles which are suitable for administration to an animal: e.g., physiological saline. A therapeutically effective amount of a compound is an amount which is capable of producing a medically desirable result such as reduced production of an ICT 1003 or ICT-1024 or ICT 1025 or ICT1031 gene product or a reduction in cellular proliferation in a treated animal.

Parenteral administration, such as intravenous, subcutaneous, intramuscular, and intraperitoneal delivery routes, may be used to deliver nucleic acids or ICT 1003 or ICT-1024 or ICT 1025 or ICT1031-inhibitory peptides on non-peptide compounds. Liposome formulations of therapeutic compounds may also facilitate activity.

Dosages for any one patient depends upon many factors, including the patient's size, body surface area, age, the particular nucleic acid to be administered, sex, time and route of administration, general health, and other drugs being administered concurrently. Dosage for intravenous administration of nucleic acids is from approximately 106 to 1022 copies of the nucleic acid molecule.

RNA interference (RNAi) is a post-transcriptional process where the double-stranded RNA (dsRNA) inhibits gene expression in a sequence specific fashion. The RNAi process occurs in at least two steps: in first step, the longer dsRNA is cleaved by an endogenous ribonuclease into shorter, less than 100-, 50-, 30-, 23-, or 21-nucleotide-long dsRNAs, termed "small interfering RNAs" or siRNAs. In second step, the smaller siRNAs mediate the degradation of the target mRNA molecule. This RNAi effect can be achieved by introducing either longer dsRNA or shorter siRNA to the target sequence within cells. It is also demonstrated that RNAi effect can be achieved by introducing plasmids that generate dsRNA complementary to target gene. The RNAi have been sucessfully used in gene function determination in *Drosophila* (Kennerdell et al. (2000) Nature Biotech 18: 896-898; Worby et al. (2001) *Sci STKE* Aug. 14, 2001(95):PL1; Schmid et al. (2002) *Trends Neurosci* 25(2):71-74; Hammond et al. (2000). Nature, 404: 293-298), C. elegans (Tabara et al. (1998) Science 282: 430-431; Kamath et al. (2000) *Genome Biology* 2: 2.1-2.10; Grishok et al. (2000) *Science* 287: 2494-2497), and Zebrafish (Kennerdell et al. (2000) *Nature Biotech* 18: 896-898). In those model organisms, it has been reported that both the chemically synthesized shorter siRNA or in vitro transcripted longer dsRNA can effectively inhibit target gene expression. There are increasing reports on successfully achieved RNAi effects in non-human mammalian and human cell cultures (Manche et al. (1992). *Mol. Cell. Biol.* 12:5238-5248; Minks et al. (1979). *J. Biol. Chem.* 254:10180-10183; Yang et al. (2001) *Mol. Cell. Biol.* 21(22):7807-7816; Paddison et al. (2002). *Proc. Natl. Acad. Sci.* USA 99(3):1443-1448; Elbashir et al. (2001) *Genes Dev* 15(2):188-200; Elbashir et al. (2001) *Nature* 411: 494-498; Caplen et al. (2001) *Proc. Natl. Acad. Sci.* USA 98: 9746-9747; Holen et al. (2002) *Nucleic Acids Research* 30(8):1757-1766; Elbashir et al. (2001) EMBO J 20: 6877-6888; Jarvis et al. (2001) *TechNotes* 8(5): 3-5; Brown et al. (2002) *TechNotes* 9(1): 3-5; Brummelkamp et al. (2002) *Science* 296:550-553; Lee et al. (2002) *Nature Biotechnol.* 20:500-505; Miyagishi et al. (2002) *Nature Biotechnol.* 20:497-500; Paddison et al. (2002) *Genes & Dev.* 16:948-958; Paul et al. (2002) *Nature Biotechnol.* 20:505-508; Sui et al. (2002) *Proc. Natl. Acad. Sci.* USA 99(6):5515-5520; Yu et al. (2002) *Proc. Natl. Acad. Sci.* USA 99(9):6047-6052). The two siRNA duplexes we have used can effectively silence ICT1024 or EGF-AP expression in both cell based assay and xenograft tumor model. However, there are regions of mRNA of ICT 1003 or ICT-1024 or ICT 1025 or ICT1031 are useful for siRNA targeted knockdown.

In another aspect, the invention provides methods for inhibiting cancer or precancerous growth in a mammalian tissue, comprising contacting the tissue with an inhibitor that interacts with the target ICT 1003 or ICT-1024 or ICT 1025 or ICT1031 DNA or RNA and thereby inhibits the target ICT 1003 or ICT-1024 or ICT 1025 or ICT1031 gene expression, wherein the tissue is breast tissue, colon tissue, prostate tissue, skin tissue, bone tissue, parotid gland tissue, pancreatic tissue, kidney tissue, uterine cervix tissue, lymph node tissue, or ovarian tissue, wherein the inhibitor is an a nucleic acid molecule, a decoy molecule, a decoy DNA, a double stranded DNA, a single-stranded DNA, a complexed DNA, an encapsulated DNA, a viral DNA, a plasmid DNA, a naked RNA, an encapsulated RNA, a viral RNA, a double stranded RNA, a molecule capable of blocking the target ICT 1003 or ICT-1024 or ICT 1025 or ICT1031 gene expression, or combinations thereof.

Another aspect of the invention provides methods of administering inhibitors to a patient in need thereof, wherein the inhibitor molecule is delivered in the form of a monoclonal antibody, a peptide antagonist, a small molecule protease blocker, a naked oligonucleotide or a vector, wherein the nucleic acid interacts with the target ICT 1003 or ICT-1024 or ICT 1025 or ICT1031 gene.

Yet another aspect of the invention provides methods of administering an inhibitor to a patient in need thereof, wherein the inhibitor molecule is delivered in the form of a naked oligonucleotide or a vector, wherein the nucleic acid interacts with the target ICT 1003 or ICT-1024 or ICT 1025 or ICT1031 gene, wherein the nucleic acid is delivered as a vector, wherein the vector is a plasmid, cosmid, bacteriophage, or a virus, for example, a retrovirus or an adenovirus based vector.

Still another aspect of the invention provides methods of blocking in vivo expression of a gene by administering a vector to a patient in need thereof, wherein the vector containing target ICT 1003 or ICT-1024 or ICT 1025 or ICT1031 gene, wherein the nucleic acid interacts with the target ICT 1003 or ICT-1024 or ICT 1025 or ICT1031 gene expression, wherein the nucleic acid inhibits the target ICT 1003 or ICT-1024 or ICT 1025 or ICT1031 gene expression in a mammalian cell, for example, a human cell.

According to another aspect of the invention, the inhibitor molecules are introduced into tissues, including breast tissue, colon tissue, prostate tissue, skin tissue, bone tissue, parotid gland tissue, pancreatic tissue, kidney tissue, uterine cervix tissue, lung tissue, lymph node tissue, or ovarian tissue.

Using Inhibitors to Block Protein Function

Antibody Inhibitors of ICT 1003 or ICT-1024 or ICT 1025 or ICT1031

The present invention provides compositions and methods for treatments or diagnostics for diseases which progress by cellular proliferation, such as proliferation or metastasis of solid tumors, arthritis in rheumatoid arthritis, diabetic retinopathy, retinopathy of prematurity, psoriasis, and the like.

The inventors of the present invention find that antibodies binding to ICT1024 and capable of recognizing an epitope present in a region of the 1st to 590th positions from the N-terminal amino acid can specifically react with the human ICT1024 by immunocyte staining, and that biological activities can be inhibited by the inhibition of binding. Diagnosis and treatment of the above-described diseases in which their morbid states progress by abnormal angiogenesis, such as proliferation or metastasis of solid tumors, arthritis in rheumatoid arthritis, diabetic retinopathy, prematurity retinopathy and psoriasis, can be carried out by using these monoclonal antibodies.

Consequently, the present invention provides antibodies which specifically react with human ICT1024. With regard to the monoclonal antibody of the present invention, a monoclonal antibody is provided that recognizes an epitope which is present in a region of the 1st to 590th, for example, between positions 161-190 or 451-480 as measured from the N-terminal amino acid. A C-terminal epitope region is between positions 740-855, for example positions 826-855. The present invention also provides a monoclonal antibody which inhibits binding of human ICT1024 and also inhibits biological activities of ICT1024.

The inventors of the present invention find that antibodies binding to ICT1025 and capable of recognizing an epitope present in a region of the 1st to 300th positions from the N-terminal amino acid can specifically react with the human ICT1025 by immunocyte staining, and that biological activities can be inhibited by the inhibition of binding. Diagnosis and treatment of the above-described diseases in which their morbid states progress by abnormal angiogenesis, such as proliferation or metastasis of solid tumors, arthritis in rheumatoid arthritis, diabetic retinopathy, prematurity retinopathy and psoriasis, can be carried out by using these monoclonal antibodies.

Consequently, the present invention provides antibodies which specifically react with human ICT1025. With regard to the monoclonal antibody of the present invention, a monoclonal antibody is provided that recognizes an epitope which is present in a region of the 1st to 300th, for example, between positions 161-190 or 251-280 as measured from the N-terminal amino acid. A C-terminal epitope region is between positions 700-803, for example positions 726-803. The present invention also provides a monoclonal antibody which inhibits binding of human ICT1025 and also inhibits biological activities of ICT1025.

The monoclonal antibody of the present invention may be any antibody, so long as it specifically reacts with human ICT 1003 or ICT-1024 or ICT 1025 or ICT1031. Examples of the monoclonal antibody include an antibody produced by a hybridoma and a recombinant antibody produced by a transformant transformed with an expression vector containing the antibody gene. For example, those which are established with murine or rabbit hybridomas can be prepared. That is, anti-human ICT 1003 or ICT-1024 or ICT 1025 or ICT1031 monoclonal antibody can be obtained by preparing human ICT 1003 or ICT-1024 or ICT 1025 or ICT1031 protein as an antigen, immunizing an animal capable of providing a hybridoma with the antigen, such as mouse, rat, hamster, rabbit or the like, thereby inducing plasma cells having the antigen specificity, preparing a hybridoma capable of producing the monoclonal antibody through fusion of the cells with a myeloma cell line and subsequently culturing the hybridoma. Alternatively, anti-human ICT 1003 or ICT-1024 or ICT 1025 or ICT1031 monoclonal antibody can be obtained by preparing plasmids expressing human ICT 1003 or ICT-1024 or ICT 1025 or ICT1031 protein, immunizing an animal capable of providing a hybridoma with the antigen using DNA vaccination, such as mouse, rat, hamster, rabbit or the like, thereby inducing plasma cells having the antigen specificity, preparing a hybridoma capable of producing the monoclonal antibody through fusion of the cells with a myeloma cell line and subsequently culturing the hybridoma.

Alternatively, a fully human antibody that binds ICT 1003 or ICT-1024 or ICT 1025 or ICT1031 protein can be isolated from a human antibody library using phage display methods, as described in, for example, in U.S. Pat. No. 5,885,793, the contents of which are hereby incorporated by reference in their entirety. Human antibodies also can be isolated from transgenic xenomice that have been modified to encode a portion of the human immunglobulin repertoire, as described for example, in U.S. Pat. No. 6,075,181, the contents of which are hereby incorporated by reference in their entirety. Alternatively, camelid-type antibodies that lack light chains may be used, as described, for example, in U.S. Pat. No. 5,800,988 the contents of which are hereby incorporated by reference in their entirety.

The monoclonal antibody which specifically reacts with human ICT 1003 or ICT-1024 or ICT 1025 or ICT1031 of the present invention may be a recombinant antibody. Examples of the recombinant antibody includes a humanized antibody and an antibody fragment. The recombinant antibody of the present invention can be obtained by modifying the above-described monoclonal antibody of the present invention using gene recombination technique. The recombinant antibody includes antibodies produced by gene recombination, such as a humanized antibody and an antibody fragment (e.g., single chain antibody, disulfide stabilized antibody). Among these, antibodies which have the characteristics of monoclonal antibodies, show low antigenicity and have prolonged half-life in blood are preferred as therapeutic agents. The humanized antibody of the present invention includes a human chimeric antibody and a human CDR (complementarity-determining region; hereinafter referred to as "CDR")-grafted antibody. The antibody fragment of the present invention includes a fragment of antigen binding (hereinafter referred to as "Fab"), Fab', F(ab')$_2$, a single chain antibody (single chain Fv; hereinafter referred to as "scFv"), and a disulfide stabilized antibody (disulfide stabilized Fv; hereinafter referred to as "dsFv"), which specifically react with ICT1024. The antibody also may be a "diabody" of the type described in U.S. Pat. No. 5,837,242, the contents of which are hereby incorporated by reference in their entirety The antibody which reacts with human ICT 1003 or ICT-1024 or ICT 1025 or ICT1031 of the present invention may be a humanized antibody which is selected from a human chimeric antibody and a human CDR-grafted antibody.

The structure of the antibody of the present invention may belong to any immunoglobulin (Ig) class, but preferably contains the C region of IgG type immunoglobulin, particularly of IgG subclasses, such as IgG1, IgG2, IgG3, and IgG4.

In addition, the present invention relates to the following methods:

a method for immunologically detecting human, comprising reacting human ICT 1003 or ICT-1024 or ICT 1025 or ICT1031 with the antibody orpeptide of the present invention;

a method for immunologically detecting cells in which human ICT 1003 or ICT-1024 or ICT 1025 or ICT1031 is expressed on the surface thereof, comprising reacting human ICT 1003 or ICT-1024 or ICT 1025 or ICT1031 with the antibody or peptide of the present invention;

a method for inhibiting binding of human ICT 1003 or ICT-1024 or ICT 1025 or ICT1031, comprising reacting human ICT1024 with the antibody or peptide of the present invention;

a method for inhibiting biological activities of human ICT 1003 or ICT-1024 or ICT 1025 or ICT1031 with the antibody or peptide of the present invention;

a method for detecting a disease in which the morbid states progress by abnormal cell proliferation, comprising reacting a sample with the antibody or peptide of the present invention; and a method for preventing or treating a disease, comprising the step of administering to human or animal in need of such prevention or treatment an effective amount of the antibody or peptide of the present invention.

In the above method for immunologically detecting human ICT 1003 or ICT-1024 or ICT 1025 or ICT1031, the human ICT 1003 or ICT-1024 or ICT 1025 or ICT1031 or a fragment of ICT 1003 or ICT-1024 or ICT 1025 or ICT1031 may be soluble.

In the above method for inhibiting biological activities of human ICT 1003 or ICT-1024 or ICT 1025 or ICT1031, for example, the activity of human ICT 1003 or ICT-1024 or ICT 1025 or ICT1031 is inhibited.

In the above method for detecting a disease, for example, the method may comprise (a) separating human cell or a crushing solution thereof, tissue or a crushing solution thereof, serum, pleural fluid, ascites fluid, or ocular fluid to prepare a sample, (b) reacting the separated sample prepared in the step (a) with the monoclonal antibody or peptide of the present invention, (c) further reacting the reacted sample prepared in the step (b) with a labeled anti-mouse IgG antibody or binding fragment, and (d) measuring or observing the labeled sample prepared in the step (c).

In the above method for preventing or treating a disease, examples of the disease include diseases in which the morbid states progress by abnormal cellular proliferation.

Examples of the diseases in which their morbid states progress by abnormal cellular proliferation include proliferation or metastasis of solid tumor, arthritis in chronic rheumatoid arthritis, diabetic retinopathy, retinopathy of prematurity, and psoriasis. Examples of the solid tumor include breast cancer, prostatic cancer, large bowel cancer, gastric cancer and lung cancer.

The present invention relates to a composition comprising the antibody or peptide of the present invention and a diagnostic or pharmaceutical acceptable carrier.

Patients with tumors characterized as expressing or overexpressing ICT 1003 or ICT-1024 or ICT 1025 or ICT1031 such as tumors are treated by administering ICT 1003 or ICT-1024 or ICT 1025 or ICT1031 antibodies ICT 1003 or ICT-1024 or ICT 1025 or ICT1031-specific antibodies will inhibit proliferation of cells in culture and in pathological tissues. Different ICT-1024 or ICT1025-specific antibodies can be developed and demonstrated to inhibit cell proliferation. For example, tumor cells (a heptatocarcinoma cell line, a lung carcinoma cell line, and a breast carcinoma cell line) can be seeded in a 96 well plate and incubated with varying concentrations of antibody for 48 hours. The cells can be fixed and cell growth monitored using a sulforhodamine B dye binding assay. The data indicate a reduction in cell viability and proliferation in the presence of ICT 1003 or ICT-1024 or ICT 1025 or ICT1031-specific antibody compared to in its absence.

Passive Immunization

Purified antibody preparations (e.g., a purified monoclonal antibody, an antibody fragment, or single chain antibody) is administered to an individual diagnosed with a tumor or at risk of developing a tumor. The antibody preparations are administered using methods known in the art of passive immunization, e.g., intravenously or intramuscularly. The antibodies used in the methods described herein are formulated in a physiologically-acceptable excipient. Such excipients, e.g., physiological saline, are known in the art.

The antibody is preferably a high-affinity antibody, e.g., an IgG-class antibody or fragment or single chain thereof. Alternatively, the antibody is an IgM isotype. Antibodies are monoclonal, e.g., a murine monoclonal antibody or fragment thereof, or a murine monoclonal antibody, which has been humanized. The antibody is a human monoclonal antibody. The affinity of a given monoclonal antibody is further increased using known methods, e.g., by selecting for increasingly higher binding capacity (e.g., according to the method described in Boder et al., 2000, *Proc. Natl. Acad. Sci. U.S.A.* 97:10701-10705). Optionally, the antibody, antibody fragment, or high affinity single chain antibody is conjugated to a toxic moiety prior to administration. Toxic moieties suitable for conjugation include ricin, Pseudomonas toxin, Diptheria toxin as well as radioisotopes and chemotherapeutic agents known in the art. Such antibody toxins damage or kill a tumor cell upon binding to the tumor cell or upon internalization into the cytoplasm of the tumor cell.

Antibody preparations or antibody-toxin preparations are administered at doses of approximately 0.01-2 mL/kg of body weight. Doses are readministered daily, weekly, or monthly as necessary to reduce tumor load in a treated individual.

Active vaccination is the process of inducing an animal to respond to an antigen. During vaccination, cells, which recognize the antigen (B cells or cytotoxic T cells), are clonally expanded. In addition, the population of helper T cells specific for the antigen also increase. Vaccination also involves specialized antigen presenting cells, which can process the antigen and display it in a form which can stimulate one of the two pathways. Antigen recognition followed by immune cell expansion and activation leads to the production of antigen-specific antibodies and antigen-specific cellular immune responses. Successful immunization is indicated by an increase in the level of ICT 1003 or ICT-1024 or ICT 1025 or ICT1031-specific antibody titer in serum of an immunized individual compared to the level prior to immunization. Preferably, the ICT 1003 or ICT-1024 or ICT 1025 or ICT1031-specific antibody titer is at least 10%, more preferably at least 50%, more preferably at least 100%, and most preferably 200% greater than the titer prior to immunization.

For active immunization, an individual is immunized with an ICT 1003 or ICT-1024 or ICT 1025 or ICT1031 polypeptide or a polynucleotide encoding the peptide. For example, a human patient is immunized with full-length ICT 1003 or ICT-1024 or ICT 1025 or ICT1031. Standard adjuvant formulations may be simultaneously administered to enhance immunogenicity of the immunizing polypeptide. Alternatively, shorter polypeptides, e.g., immunogenic fragments of ICT 1003 or ICT-1024 or ICT 1025 or ICT1031, are used. For example, a polypeptide contains an extracellular catalytic domain of ICT-1024 (e.g., amino acids 1-590 of ICT-1024. Other immunogenic fragments of ICT-1024 include fragments within the region of amino acids 1-590. A polypeptide containing the extracellular domain of ICT 1025.

Monoclonal antibody therapy is a passive immunotherapy because the antibodies are produced in large quantities outside the body rather than by the immune system of human body itself. This type of therapy can be effective even if the immune system is weakened, which is a typical case for cancer patients. These treatments do not require the immune system to take an "active" role in fighting the cancer. Antibodies are mass-produced by fusing a myeloma cell from a mouse with a mouse B cell that makes a specific antibody. The cell that results from this fusion is called a hybridoma. The combination of a B cell that can recognize a particular antigen and a myeloma cell that lives indefinitely makes the hybridoma cell a kind of perpetual antibody-producing factory. Because the antibodies are all identical clones produced from a single (mono) hybridoma cell, they are called monoclonal antibodies. The monoclonal antibodies that react with specific antigens, e.g. ICT 1003 or ICT-1024 or ICT 1025 or ICT1031, on certain types of cancer cells, are able to neutralize the targeted protein or block its biological function. As a result, the EGF-AP is deactivated and the EGF pathway was shut down and tumor growth is inhibited.

Antibody therapy can be applied in following way: A. Naked Monoclonal Antibodies, the antibodies attach themselves to specific antigens on cancer cells. B. Conjugated monoclonal antibodies are joined to drugs, toxins, or radioactive atoms, and used as delivery vehicles to take those substances directly to the cancer cells. The MAb acts as a homing device, circulating in the body until it is attracted by, and attaches itself to, a cancer cell with a matching antigen. It delivers the toxic substance to where it is needed most, minimizing damage to normal cells in other parts of the body. But conjugated antibodies still generally cause more side effects than do naked antibodies. C. Immunotoxins are made by attaching toxins (poisonous substances from plants or bacteria) to monoclonal antibodies. Various immunotoxins have been made by attaching monoclonal antibodies to bacterial toxins such as diphtherial toxin (DT) or pseudomonal exotoxin (PE40), or to plant toxins such as ricin A or saporin. D. Until recently, the effectiveness of MAb therapies was limited by the fact that the antibodies were produced by mouse hybridoma cells. In some cases, these antibodies worked well at first. But after a while, the patient's immune system would recognize the mouse antibodies as "foreign" and would destroy them. For this reason, the humanized Mab was generated by combining the part of the mouse antibody gene responsible for recognizing a specific tumor antigen with other parts from a human antibody gene. The product of this mouse-human antibody gene, looks enough like a normal human antibody to avoid being destroyed by the patient's own immune system. This helps the antibody to be effective for longer periods. All the above stated approaches are useful for ICT1024 or EGF-AP based antibody therapy. Other approaches, like intrabody, single chain antibody and DNA vaccine can also be used to generate antibody agents for research, diagnosis and therapeutic applications.

In the present invention, two different embodiments for antibody inhibitors according to the transmembrane topology of ICT1024: N-terminal is located outside of cell, vs. N-terminal is located inside of cell. When the N-terminal is located outside the cell, a large fragment from 1st to 409th AA is preferred to be the antigen for antibody generation, either using the entire 409 AA peptides or different portion within this fragment. There are several sequences may serve as good antigens due to their ligation strength to a defined HLA type: GLSAPHTPV (174TH) (SEQ ID NO.; 43), GMQKIIDPL (151TH)(SEQ ID NO: 44), KMSFRAAAA (213)(SEQ ID NO:45) and LTAEEPSFL (30) (SEQ ID NO:46). Design the antigen peptides containing those sequence will increase the binding activity of the induced antibodies. Only several short peptide fragments will be outside of the cell in this scenario, which may not be strong antigen for generation of antibodies to bind to ICT1024. When the N-terminal is located inside of cell, another long fragment of the ICT1024 protein, from 433th to 660th AA, is presumably located outside the cell. In this case, the fragment provides a good antigen as whole, or multiple antigens selected within the region. There are several strong HLA binding motifs in the region: SQHETVDSV (433TH) (SEQ ID NO:47), GVYENVKYV (446TH)(SEQ ID NO: 48), YVQQENFWI (453TH) (SEQ ID NO:49), and LLPFLNPEV (641TH) (SEQ ID NO:50).

There is one scenario that the C-Terminal domain is located outside of cell. The short fragment from 823 to 855 AA can also serve as a peptide antigen either with the entire sequence or partial of the sequence.

Three 30 AA peptides were selected as the examples for generations of polyclonal and monoclonal antibodies:

```
                                              (SEQ ID NO:51)
N'-RGRAFRVADDTAEGLSAPHTPVTPGAASLC-C';  (161-190th)

(SEQ ID NO:52)
N'-VKYVQQENFWIGPSSEALIHLGAKFSPCMR-C';  (451-480th)

(SEQ ID NO:53)
N'-PVRCEWCEFLTCIPFTDKFCEKYELDAQLH-C'.  (826-855th)
```

The similar peptide sequences can also be selected as potential peptide antigens with size from 14 AA to more than 100 AA.

In the present invention, two different embodiments for antibody inhibitors according to the transmembrane topology of ICT1025: N-terminal is located outside of cell, vs. N-terminal is located inside of cell. When the N-terminal is located outside the cell, a large fragment from 1st to 300th AA is preferred to be the antigen for antibody generation, either using the entire 300 AA peptides or different portion within this fragment. There are several sequences may serve as good antigens due to their ligation strength to a defined HLA type:

```
ALWVLGLCC (3TH),        (SEQ ID NO:76)

VLGLCCVLL (6TH),        (SEQ ID NO:77)

LLHVTDTGV (144TH)       (SEQ ID NO:78)
and

SELIGQFGV (189TH).      (SEQ ID NO:79)
```

Design the antigen peptides containing those sequence will increase the binding activity of the induced antibodies. Only several short peptide fragments will be outside of the cell in this scenario, which may not be strong antigen for generation of antibodies to bind to ICT1025. There is one scenario that the C-Terminal domain is located outside of cell. The short fragment from 823 to 855 AA can also serve as a peptide antigen either with the entire sequence or partial of the sequence.

Three 30 AA peptides were selected as the examples for generations of polyclonal and monoclonal antibodies:

```
                                               (SEQ ID No:80)
N'-ADDEVDVDGTVEEDLGKSREGSRTDDEVVQ-C';    (21-50th)

(SEQ ID No:81)
N'-SAFLVADKVIVTSKHNNDTQHIWESDSNEF-C';    (201-230th)

(SEQ ID No:82)
N'-SEKTKESREAVEKEFEPLLNWMKDKALKDK-C'.    (701-730th)
```

The similar peptide sequences can also be selected as potential peptide antigens with size from 14 AA to more than 100 AA.

According to another aspect of the invention, the inhibitor molecules are introduced into tissues, including breast tissue, colon tissue, prostate tissue, skin tissue, bone tissue, parotid gland tissue, pancreatic tissue, kidney tissue, uterine cervix tissue, lung tissue, lymph node tissue, or ovarian tissue.

Inhibitory Protease Inhibitors

Peptide antagonists, small molecule protease inhibitors and other types of ICT1024 inhibitors are also provided to block or inhibit ICT1024 activity.

The following examples are offered to illustrate embodiments of the present invention, but should not be viewed as limiting the scope of the invention.

EXAMPLES

Example 1

Gene Delivery Method for Target Validation

Efficacy-First Discovery™ method is initiated with a known gene that acts as a key player in a defined disease pathway (for example, angiogenesis) and a well-defined disease model (for example, human tumor xenografted in nude mice). An effective gene delivery tool is crucial, that is, one with strong expression but, equally or more importantly, with little background activity from the delivery tool itself. A non-viral and polymer based delivery system can provide both strong delivery and low background for solid tumors. The pathological, pharmaceutical and histological readouts following the treatment are analyzed in comparison with gene expression and protein profiles. Based on both bioinformatics analysis and biological analysis, the genes and proteins significantly up or down regulated in the defined pathway can be carefully selected and further analyzed by the same iterative in vivo validation process. The process started with effective gene delivery into the tumor tissue. The affected tumors were first evaluated by growth rate, histological changes, and then harvested for expression profile analysis with Affymetrix Chips. The highly up- or down-regulated targets were identified for Disease-Control validation. Novel targets were validated in vivo.

The targets identified by Efficacy-First Discovery™ method are different from those identified using a conventional approach. The advantage of Efficacy-First Discovery™ method is that the targets selected by the method is associated with disease efficacy and not simply with a disease state (see FIG. 1). The expression changes of the targets are due to perturbation of delivered genes and disease process dynamic. They are better fit for drug discovery.

Example 2

Tumor Perturbation with Known Factors

The human breast cancer carcinoma cell induced xenograft tumors were perturbed with genes that are known to affect tumor growth, and forced to grow faster and slower. The xenograft tumor model was induced with MDA-MB-435 cell on Ncr nu/nu mice. This demonstration was performed using the proprietary polymer mediated IL-2 and bFGF deliveries, based on our previous data and that bFGF is a well-known drug target enhancing tumor growth, and IL-2, which is not only a target but an approved cancer inhibition drug. Four tumor samples treated with IL-2, 4 tumor samples treated with bFGF, and 2 samples treated with Luc as control were collected and processed. When tumor reached 50 mm$^3$ in size, pCI-IL-2 and pCI-bFGF were directly delivered intratumorally with pCI-Luc as a control. Tumor tissues (10 in total) were harvested at different time points and RNA samples were isolated by RNAsol, quantified and gel verified for their integrities. Data show tumor growth inhibition by IL-2 and enhancement by bFGF.

Example 3

Expression Analysis with Affymetrix Chip

The total RNA samples from tumor tissues were subjected to expression analysis using Affymetrix GeneChip U133 A. The pictures show the original array images. The treated samples were compared with the control samples and initial analytical data were further analyzed with bioinformatics effort. According to the tumor growth rate and efficacy data, combined with the bioinformatics data and literature search, we used at least two folds as a benchmark for significant regulated targets. The signals must be higher than 200.

Example 4

Novel Targets Identified

According to the perturbation effects on the tumor growth, bioinformatics analysis and literature search, only small percentage of gene targets were selected based on their expression profile changes. For example, 156 targets were selected based on about 23,000 pairs of comparisons from Affymetrix U133 A chip. The tumor tissue was harvested 24 hours after the second injection of IL-2 expressing vector. Among 156 selected targets, 111 of them were known based on UniGene database annotations, versus 45 were unknown novel targets. Within the known targets, 87% are tumor related. If the same ratio holds the truth, we expect more then 35 targets are novel tumor targets. In addition, the hits also belong to several tumorigenesis pathways.

Many of these selected targets are well known and some of them are at different stages of clinical development (see Table 1). The long list of unknown targets (no annotation in UniGene Database) holds great potential as novel tumor targets. For further validation in xenograft tumor models, more than 200 targets were selected from both IL-2 and bFGF treated samples (see Table 2). The strategy for the validation is screening those targets with established procedure followed by more comprehensive study of each of the positive hits.

Among 156 selected targets (see Table 1), many of them are well characterized and at different stages of clinical studies. These examples indicate that the targets selected either known or unknown are having great potentials.

Based on expression analyses of 8 tissue samples treated by both IL-2 and bFGF, we selected highly up-or down-regulated targets. About ⅔ of the targets are known and ⅓ are novel according to UniGene database annotations. Selected targets, either known or novel, were subjected to the Disease-Control Validation.

Example 5

Target Validation Process

Recently disclosed new technology platform, using RNAi mediated in vivo gene silencing for validating drug targets controlling tumor disease (see U.S. provisional application Ser. No. 60/401,029), was used. This invention further validates the technology platform by performing a complete set of experiments studying payloads and delivery methods on tumor-bearing mouse models.

1) Target Validation: Tumor Correlation or Control

Of the many levels of drug target validation, the ultimate is demonstration that a candidate target actually controls the disease. Disease controlling targets are the high value targets that justify drug discovery. The goal of drug development is products that selectively target key pathways and the key controlling elements of those pathways in order to provide effective therapeutic control of the disease. Validation of such key pathways and elements requires demonstration that addition or subtraction of individual candidate targets controls the disease, i.e. results in a clear increase or decrease of pathology. In vitro cell-based strategies have provided useful information in helping identify and select potential targets. However, the ability of targets to control in vitro cell models associated with disease frequently is not sufficient to prove the target actually controls the disease process, i.e. the complex interactions of multiple cell types that result in disease pathology. Definitive demonstration of disease control by targets can only be obtained by studies of those targets in a true disease model.

The process of target discovery has been greatly accelerated by genomic methods but validation remains a bottleneck. First-generation genomic methods have generated large pools of candidate targets piled up at the validation step. Many approaches are currently being used to study the function of these gene targets and to validate their role in a disease process. Many of these approaches, although having the benefit of being efficient and high throughput, often succeed only at establishing a correlation or association with disease processes rather than determining a controlling role. Newer gene knockdown and forward or inverse genomic approaches have proven useful but these identify genes whose inhibition or mutation may have a disease role, missing potential valuable information from a gene's over-expression. Furthermore, they also employ primarily in vitro cell-based phenotypes, which do not reflect the complex multi-cellular mechanisms of most diseases, such as tumor angiogenesis, and hence run the risk of missing important targets in adjacent cellular pathways or provide disease associations which are incomplete without the full biological context.

2) Rapid Definitive Target Validation

We have recently disclosed two technology platforms for validating cancer-related drug targets that addresses many of these limitations and has a valuable complementary role in the target validation process. Both unique and proprietary Target Discrimination Methods validate targets directly in animal tumor models by over-expressing transgene(s) or silencing endogenous gene(s) in tumor tissue. The methods reduce the need for the costly and slow steps of definitive validation, such as gene cloning and sequencing, generation of proteins and antibodies or transgenic animals. The combination of these two methods vastly accelerates the process, and most importantly rapidly eliminates weaker targets. Moreover, results obtained by the methods provide clear and definitive evidence that targets actually control the disease, the key validation needed to proceed to the costly steps of drug discovery. The methods can be used to complete the validation of any candidate targets such as those generated from cell culture, model organisms, transgenic animals, etc.

3) Target Discovery: Capturing Targets Missed in Preliminary Validation

Another critical consideration is that, unfortunately, many high value disease-controlling targets may be lost when in vitro or disease-association methods are employed as the first "filter" in target discovery and validation. Many disease-controller targets may only be found in the context of the entire disease model. For example, targets controlling angiogenesis of tumors will only be found at the conjunction of tumors and blood vessels. In the case of tumors, certain valuable targets may only be discovered by studying the in vivo biological system containing assembly of tumor and surrounding tissues.

4) High Throughput Target Discovery Solutions

We have also disclosed a method for discovering disease controller targets. The method is to scale-up the basic approach so that it can be applied to screen larger sets of gene targets in a higher throughput operation. By scaling the method to processing 1000 candidate genes in animal tumor models each quarter with our in vivo gene delivery technology, this approach can provide the opportunity to skip or shorten, in many cases, preliminary functional validation methods.

5) Tumor Target Elimination

The disclosed technologies also permit candidate targets to be rapidly tested for their capacity in controlling tumor growth. Those candidates showing only weak or negligible control of tumor growth can be eliminated from consideration in favor of those that have a strong effect on tumor growth. These Tumor Target Discrimination Methods rapidly discriminates targets into three categories: those enhancing tumor growth, those with little effect on tumor growth, and those inhibiting tumor growth.

Example 6

Novel Targets Validated

Both known and unknown targets (see example 4) were selected for Disease-Control Validation in the tumor models. Based on proprietary nucleic acid delivery technologies, two different platforms are established for understanding disease-control property of each target, by either knockdown or over-express the expression. Using a highly efficient method for siRNA delivery in vivo, several groups of targets have been validated. The novel tumorigenesis related targets are identified and validated (see Table 3). On the other hand, we also applied over-expression approach to validate a group of known angiogenesis related gene targets in the same xenograft tumor model with a proprietary delivery. IL-12 were clearly re-validated based on their roles in tumor growth inhibition. The same approach is currently used for novel target validation also.

Table 3. siRNA-mediated validation of several groups of targets.

Two siRNA targets were selected for each gene and verified by BLAST, and synthesized by Dharmacon (Lafayette, Co.). A 10 µg of specific siRNA for each gene was repeatedly delivered intratumorally into MDA-MB-435 xenograft model. Tumor sizes were measured with N=8 or N=10. A. Group I targets were validated using xenografted tumor model. Human VEGF and mouse VEGFR2 were used as the positive controls. Three targets were validated among the Group I targets (see Table 3, Group I). B. Group II targets were also validated with the same type assay. Two targets were validated among the Group II (see Table 3, Group II).

The Group III validation included some of previously validated targets and some novel targets. One novel target was validated in the Group III.

Figure 3:
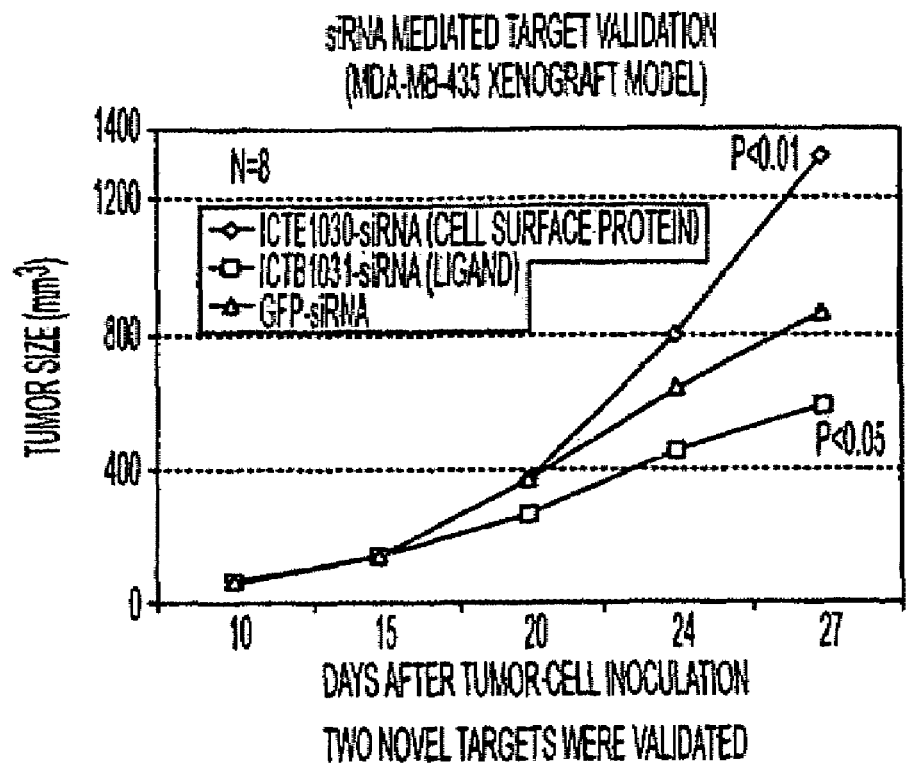
FIG. 3 shows validated two novel targets: ICT1030 and ICT1031. Among the selected targets tested with siRNA knockdown in vivo, 2 targets (ICT1030 and ICT1031) were validated with n=8 (8 tumors per cohort). Two proteins are cell surface factors with totally opposite effects. ICT1030 knockdown by specific siRNA resulted in tumor grow enhancement, versus ICT1031 knockdown triggered tumor growth inhibition. So that the former may be protein or gene therapy drug and the later could be an antibody or small molecular drug target.
Figure 4:
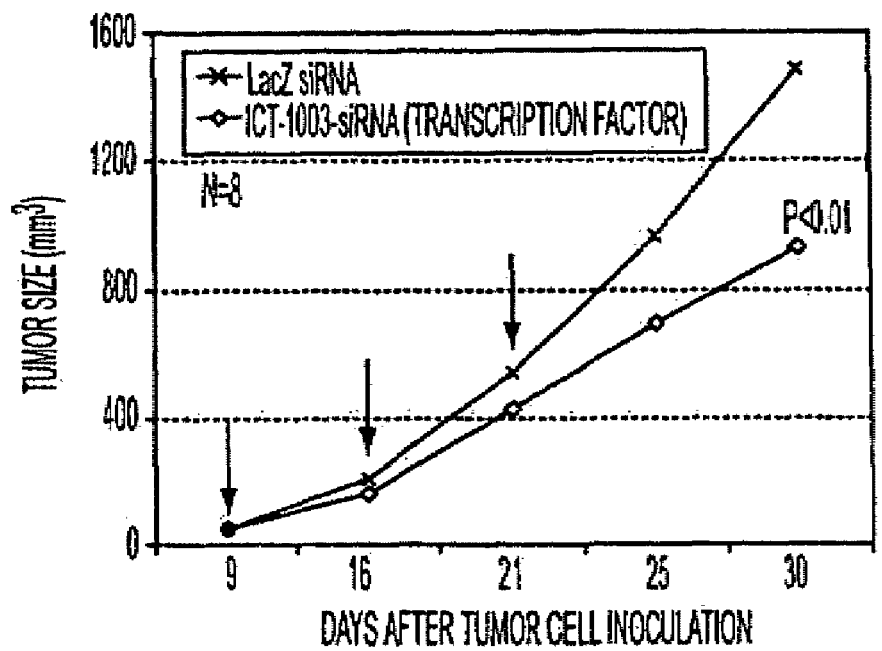
FIG. 4 shows one of the selected targets, ICT1003, which was tested with siRNA knockdown in vivo (8 tumors per cohort). The target ICT1003 is a novel zinc finger protein and may represent a transcription factor. ICT1003 knockdown by specific siRNA resulted in tumor growth inhibition. So that the protein could be a siRNA drug target or small molecular drug target.
Figure 5:
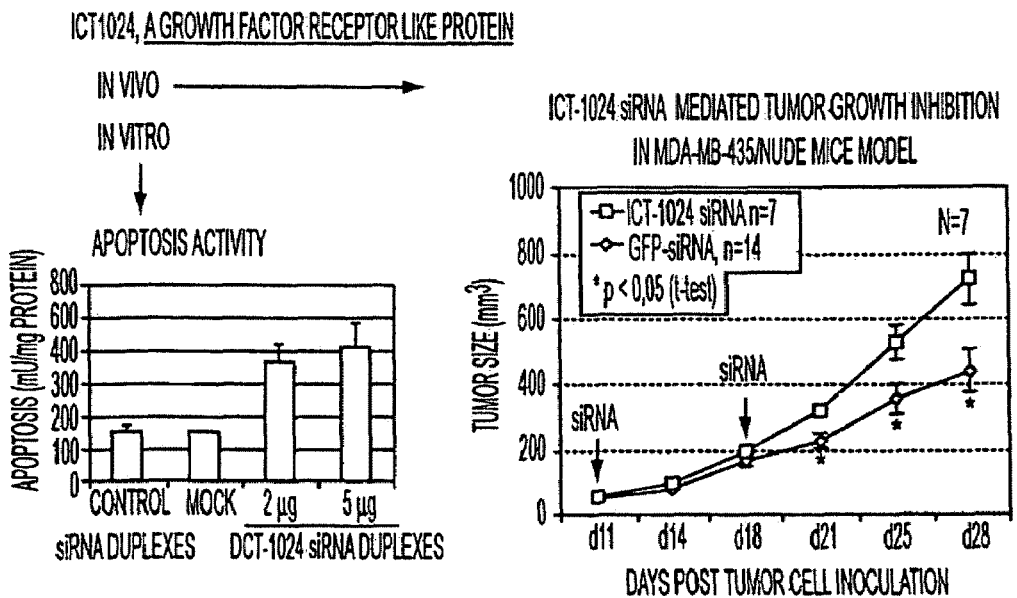
FIG. 5 shows a novel target, ICT1024, Accession No. AK026010, NM_022450, human growth factor receptor-related protein, EGFR-RP, or EGFR-RS, has been first identified by Efficacy-First discovery method due to its highly up-regulated expression in bFGF treated tumor (MDA-MB-435 cell) tissues. siRNA knockdown of this gene in the cell culture (MDA-MB-435 cell) study resulted activated apoptosis status. SiRNA knockdown of this gene in the xenograft tumors (MDA-MB-435 cell) resulted in tumor growth inhibition. The gene over expressed in several human tumors including breast and prostate cancer. The coded protein of this gene has a Rhomboid domain and a transmembrane domain.
Figure 6:
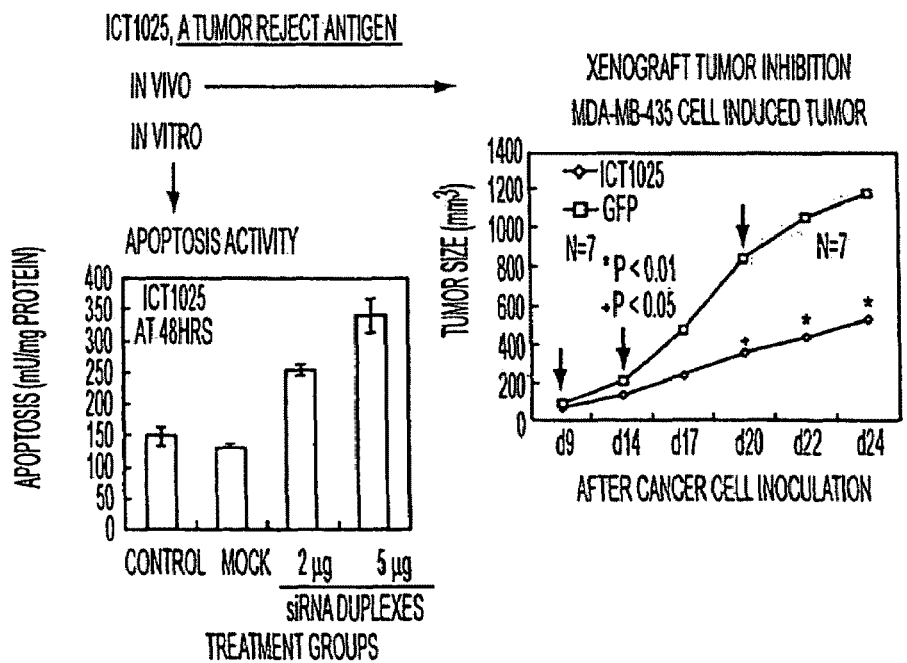
FIG. 6 shows a novel target, ICT1025, NM_003299, human tumor rejection antigen, TRA1, HSP gp96, has been first identified by Efficacy-First discovery method due to its highly up-regulated expression in bFGF treated tumor (MDA-MB-435 cell) tissues. siRNA knockdown of this gene in the cell culture (MDA-MB-435 cell) study resulted activated apoptosis status. siRNA knockdown of this gene in the xenograft tumors (MDA-MB-435 cell) resulted in tumor growth inhibition. The gene over expressed in several human tumors including brain, breast, colon, ovary and prostate cancer. The coded protein of this gene has a ATPase domain of HSP90 and the Hsp90 protein.

When the following targets, ICT1024, ICT1025, ICT1031, ICT1030, and ICT1003, were down regulated by two duplexes of specific siRNA molecules, the tumor growth rates changed. Among them, ICT1030, milk fat globule-EGF factor 8 protein or breast epithelial BA46 antigen, GeneBank Accession Nos.: NM_005928, BC003610 and their splicing derivatives, behaved more like a tumor suppressor target, or a protein therapy and gene therapy target. Since the siRNA-mediated knockdown resulted tumor growth acceleration rather than inhibition. Other targets: ICT1031 (GeneBank no.: AK090698, Tumor Necrosis Factor ligand super family member 13, or TNF related proliferation inducing ligand and their splicing variants, see FIG. 3), and ICT1003 (GeneBank no.: AK000847, human novel zinc finger protein 236 or its splicing variants), are all up regulated in fast growing tumor, and have demonstrated as the suitable targets for antibody, small molecules, antisense, siRNA and other antagonist agents.

Among the selected targets tested with siRNA knockdown in vivo, 4 targets (ICT1024, ICT1025, ICT1030 and ICT1031) were validated with n=8 and n=10 (8 and 10 tumors per cohort, respectively) (see FIGS. 3-6). Two proteins are cell surface factors with totally opposite effects. ICT1030 knockdown by specific siRNA resulted in tumor grow enhancement, versus ICT1031 knockdown triggered tumor growth inhibition. Therefore, the former may be protein or gene therapy drug and the later can be an antibody or a small molecular drug target.

One of the selected targets, ICT1003, was tested with siRNA knockdown in vivo (8 tumors per cohort). The target ICT1003 is a novel zinc finger protein and may represent a transcription factor. ICT1003 knockdown by specific siRNA resulted in tumor growth inhibition (see FIG. 4). Therefore, the protein can be a siRNA drug target or a small molecular drug target.

Example 7

Small Interfering RNA (siRNA)

Sense and antisense siRNAs duplexes are made based upon targeted region of a DNA sequence for targets ICT1024, ICT1025, ICT1030, ICT1031, or ICT1003, as disclosed herein (see, for example, SEQ ID NO:1, SEQ ID NO:3, SEQ ID NO:4, SEQ ID NO:6, SEQ ID NO:8, or a fragment thereof), are typically less than 100 base pairs ("bps") in length and constituency and preferably are about 30 bps or shorter, and are made by approaches known in the art, including the use of complementary DNA strands or synthetic approaches. SiRNA derivatives employing polynucleic acid modification techniques, such as peptide nucleic acids, also can be employed according to the invention. The siRNAs are capable of causing interference and can cause post-transcriptional silencing of specific genes in cells, for example, mammalian cells (including human cells) and in the body, for example, mammalian bodies (including humans). Exemplary siRNAs according to the invention have up to 29 bps, 25 bps, 22 bps, 21 bps, 20 bps, 15 bps, 10 bps, 5 bps or any integer thereabout or therebetween.

A targeted region is selected from the DNA sequence (for example, SEQ ID NO:1, SEQ ID NO:3, SEQ ID NO:4, SEQ ID NO:6, SEQ ID NO:8, or a fragment thereof). Various strategies are followed in selecting target regions and designing siRNA oligos, for example, 5' or 3' UTRs and regions nearby the start codon should be avoided, as these may be richer in regulatory protein binding sites. Designed sequences preferably include AA-(N21 or less nucleotides)-TT and with about 30% to 70% G/C-content. If no suitable sequences are found, the fragment size is extended to sequences AA(N29 nucleotides). The sequence of the sense siRNA corresponds to, for example, (N21 nucleotides)-TT or N29 nucleotides, respectively. In the latter case, the 3' end of the sense siRNA is converted to TT. The rationale for this sequence conversion is to generate a symmetric duplex with respect to the sequence composition of the sense and antisense 3' overhangs. It is believed that symmetric 3' overhangs help to ensure that the small interfering ribonucleoprotein particles (siRNPs) are formed with approximately equal ratios of sense and antisense target RNA-cleaving siRNPs (Elbashir et al. *Genes & Dev.* 15:188-200, 2001).

ICT1024 siRNA: Sense or antisense siRNAs are designed based upon targeted regions of a DNA sequence, as disclosed herein (see SEQ ID NO: 66), and include fragments having up to 29 bps, 25 bps, 22 bps, 21 bps, 20 bps, 15 bps, 10 bps, 5 bps or any integer thereabout or therebetween. For example, 21 bps siRNA targeting the sense strand of mRNA include:

```
                                           (SEQ ID NO:21)
    5'-AAGCTGGACATTCCCTCTGCG-3'
    and (SEQ ID NO:22)
    5'-AAGAGCCCAGCTTCCTGCAGC-3'.
```

ICT1025 siRNA: Sense or antisense siRNAs are designed based upon targeted regions of a DNA sequence, as disclosed herein (see SEQ ID NO:3), and include fragments having up to 29 bps, 25 bps, 22 bps, 21 bps, 20 bps, 15 bps, 10 bps, 5 bps or any integer thereabout or therebetween. For example, 21 bps siRNA targeting the sense strand of mRNA include:

```
                                            (SEQ ID NO:23)
     5'-AACTGTTGAGGAGCCGATGGA-3'
     and
                                            (SEQ ID NO:24)
     5'-AATCTGATGATGAAGGTGCAG-3'.
```

ICT1030 siRNA: Sense or antisense siRNAs are designed based upon targeted regions of a DNA sequence, as disclosed herein (see SEQ ID NO:3), and include fragments having up to 29 bps, 25 bps, 22 bps, 21 bps, 20 bps, 15 bps, 10 bps, 5 bps or any integer thereabout or therebetween. For example, 21 bps siRNA include:

Targeted region (base position numbers 88-108, (SEQ ID NO:9) 5'-aaccctgccacaacggtggt-3', and the corresponding sense siRNA (SEQ ID NO: 10), 5'-aaccccUgccacaacggUggU-3';

Targeted region (base position numbers 190-210, SEQ ID NO:11) 5'-aaccactgtgagacgaaatgt-3', and the corresponding sense siRNA (SEQ ID NO:12) 5'-aaccacUgUgagacgaaaUgU-3'; and continuing in this progression to the end of ICTE1030 coding sequence, as set forth herein.

A set of siRNAs/shRNAs are designed based on ICT1030-coding sequence (SEQ ID NO:3).

ICT1031 siRNA: Sense or antisense siRNAs are designed based upon targeted regions of a DNA sequence, as disclosed herein (see SEQ ID NO:4), and include fragments having up to 29 bps, 25 bps, 22 bps, 21 bps, 20 bps, 15 bps, 10 bps, 5 bps or any integer thereabout or therebetween. For example, 21 bps siRNA include:

Targeted region (base position numbers 90-110, (SEQ ID NO:13) 5'-aactgccccagcgatctctgc-3', and the corresponding sense siRNA (SEQ ID NO: 14), 5'-aacUgcccagcgaUcUcUgc-3';

Targeted region (base position numbers 330-310, (SEQ ID NO:15) 5'-aacctaattctcctgaggctg-3', and the corresponding sense siRNA (SEQ ID NO: 16) 5'-aaccUaaUUcUccUgaggcUg-3'; and continuing in this progression to the end of ICTB1031 coding sequence, as set forth herein.

A set of siRNAs/shRNAs are designed based on ICT1031-coding sequence (SEQ ID NO:4).

ICT1003 siRNA: Sense or antisense siRNAs are designed based upon targeted regions of a DNA sequence, as disclosed herein (see SEQ ID NO:6), and include fragments having up to 29 bps, 25 bps, 22 bps, 21 bps, 20 bps, 15 bps, 10 bps, 5 bps or any integer thereabout or therebetween. For example, 21 bps siRNA include:

Targeted region (base position numbers 345-365, (SEQ ID NO:17) 5'-aatgcggagaacactaattat-3', and the corresponding sense siRNA (SEQ ID NO:18), 5'-aaUgcggagaacacUaaUaU-3';

Targeted region (base position numbers 462-482, (SEQ ID NO:19) 5'-aatgacaagccacatcgatgt-3', and the corresponding sense siRNA (SEQ ID NO:20) 5'-aaugacaagccacaucgaugu-3'; and continuing in this progression to the end of ICTB1003 coding sequence, as set forth herein.

A set of siRNAs/shRNAs are designed based on ICTB1003-coding sequence (SEQ ID NO:6).

Experimental Details for Development of ICT1024 Antibodies

Generation of Expression Vectors for ICT1024 Protein or Peptide 1.1 Plasmid DNA based mammalian gene expression vectors consist of a eukaryotic gene promoter or a viral gene promoter, a multiple cloning site sequence, and a polyA signal sequence. The promoters include, but not limit to, CMV promoter, RSV promoter, SV40 promoter, EF promoter, E2F promoter, and E1 gene promoter of adenovirus. The polyA sequences include, but not limit to, bGH polyA, SV40 polyA, and synthetic polyA.

1.2 Viral vector based mammalian gene expression vectors include, but not limit to, retroviral vectors, adenoviral vectors, and baculoviral vectors.

1.3 Bacterial expression vectors include, but not limit to, pQE-based vectors, pGEX-based vectors, and pETBlue vector.

1.4 Yeast expression vectors include but not limit to, pESC vectors, p42K-TEF, and pFastBac.

1.5 Cytoplasmic expression vectors utilizing prokaryotic promoters that include, but not limit to, T7 promoter, sp6 promoter.

Example 8

Cloning of ICT1024 full-length cDNA into pCI Vector for Mammalian Cell Expression and DNA Vaccination The full-length cDNA of ICT1024 (855 aa) was generated by PCR amplification using a cDNA clone purchased from ATCC (MGC: 20194) as template. Since the full-length of ICT1024 cDNA is 2568 bp, to reduce the mutation may occur during the PCR reaction, two pairs of primers were designed to generate two shorter DNA fragments that can be ligated together to generate full-length ICT1024 cDNA.

```
Primer 1: 1024EcoUp2 (28-mer, corresponds to
111-128 nt of ICT1024 gene, GenBank Accession
Number: BC014425)
                                            (SEQ ID NO:54)
5'---C AGG AAT TCC ATG AGT GAG GCC CGC AGG---3'

Primer 2: 1024MidDn (26-mer, corresponds to
1770-1745 nt of ICT1024 gene, GenBank Accession
Number: BC014425)
                                            (SEQ ID NO:55)
5'---CC CTG GGA TCC TGG TGG CAG ACA GAG---3'

Primer 3: 1024SalDn (29-mer, corresponds to
2678-2661 nt of ICT1024 gene, GenBank Accession
Number: BC014425)
                                            (SEQ ID NO:56)
5'---CC GGC GTC GAC TCA GTG GAG CTG AGC GTC---3'

Primer 4: 1024MidUp (26-mer, corresponds to
1755-1780 nt of ICT1024 gene, GenBank Accession
Number: BC014425)
                                            (SEQ ID NO:57)
5'--- CA CCA GGA TCC CAG GGT GTG TGA TGA---3'
```

PCR reaction using Primer 1/Primer 2 and MGC 20194 template generated a 1679 bp DNA fragment that contains the 111 to 1770 nt of the ICT1024. PCR reaction using Primer 3/Primer 4 and MGC 20194 template generated a 928 bp DNA fragment that contains the 1755 to 2678 nt of the ICT1024. After purification of the PCR products, the 1679 bp DNA fragment was digested with EcoRI and BamHI, the 928 bp fragment was digested with BamHI and Sal I, then cloned into pCI vector cleaved with EcoRI and Sal I through a three-fragment legation reaction. The final product, pCI-ICT1024 plasmid DNA, was identified and its sequence was confirmed by DNA sequencing.

See FIG. 17. for restriction map of pCI-ICT1024 expression plasmid. See FIG. 25 for sequence of ICT1024 protein coding region 1670-3637 (SEQ ID NO 58).

Example 9

Cloning of the cDNA Fragment Coding the N Terminus Peptide (553 aa) of ICT1024 into pCI Vector for Mammalian Cell Expression and DNA Vaccination The CDNA coding for the N terminus 553 aa of ICT1024 was generated by a PCR amplification using a MGC20194 DNA as template. One pair of primers was used to generate the 1679 bp cDNA fragment containing a EcoRI site at its 5' and a Sal I site at its 3' end. Also, a TGA termination codon was integrated into the end of coding region to ensure correct stop of translation.

```
Primer 1: 1024EcoUp2 (28-mer, corresponds to
111-128 nt of ICT1024 gene, GenBank Accession
Number: BC014425)
                                    (SEQ ID NO:54)
5'---C AGG AAT TCC ATG AGT GAG GCC CGC AGG---3'

Primer 5: 1024MDnSal (29-mer, with SalI site +
TGA + 1769-1755 nt of ICT1024 gene, GenBank
Accession Number: BC014425)
                                    (SEQ ID NO:59)
5'---CC CTG GTCGAC TCA cct ggg atc ctg gtg---3'
```

PCR reaction using Primer 1/Primer 5 and MGC 20194 template generated a 1679 bp DNA fragment that contains the 111 to 1769 nt of the ICT1024. After purification of the PCR products, the 1679 bp DNA fragment was digested with EcoRI and Sal I, and then cloned into pCI vector cleaved with EcoRI and Sal I. The final product, pCI-ICT1024N plasmid DNA, was identified and its sequence was confirmed by DNA sequencing.

See FIG. 18 for the restriction map of pCI-ICT1024N plasmid. See FIG. 26 for the sequence of ICT1024 N Terminus 553 amino acid coding region nt. 1070-2731 (SEQ ID NO: 60)

Example 10

Cloning of ICT1024 Full-Length cDNA into pGEX-5X-3 Vector for Protein Expression in *E.coli* Host The full-length cDNA of ICT1024 (855 aa) was generated by PCR amplification using a cDNA clone purchased from ATCC (MGC: 20194) as template. Since the full-length of ICT1024 cDNA is 2568 bp, to reduce the mutation may occur during the PCR reaction, two pairs of primers were designed to generate two shorter DNA fragments that can be ligated together to generate full-length ICT1024 cDNA.

```
Primer 1: 1024EcoUp2 (28-mer, corresponds to
111-128 nt of ICT1024 gene, GenBank Accession
Number: BC014425)
                                    (SEQ ID NO:54)
5'---C AGG AAT TCC ATG AGT GAG GCC CGC AGG---3'

Primer 2: 1024MidDn (26-mer, corresponds to
1770-1745 nt of ICT1024 gene, GenBank Accession
Number: BC014425)
                                    (SEQ ID NO:55)
5'---CC CTG GGA TCC TGG TGG CAG ACA GAG---3'

Primer 3: 1024SalDn (29-mer, corresponds to
2678-2661 nt of ICT1024 gene, GenBank Accession
Number: BC014425)
                                    (SEQ ID NO:56)
5'---CC GGC GTC GAC TCA GTG GAG CTG AGC GTC---3'

Primer 4: 1024MidUp (26-mer, corresponds to
1755-1780 nt of ICT1024 gene, GenBank Accession
Number: BC014425)
                                    (SEQ ID NO:57)
5'--- CA CCA GGA TCC CAG GGT GTG TGA TGA---3'
```

PCR reaction using Primer 1/Primer 2 and MGC 20194 template generated a 1679 bp DNA fragment that contains the 111 to 1770 nt of the ICT1024. PCR reaction using Primer 3/Primer 4 and MGC 20194 template generated a 928 bp DNA fragment that contains the 1755 to 2678 nt of the ICT1024. After purification of the PCR products, the 1679 bp DNA fragment was digested with EcoRI and BamHI, the 928 bp fragment was digested with BamHI and Sal I, then cloned into pGEX-5X-3 vector (Amersham) cleaved with EcoRI and Sal I through a three-fragment legation reaction. The pGEX-5X-3 is a bacterial expression vector utilizes the bacterial tac promoter to drive the expression of a GST domain (27 Kd) fusion protein. The final product, pGEX-5X-3-ICT1024 plasmid DNA, was identified and its sequence was confirmed by DNA sequencing.

See FIG. 27 for confirmed sequence of pGEX-5X-3-ICT1024 (SEQ ID NO:61)

Example 11

Cloning of the cDNA Fragment Coding the N Terminus Peptide (553 aa) of ICT1024 into pGEX-5X-3 Vector for Protein Expression in *E.coli*

The cDNA coding for the N terminus 553aa of ICT1024 was generated by a PCR amplification using a MGC20194 DNA as template. One pair of primers was used to generate the 1679 bp cDNA fragment containing a EcoRI site at its 5' and a Sal I site at its 3' end. Also, a TGA termination codon was integrated into the end of coding region to ensure correct stop of translation.

```
Primer 1: 1024EcoUp2 (28-mer, corresponds to
111-128 nt of ICT1024 gene, GenBank Accession
Number: BC014425)
                                    (SEQ ID NO:54)
5'---C AGG AAT TCC ATG AGT GAG GCC CGC AGG---3'

Primer 5: 1024MDnSal (29-mer, with SalI site +
TGA + 1769-1755 nt of ICT1024 gene, GenBank
Accession Number: BC014425)
                                    (SEQ ID NO:59)
5'---CC CTG GTCGAC TCA cct ggg atc ctg gtg---3'
```

PCR reaction using Primer 1/Primer 5 and MGC 20194 template generated a 1679 bp DNA fragment that contains the 111 to 1769 nt of the ICT1024. After purification of the PCR products, the 1679 bp DNA fragment was digested with EcoRI and Sal I, and then cloned into pGEX-5X-3 vector cleaved with EcoRI and Sal I. The final product, pGEX-5X-3-ICT1024N plasmid DNA, was identified and its sequence was confirmed by DNA sequencing.

See FIG. 14 for restriction map of pGEX-5X-3-1024N. See FIG. 28 for sequence (SEQ ID NO:62)

Example 12

Cloning of the cDNA Fragment Coding the C Terminus Peptide (372 aa) of ICT1024 into pGEX-5X-3 Vector for Protein Expression in *E.coli*

The cDNA coding for the C-terminal 372 aa of ICT1024 was generated by a PCR amplification using a MGC20194 DNA as template. One pair of primers was used to generate the 1141 bp cDNA fragment containing a EcoRi site at its 5' and a Sal I site at its 3' end.

```
Primer 6: 1024midEcoUp (30-mer, with EcoRI site
1560-1577 nt of ICT1024 gene, GenBank Accession
Number: BC014425)
                                       (SEQ ID NO:63)
5'--- CCC AGG AAT TCC CAG GTG CAC AGC TTC ATT---3'

Primer 3: 1024SalDn (29-mer, corresponds to
2678-2661 nt of ICT1024 gene, GenBank Accession
Number: BC014425)
                                       (SEQ ID NO:56)
5'---CC GGC GTC GAC TCA GTG GAG CTG AGC GTC---3'
```

PCR reaction using Primer 6/Primer 3 and MGC 20194 template generated a 1141 bp DNA fragment that contains the 1560 to 2678 nt of the ICT1024. After purification of the PCR products, the 1141 bp DNA fragment was digested with EcoRI and Sal I, and then cloned into pGEX-5X-3 vector cleaved with EcoRI and Sal I. The final product, pGEX-5X-3-ICT1024C plasmid DNA, was identified and its sequence was confirmed by DNA sequencing.

See FIG. 15 for confirmed sequence of pGEX-5X-3-ICT1024C. See FIG. 27 for the sequence ((SEQ ID NO:64)

Example 13

Cloning of ICT1024 Full-Length cDNA into pETBlue-2 Vector for Protein Expression in *E.coli* host The full-length cDNA of ICT1024 (855 aa) was generated by PCR amplification using a cDNA clone purchased from ATCC (MGC: 20194) as template. Since the full-length of ICT1024 cDNA is 2568 bp, to reduce the mutation may occur during the PCR reaction, two pairs of primers were designed to generate two shorter DNA fragments that can be ligated together to generate full-length ICT1024 cDNA.

```
Primer 1: 1024EcoUp2 (28-mer, corresponds to
111-128 nt of ICT1024 gene, GenBank Accession
Number: BC014425)
                                       (SEQ ID NO:54)
5'---C AGG AAT TCC ATG AGT GAG GCC CGC AGG---3'

Primer 2: 1024MidDn (26-mer, corresponds to
1770-1745 nt of ICT1024 gene, GenBank Accession
Number: BC014425)
                                       (SEQ ID NO:55)
5'---CC CTG GGA TCC TGG TGG CAG ACA GAG---3'

Primer 3: 1024SalDn (29-mer, corresponds to
2678-2661 nt of ICT1024 gene, GenBank Accession
Number: BC014425)
                                       (SEQ ID NO:56)
5'---CC GGC GTC GAC TCA GTG GAG CTG AGC GTC---3'

Primer 8: 1024ClaDn (30-mer, corresponds to
2675-2658 nt of ICT-1024, GenBank Accession
Number: BC014425)
                                       (SEQ ID NO:65)
5'---CGC GGC ATC GAT GTG GAG CTG AGC GTC CAG---3'
```

PCR reaction using Primer 1/Primer 2 and MGC 20194 template generated a 1679 bp DNA fragment that contains the 111 to 1770 nt of the ICT1024. PCR reaction using Primer 3/Primer 8 and MGC 20194 template generated a 925 bp DNA fragment that contains the 1755 to 2675 nt of the ICT1024. After purification of the PCR products, the 1679 bp DNA fragment was digested with EcoRI and BamHI, the 928 bp fragment was digested with BamHI and Cla I, then cloned into pETBlue-2 vector (Novagen) cleaved with EcoRI and Cla I through a three-fragment ligation reaction. The final product, pETBlue-2-ICT1024 plasmid DNA, was identified and its sequence was confirmed by DNA sequencing.

See FIG. 28 for restriction map of pETBlue-2-ICT1024 plasmid. See FIG. 30 for sequence. (SEQ ID NO:66)

Example 14

Cloning of the cDNA Fragment Coding the N Terminus Peptide (400 aa) of ICT1024 into pETBlue-2 Vector for Protein Expression in *E.coli*

The cDNA coding for the N terminus 400 aa of ICT1024 was generated by a PCR amplification using a MGC20194 DNA as template. One pair of primers was used to generate the 1221 bp cDNA fragment containing a EcoRI site at its 5' and a Cla I site at its 3' end. No stop codon was integrated into the end of coding region since there is a stop codon downstream of the pETBlue-2 vector.

```
Primer 1: 1024EcoUp2 (28-mer, corresponds to
111-128 nt of ICT1024 gene, GenBank Accession
Number: BC014425)
                                       (SEQ ID NO:54)
5'---C AGG AAT TCC ATG AGT GAG GCC CGC AGG---3'

Primer 7: 1024Cla400Dn (30-mer, w/1293-1310 nt of
ICT1024 gene, GenBank Accession Number: BC014425)
                                       (SEQ ID NO:67)
5'---CGC GGC ATC GAT GTC CAT GTC CTC GAT CTG---3'
```

PCR reaction using Primer 1/Primer 7 and MGC 20194 template generated a 1221 bp DNA fragment that contains the 111 to 1310 nt of the ICT1024. After purification of the PCR products, the 1221 bp DNA fragment was digested with EcoRI and Cla I, and then cloned into pETBlue-2 vector cleaved with EcoRi and Cla I. The final product, pETBlue-2-ICT1024N plasmid DNA, was identified and its sequence was confirmed by DNA sequencing.

See FIG. 17 for the restriction mapof pETBlue-2-ICT1024N. See FIG. 31 for the sequence. (SEQ ID NO:68)

Example 15

Cloning of the cDNA Fragment Coding the C Terminus Peptide (372 aa) of ICT1024 into pETBlue-2 Vector for Protein Expression in *E.coli*

The cDNA coding for the C-terminal 372 aa of ICT1024 was generated by a PCR amplification using a MGC20194 DNA as template. One pair of primers was used to generate the 1139 bp cDNA fragment containing a EcoRI site at its 5' and a Cla I site at its 3' end. No stop codon was integrated into the end of coding region since there is a stop codon downstream of the pETBlue-2 vector.

```
Primer 6: 1024midEcoUp (30-mer, with EcoRI site
1560-1577 nt of ICT1024 gene, GenBank Accession
Number: BC014425)
                                      (SEQ ID NO:63)
5'--- CCC AGG AAT TCC CAG GTG CAC AGC TTC ATT---3'

Primer 8: 1024ClaDn (30-mer, corresponds to
2675-2658 nt of ICT-1024, GenBank Accession
Number: BC014425)
                                      (SEQ ID NO:65)
5'---CGC GGC ATC GAT GTG GAG CTG AGC GTC CAG---3'
```

PCR reaction using Primer 6/Primer 3 and MGC 20194 template generated a 1139 bp DNA fragment that contains the 1560 to 2675 nt of the ICT1024. After purification of the PCR products, the 1139 bp DNA fragment was digested with EcoRI and Cla I, and then cloned into pETBlue-2 vector cleaved with EcoRI and Cla I. The final product, pETBlue-2-ICT1024C plasmid DNA, was identified and its sequence was confirmed by DNA sequencing.

See FIG. 18 for restriction map of pETBlue-2-ICT1024C plasmid. See FIG. 32 for the sequence. (SEQ ID NO:69)

Production and Purification of ICT1024 Protein and Peptides

Purified ICT1024 protein or peptides are required as antigen for generating ICT1024 specific antibodies using conventional methods. The ICT1024 protein or peptides can be produced from various expression systems that include, but not limit to, mammalian culture cells, yeast, insect cells, and E.coli cells. Only purification methods that preserve protein antigenicity be used for generating ICT1024 protein or peptides. In general, the first step is to introduce the expression vectors carrying a full-length 1024 cDNA or a fragment of cDNA coding for ICT1024 peptide into their corresponding host systems. For example, the mammalian expression vectors are introduced into 293 cells using standard transfection procedures such as liposome mediated or electroporation mediated transfection. The second step is to amplify the host cells carrying the expression vector. One example is the fermentation of yeast or E.coli host cells transformed with the expression vector. The third step is to induce the expression of recombinant protein in the host cells, if inducible expression vector is used. This is particularly important if the recombinant protein is toxic to the host cells. The next step is to isolated recombinant protein from the host cells lysate. The final step is to remove the fusion domain and purify the desired recombinant protein or peptide, if the recombinant protein was generated in the form of a fusion protein.

Example 16

Production of ICT1024 Protein or Peptide using pGEX-5X-3/BL21 Cells

The Glutathione S-transferase (GST) Gene Fusion System (Amersham) is a versatile system for the expression, purification, and detection of fusion proteins produced in *Eschericia coli*. The system provides an inducible, high-level expression of genes or gene fragments as fusions with GST, with GST moiety at the amino terminus and the protein of interest at the carboxyl terminus. GST fusion proteins are purified from bacterial lysate by affinity chromatography using immobilized glutathione. GST fusion proteins are captured by the glutathione medium and the impurities are removed by washing. The reduced glutathione is used to elute fusion proteins under mild, non-denaturating conditions to preserve protein's tumorgenicity. For generating ICT1024 protein or peptides as antigen for production of antibodies, the ICT1024 protein or peptides is cleaved from GST using a site-specific protease whose recognition sequence is located immediately upstream from the multiple cloning site on the pGEX plasmids.

Screening for Proper GST expression Colonies

The pGEX-5X-3-ICT1024, pGEX-5x-3-1024N, or pGEX-5x-3-ICT1024C is transformed into host cell E.coli BL21 using standard protocol provided by Amersham.

Inoculate 12 single colonies into 2 ml in LB medium with 100 ug/ml ampicillin, incubate at 37° C. with shaking (250 rpm) until OD595 reach 0.6.

Split the culture into two 1 ml for IPTG induction (I) and un-induction (NI). To "I" tube, add IPTG to a final concentration of 0.1-0.5 mM.

Continue incubation at 37° C. with shaking (250 rpm) for 3 hours then transfer culture to a 1.5 ml micro-tube, recover cells by centrifugation at 14,000 rpm for 1 minute.

Add 200 ul of Protein Sample Buffer to the cell pellet, suspend cells, then boil sample at 100° C. for 2-5 minutes.

Load 15 ul of each sample onto a 10% SDS-PAGE gel, with protein molecular weigh markers on parallel lane. After running the gel, stain the gel with coomassie blue. The molecular weigh for GST protein alone is 26 Kd, for fusion protein of GST-ICT1024 is 122 kd, for fusion protein of GST-ICT1024N is 88 Kd, for fusion protein of GST-ICT1024C is 57 Kd.

Individual clones with highest expression levels of GST fusion protein are selected for production of respect GST fusion protein.

Isolation of GST-Fusion Protein

Inoculate a selected single colony into 100 ml LB with 100 ug/ml ampicillin, incubate at 37° C. with shaking (250 rpm) overnight.

Transfer 25 ml overnight culture into 1 liter pre-warmed LB with 100 ug/ml ampicillin in a 2-L flask, incubate at 37° C. with shaking (250 rpm) until OD595 reach 0.6.

Add IPTG to a final concentration of 0.1-0.5 mM to induce GST fusion protein expression, incubate at 37° C. with shaking (250 rpm) for 3 hours.

Harvest cells by centrifugation at 3,600 rpm for 10 minutes (Servall GS-3 rotor).

Resuspend cells in 20 ml R.S. with protease inhibitor (see appendix for R.S. buffer and R.S. buffer cocktail).

Sonicate sample for 6 times, 30 seconds each. Keep sample on ice during the sonication and mix the sample after each sonication.

Centrifuge the sonicated sample at 10,000 rpm for 10 minutes using a Servall GS-3 rotor. Transfer the supernatant to a fresh tube.

To the supernatant add glutathione-agarose beads slurry (GSH-Agarose powder, sigma G4510, 70 mg beads balanced in 4 ml RS, inversed at RT in a 15-ml tube for 1 hr to overnight, with 2-3 buffer replacements, resulting in 1 ml compact swollen beads slurry, could be stored as 50% slurry for a month. Use material from 1.5-2.0 liters of supernatant (37.5-50 ml) per 1 ml of resin in 50 ml tube.)

Mix the super/slurry gently at 40 C. on rotator for 0.5-2 hr.

Centrifuge at 1,500 rpm for 2 minutes, batch wash 2 times with 10 ml RS each. Add 10 ml RS to suspend sample, load onto a column.

Rinse the column with 10 ml RS.

Stripe the column with 50 mM GSH in RS (pH 8.0, adjusted by NaOH).

Collect 0.5 ml fractions by hand or a fraction collector. GST fusion protein should be eluted in fractions 5-11.

Locate GST fusion protein by placing 2 ul aliquots of each fraction into wells of microplates and adding 100 ul of 1× Bradford reagent (1:5 dilutions of Biorad reagent) and check the color of mixture.

To remove the GST from ICT1024 protein or peptides, the mixture of super/slurry, after batch wash, is washed 1× with thrombin cleavage buffer (T.C.B., see appendix). Then, add 2 ml T.C.B. and 10 μg (13 ul) of Thrombin (0.768 μg/μl), shaking at RT for 1.5 hours.

(Thrumbin, human, lyoph, Cat: 605195, Calbiochem Corp.)
Appendix:

| R.S. buffer (500 ml) | |
| --- | --- |
| 1M Tris.HCl, pH 7.9 | 10 ml (20 mM) |
| 0.5 M EDTA | 0.2 ml (0.2 mM) |
| NaCl | 29.22 g (1 M) |

| R.S. buffer cocktail | | | | |
| --- | --- | --- | --- | --- |
| R.S. plus the following | 500 ml | 1 liter | | Final conc. |
| 2ME (40 C.) | 1 ml | 2 ml | | 0.2% |
| NP-40 (RT) | 2.5 ml | 5 ml | | 0.5% |
| PMSF (RT) MW174.2 | 17.42 mg (in EtOH) | 34.84 mg | | 0.2 mM |
| Aprotinin (−200 C., H2O) | 1 mg (freely in water) | 2 mg | | 2 μg/ml |
| Leupeptin (40 C. or −200 C.) | 1 mg (in water, 1 mg/ml) | 2 mg | | 2 μg/ml |
| Pepstatin-A (40 C. or −200 C.) | 1 mg (in EtOH, up to 1 mg/ml) | 2 mg | | 2 μg/ml |

T.C.B. (Thrombin cleavage buffer), for 30 ml:

| 1 M Tris, pH 8.0 | 1.5 ml (1:20.50 mM) |
| --- | --- |
| 4 M NaCl | 1.125 ml (0.15 M) |
| 1 M CaCl2 | 0.075 ml (2.5 mM) |
| 2ME | 0.03 ml (0.1%) |

Example 17

Production of ICT1024 Protein or Peptide using pETBlue-2/BL21 Cells

ICT1024 is a membrane-associated proteinase belongs to the RHO family. Our preliminary data in pGEX-5X-3/BL21 expression system indicated that the GST-ICT1024 fusion protein is very toxic to the bacterial host, and therefore it is difficult to get the high levels of GST-ICT1024 fusion protein expression by IPTG induction in DH5α-T1 or BL21 cells. The pETBlue system (Novagen) may likely help us to solve the toxicity problem. The pET-Blue2 vector employs the bacteriophage T7 promoter to drive the expression of the interested gene. The bacteriophage T7 polymerase only will be expressed in BL(DE3) cells when induced by IPTG. When BL21(DE3)pLysS cells are used, the T7 polymerase activity will be further contained by the expressed T7 lysozyme. All these features of this system make the expression of the interested protein very selective and tightly controlled, that favors my present purpose: to express otherwise very toxic proteins. Another advantage of using the pETBlue-2 is the utilization of α-complementation of LacZ gene product, β-Galactosidase, to use blue/white colony based selection of plasmid constructs. Additionally, the C'-end of the engineered fusion protein contains the in-frame tags: HSV Tag and His.Tag that are linked in tandem. These tags can be used for purification and detection of the fusion products, respectively.

The pETBlue-2-ICT1024, pETBlue-2-1024N, or pETBlue-2-ICT1024C plasmid DNA is transformed into host cell E.coli BL21 using standard protocol provided by Novagen. The transformed clones are easily visual identified by blue/white colony screening, since pETBlue-2 vector uses a weak constitutive E. coli promoter (tet) to drive expression of the lacZ alpha-peptide, whereas expression of ICT1024 gene is driven by a T7lac promoter in the opposite orientation. Insertion of ICT1024 sequences into the multiple cloning site (MCS) disrupts expression of the lacZ alpha-peptide and produces a white colony phenotype in strain DH5a when plated in the presence of X-gal. Colonies derived from the unmodified vector turn blue. Because T7-driven protein expression requires inserts to be cloned in an antisense orientation relative to the tet promoter, basal expression of ICT1024 sequences is virtually absent. The high copy number pUC origin of replication present on the pETBlue-2 plasmids greatly increases plasmid yields and therefore the expressed ICT1024 protein or peptides.

The ICT1024 gene or fragments in pETBlue-2 vector are expressed at high levels, because the inserted sequences are in the sense orientation relative to the T7lac promoter, and the reading frame meet the translation requirements of pET-Blue-2 vector. Protein expression is accomplished by transforming the recombinant pETBlue-2 plasmids into the host strains Tuner™(DE3)pLacI or Origami™(DE3)pLacI followed by induction with IPTG. These hosts carry a chromosomal copy of the T7 RNA polymerase gene under lacUV5 control, and supply sufficient lac repressor via the compatible pLacI plasmid to ensure low level uninduced expression. The lacY status of the Tuner strain allows uniform dose-dependent IPTG induction of the target protein throughout the culture, and Origami strains enhance cytoplasmic disulfide bond formation.

Furthermore, since the ICT1024, ICT1024N, and ICT1024C inserts all lack an internal stop codon and were cloned in-frame with the C-terminal HSV○Tag® epitope and His○Tag® sequences. The ICT1024 protein or peptides are expressed in the form of fusion protein with HSV Tag and His Tag at its C-terminal. The ICT1024 protein and peptides are isolated and purified following Novagen's standard procedure.

Example 18

Production of ICT1024 Protein or Peptide using 293 Cells

Even through mild, non-denaturing conditions were used for purify recombinant proteins from E. coli to preserve their antigenicity, too many times that the purified protein lost their antigenicity due to lower solubility or unsatisfied un-folding of the recombinant protein. Utilizing mammlian culture system for expression recombinant protein can overcome this hurdle, though the yield of recombinant protein from such a system usually is much lower than the E.coli expression system.

I. Transfection of HEK 293 Cells using Electroporation Approach

Grow cells in RPMI 1640 medium containing 10% FBS.

Wash cells with FBS free RPMI 1640 media, add trypsin;

Inactivate trypsin with RPMI 1640 medium containing 10% FBS.

Wash cells times using RPMI 1640 media with 2.5% FBS (no antibiotics).

Resuspend the cells in RPMI 1640 media with 2.5% FBS at a density of 5×106 cells/ml.

Transfer 200 ul cells into an sterile electroporation cuvette (BTX Cuvettes Model #620: 2 mm gap). Add 10 ug of plasmide DNA (pCI-ICT1024, pCI-ICT1024N, or pCI-ICT1024C) into the cuvettes and mix well. Incubate cells and DNA for 10 minutes at room temperature before electroporation.

Electroporation Settings:

| Electroporation generator | BTX ECM 830 |
|---|---|
| Voltage (V) | 1200 HV |
| Pulse Length (μs) | 50 μs |
| No. of pulses (n) | 1 |

After electroporation, let the cells recover for 10 minute incubation at room temperature.

Place the transfected cells (1×106) into in a single well of a 6-well plate containing 2 ml of prewarmed RPMI medium with 10% serum, and incubate in 37° C., 5% CO2 incubator for 48 hours.

II. Protein Extraction from Cell Membrane

Since ICT1024 protein is a membrane associated protein with majority of its C terminus residues in the membrane, the ICT1204 protein and the C terminus peptides expressed in the transfected cells need to be extracted from cell memberane using a M-PER Eukaryotic membrane Protein Extraction Reagent kit (Cat No: 89826, PIERCE).

Isolate 5×106 cells per sample by centrifuging harvested cell suspensions at 850×g for 2 minutes. Pellet cells (washed in PBS) in 1.7 ml conical microcentrifuge tubes.

Carefully remove and discard the supernatant.

Add 150 μl of Reagent A to the cell pellet. Pipette up and down to obtain a homogeneous cell suspension. Incubate 10 minutes at room temperature with occasional vortexing.

Place lysed cells on ice.

Dilute 2 parts Reagent C with 1 part Reagent B, making sufficient mixture for each sample to receive 450 μl (e.g., for 10 extractions, combine 3.33 ml of Reagent C with 1.67 ml of Reagent B). Note: Keep Reagent C at 4° C. or on ice at all times.

Add 450 μl of diluted Reagent C to each tube of lysed cells and vortex. Incubate tubes on ice for 30 minutes, vortexing every 5 minutes.

Centrifuge tubes at 10,000×g for 3 minutes at 4° C. Transfer supernatant to new tubes.

Incubate supenatant for 10 minutes at 37° C. to separate the membrane protein fraction.

Centrifuge tubes at room temperature for 2 minutes at 10,000×g to isolate the hydrophobic fraction (i.e., the fraction containing membrane protein of interest) from the hydrophilic fraction.

Carefully remove the hydrophilic phase (top layer) from the hydrophobic protein phase (bottom layer) and save in a new tube. Perform the phase separations as quickly as possible because the interface between the layers slowly disappears at room temperature. Place the separated fractions on ice.

Note: The majority of membrane protein should be found in the lower viscous phase.

Note: The hydrophobic fraction can now be used for membrane protein(s) analysis.

III. Protein Extraction from Whole Cells

The N terminus peptides of ICT1024 is likely not tightly associated with the cell membrane, therefore, it is much easy to isolated from the cell lysates using a M-PER Mammalian Protein Extraction Reagent (Cat No: 78501, PIERCE)

Carefully remove (decant) culture medium from the adherent cells.

Wash the cells once with PBS.

Add an 300 ul of M-PER™ Reagent to each plate well (6-well plate).

Shake gently for 5 minutes.

Collect the lysate and transfer to a microcentrifuge tube.

Centrifuge samples at 27,000 g for 5-10 minutes to pellet the cell debris.

Transfer supernatant to a clean tube for further analysis (SDS page or western blotting).

IV. Isolation of ICT1024 Protein or Peptides from SDS-Page Gel

Dilute the protein sample 1:1 with 2× SDS Sample Buffer, heat the samples and the molecular weight standards for 5 minutes at 100° C.

The samples are loaded onto a 10% SDS-Page gel.

Run the gel at 10 mA until the dye enters the separating gel. Then increase the current to 15 mA. When the dye reaches the bottom of the separating gel, turn off the power supply, and remove the gel sandwich.

Carefully open the sandwich by using one of the spacers to pry the plates apart. Gently cut away the stacking gel and place the separating gel in a small plastic container for staining.

Cover the gel with fixing solution and shake gently for 15 minutes.

Pour off the fixer and cover the gel with Coomassie blue staining solution. Shake gently for at least 2 hours. Pour off the staining solution and cover the gel with the wash solution.

Cut of the gel fragment containing the desired protein band, extract protein from the gel using standard procedures.

Example 19

Production of ICT1024 Antibodies

The purified ICT1024 protein or peptides are used to generate ICT1024 antibodies. The mammalian expression vectors carrying ICT1024 full-length cDNA or fragment are used to generate ICT1024 antibodies directly using DNA vaccination methods. In addition, a series of ICT1024 peptides (15 aa to 30 aa) will be chemically synthesized as antigen for generating ICT1024 antibodies. Further more, since ICT1024 is a membrane protein, plasmid DNA will be constructed for expression of ICT1024 specific intrabodies (single-chain Fv fragment, scFv) within the cell and directed against ICT1024's intracellular domains.

The ICT1024 antibodies to be generated include, but not limit to, mouse polyclonal antibodies, mouse monoclonal antibodies (MAb), rabbit polyclonal antibodies, rabbit monoclonal antibodies, chicken IgY antibodies, and humanized antibodies.

Example 20

Generation of ICT1024 Antibodies by Directly DNA Vaccination of Mouse

Plasmid DNA or polynucleotides have been proved to be good alternative vaccines to traditional whole organism or purified proteins. Advantages of DNA vaccination over traditional methods are listed below:

Simple: subcloning of DNA sequence into vectors (plasmid, or viral) is much easier than tedious and often very difficult undertakes of purification of antigen proteins.

Safer: individual proteins pose little risk of causing infection. If specific epitope sequences are selected for vaccination the toxicity, if any, of natural proteins could be also minimized as well.

Natural: studies showed that antigens (proteins orpolypeptides) produced in situ from DNA vaccines would adopt a natural conformation and have necessary post-translation modifications made by host during natural infections.

Although enhanced immune responses have been reported when DNA vaccines are delivered with cationic lipids, gene gun, or jet injection, the electroporation is by far the most efficient way for DNA transfection both in vitro and in vivo. The combination of plasmid DNA injection and electroporation delivery has produced convincing positive results on different tissues, such as muscle, skin, tumor xenografts, etc.

As the combination of DNA vaccine and electroporation offers a convenient and speedy way to generate polyclonal antibodies in mice, this approach can thus be used to screen for potential antibody targets discovered in house which may have applications in disease diagnosis, or treatment.

Procedure

After Balb/c mouse is anesthetized, a stripe of skin on the back of mouse is shaved to expose the area of skin. Five location on one mouse were shaved. Two ug of pCI-ICT1024, pCI-ICT1024N, or pCI-ICT1024C plasmid DNA in 20 µl normal saline is injected into layer of skin of in each shaved area via route of subcutaneous using a 1-ml syringe and a 30.5 gauge needle. Electroporations are then applied immediately on the injected area after the injection with parameters set as: Voltage=100V, Pulse Length=20 ms, Pulse Number=3, and Pulse Interval=800 ms.

The DNA vaccination (immunization) procedure was repeated 7 days later, and repeated another time 1 month later. Blood samples are collected 7 days after the last DNA vaccination for testing of immunization effectiveness. In other experiments, the last boosting was also achieved by injecting lysates of mouse or human tumor cells that are transfected beforehand with the same DNA.

The effectiveness of immunization with DNA expression were tested with ELISA, Western, or functional assays like cell proliferation assay, apoptosis assay. For ELISA assay plastic support surface were coated with crude lysates from transfected cos-7 cells or 293 cells as source of antigen, which is then detected with antibody present in the immunoglobulins purified from the sera of immunized mice. In other experiment, the antisera collected from immunized mice were used to precipitate ICT1024 protein or peptides (antigens) presented in the lysates of transfected cos-7 or 203 cells. The precipitated targets are then detected by Western Blotting.

Specific antibodies against ICT1024 can be purified using traditional methods, DEAE ion-exchange column, Protein-A affinity column, etc. Pure antibodies can be obtained after monoclonal antibodies are produced through hybridoma technology.

Example 21

Generation of Rabbit Monoclonal Antibodies Against ICT1024

To generate rabbit monoclonal antibodies against ICT1024, the expression vectors carrying ICT1024 full-length cDNA or cDNA fragment are transfected into the rabbit cell line 240E. The resulting transfected cells are pooled and used to immunize a rabbit. Endogenous proteins from the cell line 240E do not induce immune reaction and only the expressed human proteins are recognized as antigens by the rabbit. The combination of high fusion efficiency, better stability of hybridoma and a large repertory of antibody-producing cells make it possible to multiplex antigens for immunizing a single rabbit.

Example 22

Generation of Mouse Monoclonal Antibodies Against ICT1024 using ICT1024 Protein or Peptides as Antigen Coventional methods will be employed to generate and purify mouse polyclonal antibodies and monoclonal antibodies against ICT1024 protein. We will also utilize chemically synthesized ICT1024 peptides corresponding to different domains of ICT1024 protein to generate and purify mouse polyclonal antibodies and monoclonal antibodies against ICT1024 protein. The goal of this is to screen the best monoclonal antibodies against ICT1024, indicated by high affinity of binding with ICT1024 protein and more importantly, the capability of block the biological function of ICT1024 protein through antibody/antigen specific binding.

Example 23

Cloning of ICT1025 Full-Length cDNA into pCI Vector for Mamnmalian Cell Expression and DNA Vaccination The full-length cDNA of ICT1025 (803 aa) was generated by PCR amplification using a cDNA clone purchased from ATCC (MGC: 20194) as template. Since the full-length of ICT1025 cDNA is 2780 bp, to reduce the mutation may occur during the PCR reaction, two pairs of primers were designed to generate two shorter DNA fragments that can be legated together to generate full-length ICT1025 cDNA.

See FIG. 20. The confirmed sequence of pCI-ICT1025 expression plasmid.

Production and Purification of ICT1025 Protein and Peptides

Purified ICT1025 protein or peptides are required as antigen for generating ICT1025 specific antibodies using conventional methods. The ICT1025 protein or peptides can be produced from various expression systems that include, but not limit to, mammalian culture cells, yeast, insect cells, and E.coli cells. Only purification methods that preserve protein antigenicity be used for generating ICT1025 protein or peptides. In general, the first step is to introduce the expression vectors carrying a full-length ICT1025 cDNA or a fragment of cDNA coding for ICT1025 peptide into their corresponding host systems. For example, the mammalian expression vectors are introduced into 293 cells using standard transfection procedures such as liposome mediated or electroporation mediated transfection. The second step is to amplify the host cells carrying the expression vector. One example is the fermentation of yeast or E.coli host cells transformed with the expression vector. The third step is to induce the expression of recombinant protein in the host cells, if inducible expression vector is used. This is particularly important if the recombinant protein is toxic to the host cells. The next step is to isolated recombinant protein from the host cells lysate. The final step is to remove the fusion domain and purify the desired recombinant protein or peptide, if the recombinant protein was generated in the form of a fusion protein.

Example 24

Production of ICT1025 Protein or Peptide using pGEX-5X-3/BL21 Cells

The Glutathione S-transferase (GST) Gene Fusion System (Amersham) is a versatile system for the expression, purification, and detection of fusion proteins produced in *Eschericia coli*. The system provides an inducible, high-level expression of genes or gene fragments as fusions with GST, with GST moiety at the amino terminus and the protein of interest at the carboxyl terminus. GST fusion proteins are purified from bacterial lysate by affinity chromatography using innobilized glutathione. GST fusion proteins are captured by the glutathione medium and the impurities are removed by washing. The reduced glutathione is used to elute fusion proteins under mild, non-denaturating conditions to preserve protein's tumorgenicity. For generating ICT1025 protein orpeptides as antigen for production of antibodies, the ICT1025 protein or peptides is cleaved from GST using a site-specific protease whose recognition sequence is located immediately upstream from the multiple cloning site on the pGEX plasmids.

Screening for Proper GST Expression Colonies

The pGEX-5X-3-ICT1024, pGEX-5x-3-1024N, or pGEX-5x-3-ICT1024C is transformed into host cell *E.coli* BL21 using standard protocol provided by Amersham.

Inoculate 12 single colonies into 2 ml in LB medium with 100 ug/ml ampicillin, incubate at 37° C. with shaking (250 rpm) until OD595 reach 0.6.

Split the culture into two 1 ml for IPTG induction (I) and un-induction (NI). To "I" tube, add IPTG to a final concentration of 0.1-0.5 mM.

Continue incubation at 37° C. with shaking (250 rpm) for 3 hours then transfer culture to a 1.5 ml micro-tube, recover cells by centrifugation at 14,000 rpm for 1 minute.

Add 200 ul of Protein Sample Buffer to the cell pellet, suspend cells, then boil sample at 100° C. for 2-5 minutes.

Load 15 ul of each sample onto a 10% SDS-PAGE gel, with protein molecular weigh markers on parallel lane. After running the gel, stain the gel with coomassie blue. The molecular weigh for GST protein alone is 26 Kd, for fusion protein of GST-ICT1025 is 122 kd, for fusion protein of GST-ICT1024N is 88 Kd, for fusion protein of GST-ICT1024C is 57 Kd.

Individual clones with highest expression levels of GST fusion protein are selected for production of respect GST fusion protein.

Isolation of GST-Fusion Protein

Inoculate a selected single colony into 100 ml LB with 100 ug/ml ampicillin, incubate at 37° C. with shaking (250 rpm) overnight.

Transfer 25 ml overnight culture into 1 liter pre-warmed LB with 100 ug/ml ampicillin in a 2-L flask, incubate at 37° C. with shaking (250 rpm) until OD595 reach 0.6.

Add IPTG to a final concentration of 0.1-0.5 mM to induce GST fusion protein expression, incubate at 37° C. with shaking (250 rpm) for 3 hours.

Harvest cells by centrifugation at 3,600 rpm for 10 minutes (Servall GS-3 rotor).

Resuspend cells in 20 ml R.S. with protease inhibitor (see appendix for R.S. buffer and R.S. buffer cocktail).

Sonicate sample for 6 times, 30 seconds each. Keep sample on ice during the sonication and mix the sample after each sonication.

Centrifuge the sonicated sample at 10,000 rpm for 10 minutes using a Servall GS-3 rotor. Transfer the supernatant to a fresh tube.

To the supernatant add glutathione-agarose beads slurry (GSH-Agarose powder, sigma G4510, 70 mg beads balanced in 4 ml RS, inversed at RT in a 15-ml tube for 1 hr to overnight, with 2-3 buffer replacements, resulting in 1 ml compact swollen beads slurry, could be stored as 50% slurry for a month. Use material from 1.5-2.0 liters of supernatant (37.5-50 ml) per 1 ml of resin in 50 ml tube.)

Mix the super/slurry gently at 40 C. on rotator for 0.5-2 hr.

Centrifuge at 1,500 rpm for 2 minutes, batch wash 2 times with 10 ml RS each. Add 10 ml RS to suspend sample, load onto a column.

Rinse the column with 10 ml RS.

Stripe the column with 50 mM GSH in RS (pH 8.0, adjusted by NaOH).

Collect 0.5 ml fractions by hand or a fraction collector. GST fusion protein should be eluted in fractions 5-11.

Locate GST fusion protein by placing 2 ul aliquots of each fraction into wells of microplates and adding 100 ul of 1× Bradford reagent (1:5 dilutions of Biorad reagent) and check the color of mixture.

To remove the GST from ICT1025 protein or peptides, the mixture of super/slurry, after batch wash, is washed 1× with thrombin cleavage buffer (T.C.B., see appendix). Then, add 2 ml T.C.B. and 10 μg (13 ul) of Thrombin (0.768 μg/ul), shaking at RT for 1.5 hours. (Thrumbin, human, lyoph, Cat: 605195, Calbiochem Corp.).

Example 25

Production of ICT1025 Protein or Peptide using pETBlue-2/BL21 Cells

ICT1025 is a membrane-associated proteinase belongs to the RHO family. Our preliminary data in pGEX-5X-3/BL21 expression system indicated that the GST-ICT1025 fusion protein is very toxic to the bacterial host, and therefore it is difficult to get the high levels of GST-ICT1025 fusion protein expression by IPTG induction in DH5α-T1 or BL21 cells. The pETBlue system (Novagen) may likely help us to solve the toxicity problem. The pET-Blue2 vector employs the bacteriophage T7 promoter to drive the expression of the interested gene. The bacteriophage T7 polymerase only will be expressed in BL(DE3) cells when induced by IPTG. When BL21(DE3)pLysS cells are used, the T7 polymerase activity will be further contained by the expressed T7 lysozyme. All these features of this system make the expression of the interested protein very selective and tightly controlled, that favors my present purpose: to express otherwise very toxic proteins. Another advantage of using the pETBlue-2 is the utilization of a-complementation of LacZ gene product, β-Galactosidase, to use blue/white colony based selection of plasmid constructs. Additionally, the C'-end of the engineered fusion protein contains the in-frame tags: HSV Tag and His.Tag that are linked in tandem. These tags can be used for purification and detection of the fusion products, respectively.

The pETBlue-2-ICT1025, pETBlue-2-1025N, or pET-Blue-2-ICT1025C plasmid DNA is transformed into host cell E.coli BL21 using standard protocol provided by Novagen. The transformed clones are easily visual identified by blue/white colony screening, since pETBlue-2 vector uses a weak constitutive E. coli promoter (tet) to drive expression of the lacZ alpha-peptide, whereas expression of ICT1025 gene is driven by a T7lac promoter in the opposite orientation. Insertion of ICT1025 sequences into the multiple cloning site (MCS) disrupts expression of the lacZ alpha-peptide and produces a white colony phenotype in strain DH5a when plated in the presence of X-gal. Colonies derived from the unmodified vector turn blue. Because T7-driven protein expression requires inserts to be cloned in an antisense orientation relative to the tet promoter, basal expression of ICT1025 sequences is virtually absent. The high copy number pUC origin of replication present on the pETBlue-2 plasmids greatly increases plasmid yields and therefore the expressed ICT1025 protein or peptides.

The ICT1025 gene or fragments in pETBlue-2 vector are expressed at high levels, because the inserted sequences are in the sense orientation relative to the T7lac promoter, and the reading frame meet the translation requirements of pET-Blue-2 vector. Protein expression is accomplished by transforming the recombinant pETBlue-2 plasmids into the host strains Tuner™(DE3)pLacI or Origami™(DE3)pLacI followed by induction with IPTG. These hosts carry a chromosomal copy of the T7 RNA polymerase gene under lacUV5 control, and supply sufficient lac repressor via the compatible pLacI plasmid to ensure low level uninduced expression. The lac Y status of the Tuner strain allows uniform dose-dependent IPTG induction of the target protein throughout the culture, and Origami strains enhance cytoplasmic disulfide bond formation. Refer to FIG. 19 for ICT1025 protein purified with above-described procedures.

Furthermore, since the ICT1025, ICT1025N, and ICT1025C inserts all lack an internal stop codon and were cloned in-frame with the C-terminal HSV●Tag® epitope and His●Tag® sequences. The ICT1025 protein or peptides are expressed in the form of fusion protein with HSV Tag and His Tag at its C-terminal. The ICT1025 protein and peptides are isolated and purified following Novagen's standard procedure.

Example 26

Production of ICT1025 Protein or Peptide using 293 Cells

Even through mild, non-denaturing conditions were used for purify recombinant proteins from E. coli to preserve their antigenicity, too many times that the purified protein lost their antigenicity due to lower solubility or unsatisfied un-folding of the recombinant protein. Utilizing mammlian culture system for expression recombinant protein can overcome this hurdle, though the yield of recombinant protein from such a system usually is much lower than the E.coli expression system.

I. Transfection of HEK 293 Cells using Electroporation Approach

Grow cells in RPMI 1640 medium containing 10% FBS.
Wash cells with FBS free RPMI 1640 media, add trypsin;
Inactivate trypsin with RPMI 1640 medium containing 10% FBS.
Wash cells times using RPMI 1640 media with 2.5% FBS (no antibiotics).
Resuspend the cells in RPMI 1640 media with 2.5% FBS at a density of 5×106 cells/ml.

Transfer 200 ul cells into an sterile electroporation cuvette (BTX Cuvettes Model #620: 2 mm gap). Add 10 ug of plasmide DNA (pCI-ICT1025, pCI-ICT1025N, or pCI-ICT1025C) into the cuvettes and mix well. Incubate cells and DNA for 10 minutes at room temperature before electroporation.

Electroporation Settings:

| Electroporation generator | BTX ECM 830 |
| Voltage (V) | 1200 HV |
| Pulse Length | 50 μs |
| No. of pulses (n) | 1 |

After electroporation, let the cells recover for 10 minute incubation at room temperature.

Place the transfected cells (1×106) into in a single well of a 6-well plate containing 2 ml of prewarmed RPMI medium with 10% serum, and incubate in 37° C., 5% CO2 incubator for 48 hours.

II. Protein Extraction from Cell Membrane

Since ICT1025 protein is a membrane associated protein with majority of its C terminus residues in the membrane, the ICT1205 protein and the C terminus peptides expressed in the transfected cells need to be extracted from cell memberane using a M-PER Eukaryotic membrane Protein Extraction Reagent kit (Cat No: 89826, PIERCE).

Isolate 5×106 cells per sample by centrifuging harvested cell suspensions at 850×g for 2 minutes. Pellet cells (washed in PBS) in 1.7 ml conical microcentrifuge tubes.

Carefully remove and discard the supernatant.

Add 150 μl of Reagent A to the cell pellet. Pipette up and down to obtain a homogeneous cell suspension. Incubate 10 minutes at room temperature with occasional vortexing.

Place lysed cells on ice.

Dilute 2 parts Reagent C with 1 part Reagent B, making sufficient mixture for each sample to receive 450 μl (e.g., for 10 extractions, combine 3.33 ml of Reagent C with 1.67 ml of Reagent B). Note: Keep Reagent C at 4° C. or on ice at all times.

Add 450 μl of diluted Reagent C to each tube of lysed cells and vortex. Incubate tubes on ice for 30 minutes, vortexing every 5 minutes.

Centrifuge tubes at 10,000×g for 3 minutes at 4° C. Transfer supernatant to new tubes.

Incubate supernatant for 10 minutes at 37° C. to separate the membrane protein fraction.

Centrifuge tubes at room temperature for 2 minutes at 10,000×g to isolate the hydrophobic fraction (i.e., the fraction containing membrane protein of interest) from the hydrophilic fraction.

Carefully remove the hydrophilic phase (top layer) from the hydrophobic protein phase (bottom layer) and save in a new tube. Perform the phase separations as quickly as possible because the interface between the layers slowly disappears at room temperature. Place the separated fractions on ice.

Note: The majority of membrane protein should be found in the lower viscous phase.

Note: The hydrophobic fraction can now be used for membrane protein(s) analysis.

III. Protein Extraction from Whole Cells

The N terminus peptides of ICT1025 is likely not tightly associated with the cell membrane, therefore, it is much easy to isolated from the cell lysates using a M-PER Mammalian Protein Extraction Reagent (Cat No: 78501, PIERCE)

Carefully remove (decant) culture medium from the adherent cells.

Wash the cells once with PBS.

Add an 300 ul of M-PER™ Reagent to each plate well (6-well plate).

Shake gently for 5 minutes.

Collect the lysate and transfer to a microcentrifuge tube.

Centrifuge samples at 27,000 g for 5-10 minutes to pellet the cell debris.

Transfer supernatant to a clean tube for further analysis (SDS page or western blotting).

IV. Isolation of ICT1025 Protein or Peptides from SDS-Page Gel

Dilute the protein sample 1:1 with 2× SDS Sample Buffer, heat the samples and the molecular weight standards for 5 minutes at 100° C.

The samples are loaded onto a 10% SDS-Page gel.

Run the gel at 10 mA until the dye enters the separating gel. Then increase the current to 15 mA. When the dye reaches the bottom of the separating gel, turn off the power supply, and remove the gel sandwich.

Carefully open the sandwich by using one of the spacers to pry the plates apart. Gently cut away the stacking gel and place the separating gel in a small plastic container for staining.

Cover the gel with fixing solution and shake gently for 15 minutes.

Pour off the fixer and cover the gel with Coomassie blue staining solution. Shake gently for at least 2 hours. Pour off the staining solution and cover the gel with the wash solution.

Cut of the gel fragment containing the desired protein band, extract protein from the gel using standard procedures.

Example 27

Production of ICT1025 Antibodies

The purified ICT1025 protein or peptides are used to generate ICT1025 antibodies. The mammalian expression vectors carrying ICT1025 full-length cDNA or fragment are used to generate ICT1025 antibodies directly using DNA vaccination methods. In addition, a series of ICT1025 peptides (15 aa to 30 aa) will be chemically synthesized as antigen for generating ICT1025 antibodies. Further more, since ICT1025 is a membrane protein, plasmid DNA will be constructed for expression of ICT1025 specific intrabodies (single-chain Fv fragment, scFv) within the cell and directed against ICT1025's intracellular domains.

The ICT1025 antibodies to be generated include, but not limit to, mouse polyclonal antibodies, mouse monoclonal antibodies (MAb), rabbit polyclonal antibodies, rabbit monoclonal antibodies, chicken IgY antibodies, and humanized antibodies.

Example 28

Generation of ICT1025Antibodies by Directly DNA Vaccination of Mouse

Plasmid DNA or polynucleotides have been proved to be good alternative vaccines to traditional whole organism or purified proteins. Advantages of DNA vaccination over traditional methods are listed below:

Simple: subcloning of DNA sequence into vectors (plasmid, or viral) is much easier than tedious and often very difficult undertakes of purification of antigen proteins.

Safer: individual proteins pose little risk of causing infection. If specific epitope sequences are selected for vaccination the toxicity, if any, of natural proteins could be also minimized as well.

Natural: studies showed that antigens (proteins or polypeptides) produced in situ from DNA vaccines would adopt a natural conformation and have necessary post-translation modifications made by host during natural infections.

Although enhanced immune responses have been reported when DNA vaccines are delivered with cationic lipids, gene gun, or jet injection, the electroporation is by far the most efficient way for DNA transfection both in vitro and in vivo. The combination of plasmid DNA injection and electroporation delivery has produced convincing positive results on different tissues, such as muscle, skin, tumor xenografts, etc.

As the combination of DNA vaccine and electroporation offers a convenient and speedy way to generate polyclonal antibodies in mice, this approach can thus be used to screen for potential antibody targets discovered in house which may have applications in disease diagnosis, or treatment.

After Balb/c mouse is anesthetized, a stripe of skin on the back of mouse is shaved to expose the area of skin. Five location on one mouse were shaved. Two ug of pCI-ICT1025, pCI-ICT1025N, or pCI-ICT1025C plasmid DNA in 20 μl normal saline is injected into layer of skin of in each shaved area via route of subcutaneous using a 1-ml syringe and a 30.5 gauge needle. Electroporations are then applied immediately on the injected area after the injection with parameters set as: Voltage=100V, Pulse Length=20 ms, Pulse Number=3, and Pulse Interval=800 ms.

The DNA vaccination (immunization) procedure was repeated 7 days later, and repeated another time 1 month later. Blood samples are collected 7 days after the last DNA vaccination for testing of immunization effectiveness. In other experiments, the last boosting was also achieved by injecting lysates of mouse or human tumor cells that are transfected beforehand with the same DNA.

The effectiveness of immunization with DNA expression were tested with ELISA, Western, or functional assays like cell proliferation assay, apoptosis assay. For ELISA assay plastic support surface were coated with crude lysates from transfected cos-7 cells or 293 cells as source of antigen, which is then detected with antibody present in the immunoglobulins purified from the sera of immunized mice. In other experiment, the antisera collected from immunized mice were used to precipitate ICT1025 protein or peptides (antigens) presented in the lysates of transfected cos-7 or 203 cells. The precipitated targets are then detected by Western Blotting.

Specific antibodies against ICT1025 can be purified using traditional methods, DEAE ion-exchange column, Protein-A affinity column, etc. Pure antibodies can be obtained after monoclonal antibodies are produced through hybridoma technology.

Example 29

Generation of Rabbit Monoclonal Antibodies Against ICT1025

To generate rabbit monoclonal antibodies against ICT1025, the expression vectors carrying ICT1025 full-length cDNA or cDNA fragment are transfected into the rabbit cell line 240E. The resulting transfected cells are pooled and used to immunize a rabbit. Endogenous proteins from the cell line 240E do not induce immune reaction and only the expressed human proteins are recognized as antigens by the rabbit. The combination of high fusion efficiency, better stability of hybridoma and a large repertory of antibody-producing cells make it possible to multiplex antigens for immunizing a single rabbit.

Example 30

Generation of Mouse Monoclonal Antibodies Against ICT1025 using ICT1025 Protein or Peptides as Antigen Coventional methods will be employed to generate and purify mouse polyclonal antibodies and monoclonal antibodies against ICT1025 protein. We will also utilize chemically synthesized ICT1025 peptides corresponding to different domains of ICT1025 protein to generate and purify mouse polyclonal antibodies and monoclonal antibodies against ICT1025 protein. The goal of this is to screen the best monoclonal antibodies against ICT1025, indicated by high affinity of binding with ICT1025 protein and more importantly, the capability of block the biological function of ICT1025 protein through antibody/antigen specific binding.

Generation of Hybridomas Producing ICT1025 mAb

Mouse monoclonal antibody (mAb) against human ICT1025 protein was generated using a standard procedure. Briefly, the human ICT1025 protein was purified from E.coli cells that transformed with a prokaryotic expression vector for human ICT1025 cDNA. The purified human ICT1025 protein was then used to immunize mouse. After several immunizations, when the ICT1025 antibody titer in the serum of immunized mice exceeded 10,000, the mice were sacrificed and the spleen cells were harvested to generate hybridoma clones. Individual hybridoma clone was then amplified and the culture supernatant was collected for verifying mAb against the ICT1025 protein using an ELISA based assay. From one mouse immunized with ICT1025 protein, 40 hybridoma clones were confirmed to produce mAb specific to human ICT1025 protein.

Selection of ICT1025 mAb with Cell Surface Binding Activity

It has been demonstrated that the expression levels of ICT1025 are up-regulated in tumor cells. More importantly, it is believed that migration of ICT1025 protein from cytoplasm to the cell membrane and exposure to the extracellular compartment occurs selectively in tumor cells. Therefore, to be effective for therapeutics or diagnosis, a ICT1025 mAb must be able to bind to the extracellular domin(s) of the ICT1025 protein. A Living Cell Surface Staining ELISA was used to screen the ICT1025 mAb that can bind to the cell surface domain(s) of ICT1025 protein.

Two cell lines, a human breast tumor cell line MDA-MB-435 and a human colon tumor cell line HT29, both of them over-expressing ICT1025 protein, were used in the mAb screening studies. Culture supernatants from the 40 ICT1025 mAb secreting hybridoma clones were screened for cell surface staining ELISA assay (FIGS. 36 and 37). Mouse IgG at various concentrations were used as non-specific controls. Also, the supernatants from three GST mAb secreting hybrisoma clones (2H2, 1H2, and 3G3) were used as negative controls (FIG. 37). The data from mAb screening using hybridoma culture supernatant in MDA-MB-435 cells (FIG. 36) and HT29 cells (FIG. 37) demonstrated that there are great variations in surface binding activies among the 40 mAb, with the data from one cell line confirmed the data from the other cell line. The clones with the highest cell surface binding activities (Absorbance value) were selected for mAb purification.

Six hybridoma clones (Table 1) with the highest cell surface binding activities were selected for production and purification of mAb for further in vitro and in vivo characterization. One hybridoma (Table 1) with no cell surface binding activity was also selected for production and purification of mAb as the control mAb in future functional studies.

The effect of 1025 inhibition on tumorigenesis and tumor growth was determined by treating the human breast tumor cell line MDA-MB-435 with either agent and inoculating treated cells into nude mice. For antibody treatment, 5 million MDA-MB-435 cells were pre-incubated with 100 ug of 1025 mAb or rat IgG in a total volume of 1 ml culture medium at 37° C. for 4 hours. After washing with PBS, the cells were inoculated into the fat pads of nude mice at 0.4 million cells per site. For siRNA treatment, 5 million MDA-MB-435 cells were transfected with 10 ug of 1025 siRNA or GFP siRNA using electroporation. Then cells were incubated in a total volume of 1 ml culture medium at 37° C. for 4 hours. After washing with PBS, the cells were inoculated into the fat pads of nude mice at 0.4 million cells per site. For the control group, 5 million MDA-MB-435 cells were incubated at 37° C. for 4 hours. After washing with PBS, the cells were inoculated into the fat pads of nude mice at 0.4 million cells per site. The tumors formed from treated cells showed substantial inhibition in growth rate compared with cells treated by negative controls (FIG. 38) and confirmed the 1025 inhibition effect on cells in culture also applies to tumorigenesis and tumor growth.

Other embodiments and uses of the invention will be apparent to those skilled in the art from consideration of the specification and practice of the invention disclosed herein. All references and materials cited herein, including all U.S. and foreign patents and patent applications, are specifically and entirely hereby incorporated herein by reference. It is intended that the specification and examples be considered exemplary only, with the true scope and spirit of the invention indicated by the following claims

TABLE 1

Search query: TGGCCAATAA (SEQ ID NO:36)

| Color Code | | | | | | | | | | |
|---|---|---|---|---|---|---|---|---|---|---|
| Tags per 200,000 | <2 | <4 | <8 | <16 | <32 | <64 | <128 | <256 | <512 | >512 |

| I. Library | Total Tags in Library | Tags per 200,000 | Color Code |
|---|---|---|---|
| SAGE_White_Blood_Cells_normal_AP | 31985 | 43 | |
| SAGE_Breast_carcinoma_metastasis_B_2 | 49794 | 40 | |

TABLE 1-continued

| | | | |
|---|---|---|---|
| SAGE_Breast_metastatic_carcinoma_B_95-260 | 45087 | 35 | |
| SAGE_Breast_carcinoma_CL_ZR75_1_tamoxifen | 40052 | 34 | |
| SAGE_Breast_carcino_myoepithelium_AP_DCIS7 | 37435 | 32 | |
| SAGE_Breast_carcinoma_AP_DCIS-2 | 28719 | 27 | |
| SAGE_Breast_carcinoma_B_IDC-5 | 60451 | 26 | |
| SAGE_Breast_carcinoma_CL_ZR75_1_estrogen | 38797 | 25 | |
| SAGE_Placenta_normal_B_1 | 118083 | 23 | |
| SAGE_Breast_carcinoma_B_95-348 | 60343 | 19 | |
| SAGE_Breast_carcinoma_B_DCIS-4 | 60605 | 19 | |
| SAGE_Stomach_cancer_B_G189 | 63075 | 19 | |
| SAGE_Pancreas_normal_CS_HX | 31985 | 18 | |
| SAGE_Peritoneum_normal_B_13 | 53527 | 18 | |
| SAGE_Prostate_adenocarcinoma_MD_PR317 | 64951 | 18 | |
| SAGE_Prostate_carcinoma_CL_LNCaP-T | 43542 | 18 | |
| SAGE_Brain_glioblastoma_CL_H54+LacZ | 66908 | 17 | |
| SAGE_Breast_carcinoma_myoepithelium_AP_DCIS6 | 81452 | 17 | |
| SAGE_Vascular_normal_CS_VEGF+ | 57316 | 17 | |
| SAGE_Breast_carcinoma_CL_MCF7estradiol_10H | 59583 | 16 | |
| SAGE_Breast_carcinoma_CL_MCF7estradiol_3h | 59583 | 16 | |
| SAGE_Brain_astrocytoma_grade_II_B_H563 | 88568 | 15 | |
| SAGE_Breast_carcinoma_B_95-259 | 39364 | 15 | |
| SAGE_Universal_reference_human_RNA_CL | 51729 | 15 | |
| SAGE_Breast_carcinoma_MD_DCIS | 40783 | 14 | |
| SAGE_Ovary_adenocarcinoma_B_OVT-6 | 41443 | 14 | |
| SAGE_Brain_astrocytoma_grade_II_B_H388 | 106285 | 13 | |

1. Table 2 - Virtual Northern Expression Pattern for cluster Hs.57988 Text Legend

| Tissue | EST Data | | SAGE Data | | EST Data | | | SAGE Data | | |
|---|---|---|---|---|---|---|---|---|---|---|
| | Normal | Cancer | Normal | Cancer | Normal | Cancer | P | Normal | Cancer | P |
| ALL TISSUES | | | | | 46/1989425 | 77/2012352 | 0.00 | 78/2516172 | 196/4801392 | 0.02 |
| brain | | | ' | | 6/224322 | 3/146887 | 0.38 | 2/309734 | 45/1697717 | 0.02 |
| cerebelium | | | ' | | 0/4079 | 0/0 | — | 1/90885 | 5/252749 | 0.35 |
| cervix | | | — | — | 0/1052 | 0/41849 | — | — | — | — |

-continued

1. Table 2 - Virtual Northern Expression Pattern for cluster Hs.57988 Text Legend

| Tissue | EST Data Normal | EST Data Cancer | SAGE Data Normal | SAGE Data Cancer | EST Data Normal | EST Data Cancer | P | SAGE Data Normal | SAGE Data Cancer | P |
|---|---|---|---|---|---|---|---|---|---|---|
| colon | | ● | ● | ● | 0/17509 | 17/145347 | 0.14 | 4/98089 | 4/325836 | 0.13 |
| eye | | ● | — | — | 2/56429 | 0/45229 | 0.28 | — | — | — |
| heart | | ● | — | — | 2/57248 | — | — | 3/83063 | — | — |
| kidney | ● | ● | ● | | 3/63353 | 2/75055 | 0.34 | 2/106467 | 0/ | — |
| liver | | ● | | | 0/53158 | 2/72873 | 0.29 | 0/66308 | 0/ | — |
| lung | | ● | ● | — | 4/103278 | 4/161191 | 0.33 | 2/88708 | — | — |
| lymph node | | | | — | 0.77166 | 0/48390 | — | 0/ | — | — |
| mammary gland | ● | ● | ● | ● | 1/41075 | 3/88612 | 0.43 | 13/375224 | 100/1256825 | 0.00 |
| ovary | | ● | ● | ● | 0/8152 | 4/83675 | 0.39 | 3/94887 | 5/179472 | 0.46 |
| pancreas | | ● | ● | ● | 0/7614 | 3/61447 | 0.40 | 5/64208 | 5/189999 | 0.11 |
| pineal gland | | ● | — | — | 0/6287 | 2/8491 | 0.28 | — | — | — |
| placenta | | ● | ● | — | 7/190882 | 2/40610 | 0.43 | 16/207348 | — | — |
| pooled tissue | | ● | | — | 6/303542 | 2/28022 | 0.22 | — | — | — |
| prostate | | ● | ● | ● | 0/62862 | 6/53816 | 0.04 | 7/266949 | 15/491794 | 0.38 |

TABLE III

Transmembrane analysis based on SOSUI search:

Query title: ICT-1 24
Total length: 855 A. A.
Average of hydrophobicity: -0.269240
2. This amino acid sequence is of a MEMBRANE PROTEIN which have 6 transmembrane helices.

| No. | N terminal | transmembrane region | C terminal | type | length |
|---|---|---|---|---|---|
| 1 | 409 | WLTFVHSLVTILAVCIYGIAPVG | 431 | PRIMARY | 23 |
| 2 | 656 | LWLSLFLHAGILHCLVSICFQMT | 678 | PRIMARY | 23 |
| 3 | 698 | LSGVTGNLASAIFLPYRAEVGPA | 720 | SECONDARY | 23 |
| 4 | 745 | WRAFFKLLAVVLFLFTFGLLPWI | 767 | PRIMARY | 23 |
| 5 | 773 | ISGFISGLFLSFAFLPYISFGK | 794 | SECONDARY | 22 |
| 6 | 803 | QIIIFQVVFLGLLAGLVVLFYVY | 825 | PRIMARY | 23 |

TABLE 4

Hybidoma clones selected for production and purification of mAb based on cell surface binding activities

| Name of hybridoma | ICT1025 protein binding activity | Cell surface binding activity in MDA-MB-435 cells | Cell surface binding activity in HT29 cells |
|---|---|---|---|
| ICT1025-4G4 | Yes | Very high (1.5) | Very high (1.3) |
| ICT1025-1A7 | Yes | High (1.1) | High (0.8) |
| ICT1025-3C9 | Yes | High (1.1) | Medium (0.6) |
| ICT1025-1D9 | Yes | High (0.9) | Medium (0.5) |
| ICT1025-5F9 | Yes | High (1.0) | High (1.0) |
| ICT1025-5E8 | Yes | High (0.9) | Medium (0.6) |
| ICT1025-4H3 | Yes | No (<0.1) | No (<0.1) |

What is claimed is:

1. A method for reducing ICT1024 expression in a mammalian tissue, comprising administering an inhibitor that interacts with ICT1024 DNA or RNA and thereby reduces ICT1024-expression, wherein the inhibitor is an siRNA, an shRNA, an antisense RNA, an antisense DNA, a decoy molecule, a decoy DNA, a double stranded DNA, a single-stranded DNA, a complexed DNA, an encapsulated DNA, a viral DNA, a plasmid DNA, a naked RNA, an encapsulated RNA, a viral RNA, a double stranded RNA, a molecule capable of generating RNA interference, or combinations thereof.

2. The method according to claim 1, wherein the tissue is breast tissue, colon tissue, prostate tissue, skin tissue, bone tissue, parotid gland tissue, pancreatic tissue, kidney tissue, uterine cervix tissue, lymph node tissue, or ovarian tissue.

3. The method according to claim 1, wherein the inhibitor is a nucleic acid molecule that is double stranded and has a length of about one hundred base pairs or less.

4. The method according to claim 1, wherein the inhibitor comprises an siRNA or an shRNA or a nucleic acid molecule encoding an siRNA or an shRNA.

5. The method according to claim 1, wherein the inhibitor comprises a nucleic acid molecule encoding a siRNA or an shRNA, and wherein the nucleic acid molecule is associated with a liposome, a cationic polymer, a receptor-mediated delivery system, a plasmid, a cosmid, a bacteriophage, or a viral vector.

6. The method according to claim 5, wherein the viral vector is a retroviral or adenoviral vector.

7. The method according to claim 1, wherein the inhibitor is an siRNA or an shRNA, and wherein the inhibitor causes post-transcriptional silencing of ICT1024 in the mammalian tissue.

8. The method according to claim 1, wherein the mammalian tissue is human tissue.

9. The method according to claim 1, wherein the inhibitor is an siRNA molecule and is delivered in the form of a naked oligonucleotide.

10. A method of inhibiting in vivo expression of ICT1024 by administering siRNA that specifically binds and inhibits ICT1024 to a patient in need thereof.

11. The method of claim 10, wherein the patient is a human.

12. The method according to claim 10, wherein the nucleic acid molecule is double stranded and has a length of up to 25 base pairs.

13. The method according to claim 1, wherein the inhibitor is a nucleic acid molecule that is double stranded and has a length of up to 25 base pairs.

14. The method according to claim 10, wherein the siRNA is part of a complex comprising a cationic polymer.

15. The method according to claim 1 or 10, wherein the siRNA comprises an antisense strand that is complementary to the nucleic acid sequence of SEQ ID NO: 21 or SEQ ID NO: 22.

16. The method according to claim 1, wherein the inhibitor is administered directly to the tissue.

17. A method for reducing ICT1024 expression in a cell, comprising administering an inhibitor of ICT1024 polypeptide, DNA or RNA, wherein the inhibitor is a nucleic acid composition and reduces the expression of the ICT1024 polypeptide, DNA or RNA.

18. An antisense nucleic acid molecule for targeting ICT1024, wherein the antisense nucleic acid molecule comprises a sequence that is complementary to a nucleic acid sequence of SEQ ID NO: 21 or SEQ ID NO: 22.

19. A double-stranded nucleic acid molecule comprising the antisense nucleic acid molecule of claim 18 and its corresponding sense strand.

20. The method according to claim 1, wherein the nucleic acid molecule comprises at least one modified nucleotide.

21. The method according to claim 10, wherein the siRNA comprises at least one modified nucleotide.

22. The antisense nucleic acid molecule according to claim 18, wherein the antisense nucleic acid molecule comprises at least one modified nucleotide.

23. The double-stranded nucleic acid molecule according to claim 19, wherein the double-stranded nucleic acid molecule comprises at least one modified nucleotide.

24. The method according to claim 20, wherein the at least one modified nucleotide stabilizes the nucleic acid molecule.

25. The method according to claim 21, wherein the at least one modified nucleotide stabilizes the siRNA.

26. The method according to claim 20, wherein the at least one modified nucleotide protects the nucleic acid molecule against degradation.

27. The method according to claim 21, wherein the at least one modified nucleotide protects the siRNA against degradation.

28. The antisense nucleic acid molecule according to claim 22, wherein the at least one modified nucleotide stabilizes the antisense nucleic acid molecule.

29. The double-stranded nucleic acid molecule according to claim 23, wherein the at least one modified nucleotide stabilizes the double-stranded nucleic acid molecule.

30. The antisense nucleic acid molecule according to claim 22, wherein the at least one modified nucleotide protects the antisense nucleic acid molecule against degradation.

31. The double-stranded nucleic acid molecule according to claim 23, wherein the at least one modified nucleotide protects the double-stranded nucleic acid molecule against degradation.

* * * * *